United States Patent
Ray et al.

(10) Patent No.: US 11,478,558 B2
(45) Date of Patent: *Oct. 25, 2022

(54) PROSTATE-SPECIFIC MEMBRANE ANTIGEN TARGETED HIGH-AFFINITY AGENTS FOR ENDORADIOTHERAPY OF PROSTATE CANCER

(71) Applicant: The Johns Hopkins University, Baltimore, MD (US)

(72) Inventors: Sangeeta Ray, Ellicott City, MD (US); Martin G. Pomper, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/617,244

(22) PCT Filed: May 30, 2018

(86) PCT No.: PCT/US2018/035220
§ 371 (c)(1),
(2) Date: Nov. 26, 2019

(87) PCT Pub. No.: WO2018/222778
PCT Pub. Date: Dec. 6, 2018

(65) Prior Publication Data
US 2020/0306391 A1 Oct. 1, 2020

Related U.S. Application Data

(60) Provisional application No. 62/512,515, filed on May 30, 2017.

(51) Int. Cl.
| | | |
|---|---|---|
| *A61K 51/04* | (2006.01) | |
| *A61P 35/00* | (2006.01) | |
| *C07B 59/00* | (2006.01) | |
| *C07F 5/00* | (2006.01) | |
| *C07F 7/24* | (2006.01) | |

(52) U.S. Cl.
CPC .......... *A61K 51/0482* (2013.01); *A61P 35/00* (2018.01); *C07B 59/002* (2013.01); *C07F 5/003* (2013.01); *C07F 7/24* (2013.01); *C07B 2200/05* (2013.01)

(58) Field of Classification Search
CPC ............ A61K 51/0402; A61K 51/0497; A61K 51/0482; A61P 35/00; C07D 257/02; C07D 401/12; C07F 5/003; C07F 7/24; C07B 59/002; C07B 2200/05
See application file for complete search history.

(56) References Cited

U.S. PATENT DOCUMENTS

| | | | |
|---|---|---|---|
| 8,211,401 B2 * | 7/2012 | Babich | A61K 51/041 |
| | | | 424/1.65 |
| 9,044,468 B2 * | 6/2015 | Pomper | A61K 31/145 |
| 9,056,841 B2 * | 6/2015 | Pomper | C07D 209/12 |
| 9,371,360 B2 * | 6/2016 | Pomper | C07K 5/0815 |
| 9,694,091 B2 * | 7/2017 | Pomper | A61K 51/0406 |
| 9,884,132 B2 * | 2/2018 | Pomper | A61K 38/06 |
| 2013/0034494 A1 * | 2/2013 | Babich | C07D 257/02 |
| | | | 424/1.65 |
| 2014/0255306 A1 | 9/2014 | Babich et al. | |
| 2016/0067361 A1 * | 3/2016 | Babich | A61P 35/00 |
| | | | 424/1.85 |
| 2018/0273441 A1 * | 9/2018 | Musthakahmed | C07B 59/008 |

FOREIGN PATENT DOCUMENTS

| | | |
|---|---|---|
| WO | WO 2009/002529 | 12/2008 |
| WO | WO 2009/070302 | 4/2009 |
| WO | WO 2010/108125 | 9/2010 |
| WO | WO 2015/055318 | 4/2015 |
| WO | WO 2015/171792 | 11/2015 |
| WO | WO 2017/165473 | 9/2017 |

OTHER PUBLICATIONS

Eder et al., Bioconjugate Chem., 2012, 23, 688-697. (Year: 2012).*
Tykvart et al., Bioorg. And Med. Chem., 2014, 22(15), p. 4099-4108. (Year: 2014).*
Afshar-Oromieh et al., The diagnostic value of PET/CT imaging with the 68Ga-labelled PSMA ligand HBED-CC in the diagnosis of recurrent prostate cancer. European Journal of Nuclear Medicine and Molecular Imaging 2015, 42, 197-209.
Afshar-Oromieh et al., The Theranostic PSMA Ligand PSMA-617 in the Diagnosis of Prostate Cancer by PET/CT: Biodistribution in Humans, Radiation Dosimetry, and First Evaluation of Tumor Lesions. Journal of Nuclear Medicine 2015, 56, 1697-1705.
Banerjee et al., Preclinical evaluation of 86Y-labeled inhibitors of prostate-specific membrane antigen for dosimetry estimates. Journal of nuclear medicine 2015, 56, 628-34.
Banerjee et al., (2014) (6)(4)Cu-labeled inhibitors of prostate-specific membrane antigen for PET imaging of prostate cancer. J Med Chem 57, 2657-2669.
Banerjee et al., 68Ga-labeled inhibitors of prostate-specific membrane antigen (PSMA) for imaging prostate cancer. J Med Chem Jul. 22, 2010; 53(14): 5333-5341.
Banerjee et al., A modular strategy to prepare multivalent inhibitors of prostate-specific membrane antigen (PSMA). Oncotarget Dec. 2011; 2(12): 1244-1253.
Banerjee et al., Effect of chelators on the pharmacokinetics of (99m)Tc-labeled imaging agents for the prostate-specific membrane antigen (PSMA). J Med Chem 2013, 56, 6108-21.

(Continued)

*Primary Examiner* — Michael G. Hartley
*Assistant Examiner* — Leah H Schlientz
(74) *Attorney, Agent, or Firm* — Casimir Jones, S.C.; Jeffrey W. Childers

(57) ABSTRACT

Prostate-specific membrane antigen targeted high-affinity agents for endoradiotherapy of prostate cancer are disclosed.

12 Claims, 25 Drawing Sheets
(24 of 25 Drawing Sheet(s) Filed in Color)

(56) References Cited

OTHER PUBLICATIONS

Banerjee et al., Preclinical Comparative Study of (68)Ga-Labeled DOTA, NOTA, and HBED-CC Chelated Radiotracers for Targeting PSMA. Bioconjug Chem Jun. 15, 2016;27(6):1447-55.
Banerjee et al., Sequential SPECT and Optical Imaging of Experimental Models of Prostate Cancer with a Dual Modality Inhibitor of the Prostate-Specific Membrane Antigen. Angewandte Chemie 2011, 50, 9167-70.
Banerjee et al., Synthesis and evaluation of technetium-99m- and rhenium-labeled inhibitors of the prostate-specific membrane antigen (PSMA). Journal of medicinal chemistry 2008, 51, 4504-17.
Baum et al., 177Lu-Labeled Prostate-Specific Membrane Antigen Radioligand Therapy of Metastatic Castration-Resistant Prostate Cancer: Safety and Efficacy. Journal of nuclear medicine Jul. 2016;57(7):1006-13.
Benesova et al., Albumin-Binding PSMA Ligands: Optimization of the Tissue Distribution Profile. Mol Pharm. Mar. 5, 2018;15(3):934-946.
Benesova et al., Preclinical Evaluation of a Tailor-Made DOTA-Conjugated PSMA Inhibitor with Optimized Linker Moiety for Imaging and Endoradiotherapy of Prostate Cancer (2015) Journal of nuclear medicine 56, 914-20.
Berge et al., "Pharmaceutical Salts", Journal of Pharmaceutical Science, 1977, 66, 1-19.
Chandran et al., Prostate specific membrane antigen targeted nanoparticles for therapy of prostate cancer, published Jun. 4, 2009.
Chang et al., Overview of Prostate-Specific Membrane Antigen. Reviews in Urology 2004, 6, S13-S18.
Chatalic et al., Towards Personalized Treatment of Prostate Cancer: PSMA I&T, a Promising Prostate-Specific Membrane Antigen-Targeted Theranostic Agent. Theranostics 2016, 6, 849-61.
Chen et al., 2-(3-{1-Carboxy-5-[(6-[18F]fluoro-pyridine-3-carbonyl)-amino]-pentyl}-ureido)-pen tanedioic acid, [18F]DCFPyL, a PSMA-based PET imaging agent for prostate cancer. Clinical cancer research 2011, 17, 7645-53.
Chen et al., A low molecular weight PSMA-based fluorescent imaging agent for cancer. Biochemical and biophysical research communications Dec. 18, 2009;390(3):624-9.
Chen et al., Radiohalogenated Prostate-Specific Membrane Antigen (PSMA)-Based Ureas as Imaging Agents for Prostate Cancer. Journal of Medicinal Chemistry Dec. 25, 2008;51(24):7933-43.
Chen et al., Synthesis and biological evaluation of low molecular weight fluorescent imaging agents for the prostate-specific membrane antigen. Bioconjug Chem 2012 Dec. 19, 2012;23(12):2377-85.
Choy et al., (177)Lu-Labeled Phosphoramidate-Based PSMA Inhibitors: The Effect of an Albumin Binder on Biodistribution and Therapeutic Efficacy in Prostate Tumor-Bearing Mice. Theranostics Apr. 27, 2017;7(7):1928-1939.
Dennis et al., Albumin binding as a general strategy for improving the pharmacokinetics of proteins. The Journal of biological chemistry Sep. 20, 2002;277(38):35035-43.
Dennis et al., Imaging tumors with an albumin-binding Fab, a novel tumor-targeting agent. Cancer research Jan. 1, 2007;67(1):254-61.
Eder et al. 68Ga-Complex Lipophilicity and the Targeting Property of a Urea-Based PSMA Inhibitor for PET Imaging. Bioconjugate Chemistry Apr. 18, 2012;23(4):688-97.
Haberkorn et al., P8.01 PSMA ligands for diagnosis and therapy of prostate cancer. Annals of Oncology. 2015;26(Suppl. 2):ii33-ii35.
Haberkorn, et al., New Strategies in Prostate Cancer: Prostate-Specific Membrane Antigen (PSMA) Ligands for Diagnosis and Therapy. Clinical cancer research 2016, 22, 9-15.
Herrmann et al., Biodistribution and radiation dosimetry for a probe targeting prostate-specific membrane antigen for imaging and therapy. Journal of nuclear medicine 2015, 56, 855-61.
Hillier et al., [131I]MIP-1466, a small molecule prostate-specific membrane antigen (PSMA) inhibitor for targeted radiotherapy of prostate cancer (PCa).Meeting Abstract. Journal of Nuclear Medicine May 2012;53(supplement 1):170.

Hillier et al., 123I-MIP-1072, a small-molecule inhibitor of prostate-specific membrane antigen, is effective at monitoring tumor response to taxane therapy. Journal of nuclear medicine 2011, 52, 1087-93.
Kelly et al., Trifunctional PSMA-targeting constructs for prostate cancer with unprecedented localization to LNCaP tumors. Eur J Nucl Med Mol Imaging 2018.
Kiess et al., (2S)-2-(3-(1-Carboxy-5-(4-211At-Astatobenzamido)Pentyl)Ureido)-Pentanedioic Acid for PSMA-Targeted alpha-Particle Radiopharmaceutical Therapy. Journal of nuclear medicine 2016, 57, 1569-1575.
Kiess, et al., Prostate-specific membrane antigen as a target for cancer imaging and therapy. Q J Nucl Med Mol Imaging. Sep. 2015;59(3):241-68.
Kratochwil et al., [(1)(7)(7)Lu]Lutetium-labelled PSMA ligand-induced remission in a patient with metastatic prostate cancer. Eur J Nucl Med Mol Imaging Jan. 9, 2015;42:987-8.
Kratochwil et al., Targeted Alpha Therapy of mCRPC with 225Actinium-PSMA-617: Dosimetry estimate and empirical dose finding. Journal of Nuclear Medicine 2017.
Kulkarni et al., PSMA-Based Radioligand Therapy for Metastatic Castration-Resistant Prostate Cancer: The Bad Berka Experience Since 2013. Journal of nuclear medicine 2016, 57, 97s-104s.
Muller et al., DOTA conjugate with an albumin-binding entity enables the first folic acid-targeted 177Lu-radionuclide tumor therapy in mice. J Nucl Med 2013, 54, 124-31.
Rowe et al., Comparison of Prostate-Specific Membrane Antigen-Based 18F-DCFBC PET/CT to Conventional Imaging Modalities for Detection of Hormone-Naïve and Castration-Resistant Metastatic Prostate Cancer. Journal of nuclear medicine 2016, 57, 46-53.
Shallal et al., Heterobivalent agents targeting PSMA and integrin-alphavbeta3. Bioconjug Chem 2014, 25, 393-405.
Song et al., Radioimmunotherapy of breast cancer metastases with alpha-particle emitter 225Ac: comparing efficacy with 213Bi and 90Y. Cancer Res 2009, 69, 8941-8.
Soydal et al., Marked Response to 177Lu Prostate-Specific Membrane Antigen Treatment in Patient With Metastatic Prostate Cancer. Clin Nucl Med. Feb. 2016;41(2):159-60.
Sterzing et al., (68)Ga-PSMA-11 PET/CT: a new technique with high potential for the radiotherapeutic management of prostate cancer patients. Eur J Nucl Med Mol Imaging 2016, 43, 34-41.
Szabo et al., Initial Evaluation of [18F]DCFPyL for Prostate-Specific Membrane Antigen (PSMA)-Targeted PET Imaging of Prostate Cancer. Molecular Imaging and Biology 2015, 1-10.
Trover et al., Detection and characterization of the prostate-specific membrane antigen (PSMA) in tissue extracts and body fluids. Int J Cancer. Sep. 4, 1995;62(5):552-8.
Tykvart et al., Design of Highly Potent Urea-Based, Exosite-Binding Inhibitors Selective for Glutamate Carboxypeptidase II. Journal of medicinal chemistry 58, 4357-63.
Tykvart et al., Rational design of urea-based glutamate carboxypeptidase II (GCPII) inhibitors as versatile tools for specific drug targeting and delivery. Bioorganic & Medicinal Chemistry 2014, 22, 4099-4108.
Umbricht et al., Preclinical Development of Novel PSMA-Targeting Radioligands: Modulation of Albumin-Binding Properties To Improve Prostate Cancer Therapy. Mol. Pharmaceutics Apr. 23, 2018;15(6):2297-2306.
Weineisen et al., 68Ga- and 177Lu-labeled PSMA I&T: Optimization of a PSMA targeted theranostic concept and first proof of concept human studies. Journal of nuclear medicine 2015, 56, 1169-76.
Weineisen et al., Synthesis and preclinical evaluation of DOTAGA-conjugated PSMA ligands for functional imaging and endoradiotherapy of prostate cancer. EJNMMI Res 4, 1-15.
Zechmann et al., Radiation dosimetry and first therapy results with a (124)I/(131)I-labeled small molecule (MIP-1095) targeting PSMA for prostate cancer therapy. Eur J Nucl Med Mol Imaging 2014, 41, 1280-92.
International Search Report and Written Opinion for PCT/US2018/035220, dated Sep. 13, 2018, 17 pages.
Extended EP Search Report for EP18808999.9, dated Feb. 11, 2021, 8 pages.

* cited by examiner

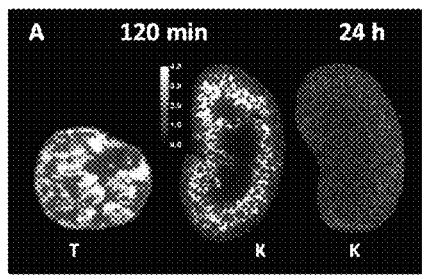 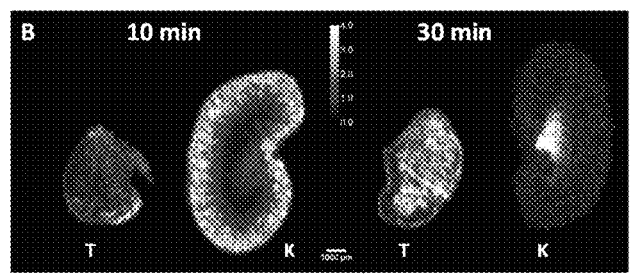
FIG. 11A  FIG. 11B
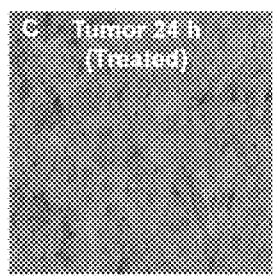 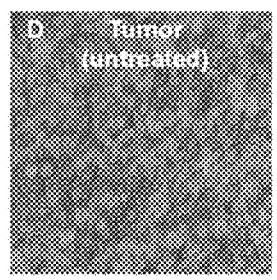
FIG. 11C  FIG. 11D
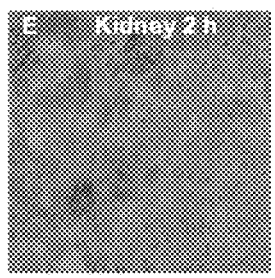
FIG. 11E

*FIG. 13A and FIG. 13B*
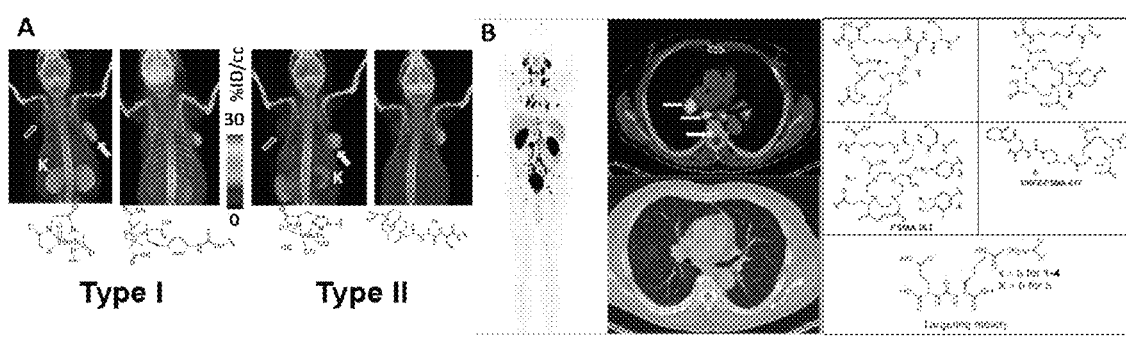
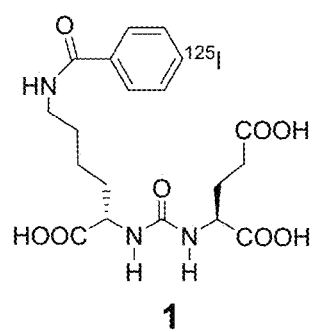
*FIG. 13A and FIG. 13B*

FIG. 18A
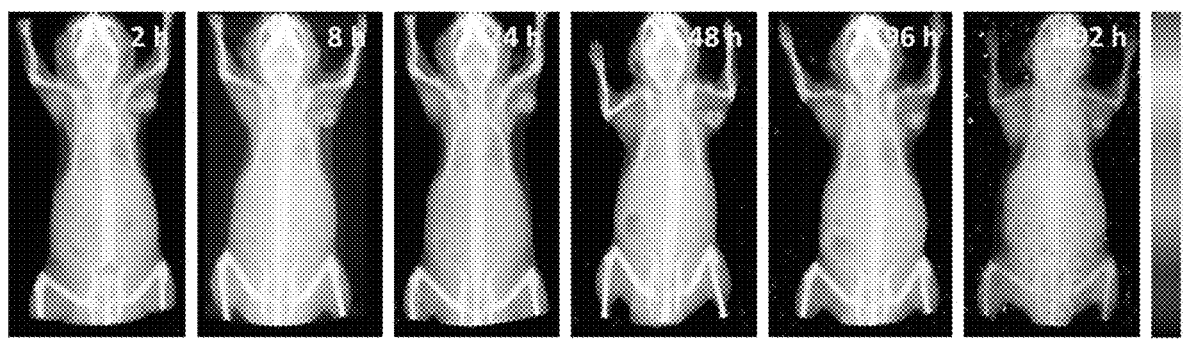
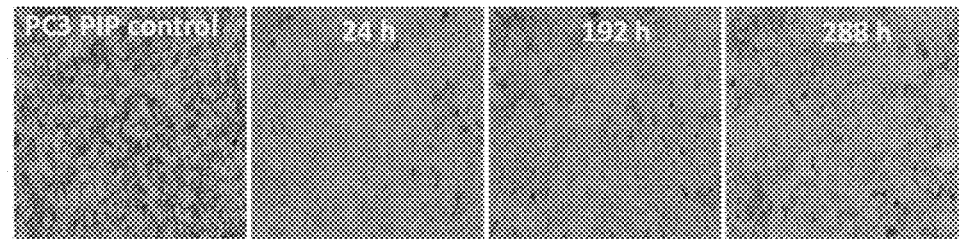
FIG. 18B

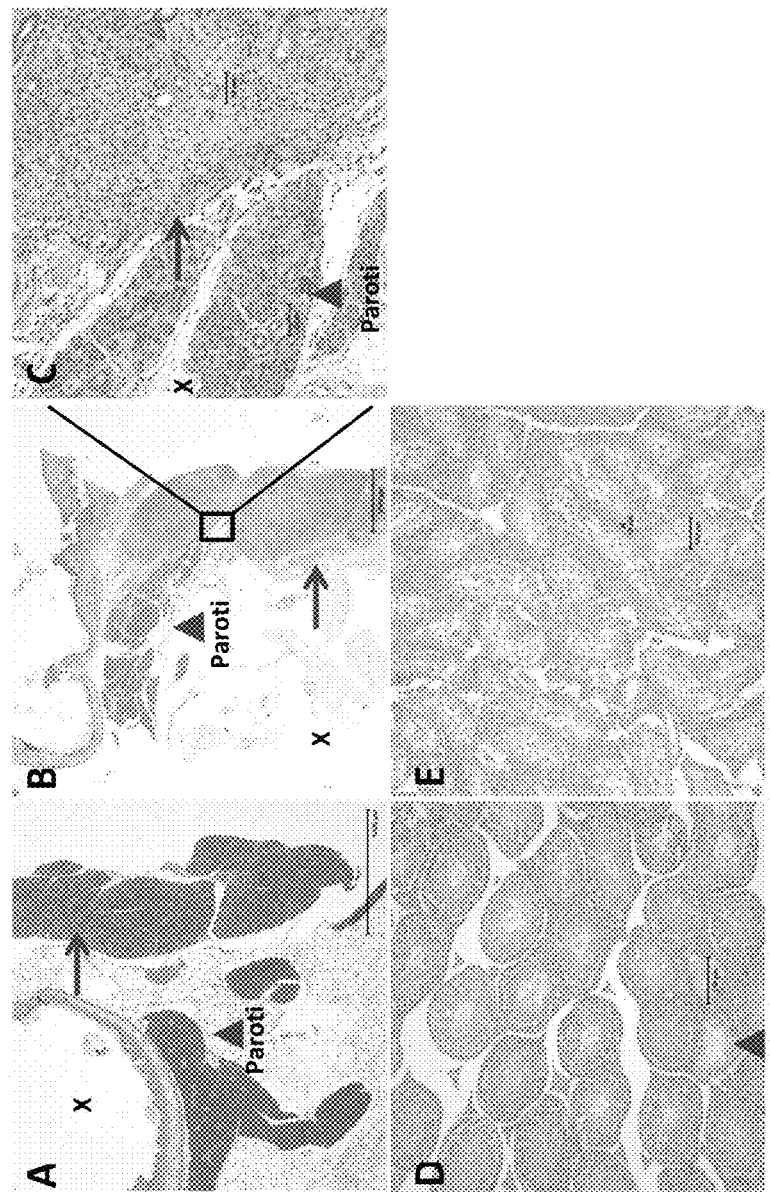

PROSTATE-SPECIFIC MEMBRANE ANTIGEN TARGETED HIGH-AFFINITY AGENTS FOR ENDORADIOTHERAPY OF PROSTATE CANCER

CROSS-REFERENCE TO RELATED APPLICATIONS

This application is a § 371 U.S. National Entry application of PCT/US2018/035220, filed May 30, 2018, which claims the benefit of U.S. Provisional Application No. 62/512,515 filed May 30, 2017, each of which is incorporated herein by reference in its entirety.

FEDERALLY SPONSORED RESEARCH OR DEVELOPMENT

This invention was made with government support under CA148901 and CA1346751 awarded by the National Institutes of Health. The government has certain rights in the invention.

BACKGROUND

Prostate cancer is the leading cancer in the U.S. population and the second leading cause of cancer death in men. Therapy for locally advanced disease remains contentious and an increasing number of disparate options are available. New, high-affinity, radiotherapeutic agents for prostate cancer have been developed using the prostate-specific membrane antigen (PSMA) as a target. PSMA is a marker for androgen-independent disease that also is expressed on solid (nonprostate) tumor neovasculature.

SUMMARY

In some aspects, the presently disclosed subject matter provides a compound of Formula (I):

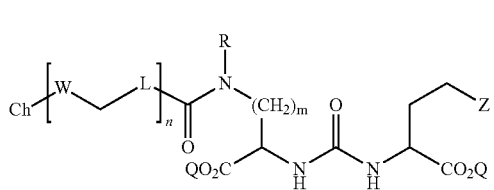

(I)

wherein: Z is tetrazole or $CO_2Q$; Q is H or a protecting group; m is an integer selected from the group consisting of 1, 2, 3, 4, and 5; R is independently H or $-CH_2-R^1$; $R^1$ is selected from the group consisting of substituted aryl, substituted pyridine, and unsubstituted isoquinoline; L is a linker selected from the group consisting of $C_1$-$C_6$ alkylene and $C_3$-$C_6$ cycloalkylene, and arylene; W is selected from the group consisting of $-NR^2-(C=O)-$, $-NR^2-(C=S)-$, $-(C=O)-NR^2-$, and $-(C=S)-NR^2-$; wherein each occurrence of L and W can be the same or different; $R^2$ is H or a $C_1$-$C_4$ alkyl; n is an integer selected from the group consisting of 1, 2, and 3; Ch is a chelating agent that can comprise a metal or a radiometal; and pharmaceutically acceptable salts thereof.

In particular aspects of the compound of the Formula (I), R, is selected from the group consisting of:

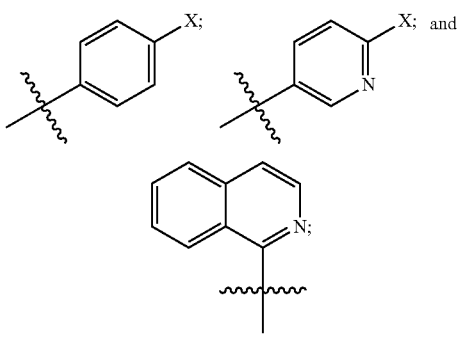

wherein X is independently Br or I.

In yet more particular aspects of the compound of the Formula (I), the chelating agent is selected from the group consisting of:

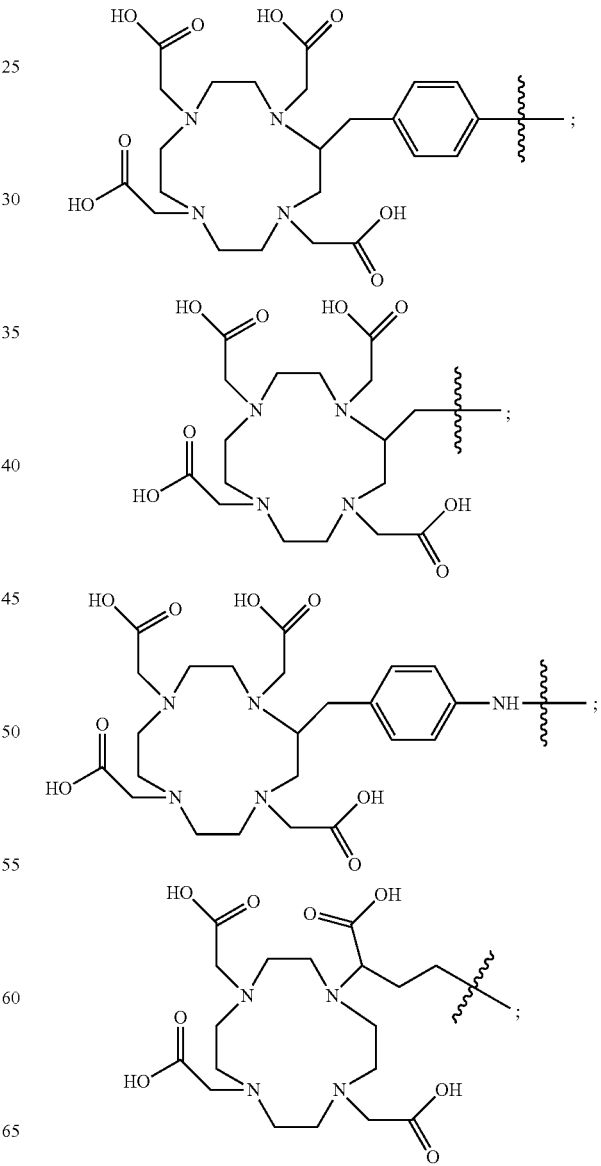

-continued

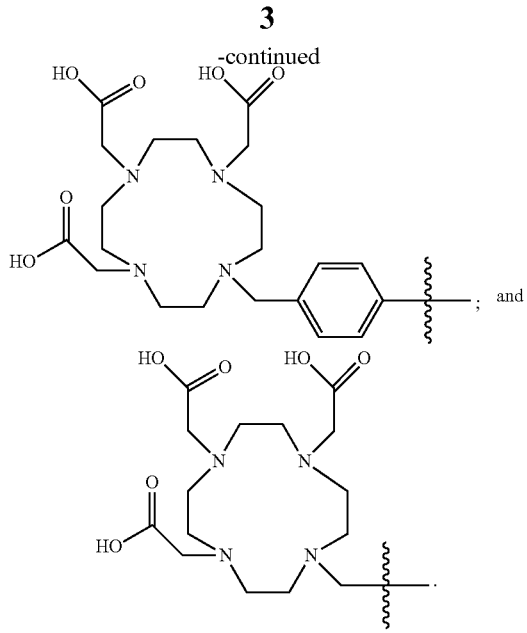

In other aspects, the presently disclosed subject matter provides a method for treating one or more PSMA expressing tumors or cells, the method comprising contacting the one or more PSMA expressing tumors or cells with an effective amount of a compound of formula (I), the compound of formula (I) comprising:

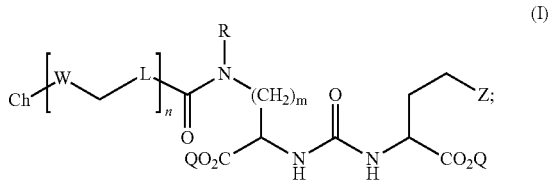

wherein: Z is tetrazole or $CO_2Q$; Q is H or a protecting group; m is an integer selected from the group consisting of 1, 2, 3, 4, and 5; R is independently H or —$CH_2$—$R^1$; $R^1$ substituted aryl, substituted pyridine, and unsubstituted isoquinoline; L is a linker selected from the group consisting of $C_1$-$C_6$ alkylene and $C_3$-$C_6$ cycloalkylene, and arylene; W is selected from the group consisting of —$NR^2$—(C=O)—, —$NR^2$—(C=S)—, —(C=O)—$NR^2$—, and —(C=S)—$NR^2$—; wherein each occurrence of L and W can be the same or different; $R^2$ is H or a $C_1$-$C_4$ alkyl; n is an integer selected from the group consisting of 1,2, and 3; Ch is a chelating agent that comprises a radiometal suitable for radiotherapy; and pharmaceutically acceptable salts thereof.

In other aspects, the presently disclosed subject matter provides a method for imaging one or more prostate-specific membrane antigen (PSMA) tumors or cells, the method comprising contacting the one or more tumor or cells, with an effective amount of a compound of Formula (I) and making an image.

In yet other aspects, the presently disclosed subject matter provides a kit comprising a compound of Formula (I).

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

The patent or application file contains at least one drawing executed in color. Copies of this patent or patent application publication with color drawings will be provided by the Office upon request and payment of the necessary fee.

Figure 1:
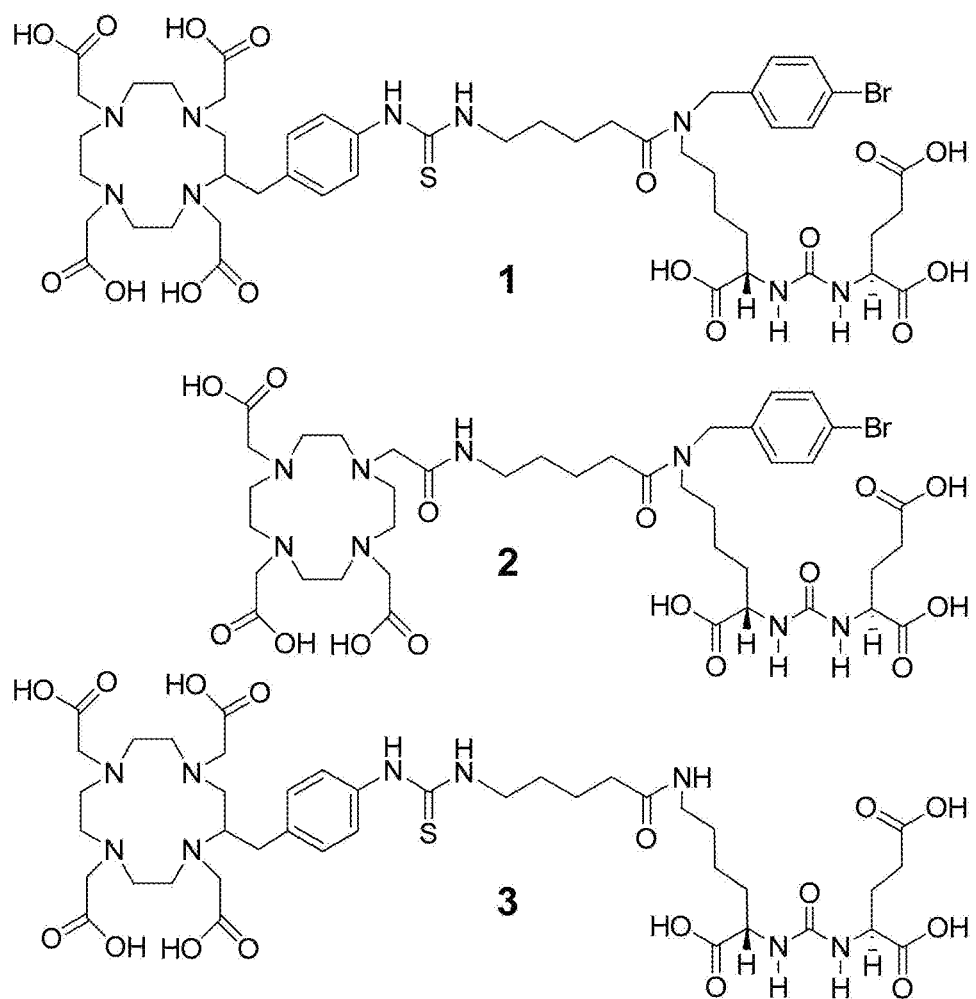
Figure 2:
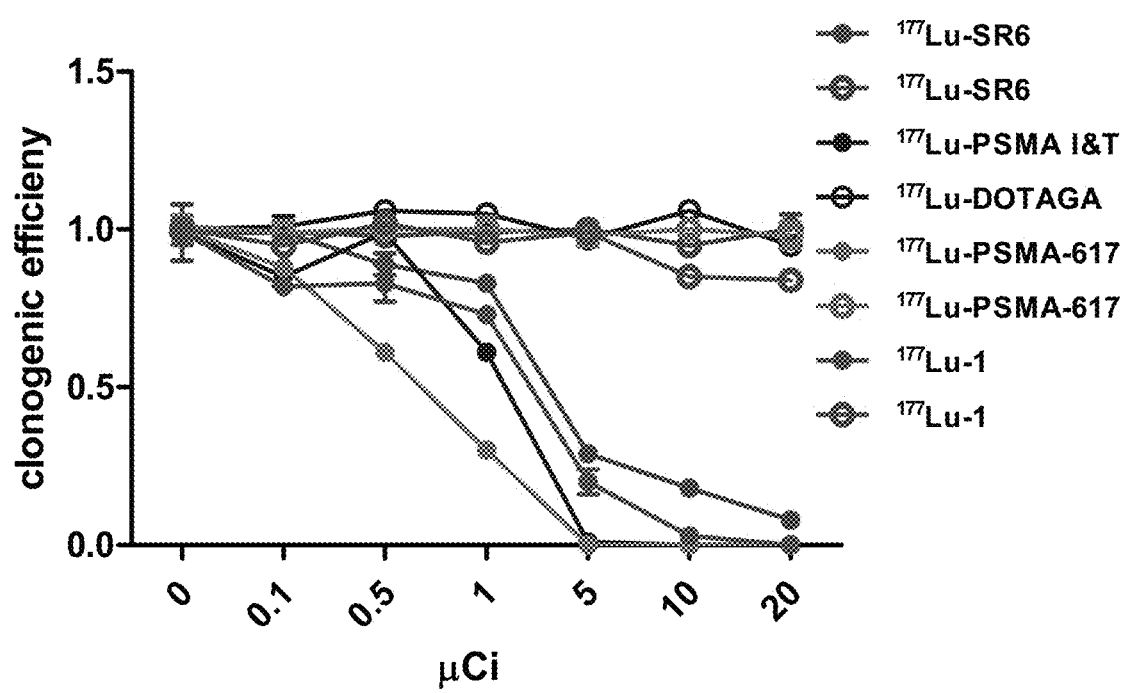
Figure 3:
Figure 4:
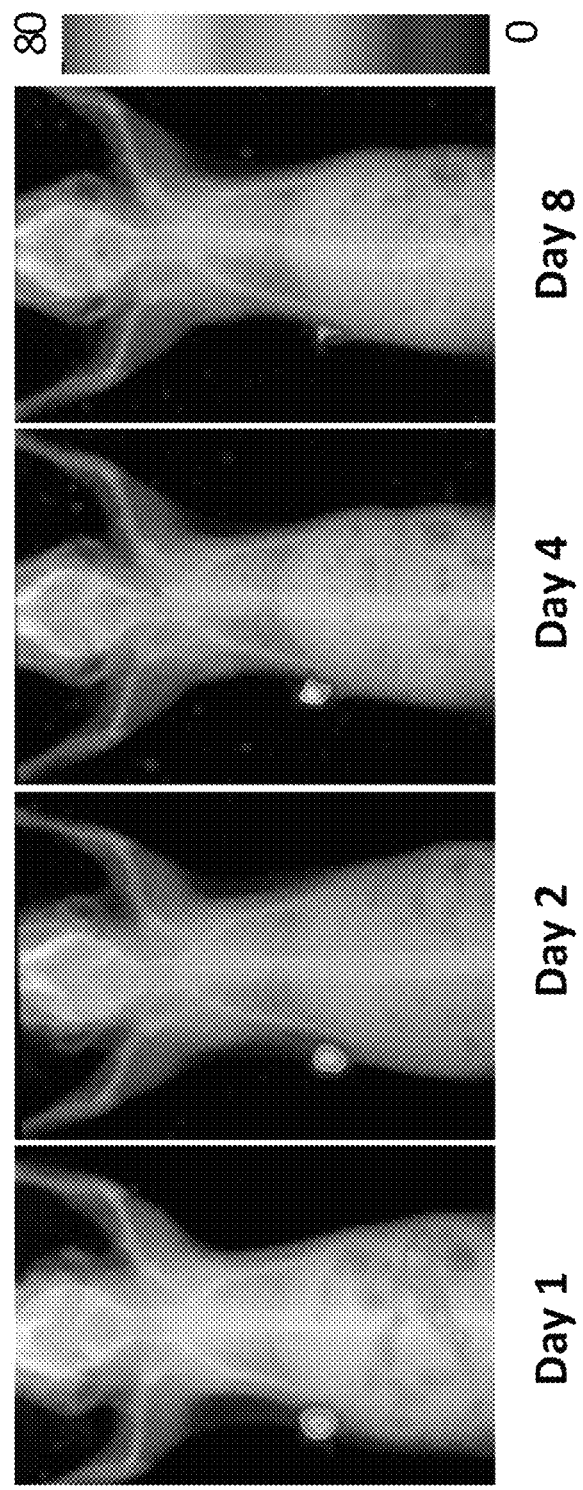
Figure 5:
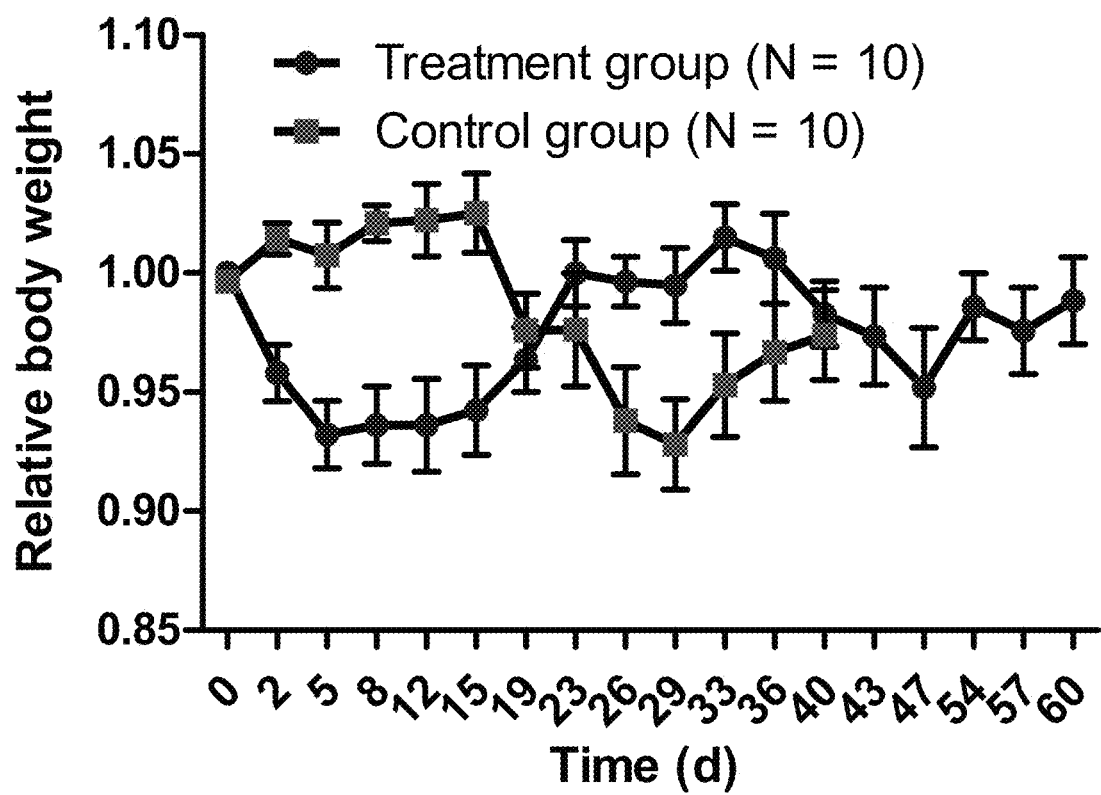
Figure 6A:
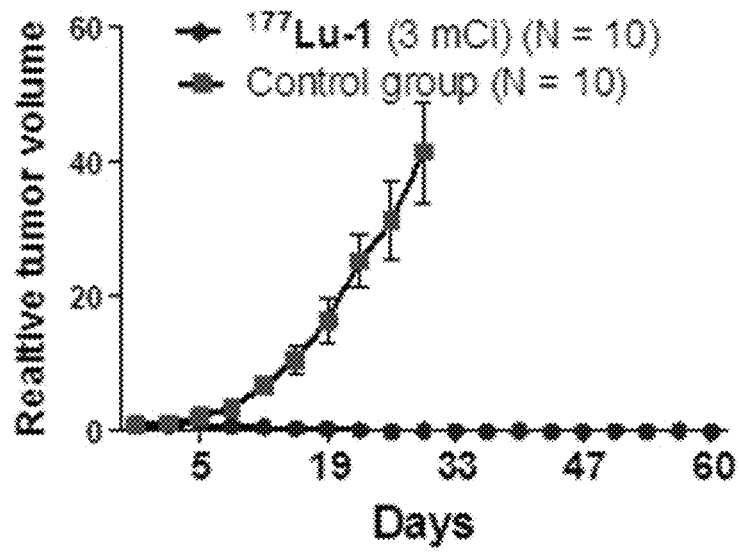
Figure 6B:
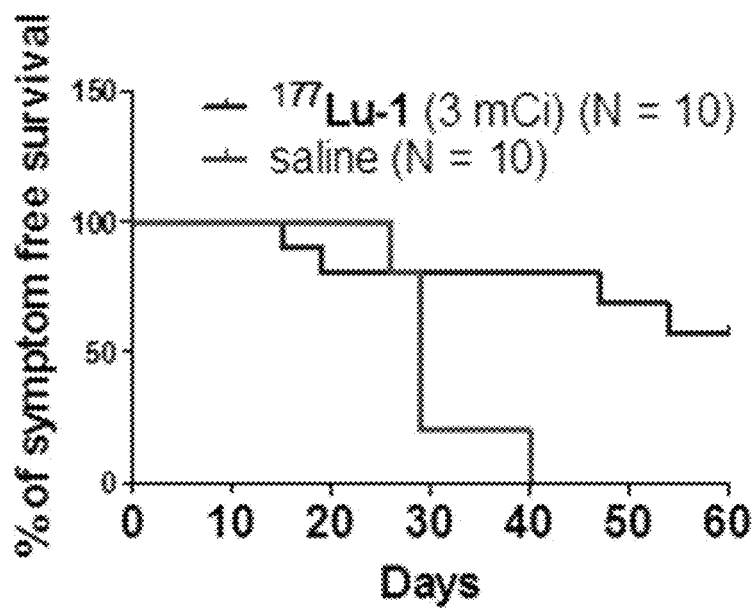
Figure 7:
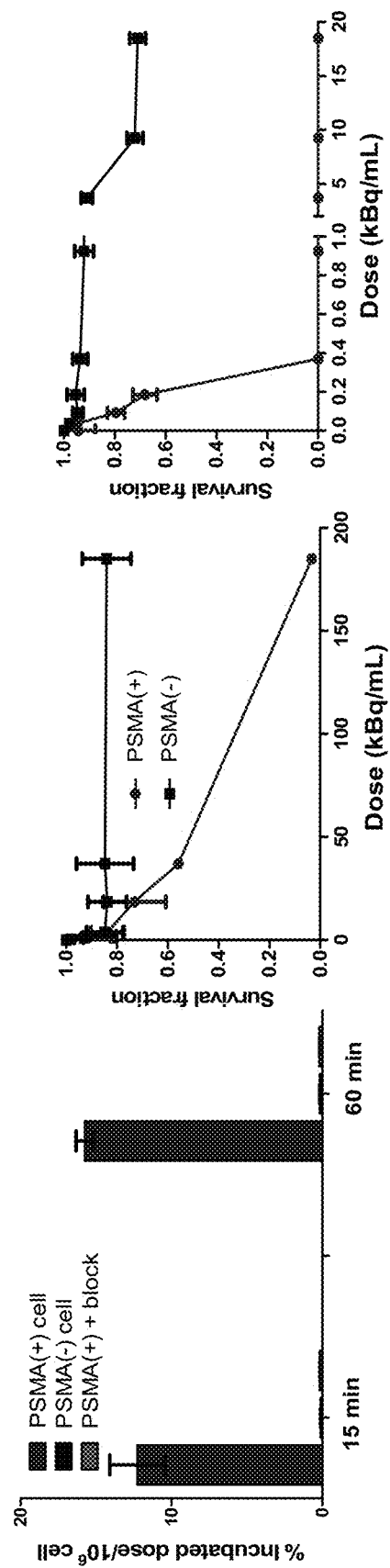
Figure 8:
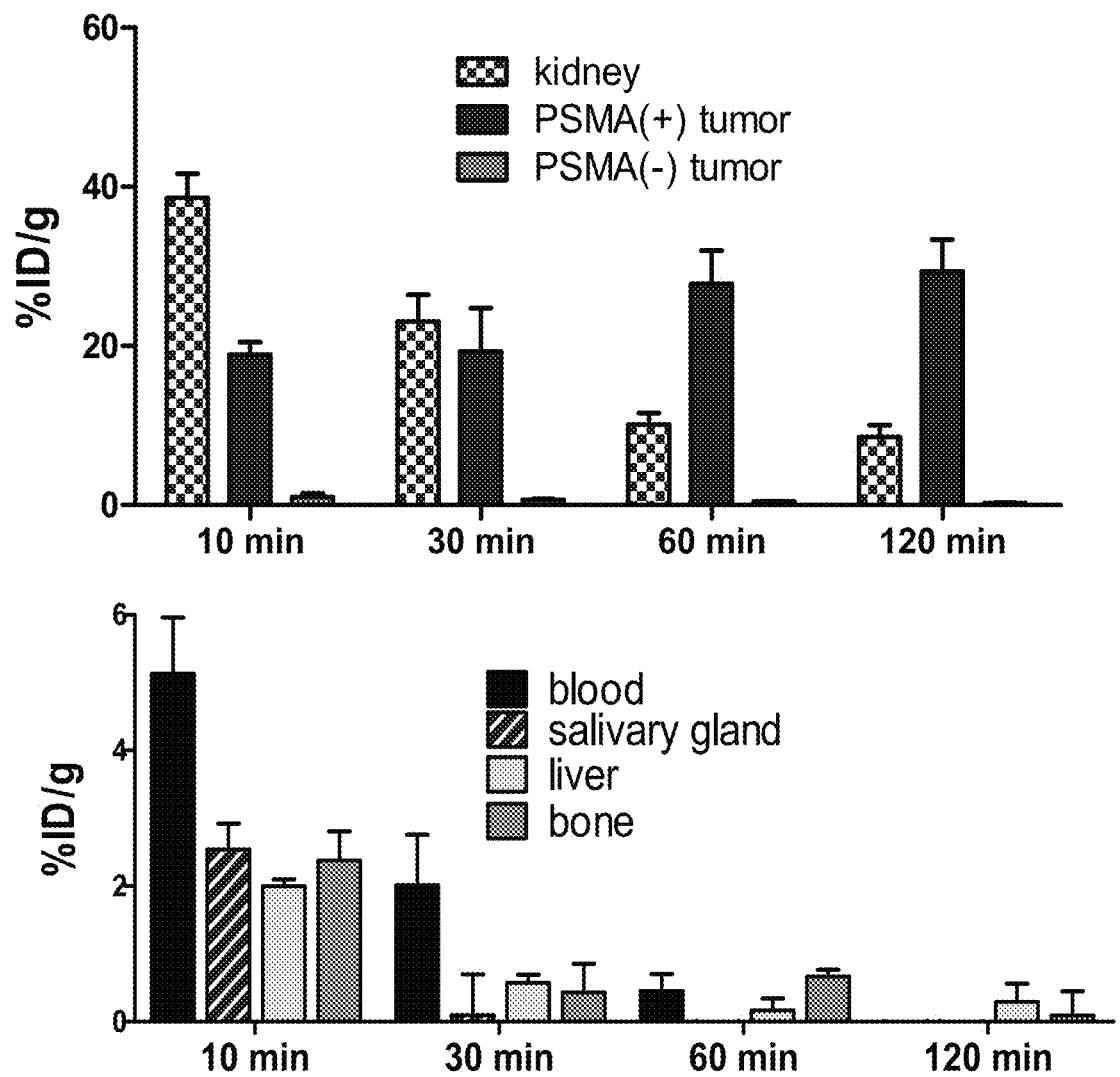
Figure 9:
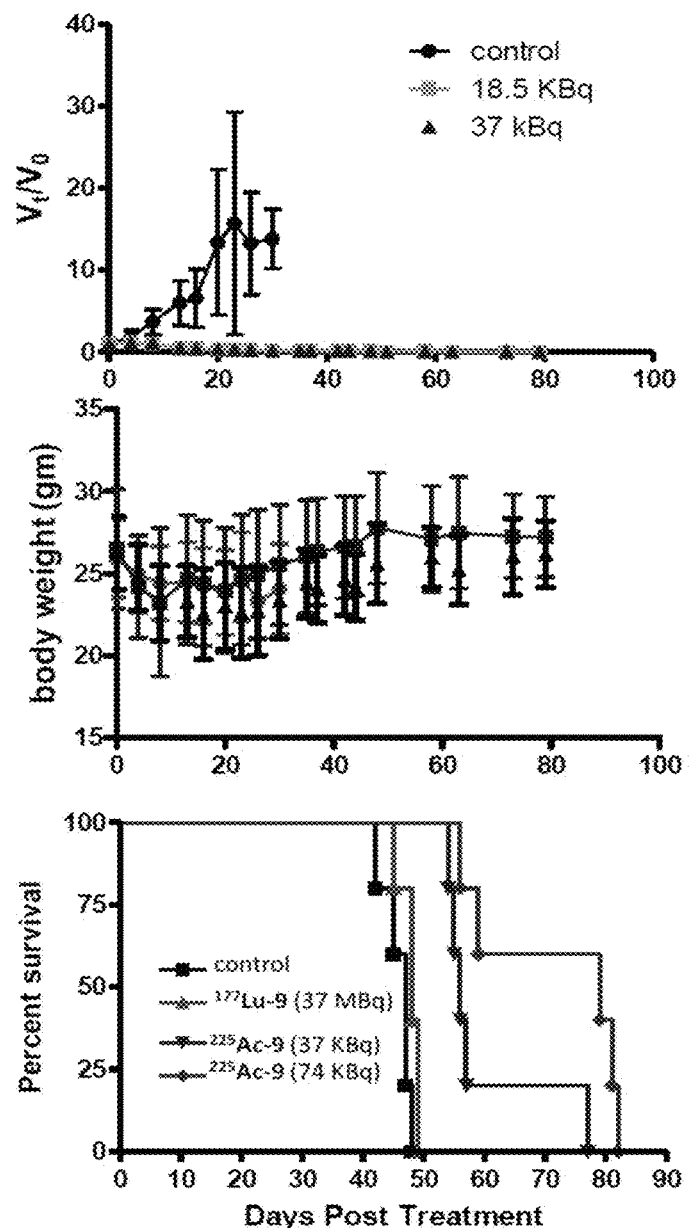
Figure 10:
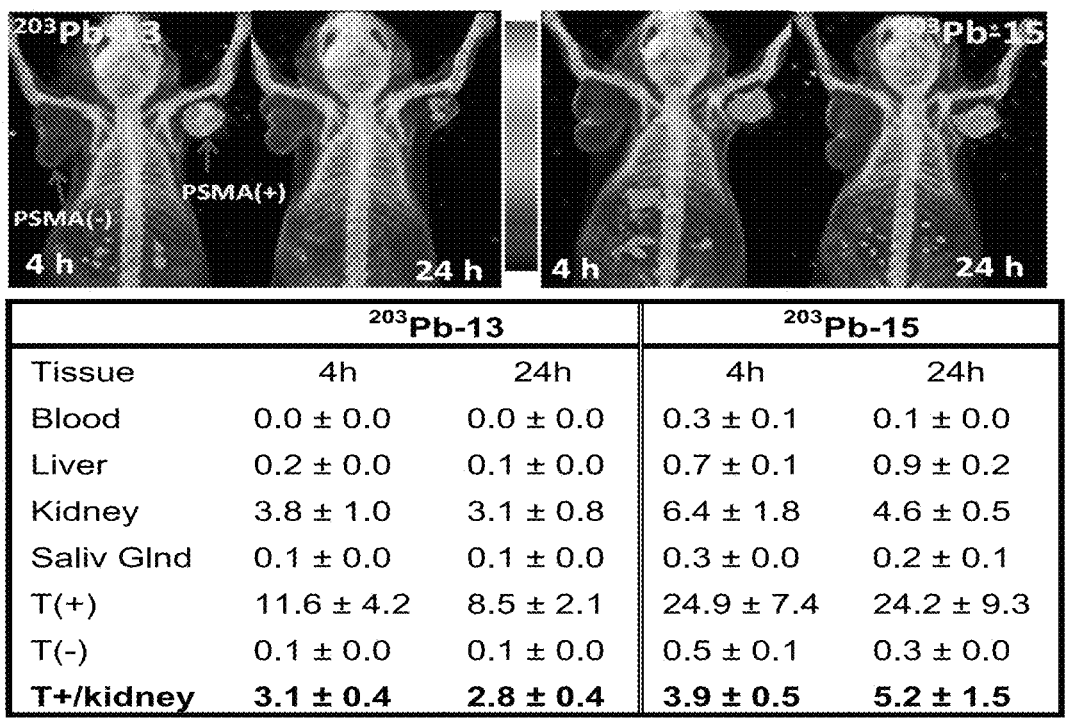
Figure 12:
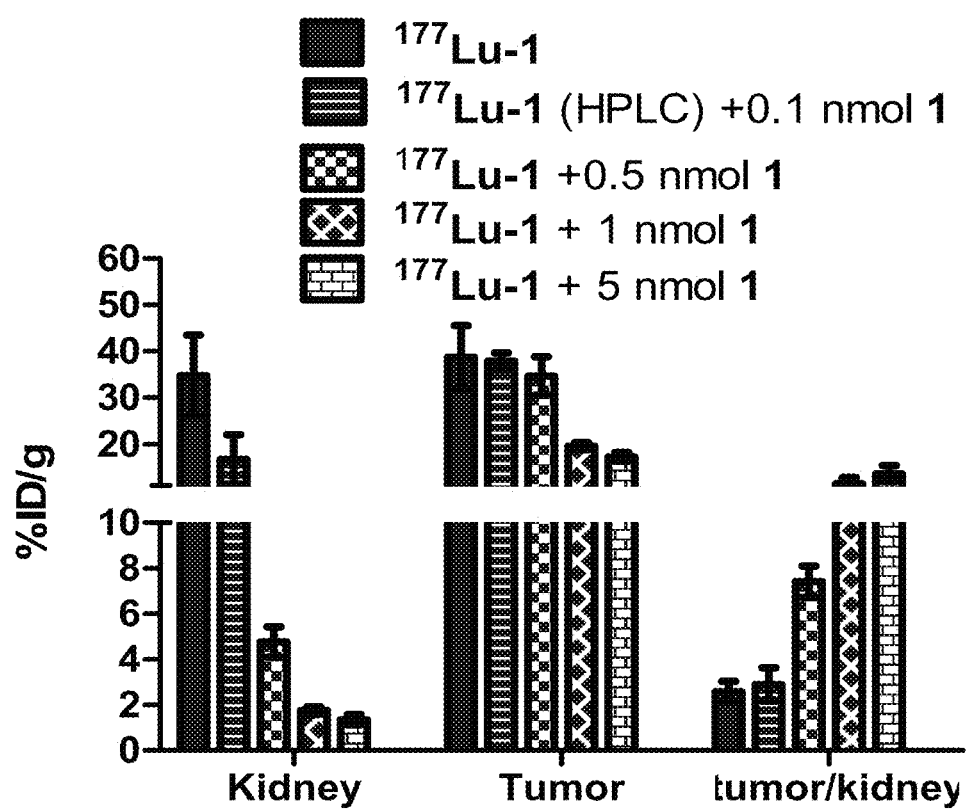
Figure 14:
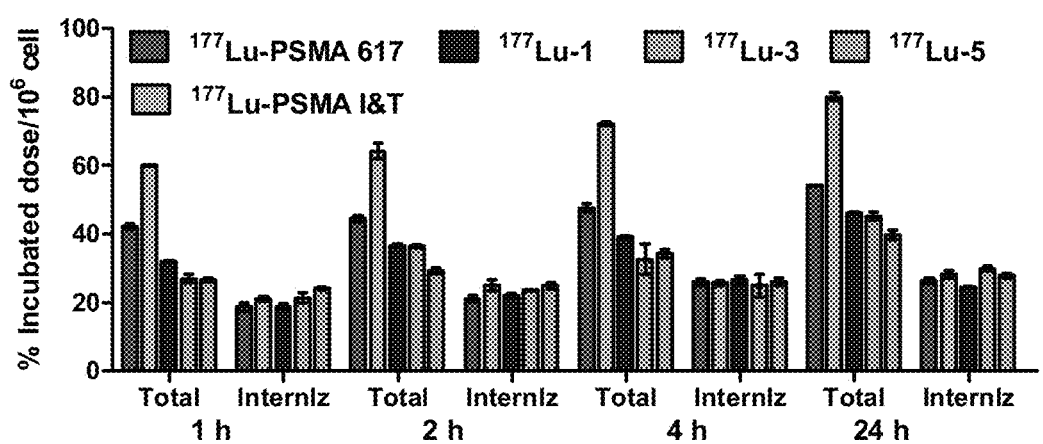
Figure 15:
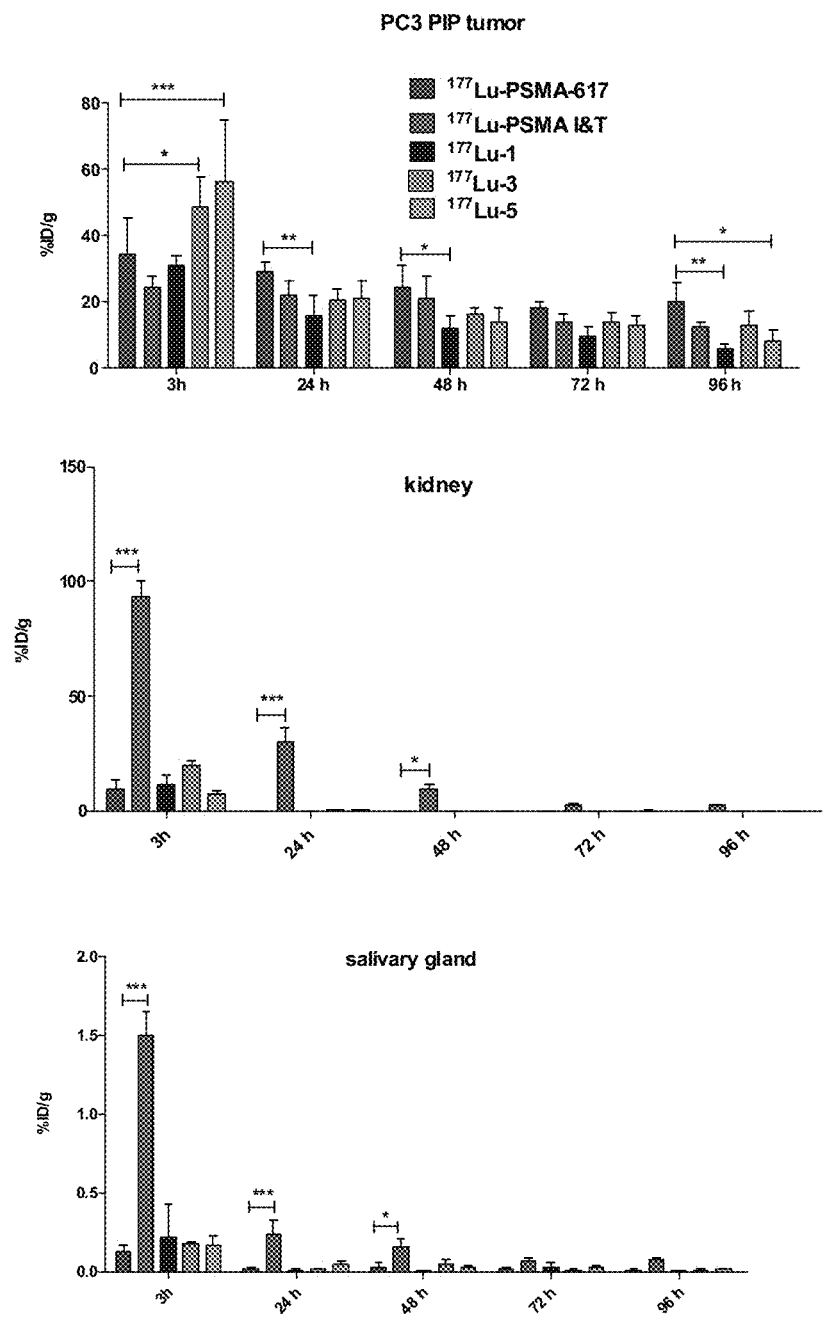
Figure 16:
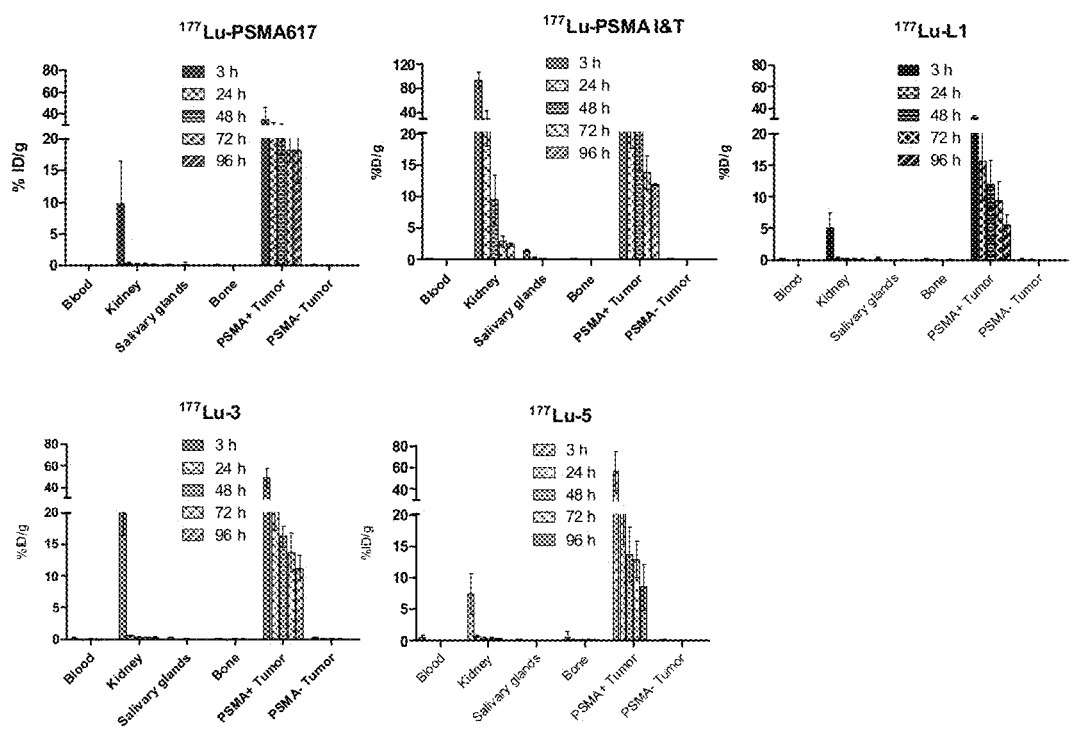
Figure 17:
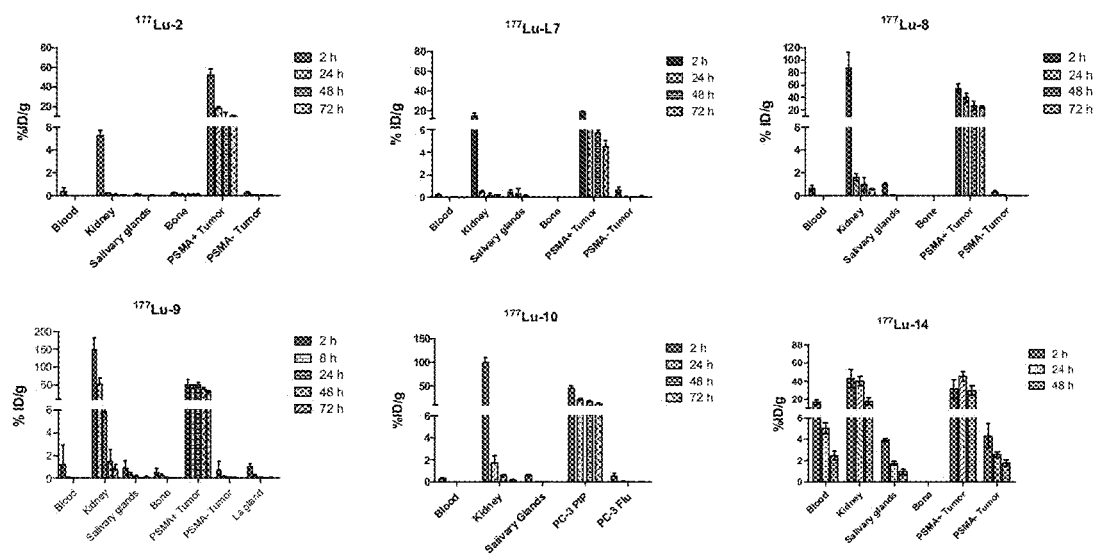
Figure 19:
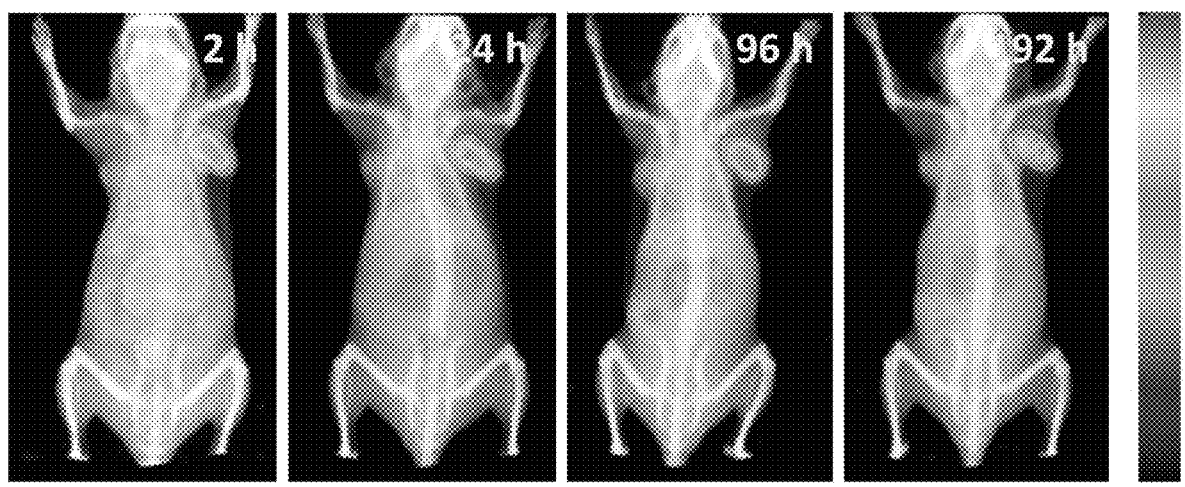
Figure 20:
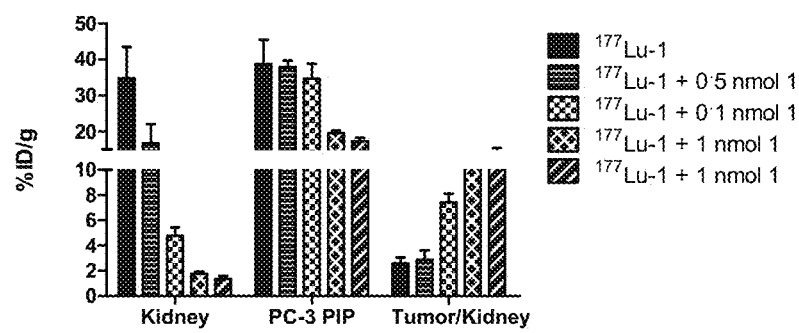
Figure 20:
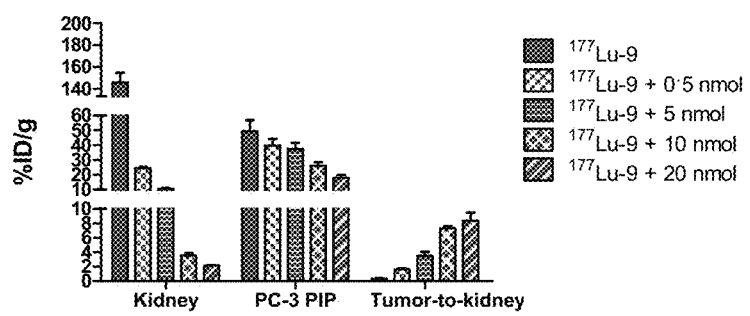
Figures 21A, 21B:
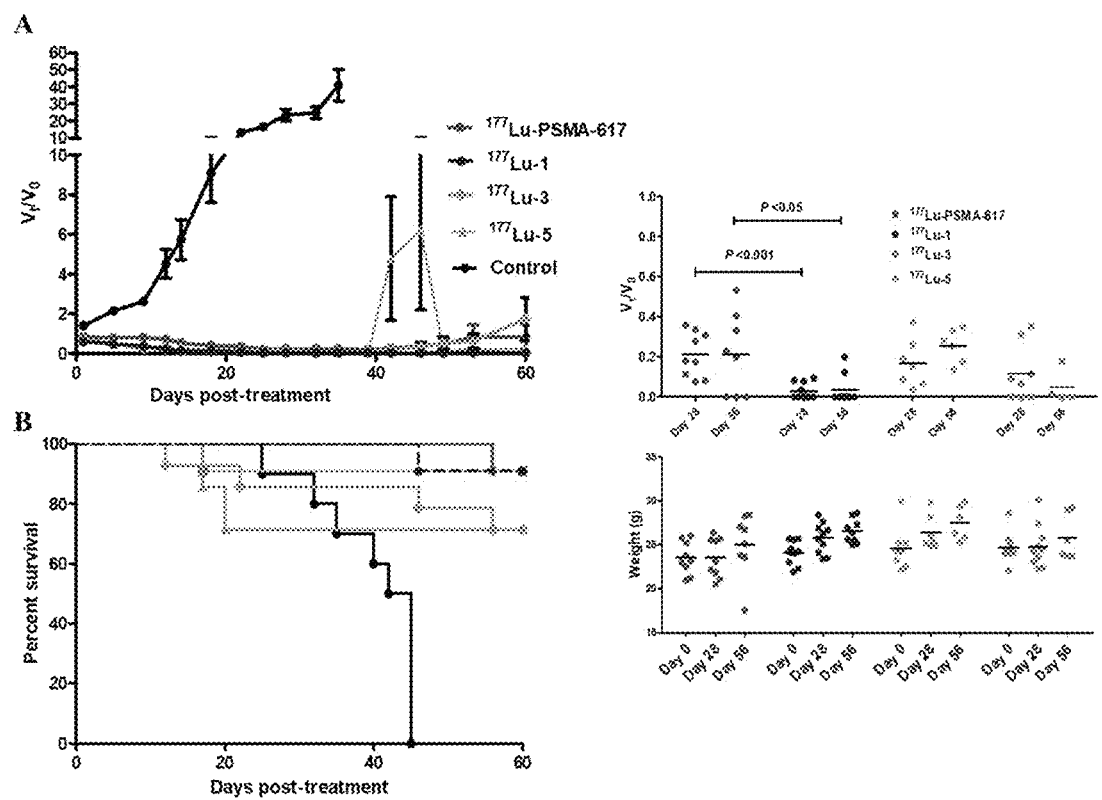
Figure 22:
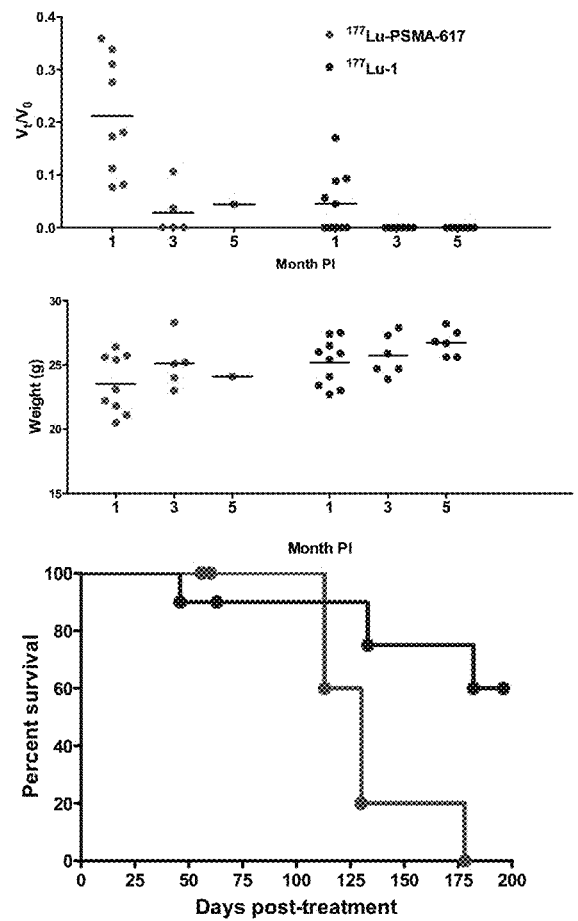
Figure 23:
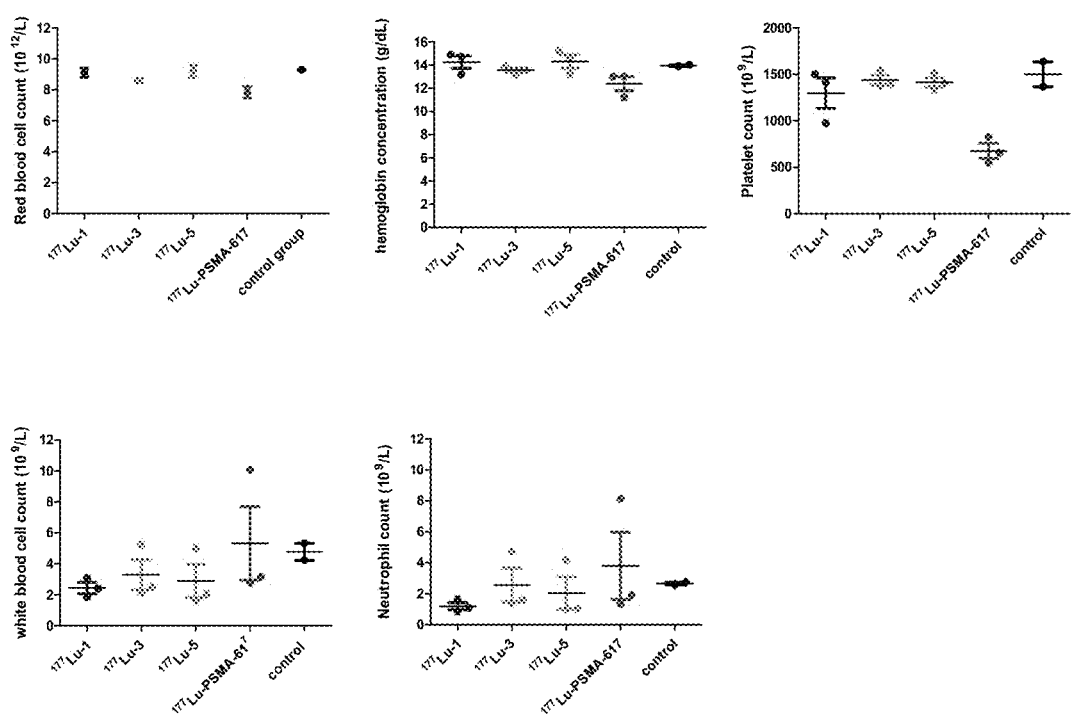
Figure 24:
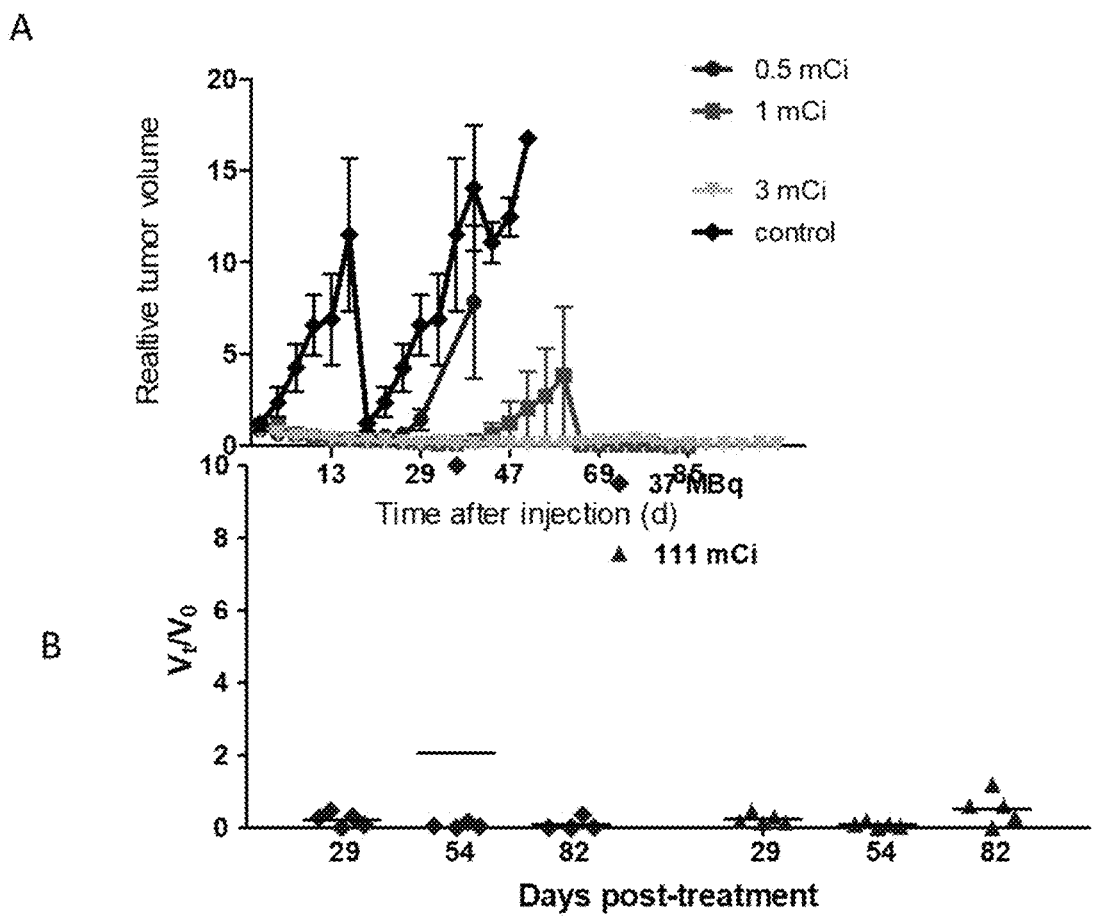

Having thus described the presently disclosed subject matter in general terms, reference will now be made to the accompanying Figures, which are not necessarily drawn to scale, and wherein:

FIG. 1 shows chemical structures of representative radiotherapeutic agents;

FIG. 2 shows a comparative study of the clonogenic efficacy of $^{177}$Lu-8, and known agents SR6, PSMA-617 and PSMA-I&T;

FIG. 3 shows PSMA+ tumor-to-kidney ratios of $^{177}$Lu-8, $^{177}$Lu-1, $^{177}$Lu—SR6, $^{177}$Lu-PSMA-617 and $^{177}$Lu-PSMA-I&T;

FIG. 4 shows SPECT-CT imaging of $^{177}$Lu-8 during treatment studies using of a single dose of 3 mCi;

FIG. 5 shows the relative body weight of the mice during the treatment studies;

FIG. 6A and FIG. 6B show the relative tumor volume of the mice (FIG. 6A) during the treatment studies and the Kaplan-Meier survival curve (FIG. 6B) up to 60 days post-treatment;

FIG. 7 shows (left) In vitro cell uptake of $^{213}$Bi-1 at 37° C. Specific cell uptake in PSMA(+) PC3 PIP cells (blue) and followed by PSMA(−) PC3 flu cell (black) and blockade with 1 mM of ZJ43, (red). (Middle and right) Specific cell kill for $^{213}$Bi-1 and $^{225}$Ac-1 after 2 h at 37° C.;

FIG. 8 shows the tissue biodistribution for $^{213}$Bi-1 (% ID/g);

FIG. 9 shows (top) Efficacy of $^{225}$Ac-1 in PSMA+PIP flank tumor model (male NSG mice). (middle) Changes in bodyweight during the treatment study. (bottom) Kaplan-Meier survival curve for treatment study in micrometastatic PC3-ML-Luc-PSMA model, median survival for 51 days (untreated) vs 52 days for $^{177}$Lu-PSMA-617 (37 MBq) and 56 days for 225Ac-1 (37 kBq) and 79 days for 225Ac-1 (74 kBq);

FIG. 10 shows (top) SPECT-CT imaging of $^{203}$Pb-2 and $^{203}$Pb-3 (14.8 MBq.) and (bottom) tissue biodistribution data. T+: PSMA(+) PC3 PIP, T(−) PC3 flu;

FIGS. 11A, 11B, 11C, 11D, and 11E show the distribution of 0.37 MBq $^{225}$Ac-1 (A) and 1.85 MBq of $^{213}$Bi-1 (+2 nmol 9) (B) in PSMA+ PC3 PIP tumor (T) and kidney (K) recorded by α-camera imaging. Co-injection of 2 nmol of 9 generated specific removal of activity from renal cortex but not from PSMA+ tumor. (C) IHC of PSMA+ tumor treated $^{225}$Ac-9 showing reduction of PSMA-expression after 24 h compared to untreated PSMA+ tumor, (D, E) PSMA+ staining (IHC) of kidney from the same mouse as (A) at 2 h;

FIG. 12 shows the biodistribution of $^{177}$Lu-1 with increased amount of 1 showing partial kidney blocking ligand at 2 h;

FIG. 13A and FIG. 13B show (FIG. 13A) Type I (with high tumor and kidney uptake) and Type II (with high tumor and low kidney uptake) imaging agents, at 2 h post-injection, and (FIG. 13B) First patient with extensive metastatic disease scanned with $^{68}$Ga-2. Note sub-centimeter perihilar and thoracic vertebral lymph node involvement (axial panels, arrows) (left) (ref. 34); selected $^{68}$Ga/$^{177}$Lu-labeled PSMA-binding agents (right);

FIG. 14 shows comparative cell uptake and internalization data for selected compounds (head-to-head study);

FIG. 15 shows comparative tissue biodistribution data for selected compounds (head-to-head study);

FIG. 16 shows comparative tissue biodistribution data for selected compounds (head-to-head study as also shown in FIG. 15);

FIG. 17 shows biodistribution data for $^{177}$Lu-1, $^{177}$Lu-7, $^{177}$Lu-8, $^{177}$Lu-9, $^{177}$Lu-10, and $^{177}$Lu-14;

FIG. 18A and FIG. 18B show (FIG. 18A) SPECT/CT imaging using $^{177}$Lu-1 (37 MBq); FIG. 18B. Immunohistochemistry of PSMA expression of PC3 PIP tumors administered without or with 37 MBq of $^{177}$Lu-1;

FIG. 19 shows SPECT/CT imaging after intravenous administration of $^{177}$Lu-14;

FIG. 20 shows partial self-blocking of $^{177}$Lu-1 and $^{177}$Lu-9 at 2 h post injection;

FIG. 21A and FIG. 21B show radionuclide therapy of PSMA-based $^{177}$Lu-labeled low molecular weight agents $^{177}$Lu-1, $^{177}$Lu-3, $^{177}$Lu-5 and $^{177}$Lu-PSMA-617. Tumor growth inhibition (FIG. 21A) and survival (FIG. 21B) after single administration of ~111 MBq via tail-vein injection of the individual agent and control with saline injection (n=10 for $^{177}$Lu-1, $^{177}$Lu-3, $^{177}$Lu-5 and n=9 for $^{177}$Lu-PSMA-617). Relative tumor volume and body weight of the individual mice are shown at 4 weeks and 8 weeks post treatment;

FIG. 22 show relative volume, body weight and survival (%) of 111 MBq of $^{177}$Lu-PSMA-617 and $^{177}$Lu-1;

FIG. 23 shows hemoglobin and blood count level eight week after radiotherapy using $^{177}$Lu-1, $^{177}$Lu-3, $^{177}$Lu-5, $^{177}$Lu-PSMA-617. Data are mean±SEM of n=3/group;

FIG. 24 shows radionuclide therapy $^{177}$Lu-1, after single administration of 111 MBq via tail-vein injection of the and control with saline injection (n=10 for $^{177}$Lu-1, $^{177}$Lu-3, $^{177}$Lu-5 and n=9 for $^{177}$Lu-PSMA-617). Relative tumor volume and body weight of the individual mice are shown at 4 weeks and 8 weeks post treatment; and FIG. 25A, FIG. 25B, FIG. 25C, FIG. 25D, and FIG. 25 E show hematoxylin and eosin (H&E) staining. (FIG. 25A, FIG. 25B, FIG. 25C) Extraorbital acrimal glands FIG. 25A. control untreated; FIG. 25B. Adjacent parotid gland (arrowhead) is spared; FIG. 25C. higher magnification of FIG. 25B, showing acinar loss, with chronic and active inflammation affecting lacrimal gland ($^{177}$Lu-PSMA-617. (FIG. 25D, and FIG. 25 E). Testis FIG. 25D. control untreated, active spermatogenesis, one tubule (arrowhead) contains only Sertoli cells. This is expected near the rete testis; FIG. 25E. there is no spermatogenesis, diffusely seminiferous tubules are smaller than in A (same magnification) and lined only by Sertoli cells, with a few germ cells in some tubules. Interstitial cells are prominent between tubules in this specimen.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Prostate-Specific Membrane Antigen Targeted High-Affinity Agents for Endoradiotherapy of Prostate Cancer A. Compounds of Formula (I)

Accordingly, in some embodiments, the presently disclosed subject matter provides a compound of Formula (I):

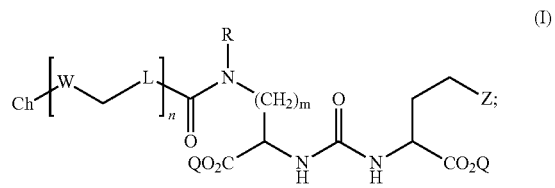

wherein: Z is tetrazole or CO$_2$Q; Q is H or a protecting group; m is an integer selected from the group consisting of 1, 2, 3, 4, and 5; R is independently H or —CH$_2$—R$^1$; R$^1$ is selected from the group consisting of substituted aryl, substituted pyridine, and unsubstituted isoquinoline; L is a linker selected from the group consisting of C$_1$-C$_6$alkylene and C$_3$-C$_6$ cycloalkylene, and arylene; W is selected from the group consisting of —NR$^2$—(C=O)—, —NR$^2$—(C=S)—, —(C=O)—NR$^2$—, and —(C=S)—NR$^2$—; wherein each occurrence of L and W can be the same or different; R$^2$ is H or a C$_1$-C$_4$ alkyl; n is an integer selected from the group consisting of 1, 2, and 3; Ch is a chelating agent that can comprise a metal or a radiometal; and pharmaceutically acceptable salts thereof.

The phrase "wherein each occurrence of L and W can be the same or different" means that when the variable "n" is 2 or 3, one "L" group can be C$_1$-C$_6$ alkylene, whereas the other "L" group or groups can be C$_3$-C$_6$ cycloalkylene or arylene, or, in other embodiments, each "L" group can be, for example, C$_1$-C$_6$ alkylene. Likewise, for example, when "n" is 2 or 3, one "W" group can be —(C=O)—NR$^2$— and the other "W" group or groups can be —(C=S)—NR$^2$—, or, in other embodiments, each "W" can be, for example, —(C=O)—NR$^2$—.

In particular embodiments of the compound of Formula (I), R$^1$ is selected from the group consisting of:

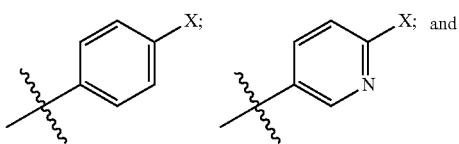

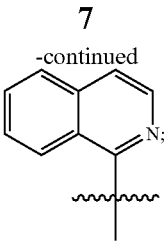

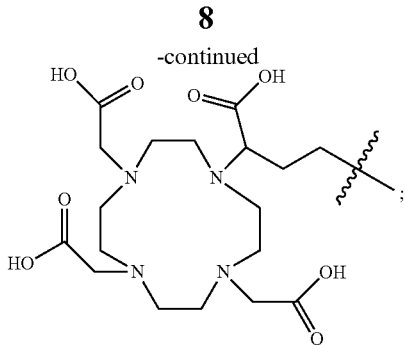

wherein X is independently Br or I.

In yet more particular embodiments of the compound of Formula (I), the chelating agent is selected from the group consisting of:

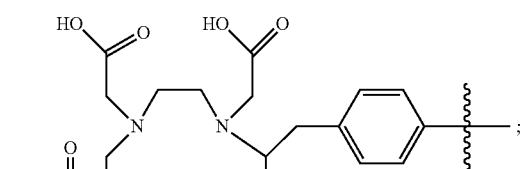

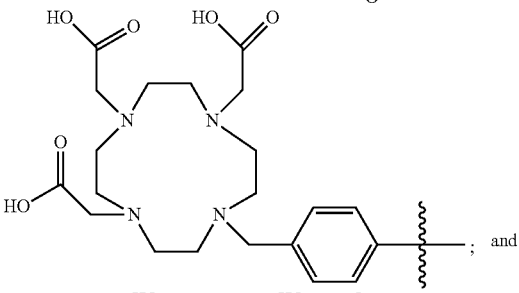

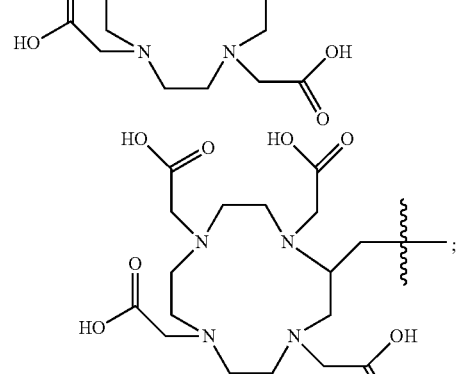

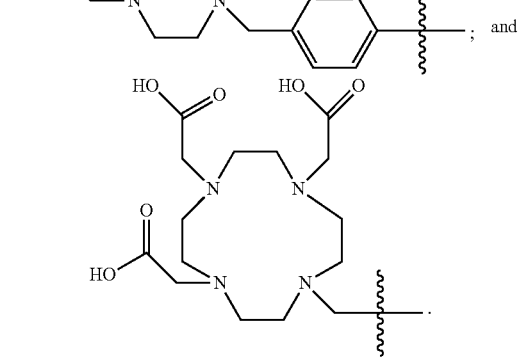

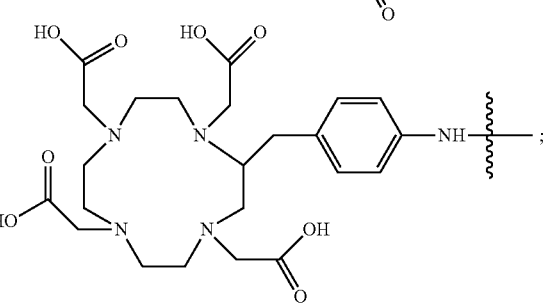

In still more particular embodiments of the compound of Formula (I), the chelating agent comprises a metal selected from the group consisting of: Y, Lu, Tc, Zr, In, Sm, Re, Cu, Pb, Ac, Bi, Al, Ga, Re, Ho and Sc. In further particular embodiments of the compound of Formula (I), the metal is a radiometal and is selected from the group consisting of: $^{68}$Ga, $^{64}$Cu, $^{86}$Y, $^{90}$Y, $^{89}$Zr, $^{111}$In, $^{99m}$Tc, $^{177}$Lu, $^{53}$Sm, $^{186}$Re, $^{188}$Re, $^{67}$Cu, $^{212}$Pb, $^{225}$Ac, $^{213}$Bi, $^{212}$Bi, $^{212}$Pb, $^{67}$Ga, $^{203}$Pb, $^{47}$Sc, and $^{166}$Ho.

In particular embodiments, the compound of Formula (I) is selected from the group consisting of:

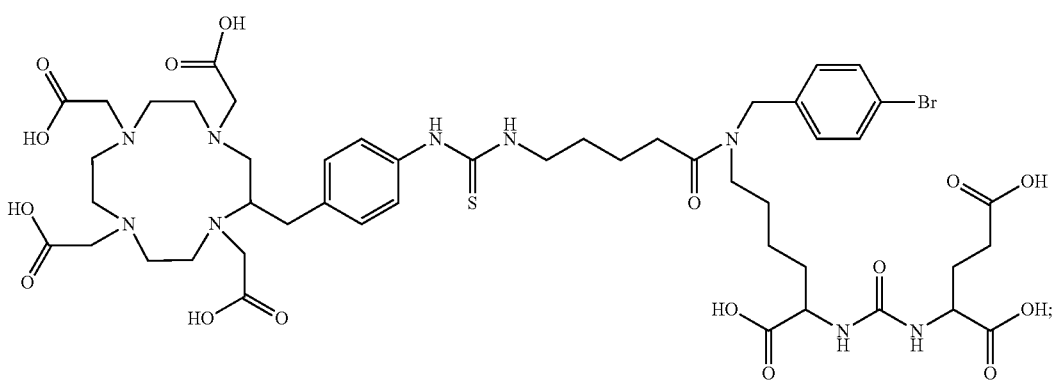

-continued
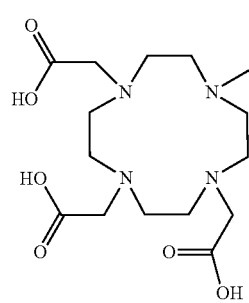
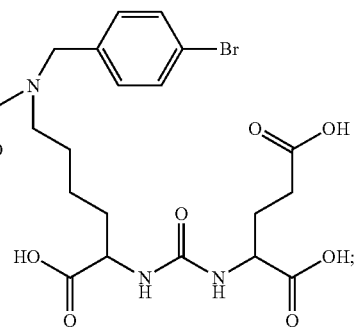
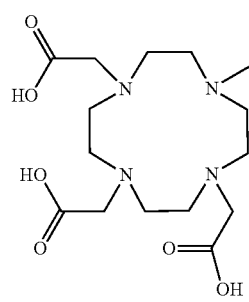
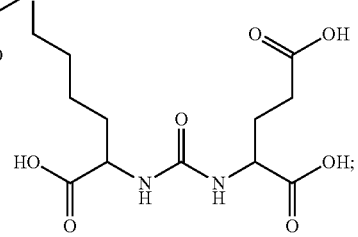
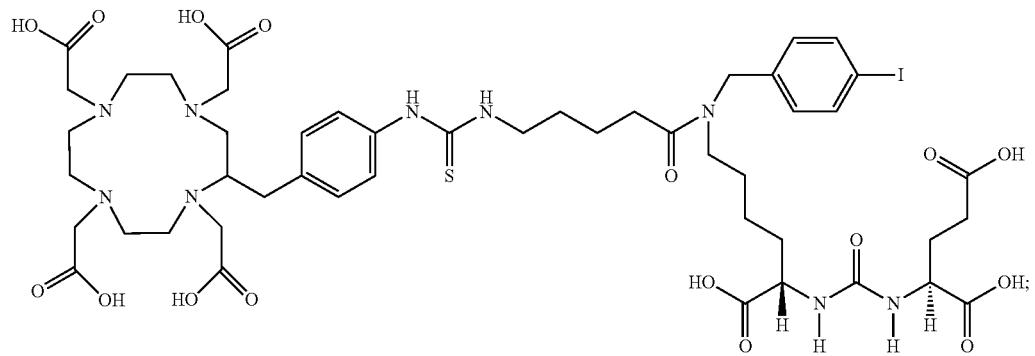
P1
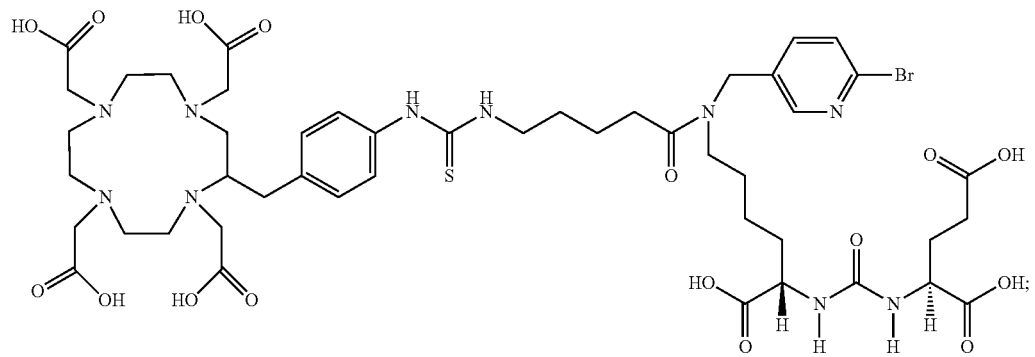
P1

-continued
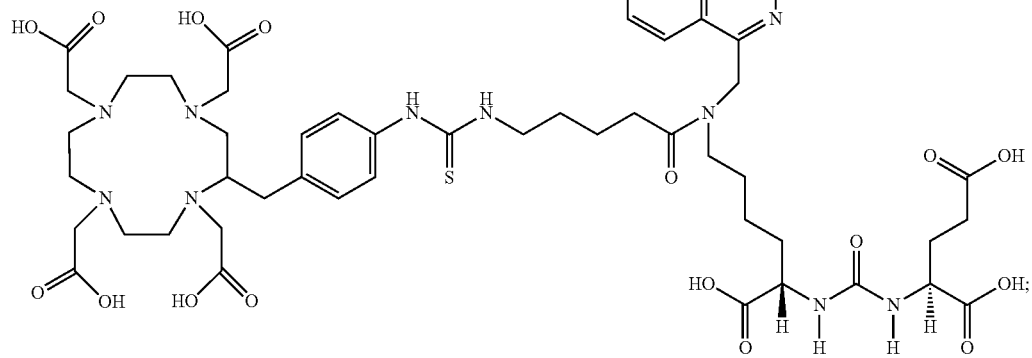
P1
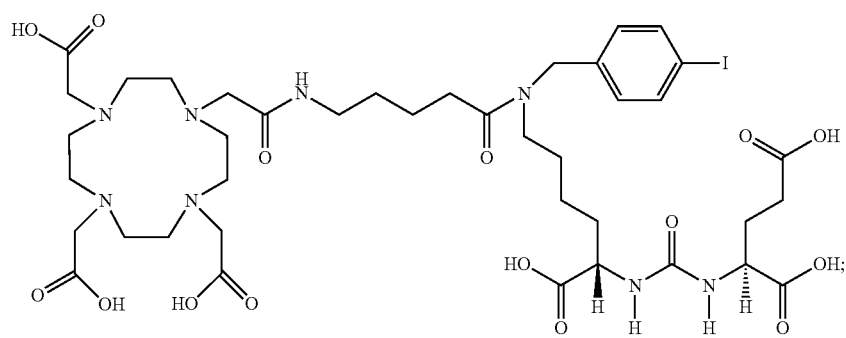
P2
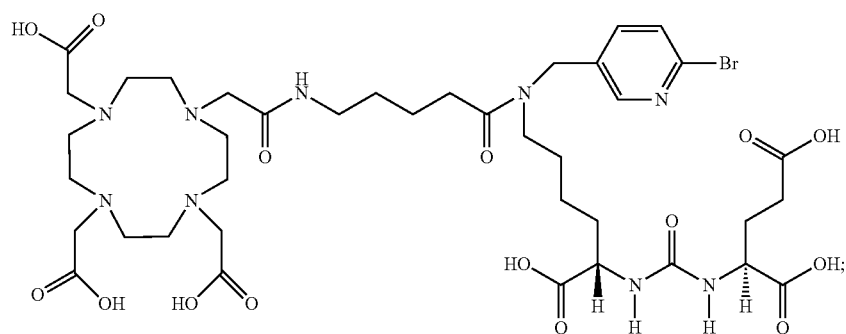
P2
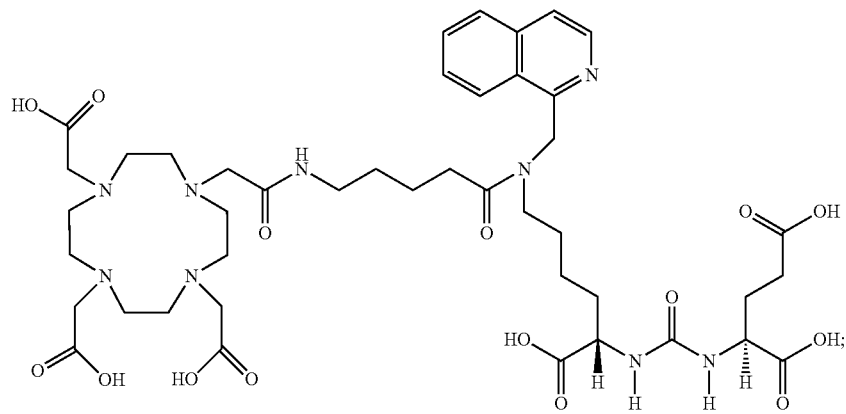
P2

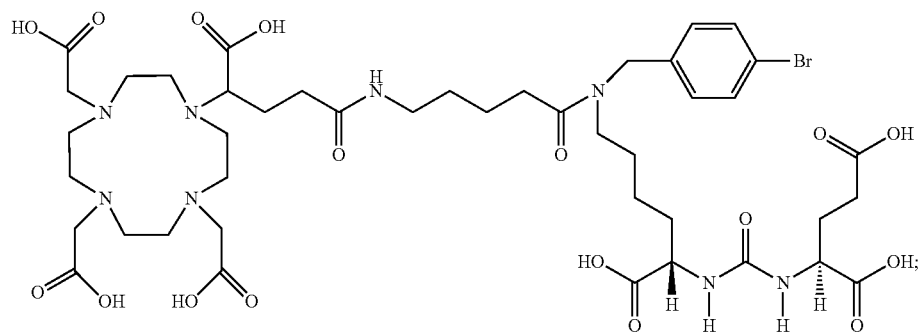
P3
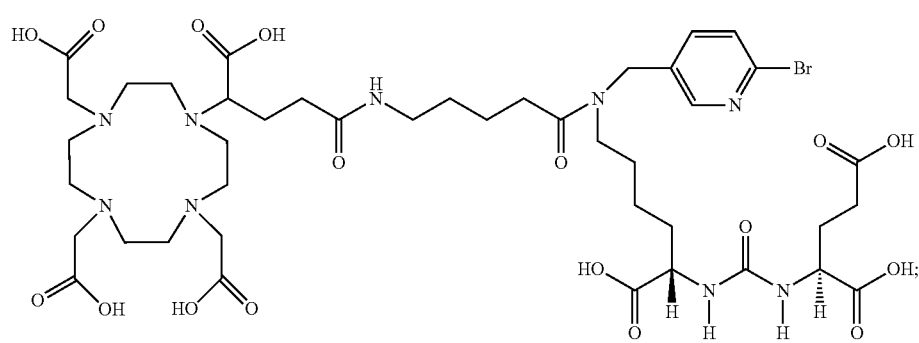
P3
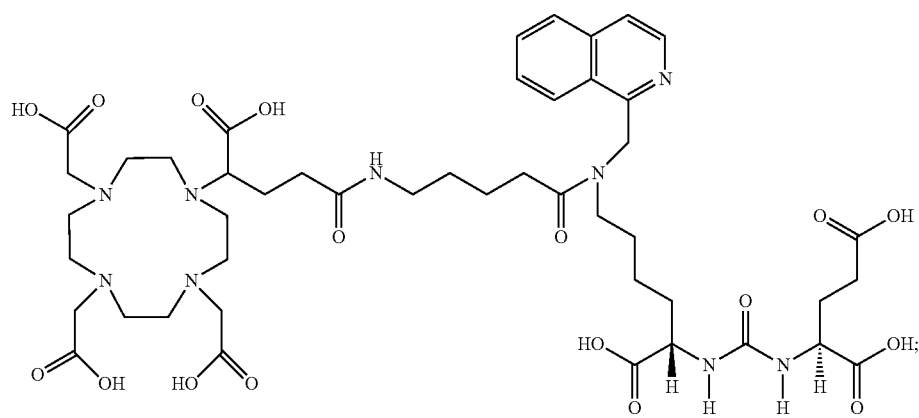
P3
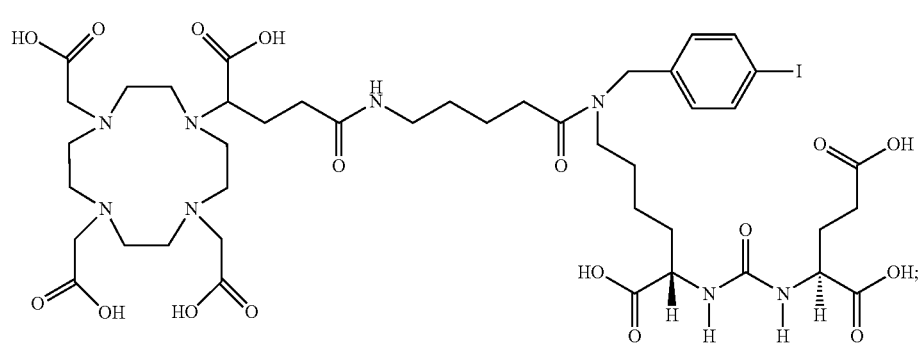
P4

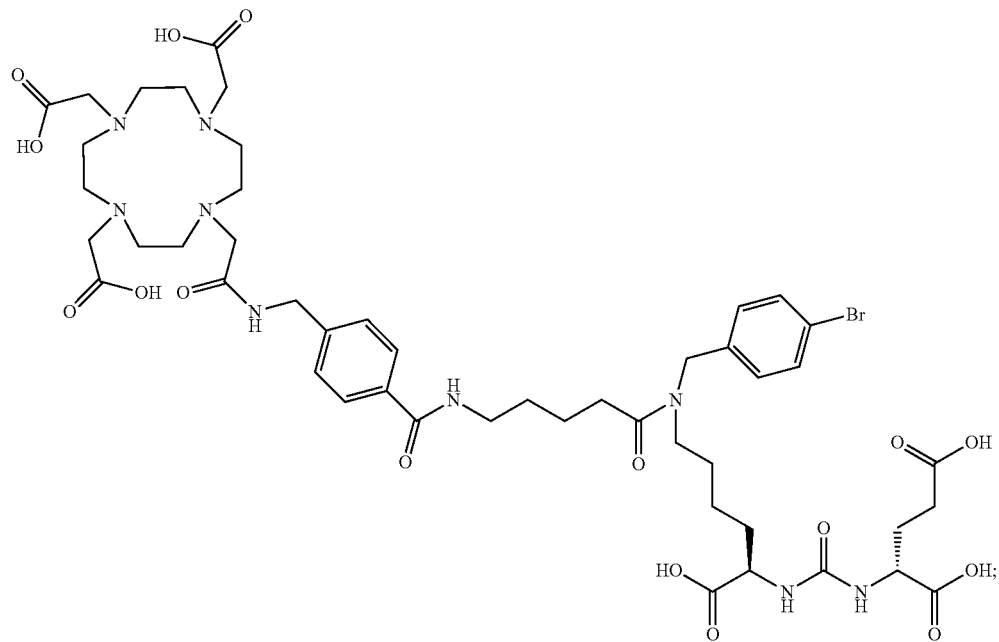
P5
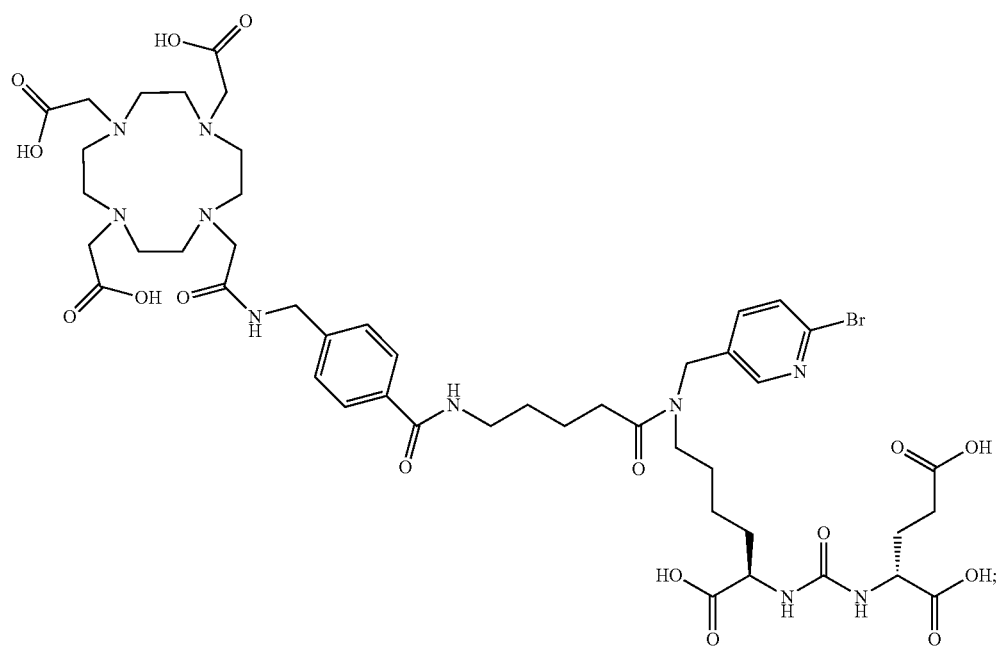
P5

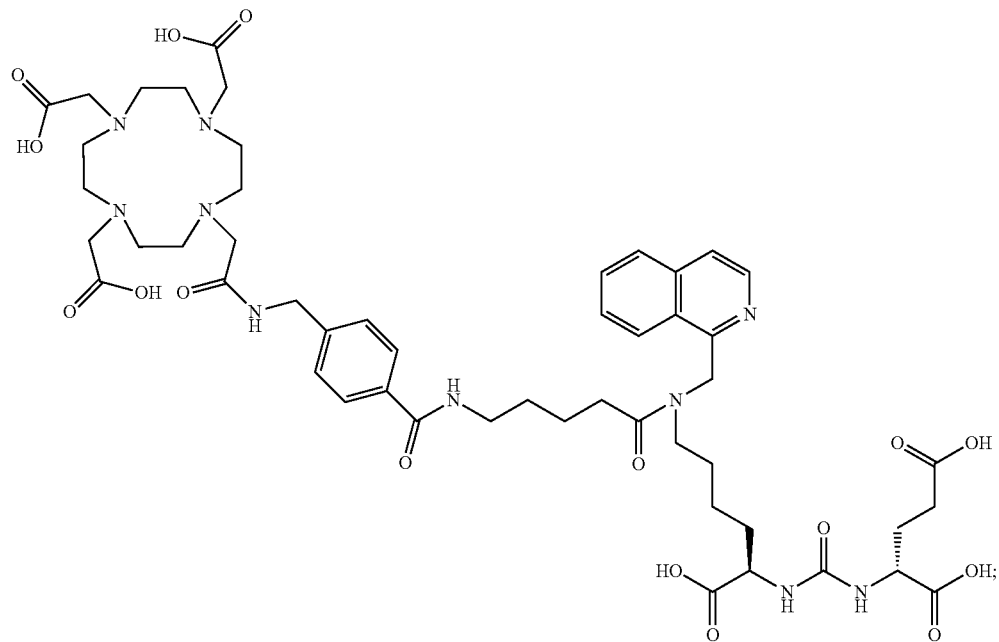
P5
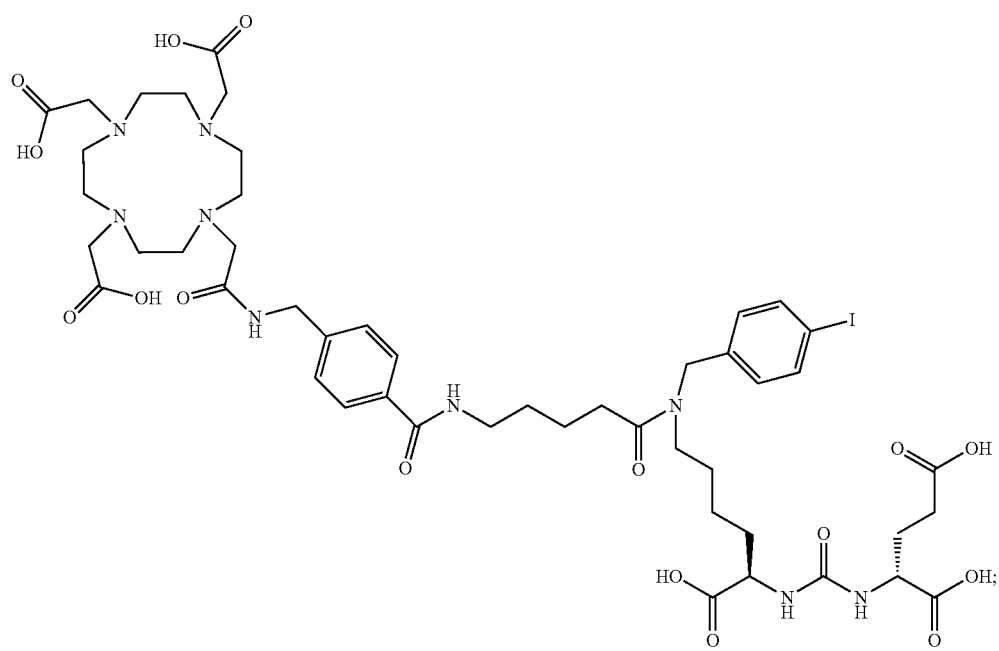
P6

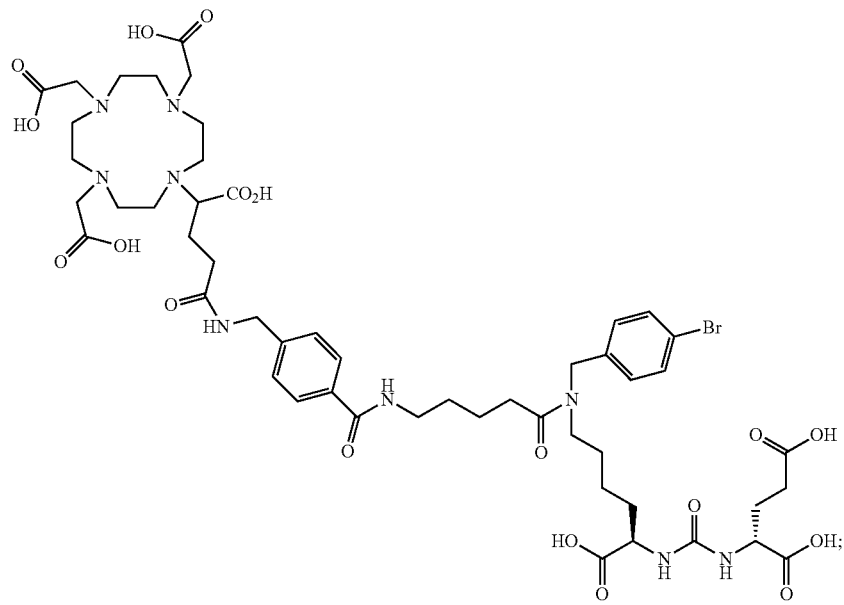
P7
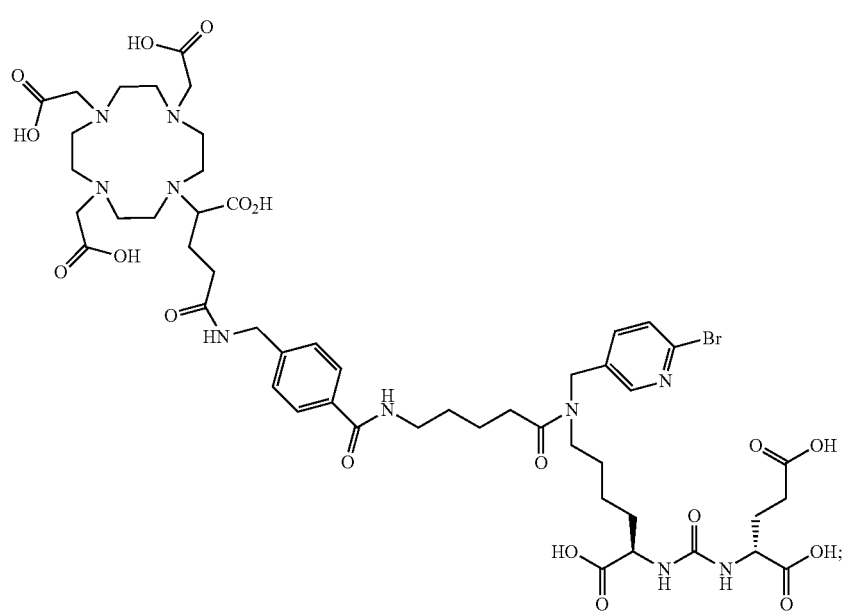
P7

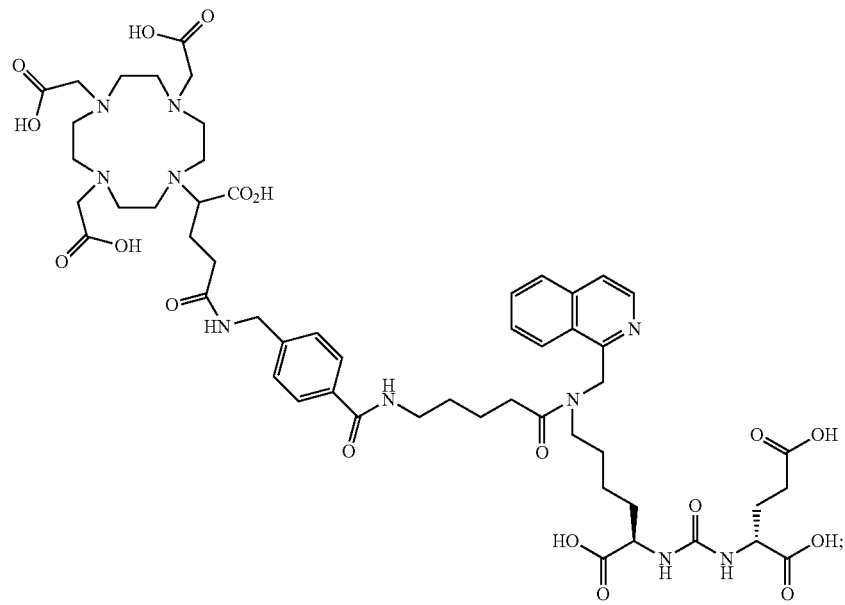
P7
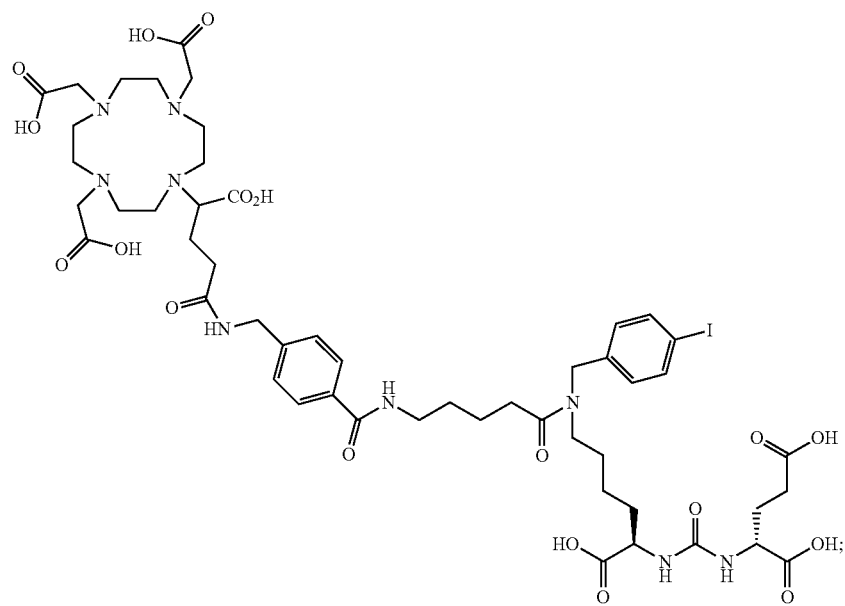
P8

-continued
P9
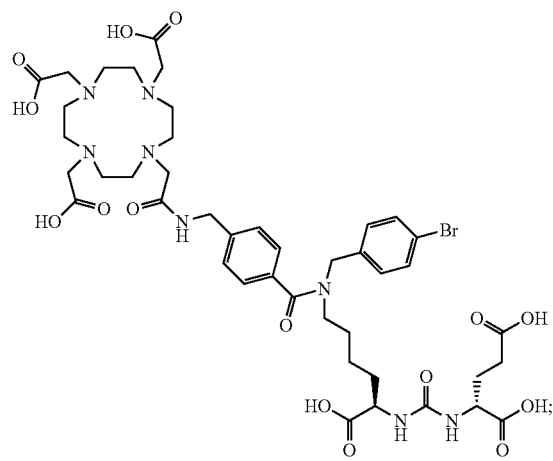
P10
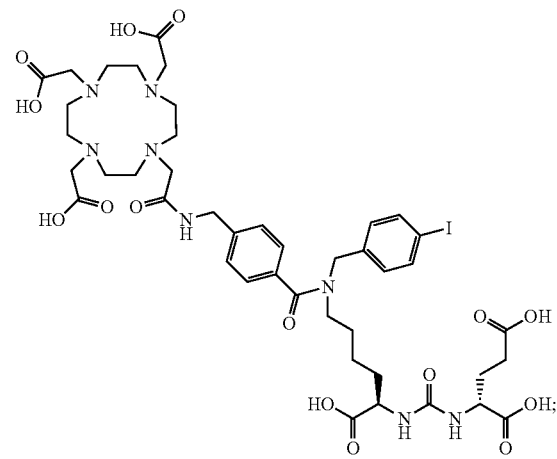
P9
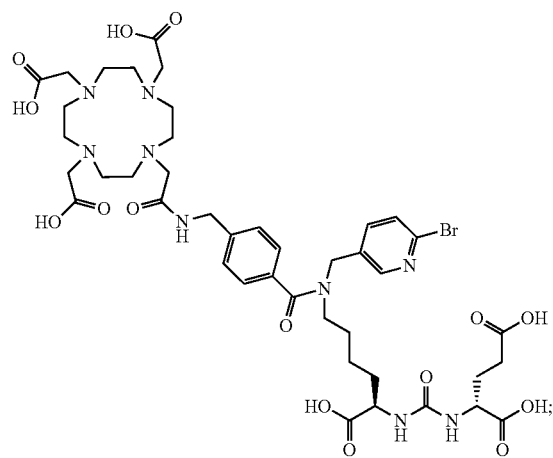
P9
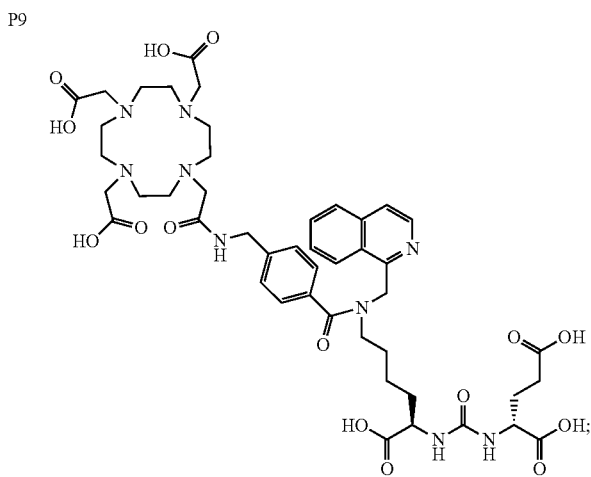
P11
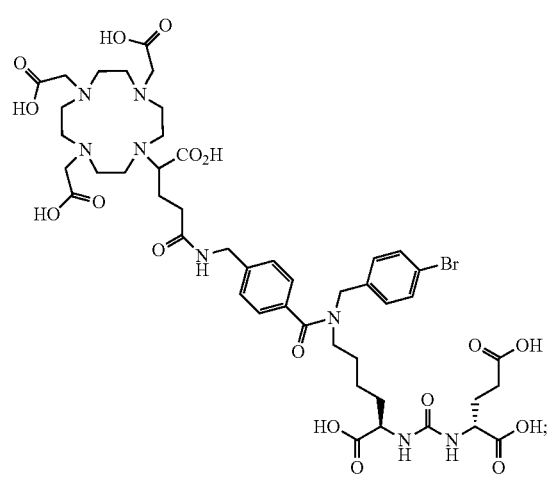
P12
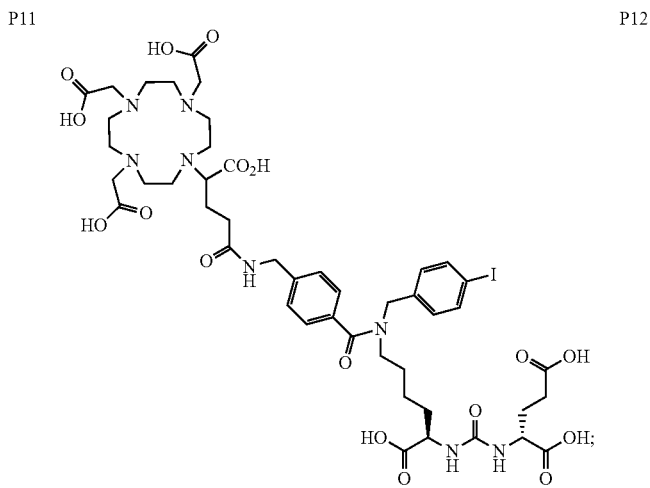

-continued
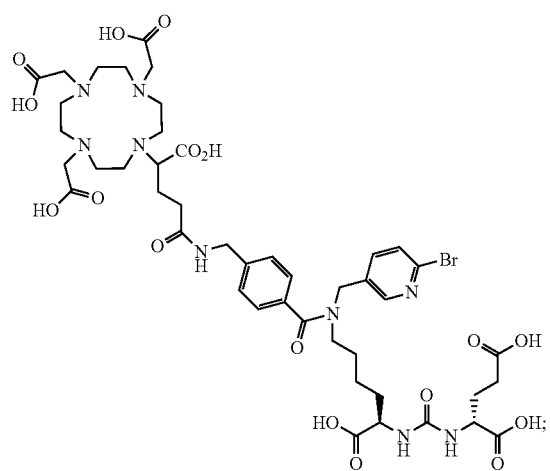
P11
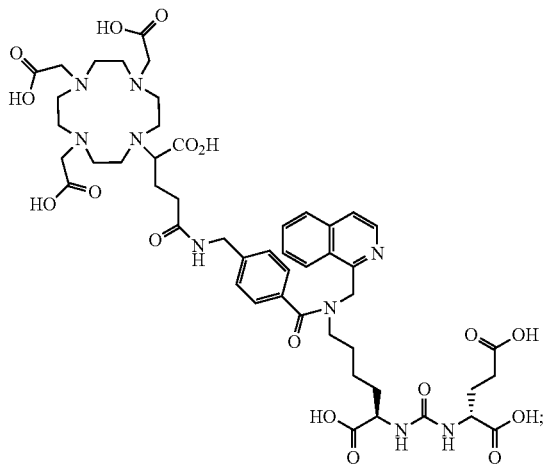
P11
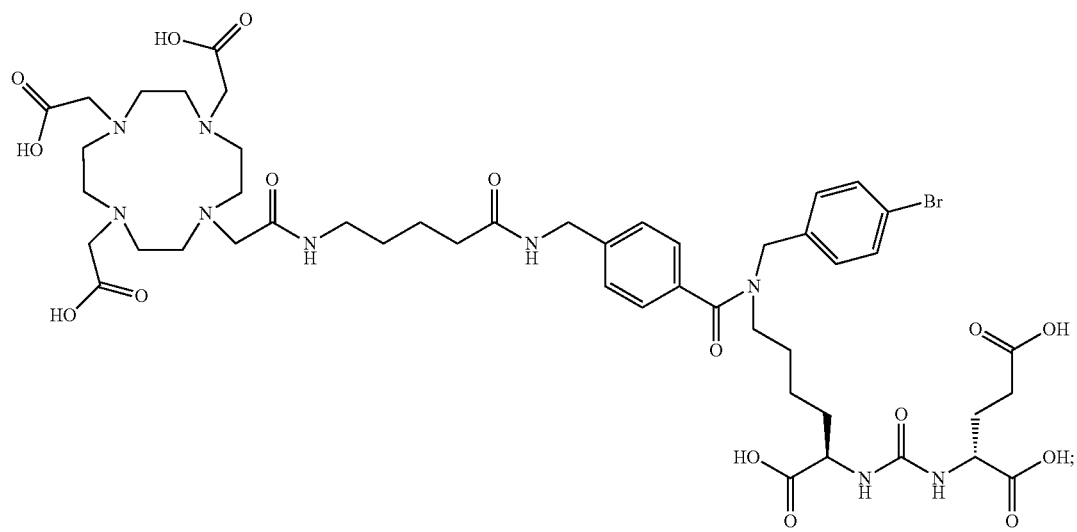
P13
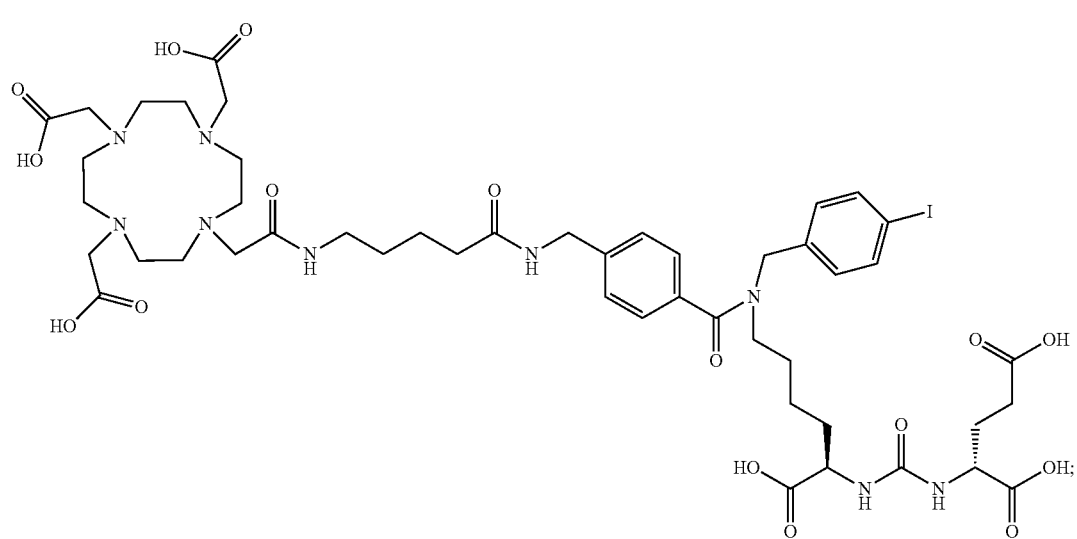
P14

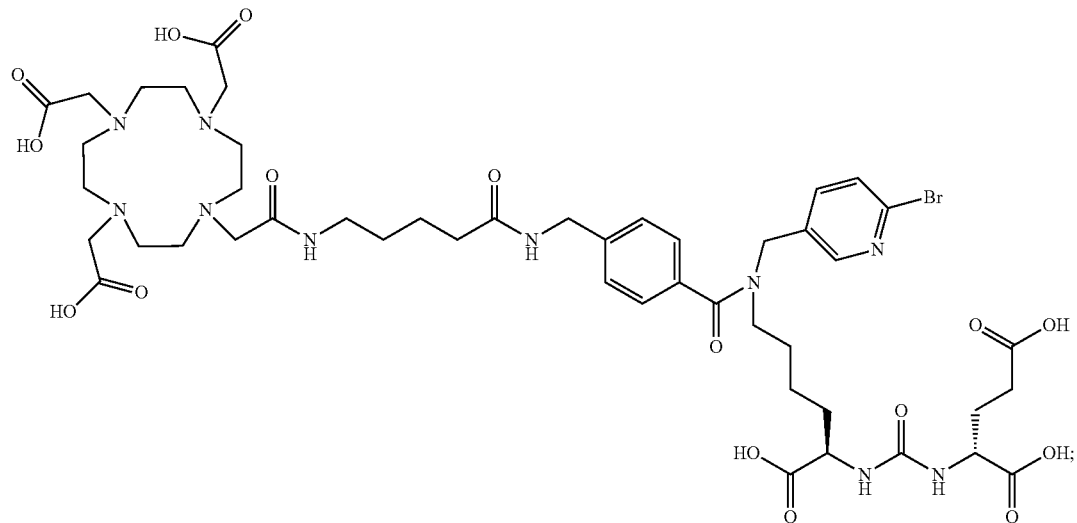
P13
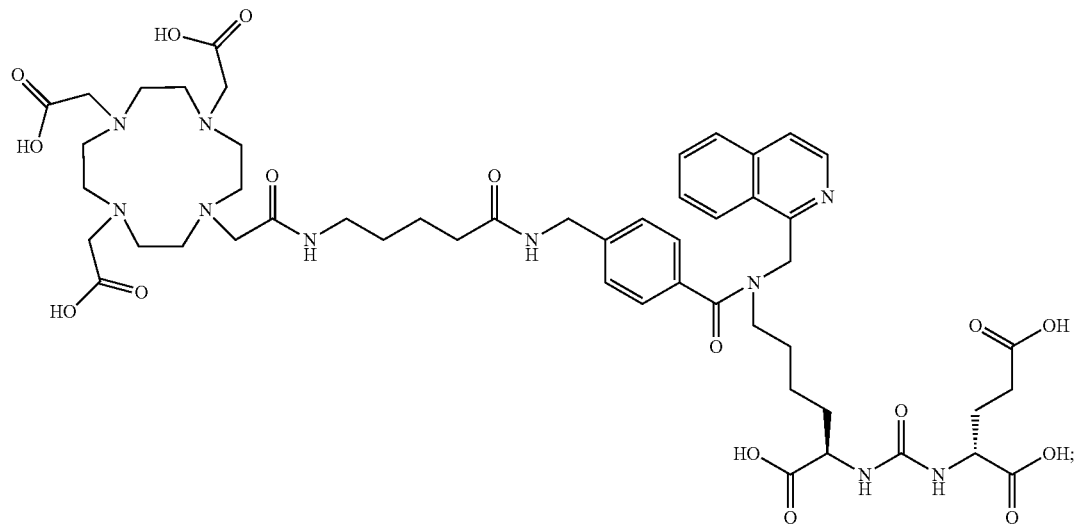
P13
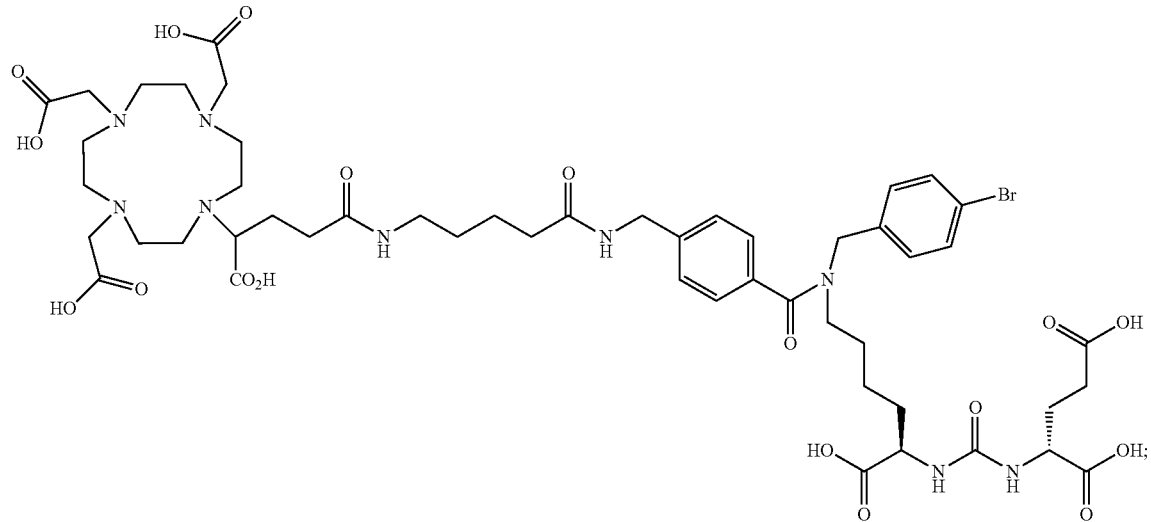
P15

-continued
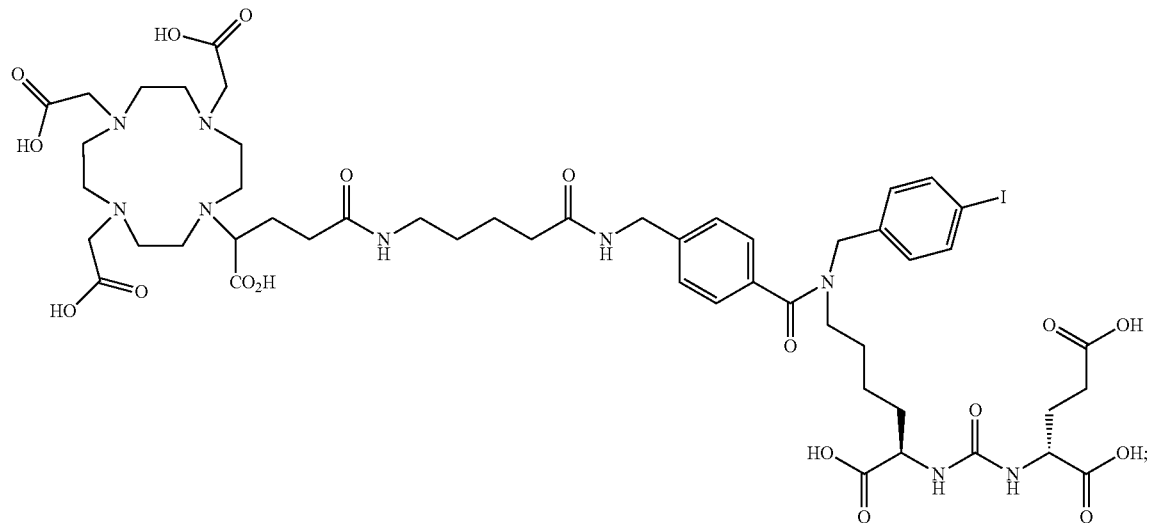
P16
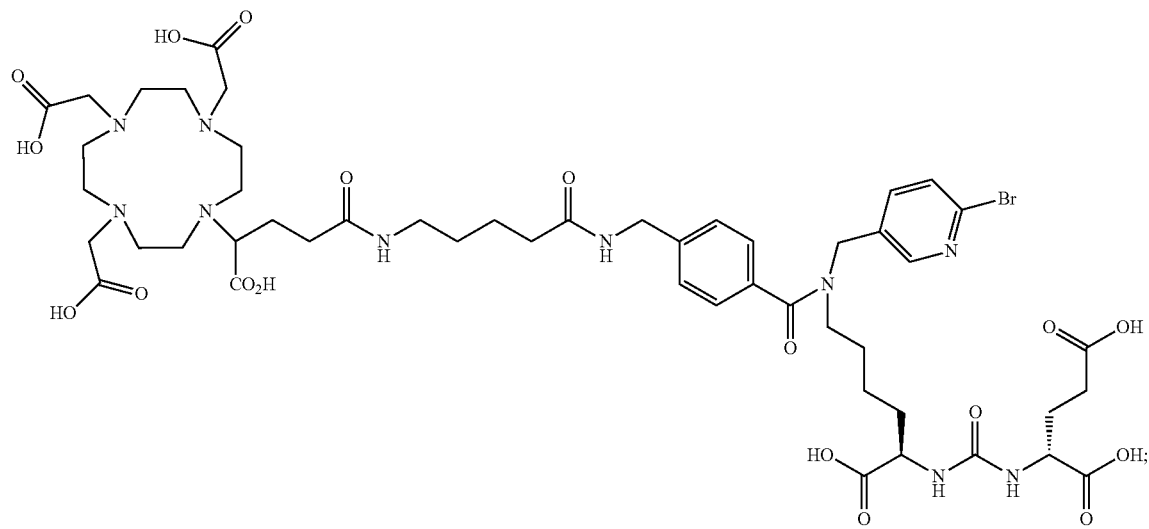
P15
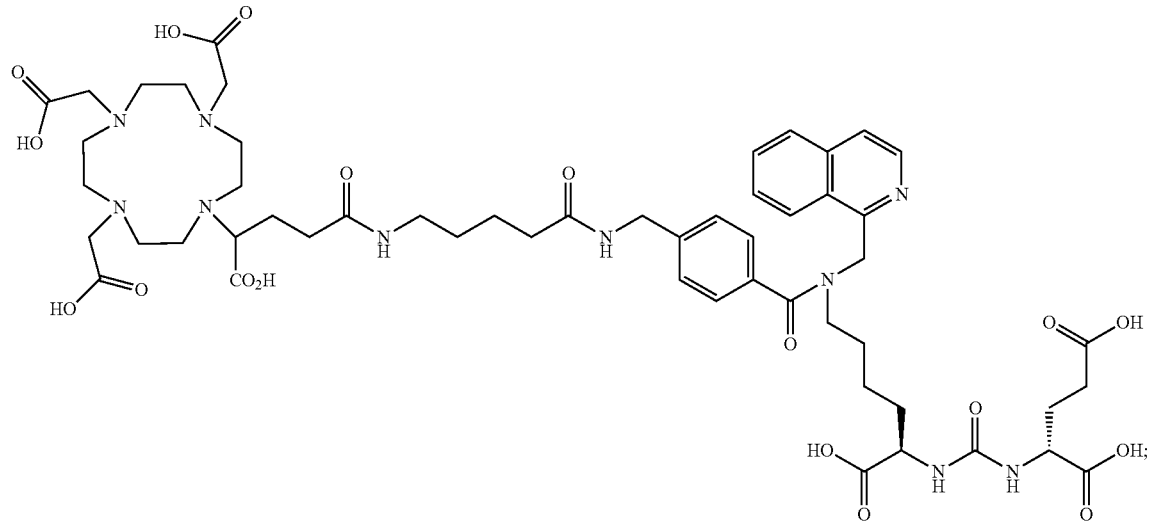
P15

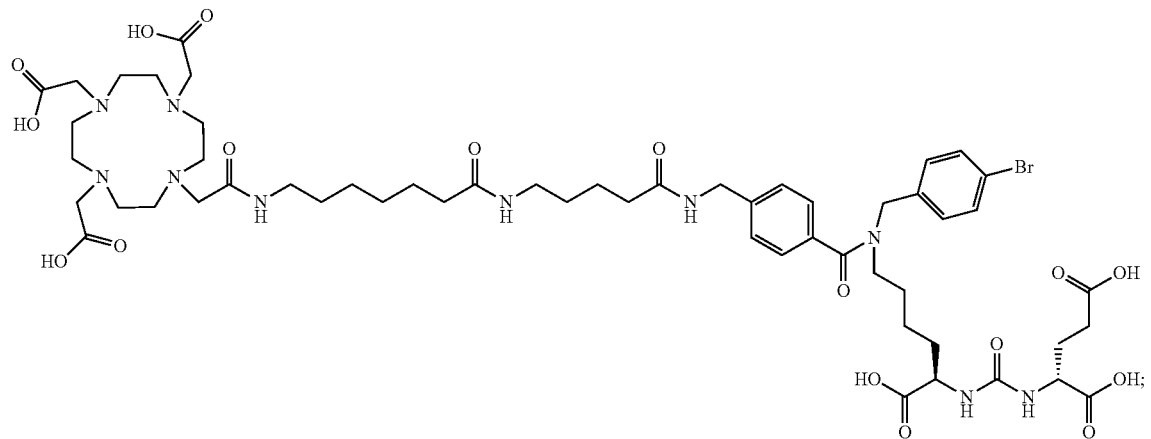
P17
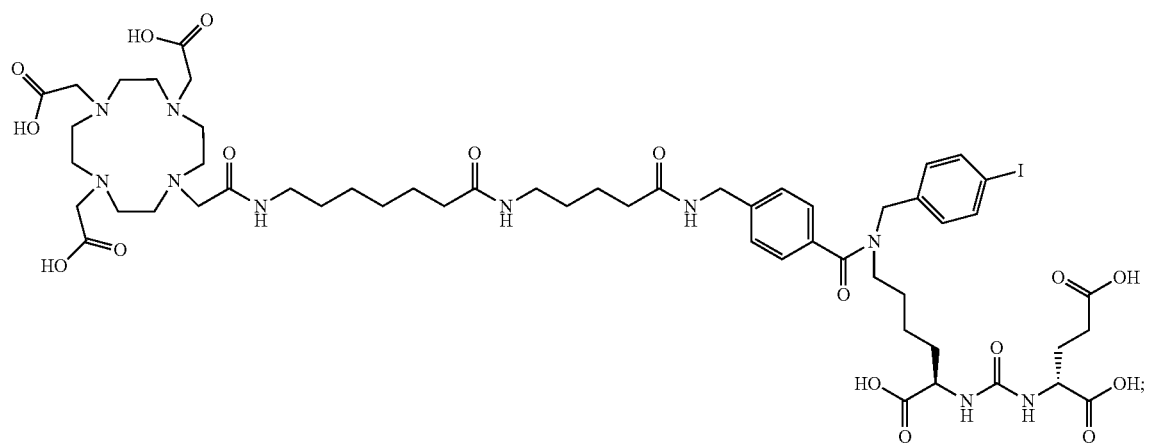
P18
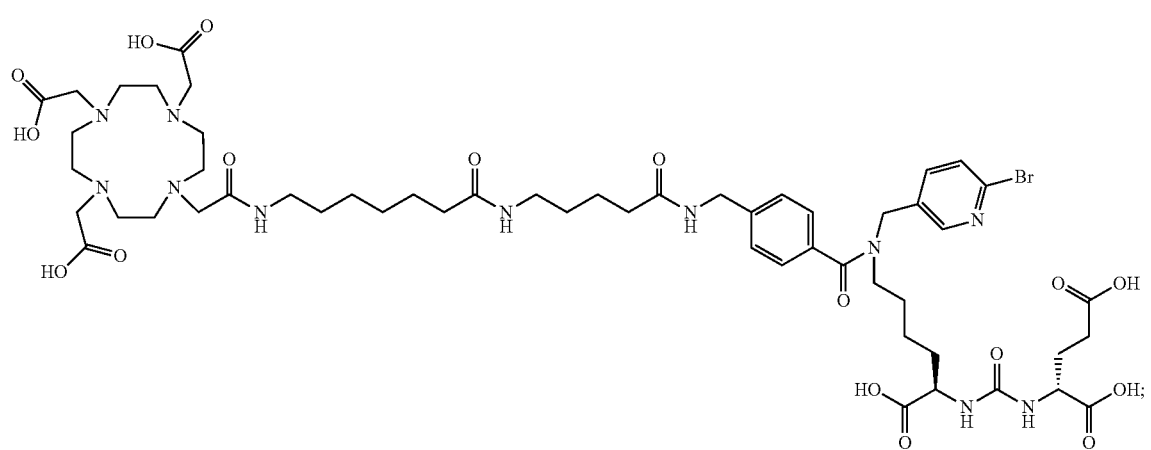
P17

-continued
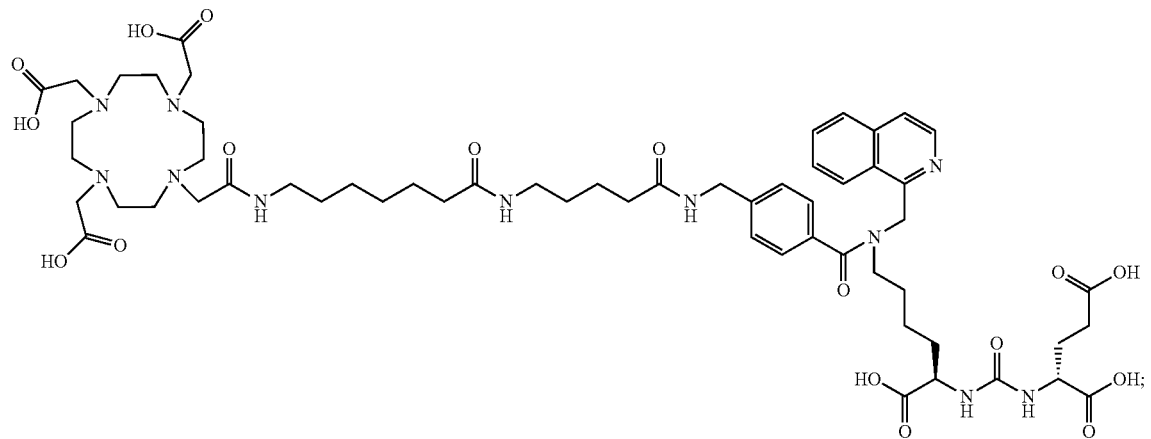
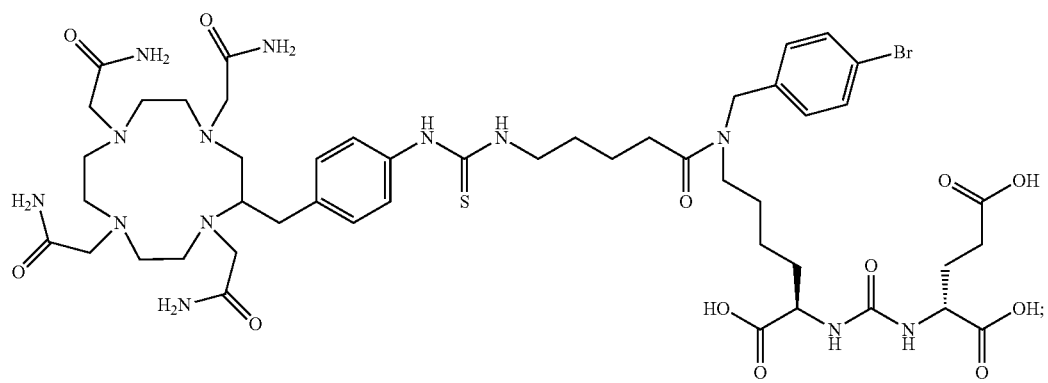
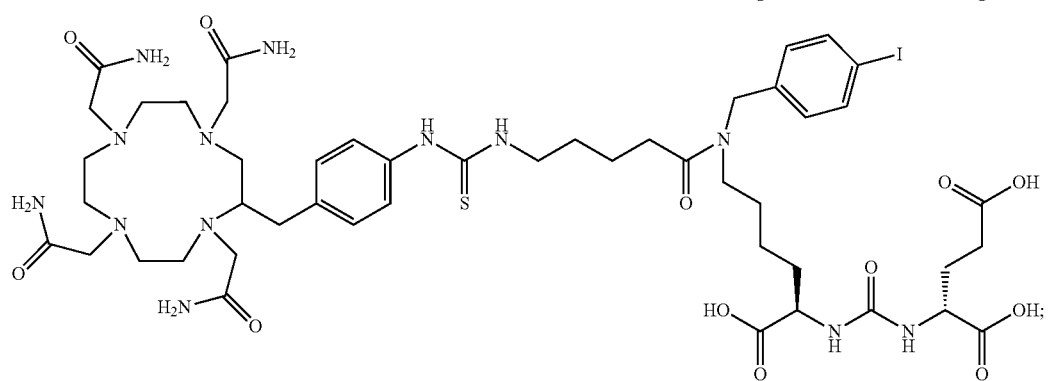
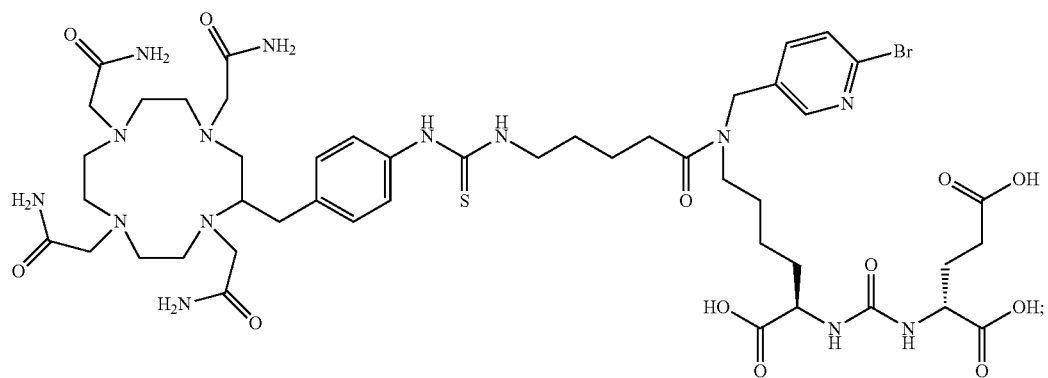

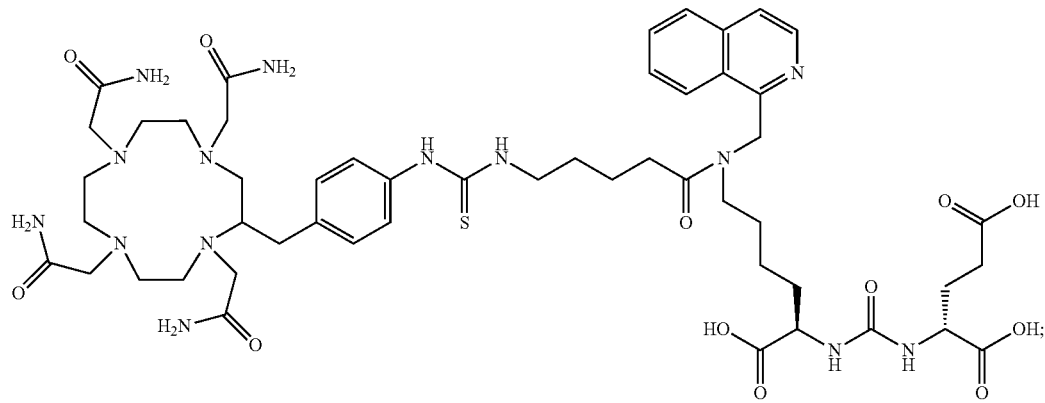
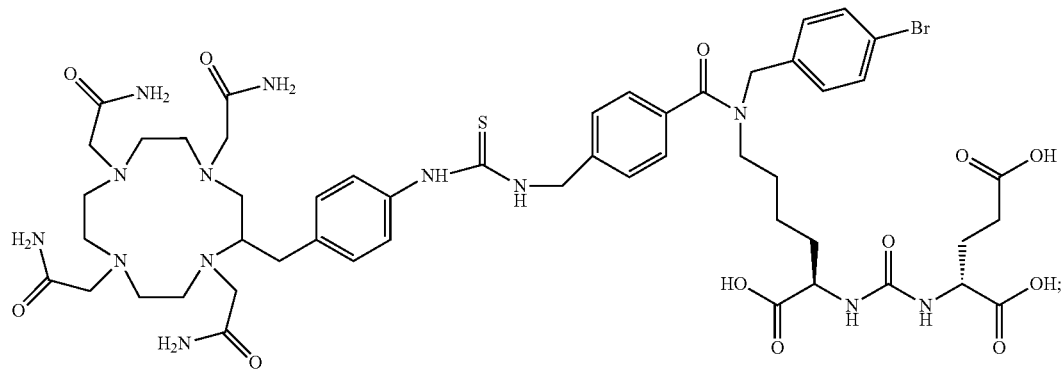
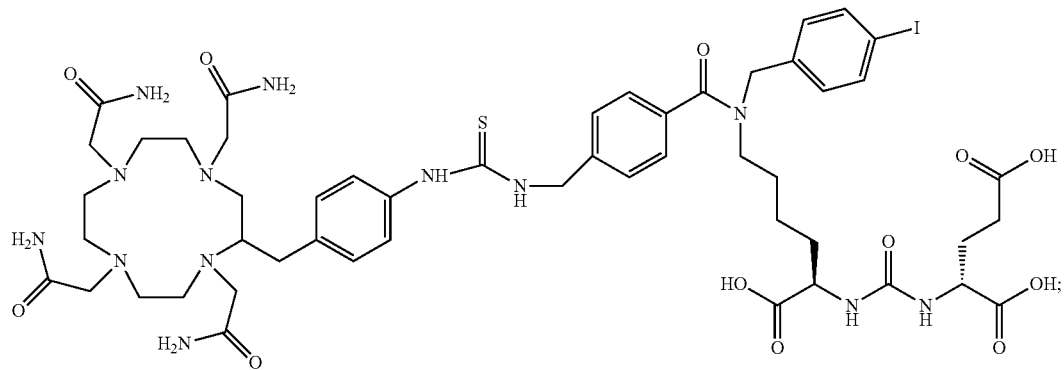
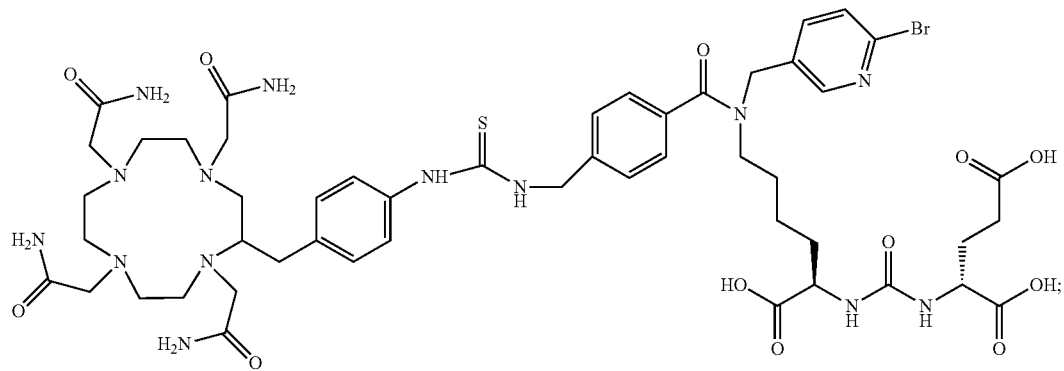

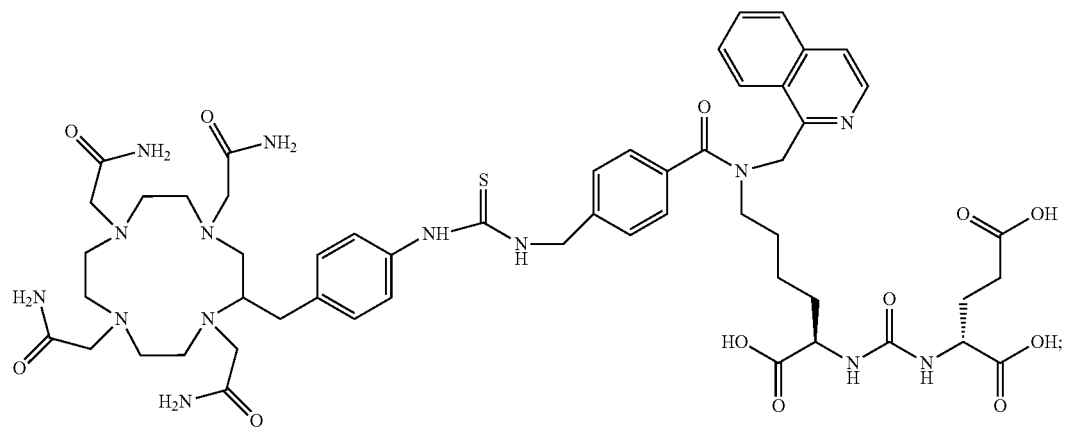
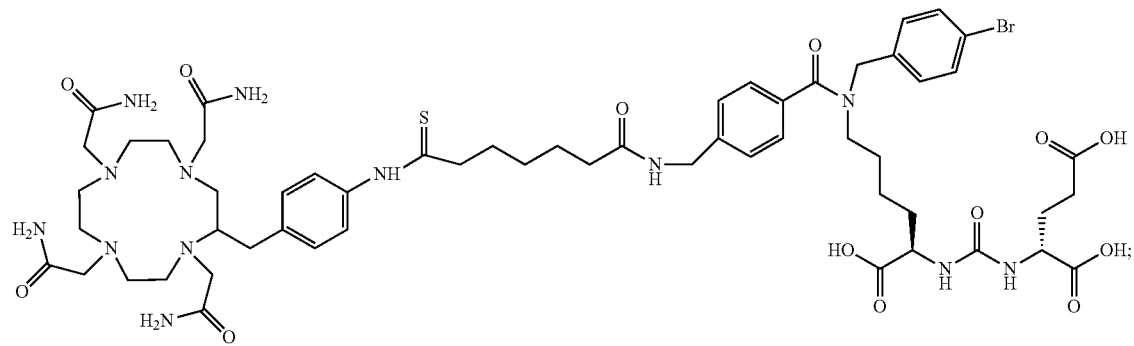
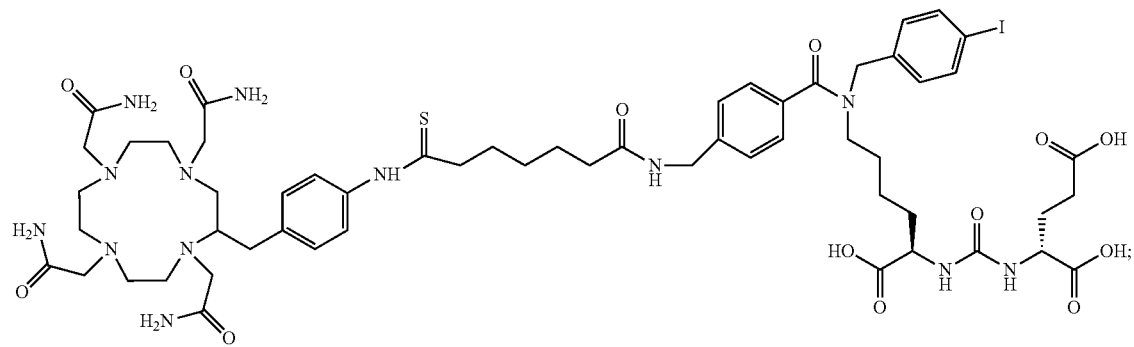
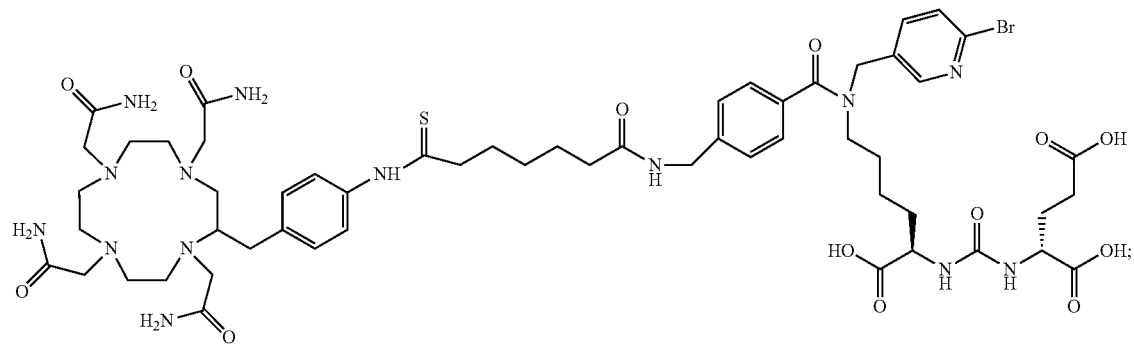

-continued
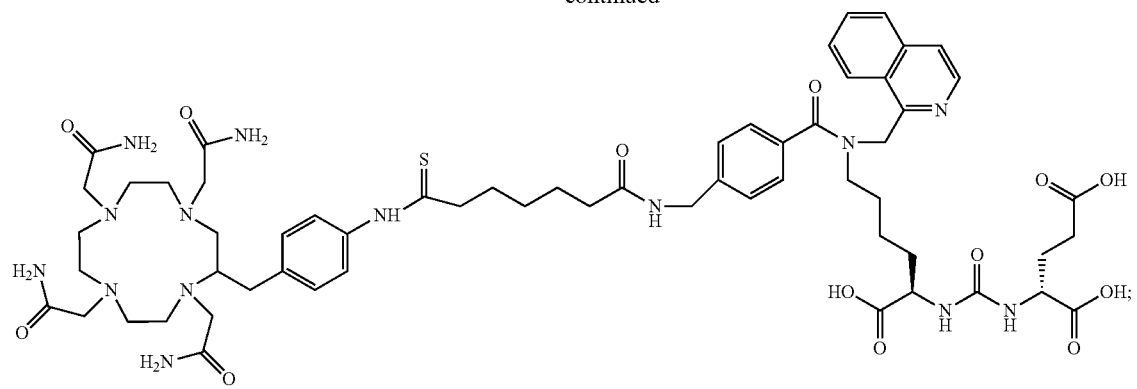
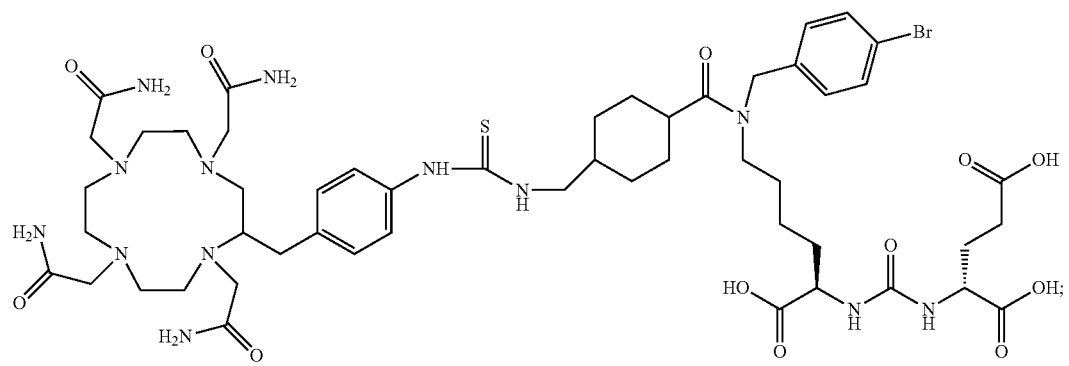
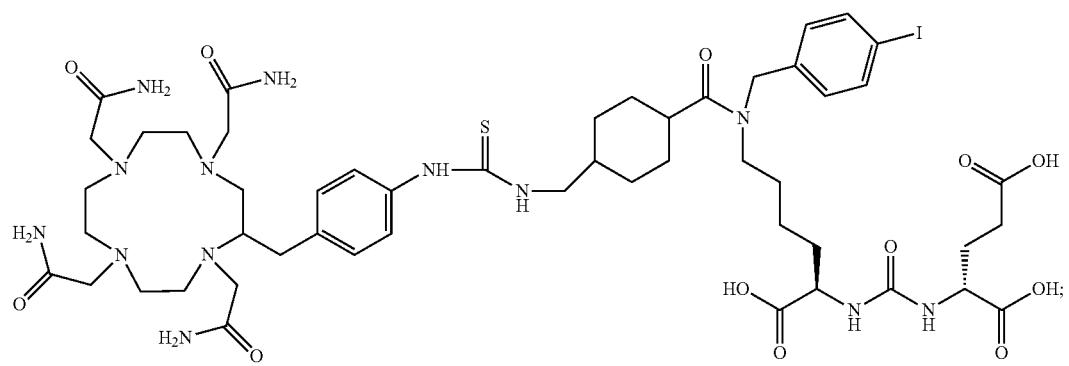
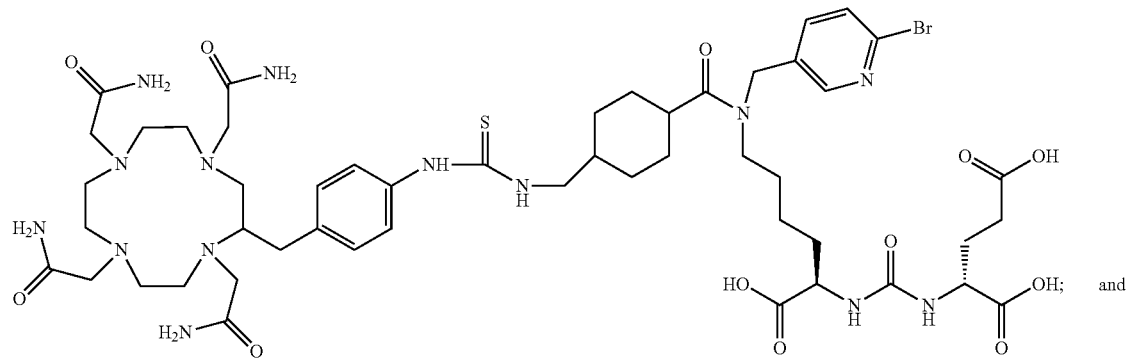

-continued

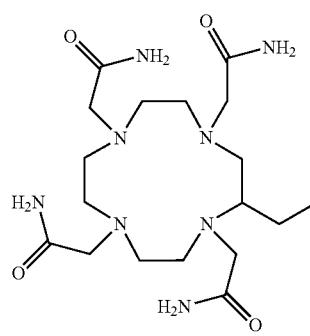 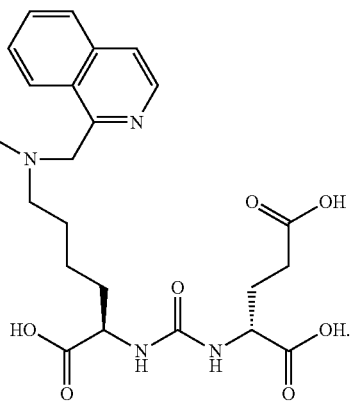

B. Methods of Using Compounds of Formula (I) for Treating One or More PSMA-Expressing Tumors or Cells In some embodiments, the presently disclosed subject matter provides a method for treating one or more PSMA expressing tumors or cells, the method comprising contacting the one or more PSMA expressing tumors or cells with an effective amount of a compound of formula (I), the compound of formula (I) comprising:

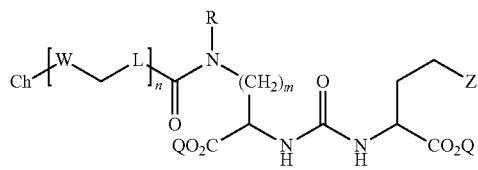

(I)

wherein: Z is tetrazole or $CO_2Q$; Q is H or a protecting group; m is an integer selected from the group consisting of 1, 2, 3, 4, and 5; R is independently H or —$CH_2$—$R^1$; $R^1$ is selected from the group consisting of substituted aryl, substituted pyridine, and unsubstituted isoquinoline; L is a linker selected from the group consisting of $C_1$-$C_6$ alkylene and $C_3$-$C_6$ cycloalkylene, and arylene; W is selected from the group consisting of —$NR^2$—(C=O)—, —$NR^2$—(C=S)—, —(C=O)—$NR^2$—, and —(C=S)—$NR^2$—; wherein each occurrence of L and W can be the same or different; $R^2$ is H or a $C_1$-$C_4$ alkyl; n is an integer selected from the group consisting of 1, 2, and 3; Ch is a chelating agent that comprises a radiometal suitable for radiotherapy; and pharmaceutically acceptable salts thereof.

"Contacting" means any action which results in at least one compound comprising the therapeutic agent of the presently disclosed subject matter physically contacting at least one PSMA-expressing tumor or cell. Contacting can include exposing the cell(s) or tumor(s) to the compound in an amount sufficient to result in contact of at least one compound with at least one cell or tumor. The method can be practiced in vitro or ex vivo by introducing, and preferably mixing, the compound and cell(s) or tumor(s) in a controlled environment, such as a culture dish or tube. The method can be practiced in vivo, in which case contacting means exposing at least one cell or tumor in a subject to at least one compound of the presently disclosed subject matter, such as administering the compound to a subject via any suitable route.

As used herein, the term "treating" can include reversing, alleviating, inhibiting the progression of, preventing or reducing the likelihood of the disease, disorder, or condition to which such term applies, or one or more symptoms or manifestations of such disease, disorder or condition. Preventing refers to causing a disease, disorder, condition, or symptom or manifestation of such, or worsening of the severity of such, not to occur. Accordingly, the presently disclosed compounds can be administered prophylactically to prevent or reduce the incidence or recurrence of the disease, disorder, or condition.

In general, the "effective amount" of an active agent refers to the amount necessary to elicit the desired biological response. A will be appreciated by those of ordinary skill in this art, the effective amount of an agent or device may vary depending on such factors as the desired biological endpoint, the agent to be delivered, the makeup of the pharmaceutical composition, the target tissue, and the like.

The term "combination" is used in its broadest sense and means that a subject is administered at least two agents, more particularly a compound of Formula (I) and at least one other active agent. More particularly, the term "in combination" refers to the concomitant administration of two (or more) active agents for the treatment of a, e.g., single disease state. As used herein, the active agents may be combined and administered in a single dosage form, may be administered as separate dosage forms at the same time, or may be administered as separate dosage forms that are administered alternately or sequentially on the same or separate days. In one embodiment of the presently disclosed subject matter, the active agents are combined and administered in a single dosage form. In another embodiment, the active agents are administered in separate dosage forms (e.g., wherein it is desirable to vary the amount of one but not the other). The single dosage form may include additional active agents for the treatment of the disease state.

In particular embodiments, $R^1$ is selected from the group consisting of:

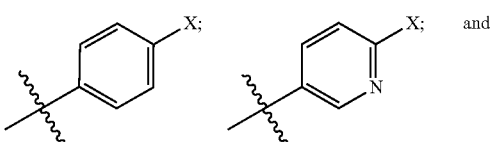

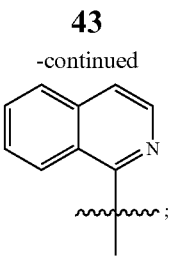

wherein X is independently Br or I.

In more particular embodiments, the chelating agent is selected from the group consisting of:

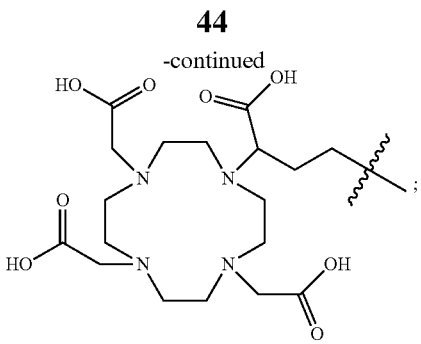

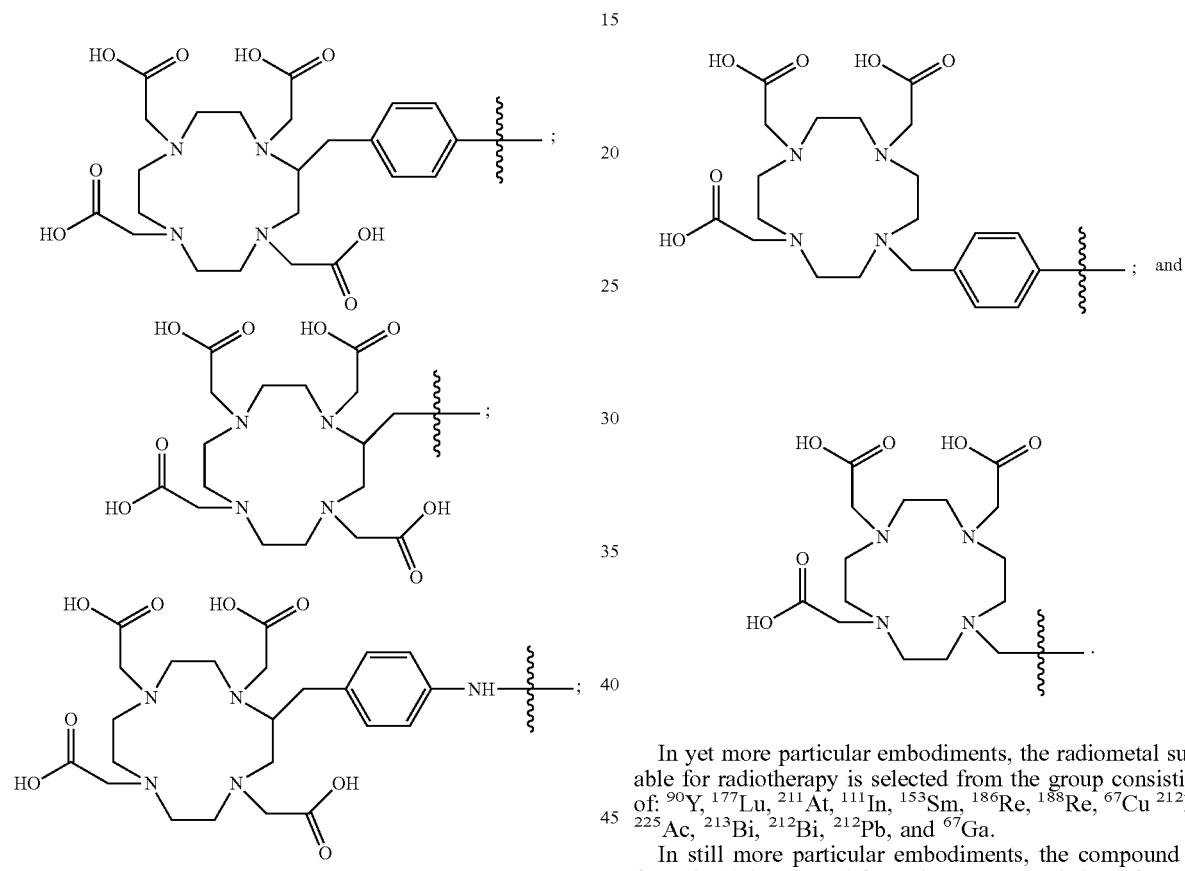

In yet more particular embodiments, the radiometal suitable for radiotherapy is selected from the group consisting of: $^{90}$Y, $^{177}$Lu, $^{211}$At, $^{111}$In, $^{153}$Sm, $^{186}$Re, $^{188}$Re, $^{67}$Cu $^{212}$Pb $^{225}$Ac, $^{213}$Bi, $^{212}$Bi, $^{212}$Pb, and $^{67}$Ga.

In still more particular embodiments, the compound of formula (I) is selected from the group consisting of:

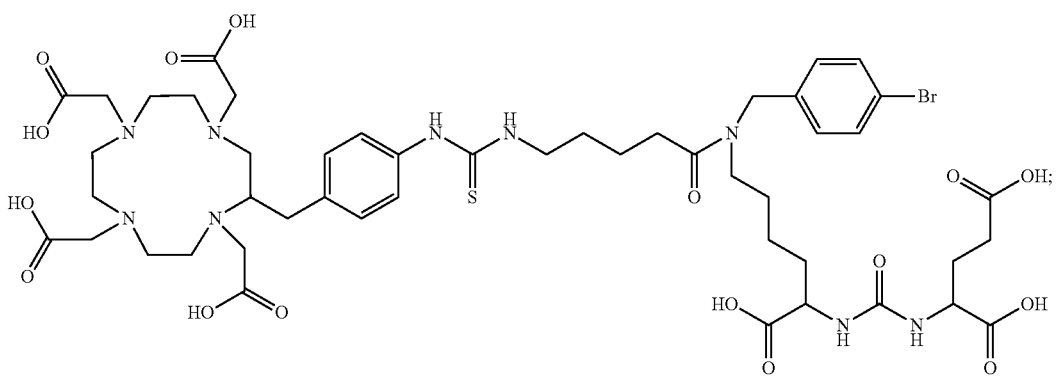

-continued
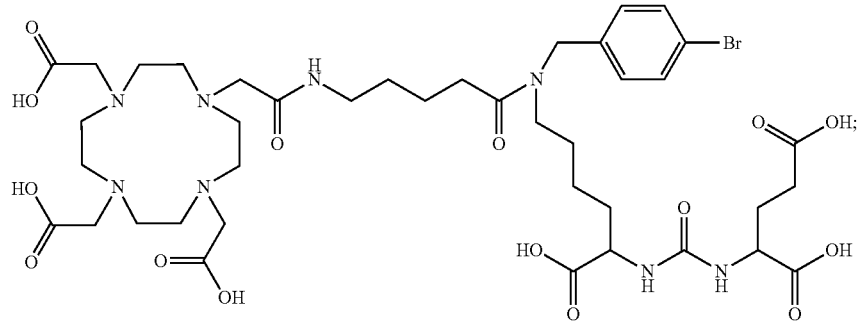
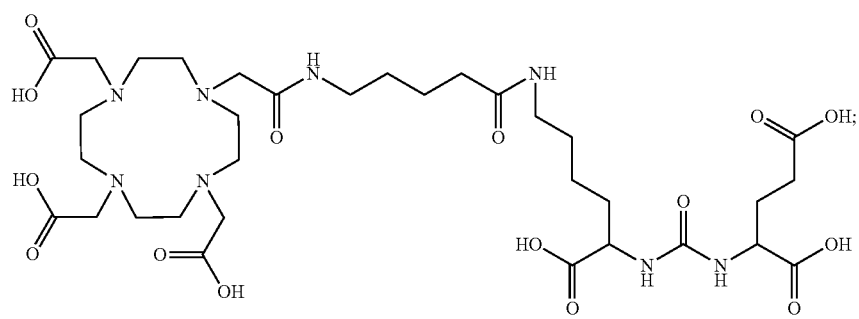
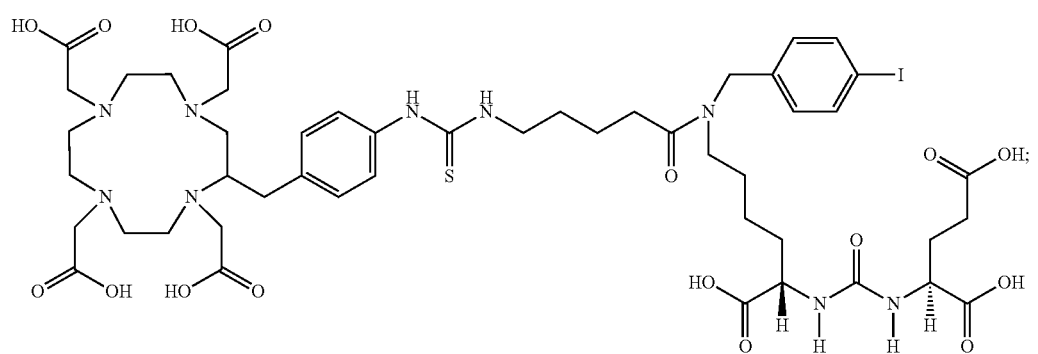
P1
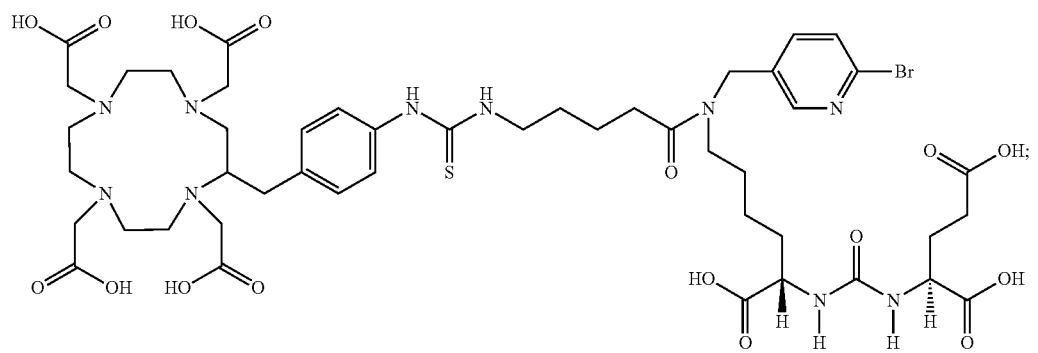
P1

-continued
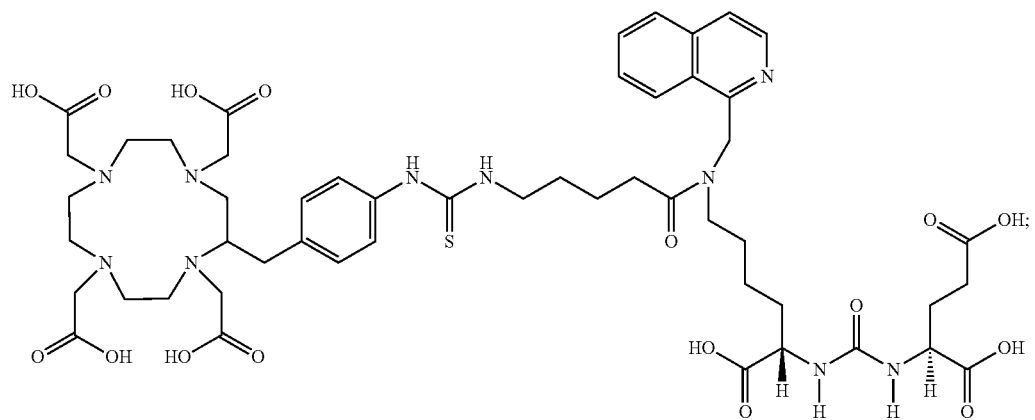
P1
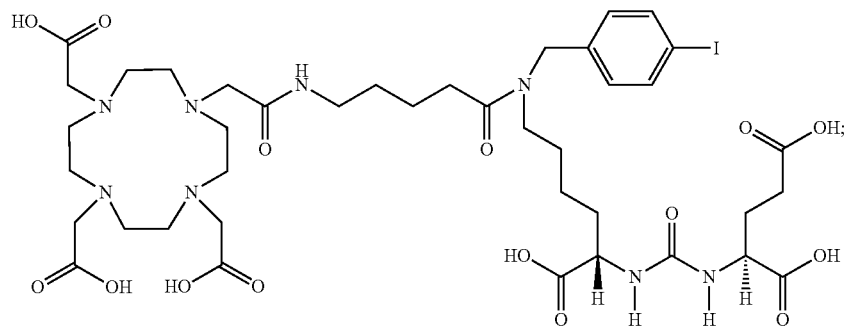
P2
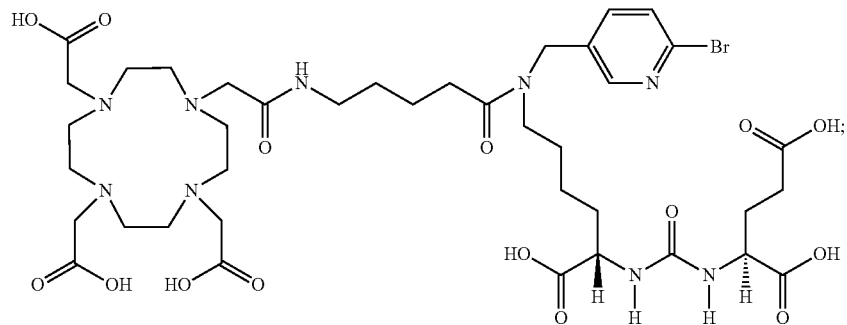
P2
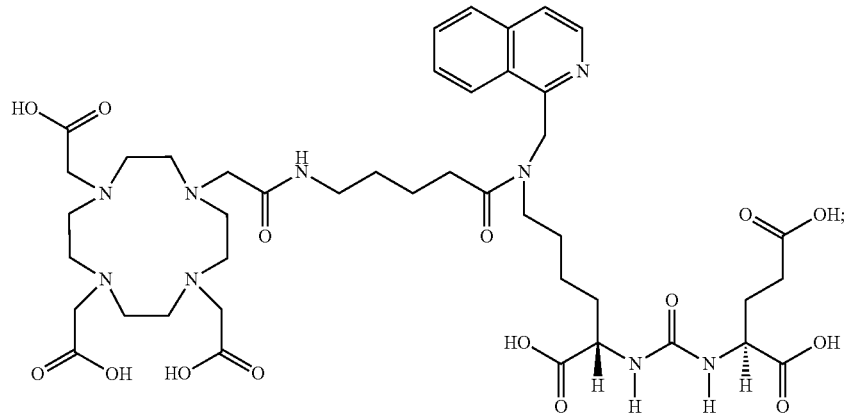
P2

-continued
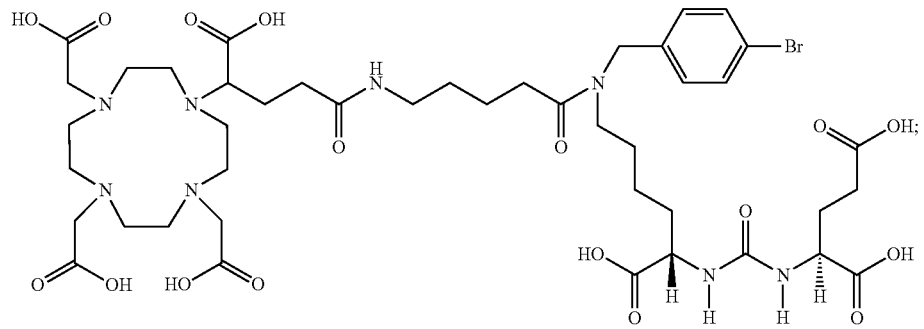
P3
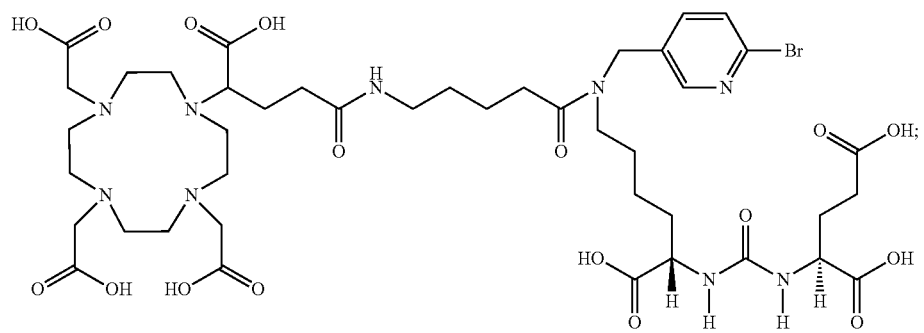
P3
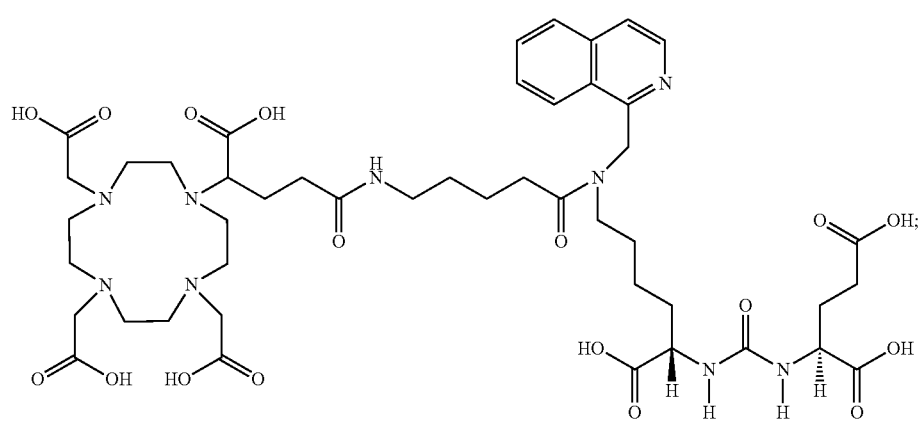
P3
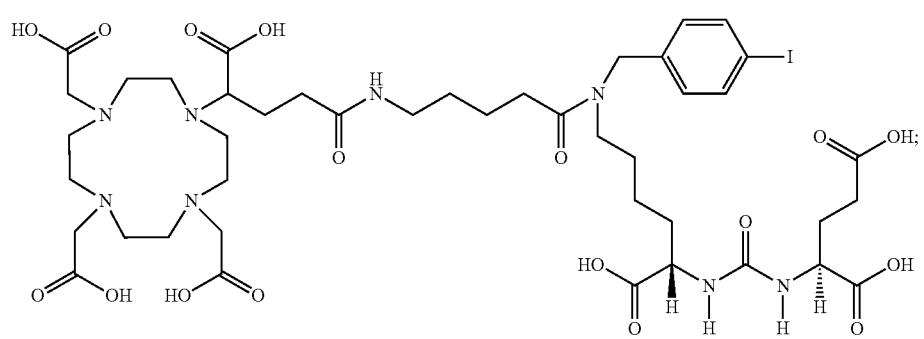
P4

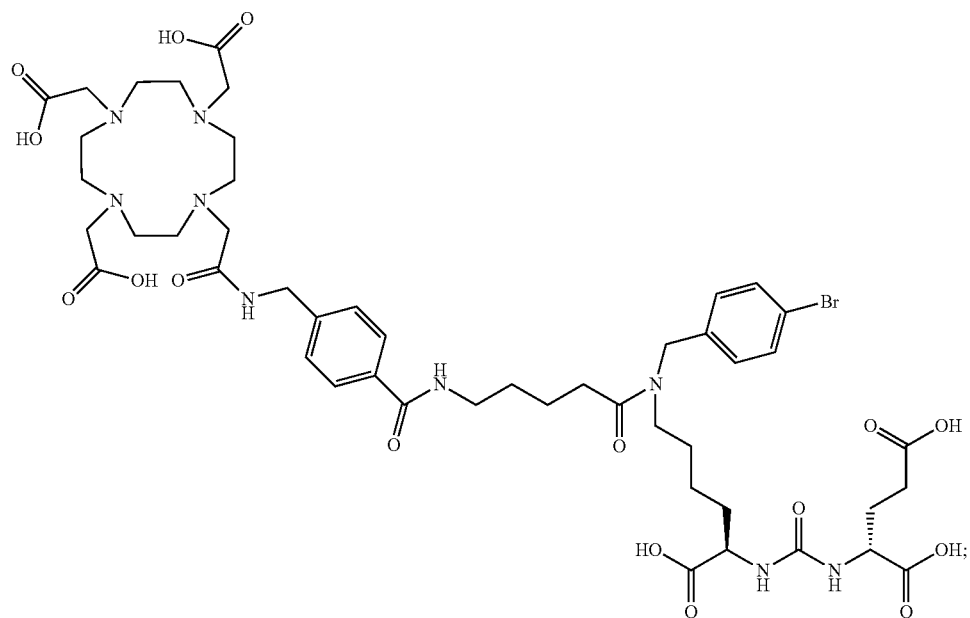
P5
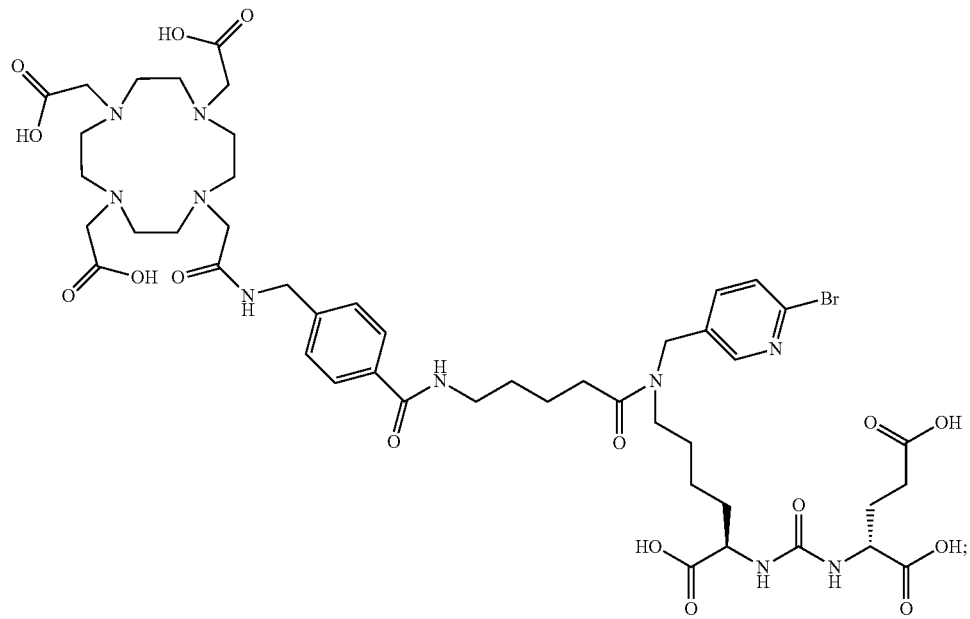
P5

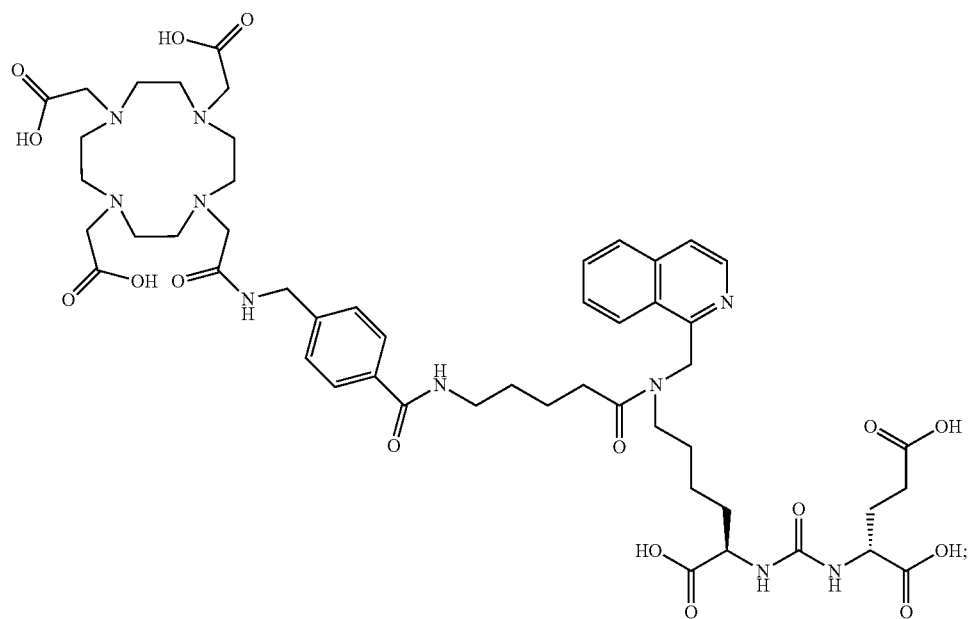
P5
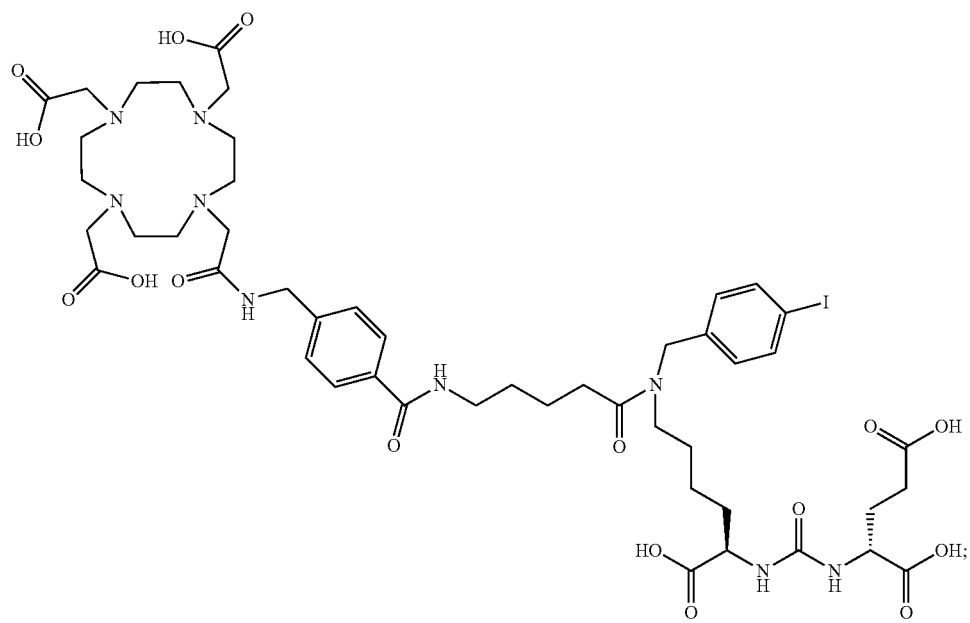
P6

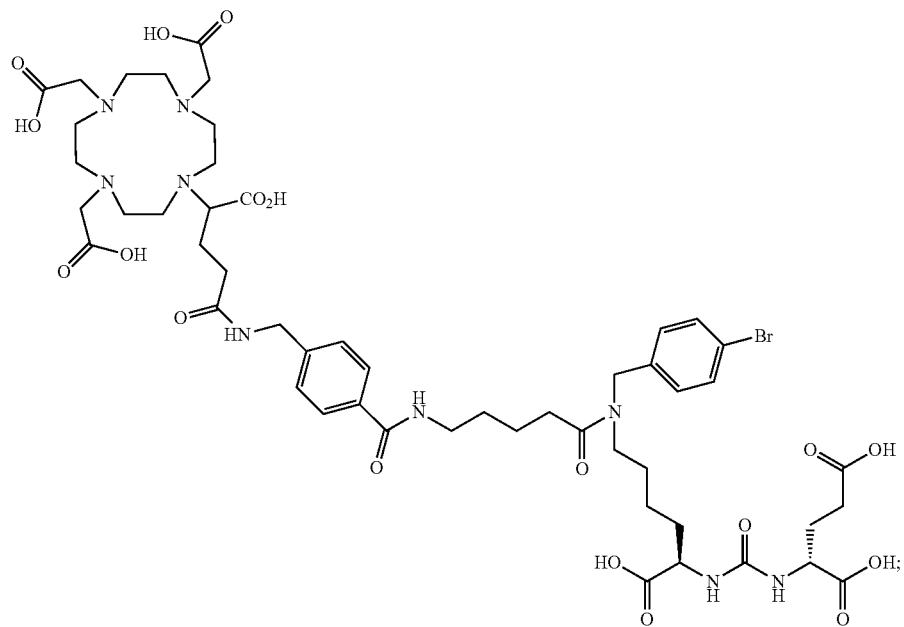
P7
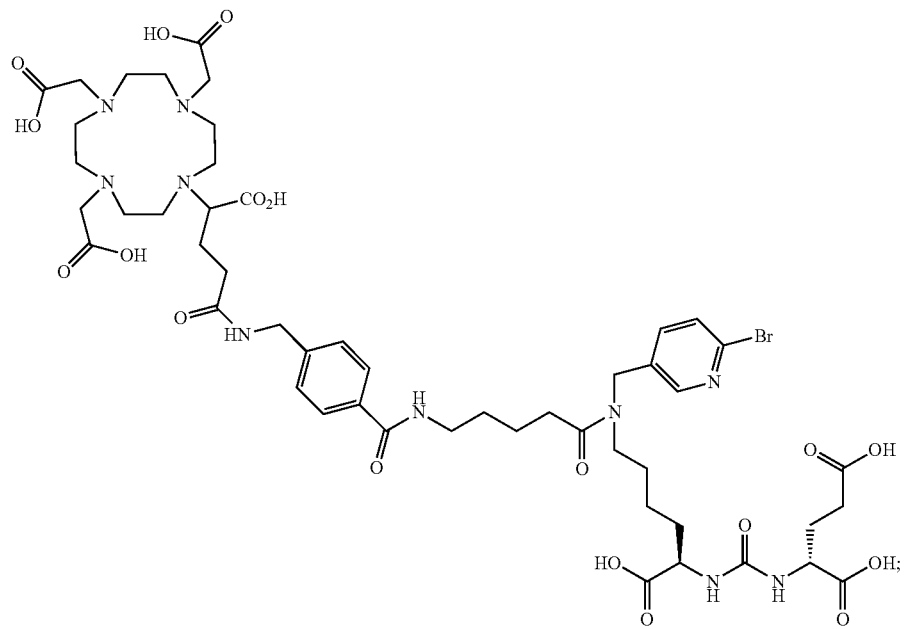
P7

P7
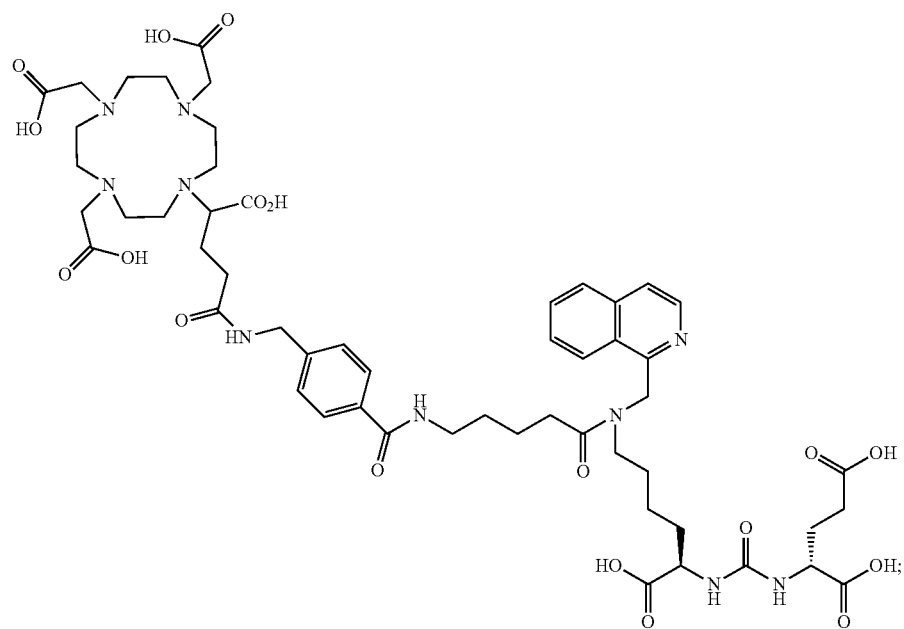
P8
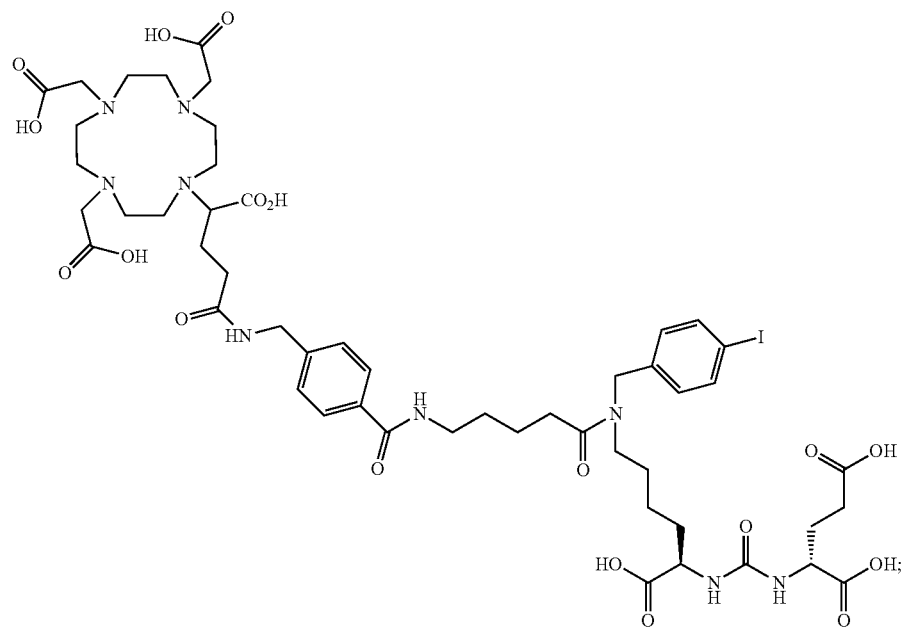

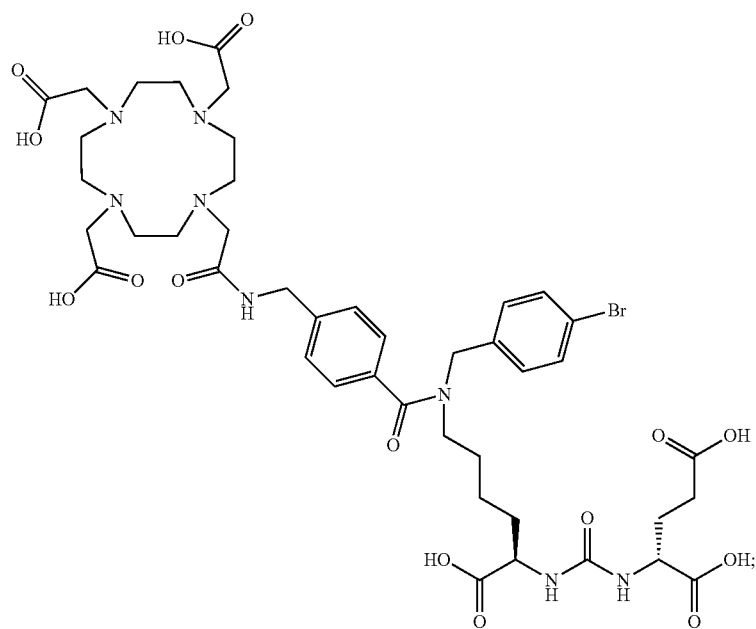
P9
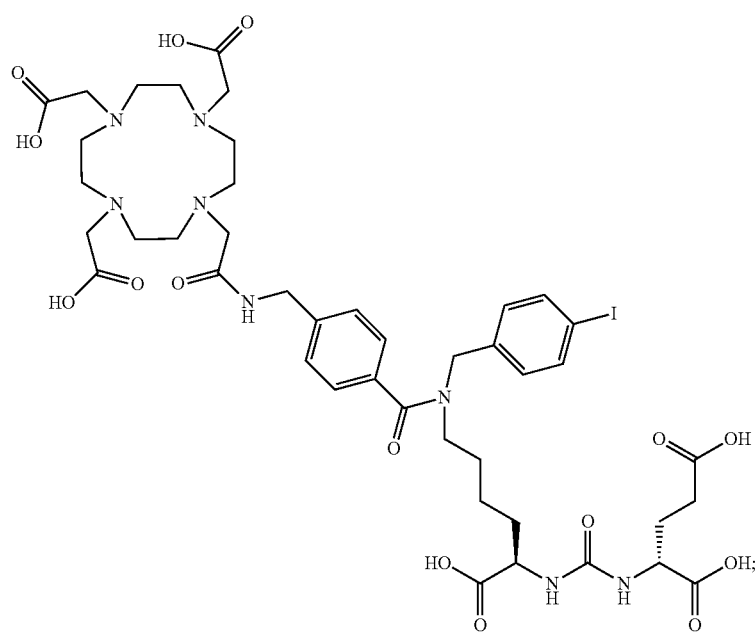
P10

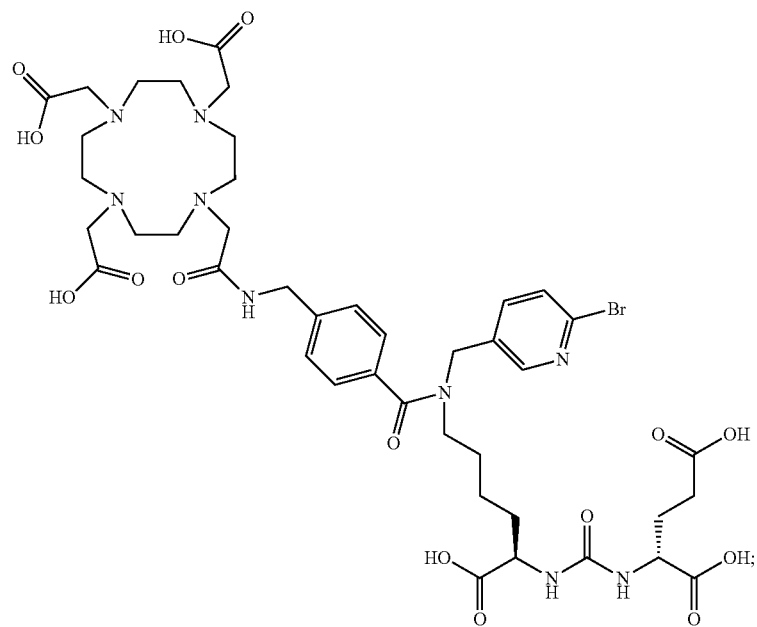
P9
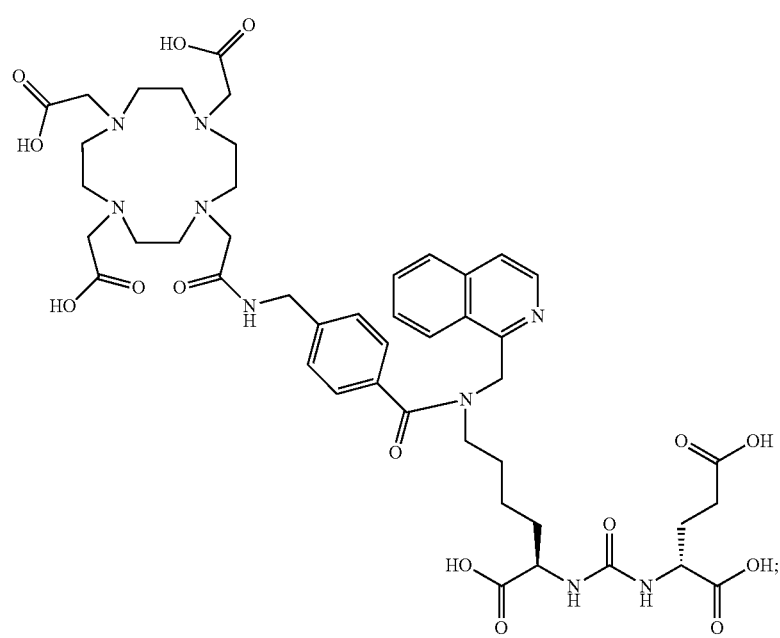
P9

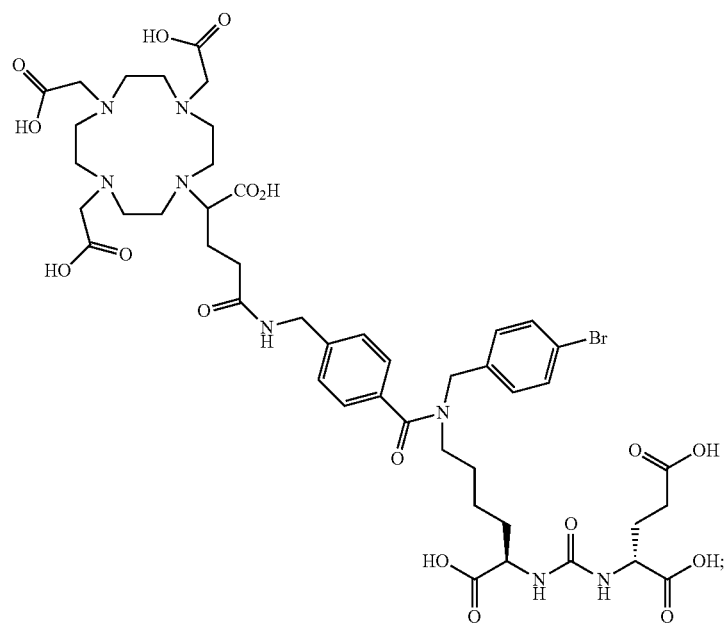
P11
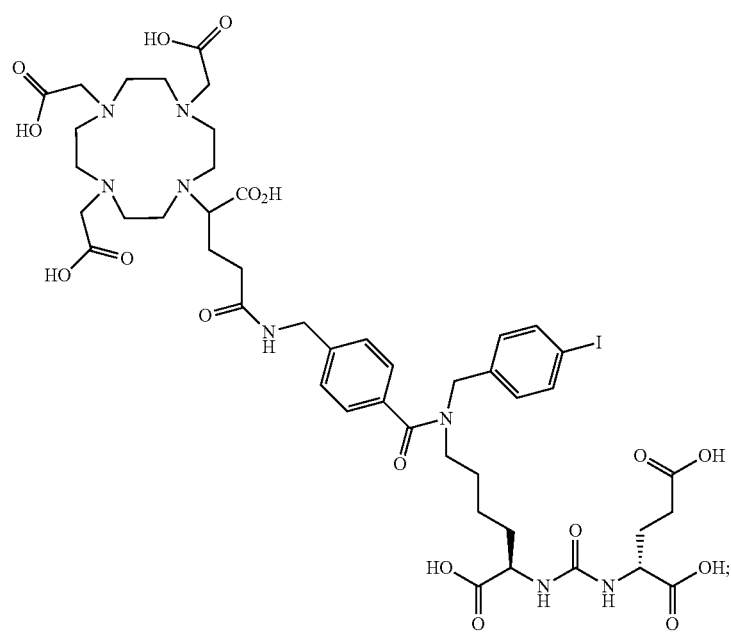
P12

-continued
P11
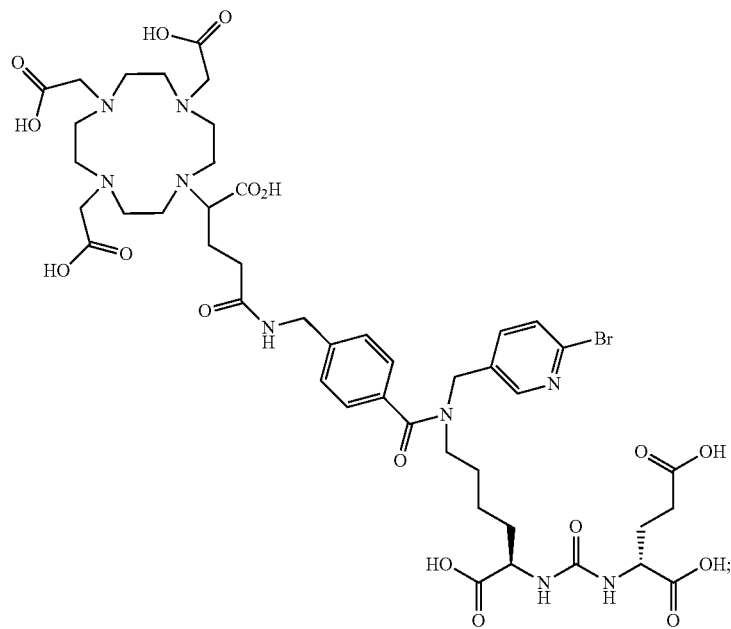
P11
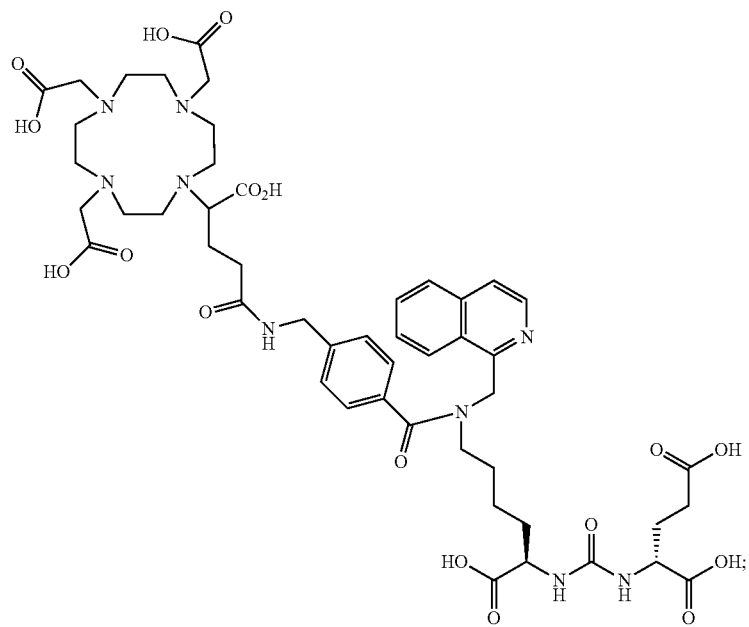

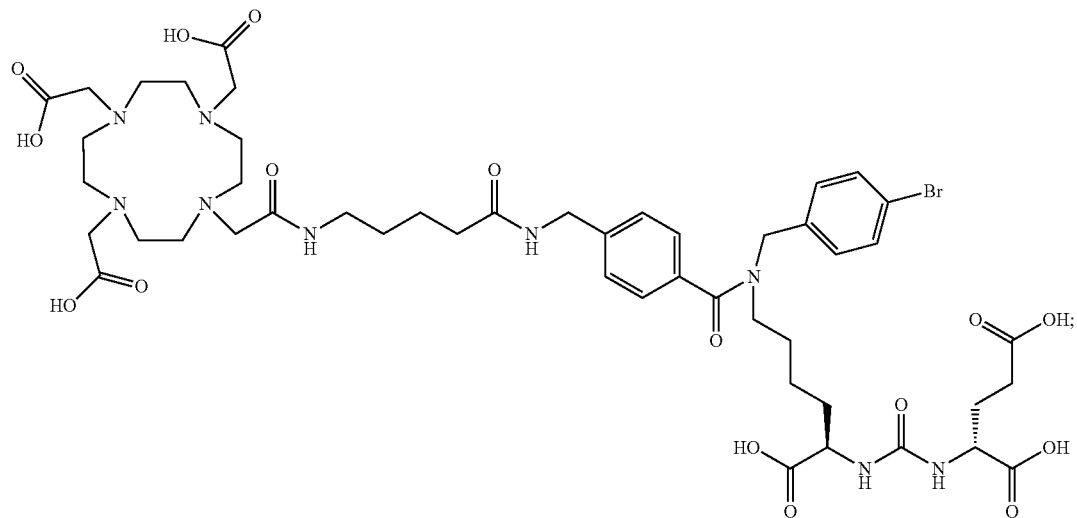
P13
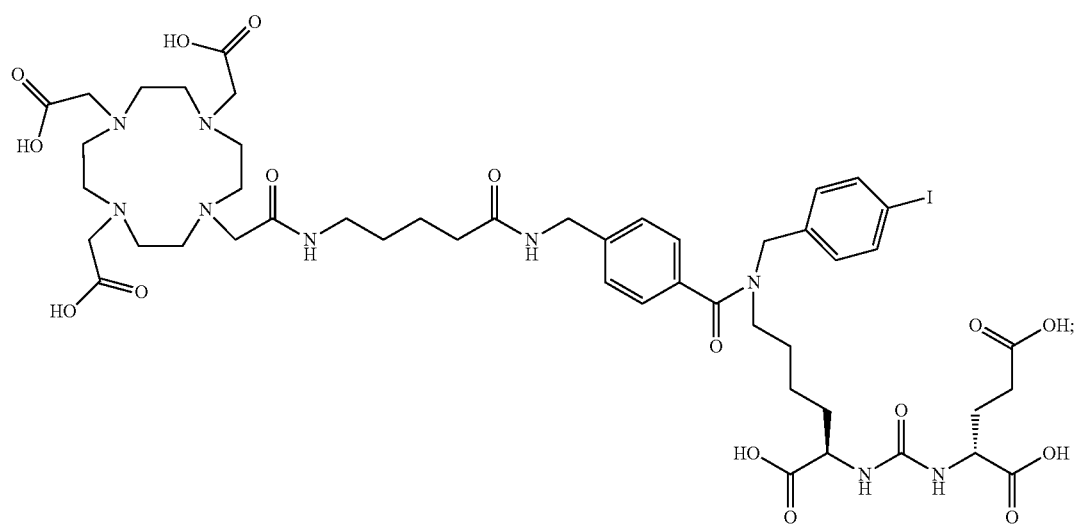
P14
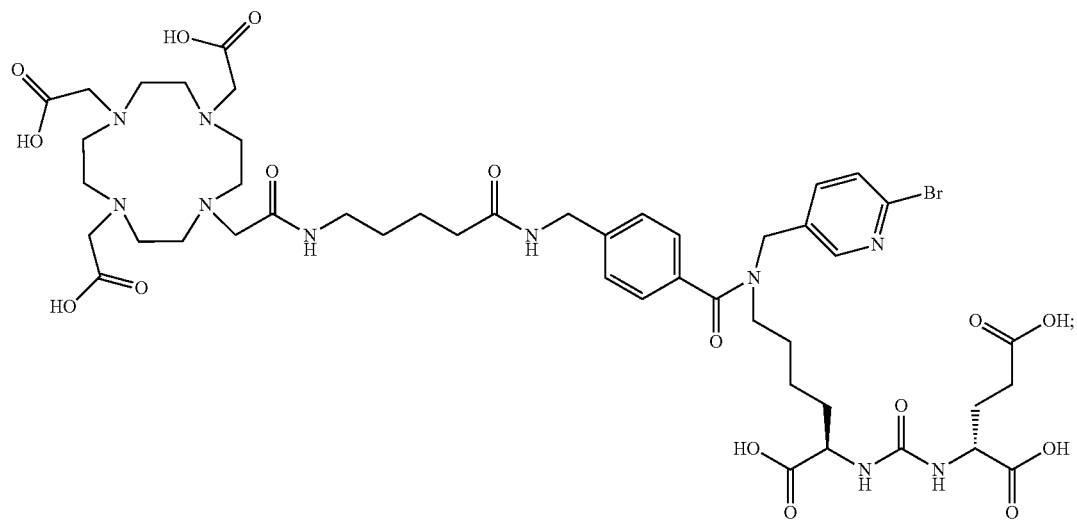
P13

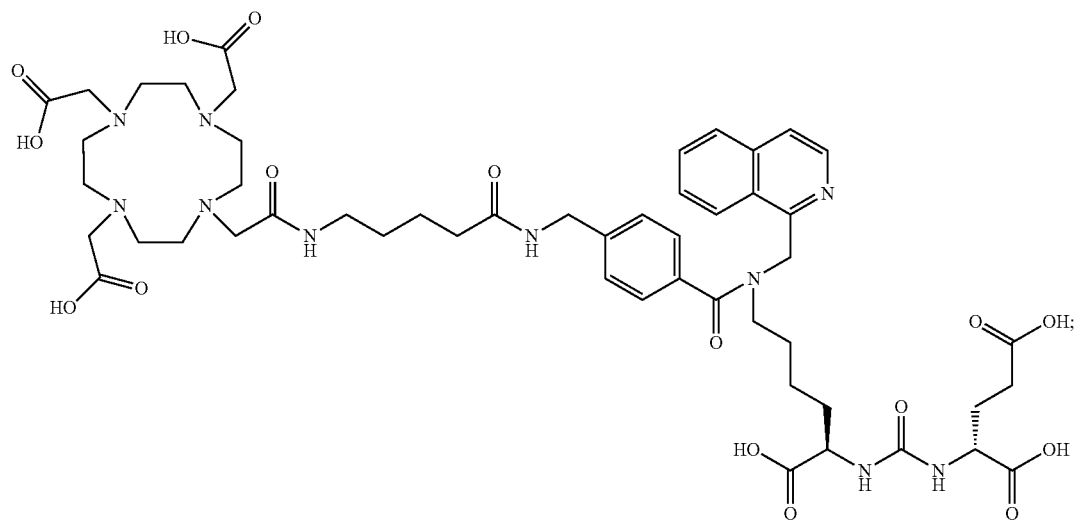
P13
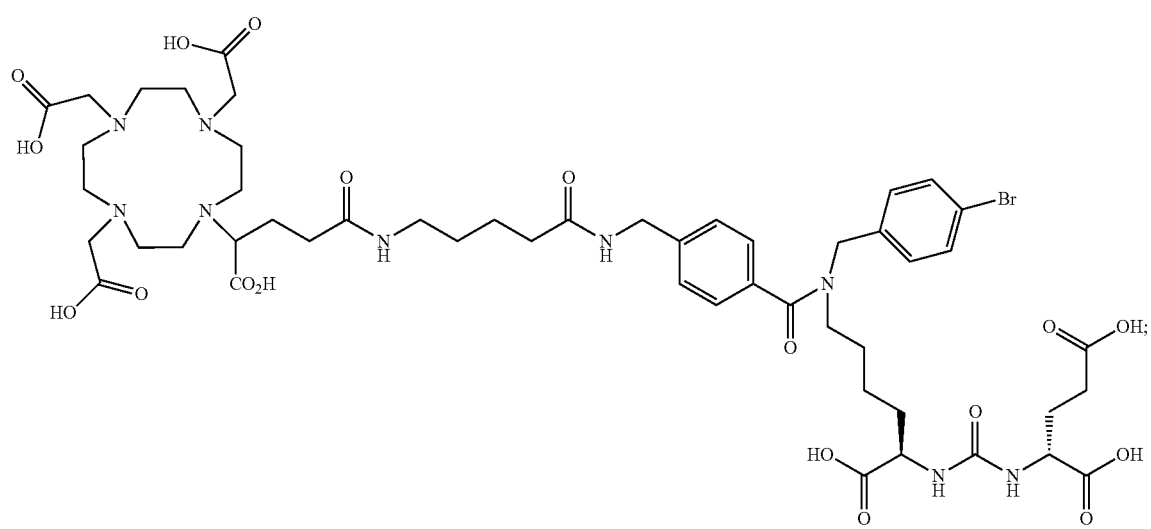
P15
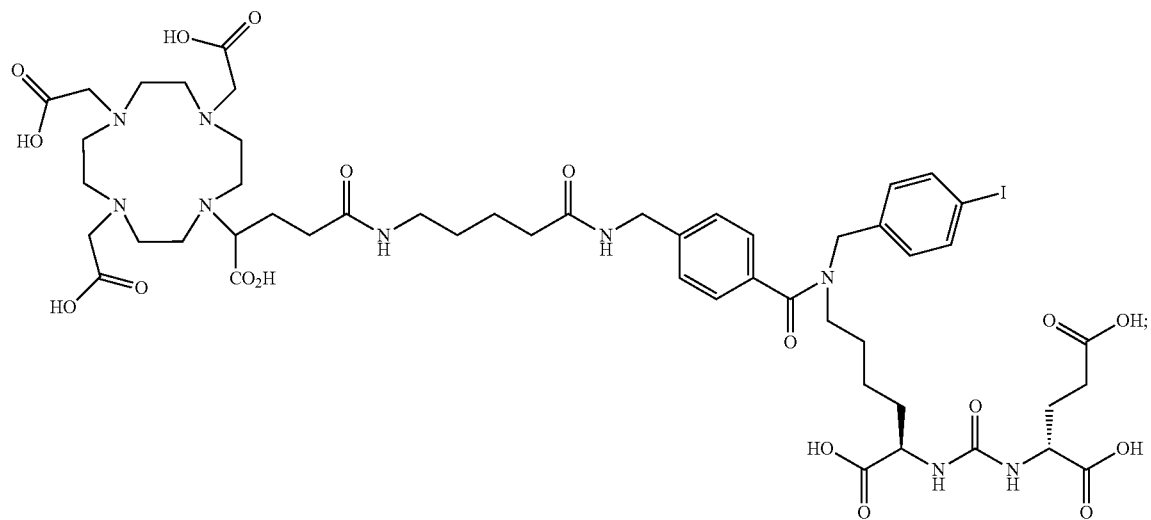
P16

P15
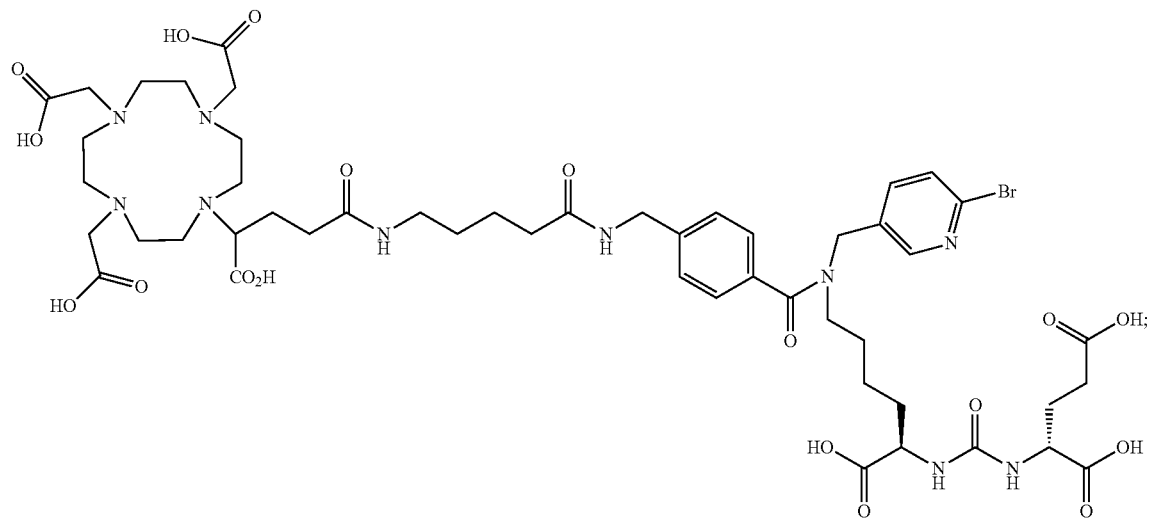
P15
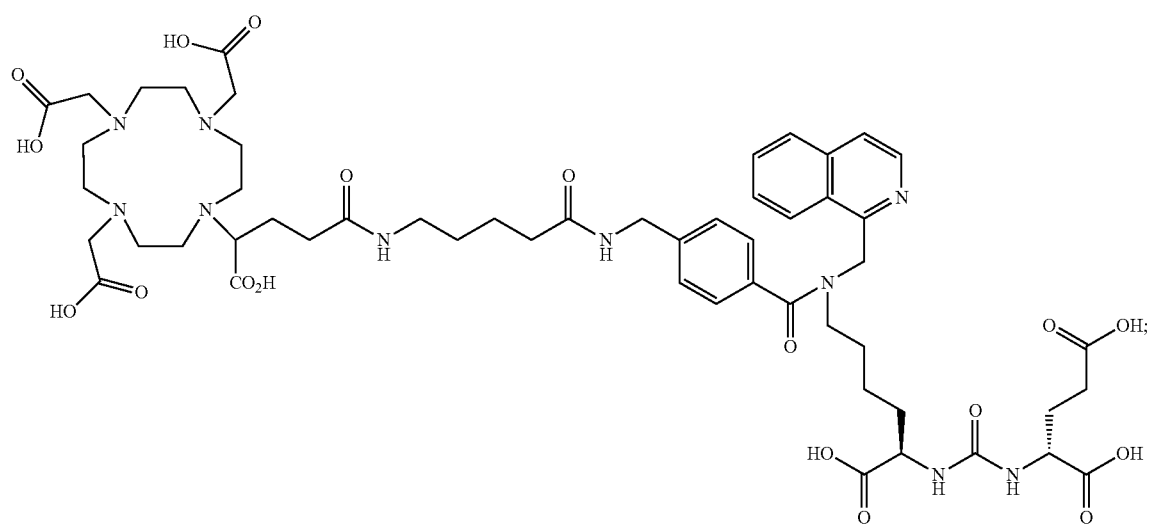
P17
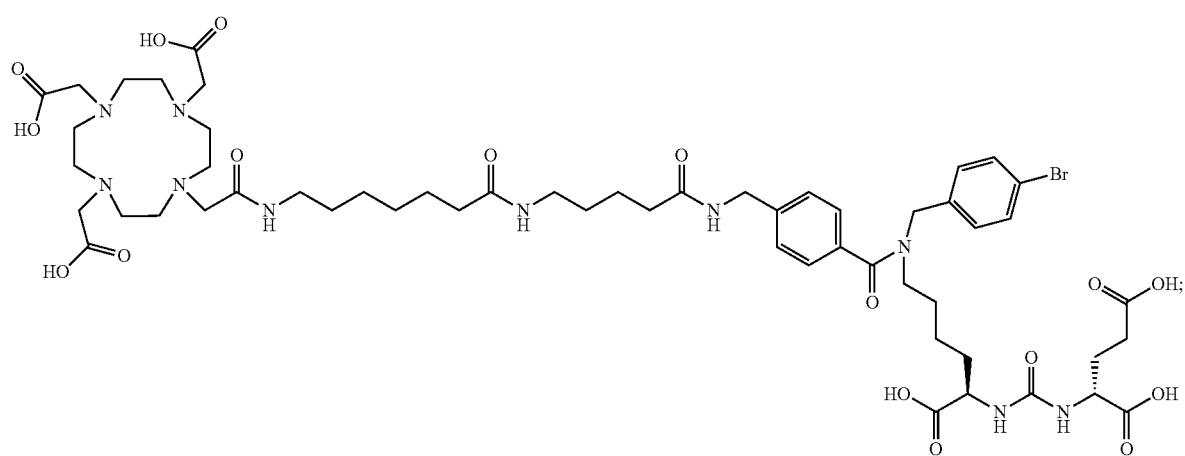

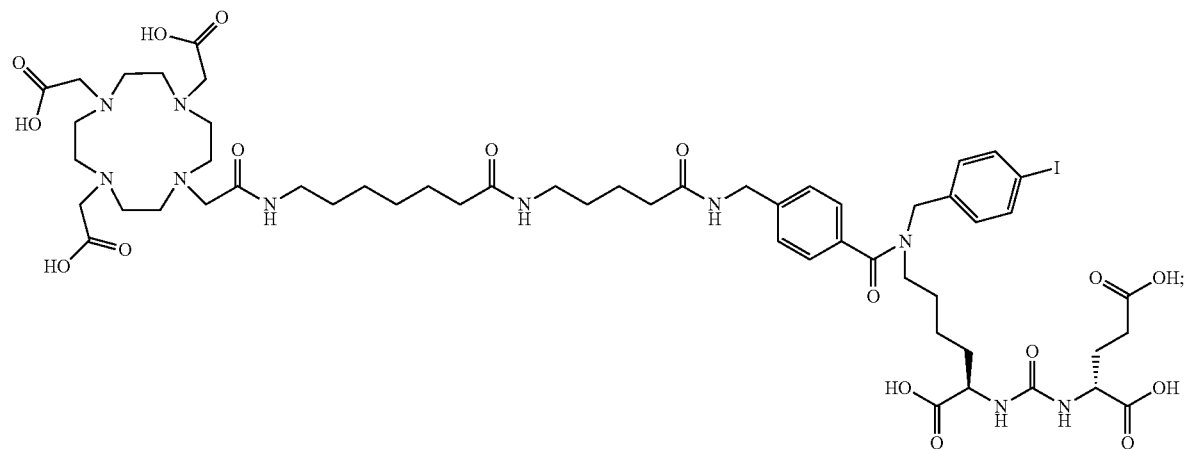
P18
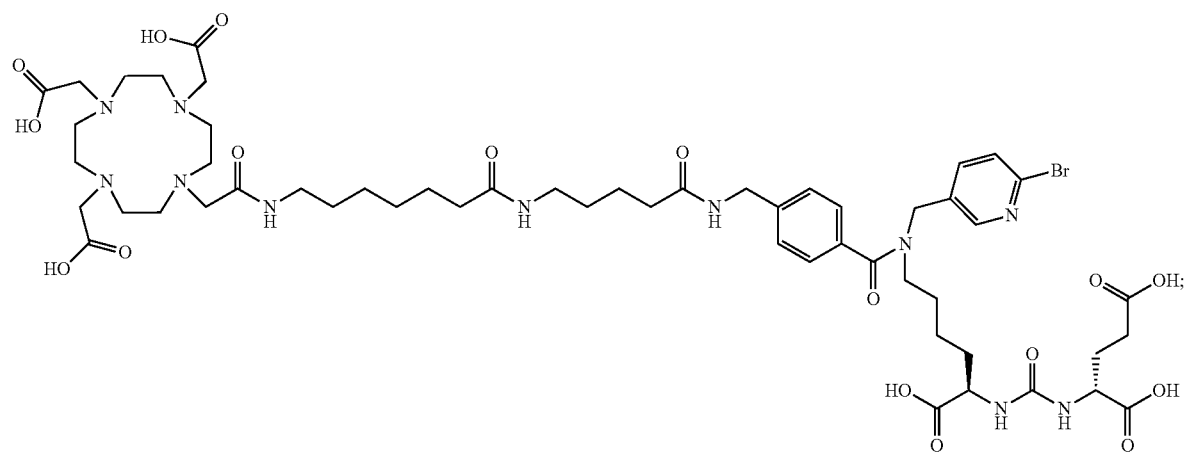
P17
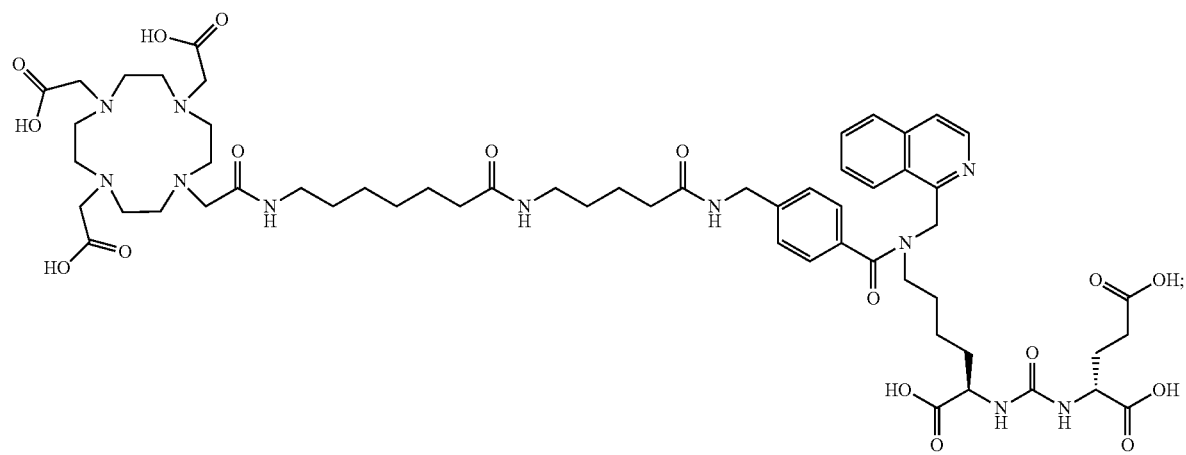
P17

-continued
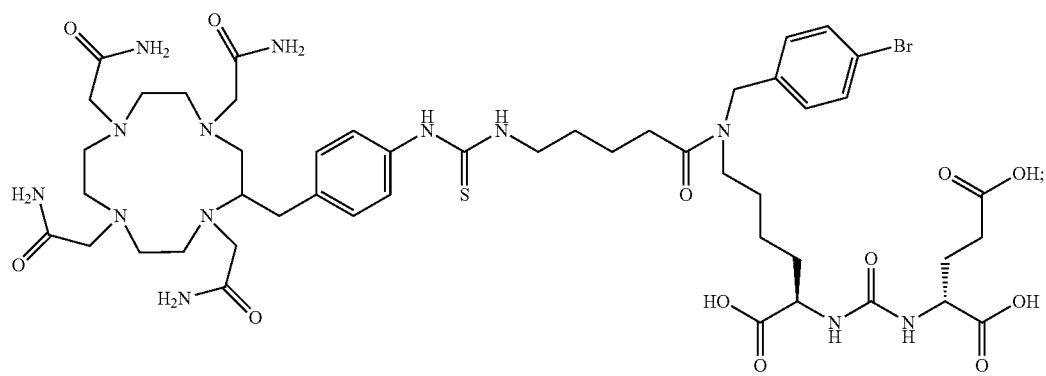
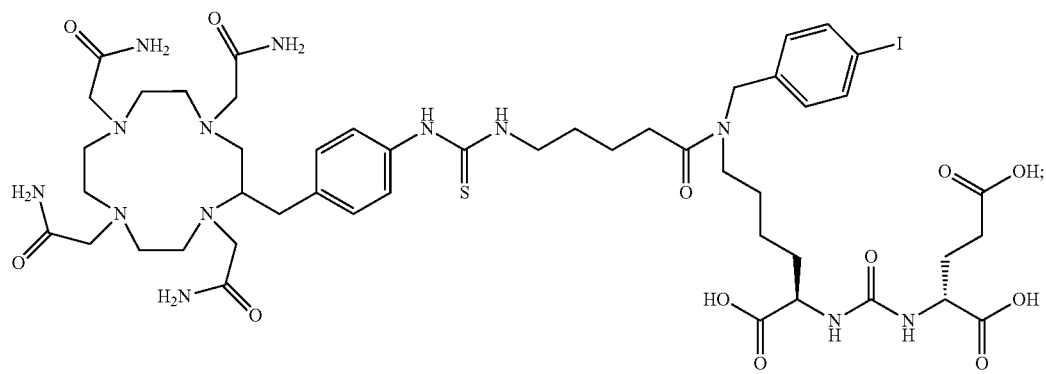
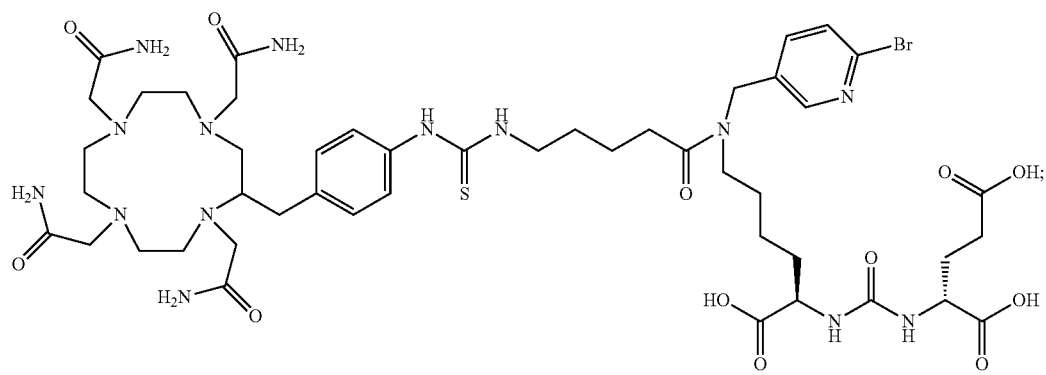
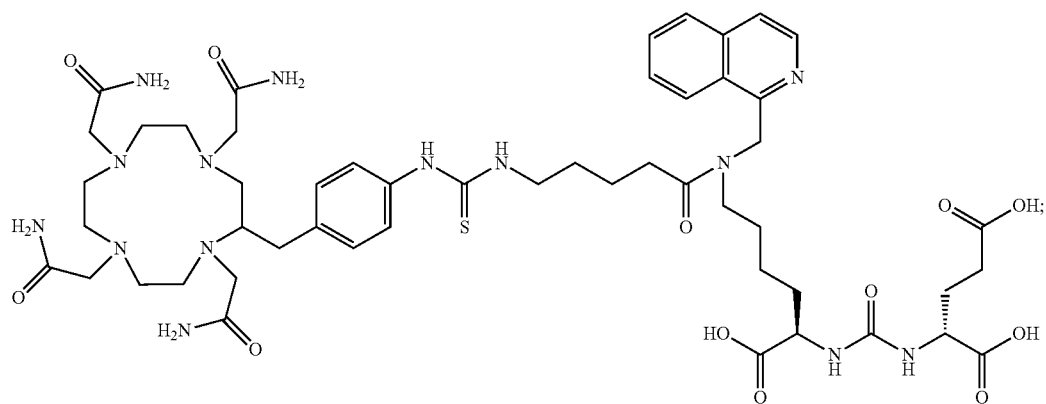

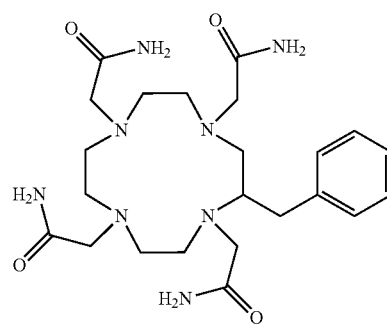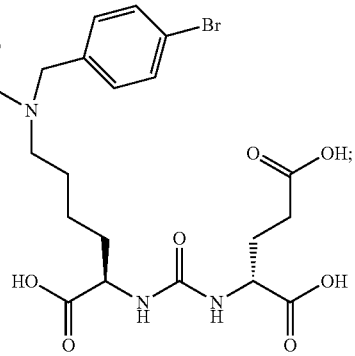
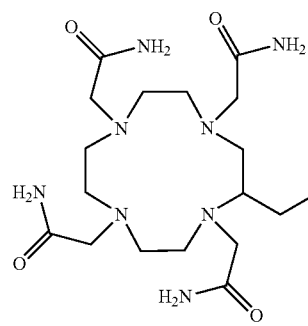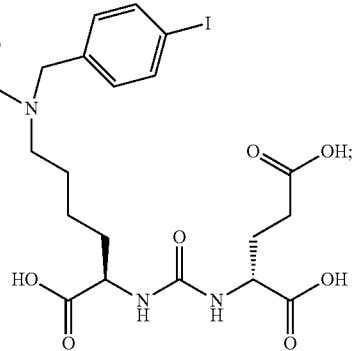
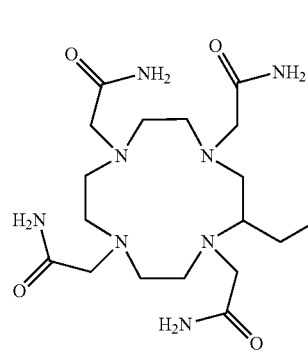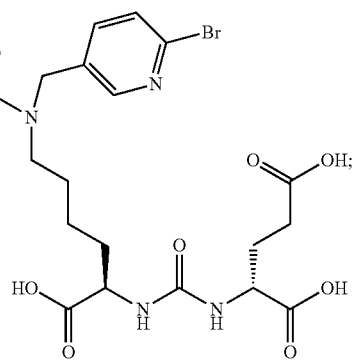
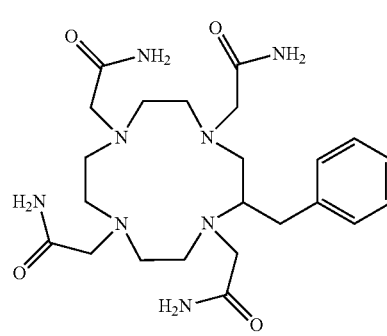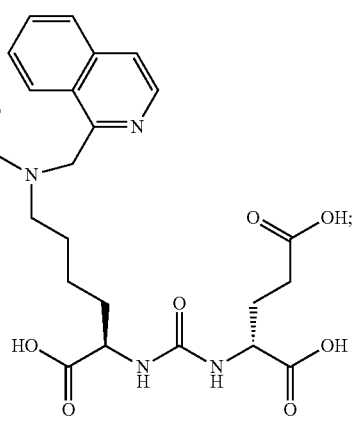

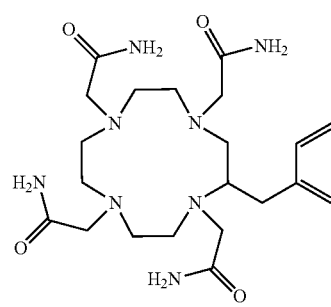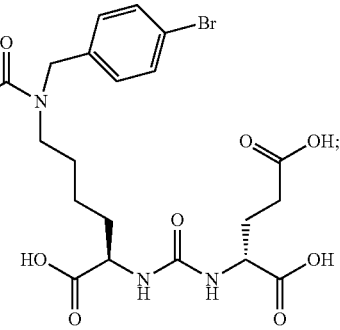
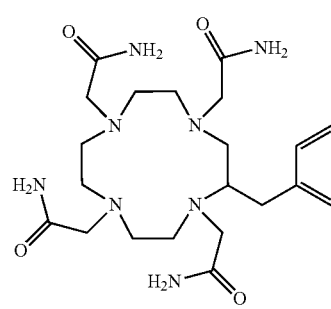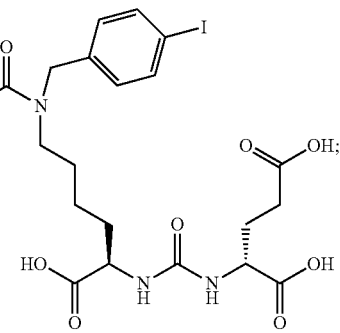
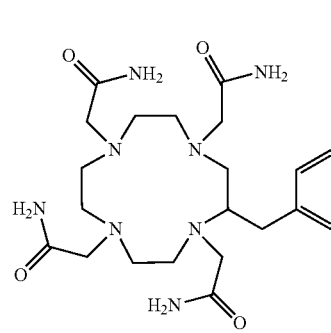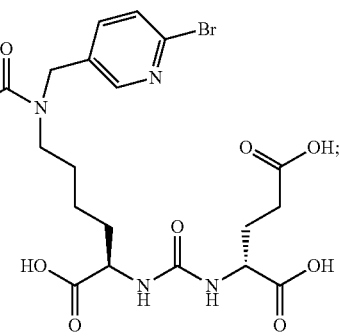
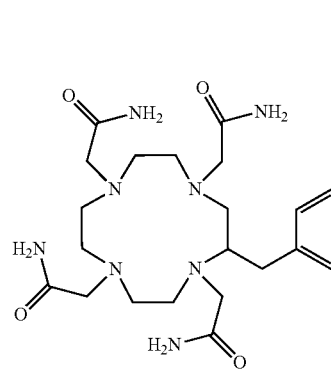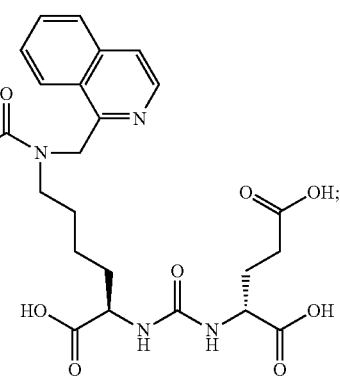

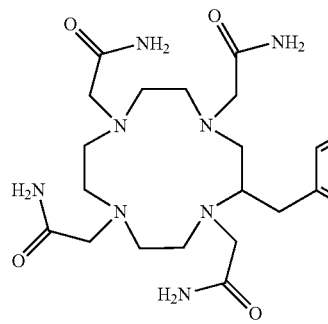 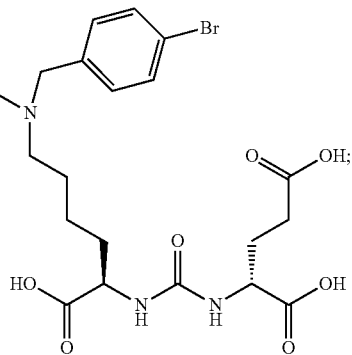

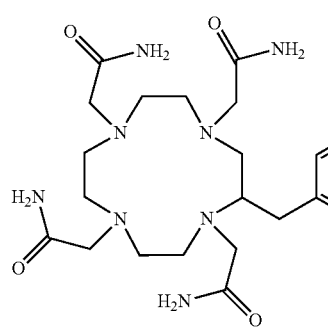 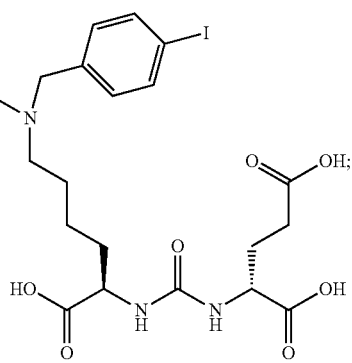

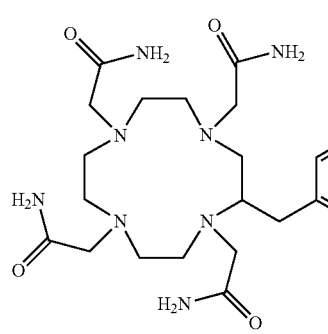 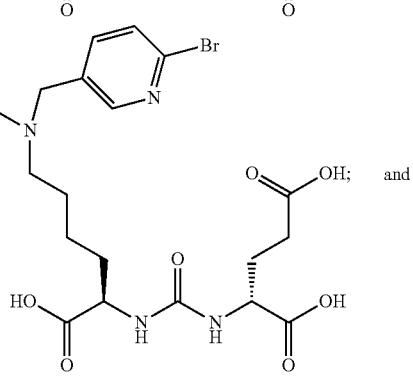

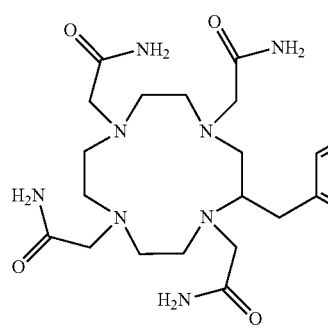 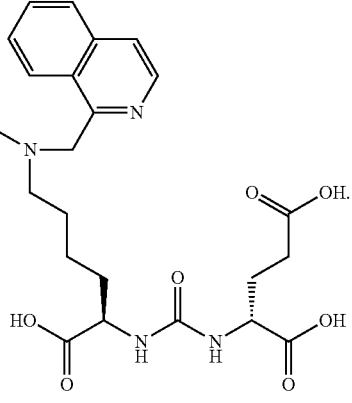

In other embodiments, the one or more PSMA-expressing tumor or cell is selected from the group consisting of: a prostate tumor or cell, a metastasized prostate tumor or cell, a lung tumor or cell, a renal tumor or cell, a glioblastoma, a pancreatic tumor or cell, a bladder tumor or cell, a sarcoma, a melanoma, a breast tumor or cell, a colon tumor or cell, a germ cell, a pheochromocytoma, an esophageal tumor or cell, a stomach tumor or cell, and combinations thereof. In some other embodiments, the one or more PSMA-expressing tumor or cell is a prostate tumor or cell.

In other embodiments, the one or more PSMA-expressing tumors or cells is in vitro, in vivo or ex-vivo. In yet other embodiments, the one or more PSMA-expressing tumor or cell is present in a subject.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal (non-human) subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

In yet some other embodiments, the method results in inhibition of the tumor growth.

C. Methods of Using Compounds of Formula (I) for Imaging One or More One or More PSMA-Expressing Tumors or Cells In other embodiments, the presently disclosed subject matter provides a method for imaging one or more prostate-specific membrane antigen (PSMA) tumors or cells, the method comprising contacting to the one or more tumors or cells, an effective amount of a compound of Formula (I) and making an image, the compound of Formula (I) comprising:

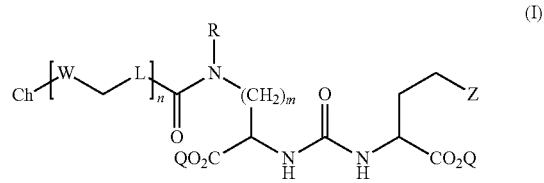

wherein: Z is tetrazole or $CO_2Q$; Q is H or a protecting group; m is an integer selected from the group consisting of 1, 2, 3, 4, and 5; R is independently H or —$CH_2$-$R^1$; $R^1$ substituted aryl, substituted pyridine, and unsubstituted isoquinoline; L is a linker selected from the group consisting of $C_1$-$C_6$ alkylene and $C_3$-$C_6$ cycloalkylene, and arylene; W is selected from the group consisting of —$NR^2$—(C=O)—, —$NR^2$—(C=S)—, —(C=O)—$NR^2$—, and —(C=S)—$NR^2$—; wherein each occurrence of L and W can be the same or different; $R^2$ is H or a $C_1$-$C_4$ alkyl; n is an integer selected from the group consisting of 1, 2, and 3; Ch is a chelating agent that comprises a radiometal suitable for imaging; and pharmaceutically acceptable salts thereof.

D. Kits

In yet other embodiments, the presently disclosed subject matter provides a kit comprising a compound of Formula (I).

In certain embodiments, the kit provides packaged pharmaceutical compositions comprising a pharmaceutically acceptable carrier and a compound of the invention. In certain embodiments the packaged pharmaceutical composition will comprise the reaction precursors necessary to generate the compound of the invention upon combination with a radio labeled precursor. Other packaged pharmaceutical compositions provided by the present invention further comprise indicia comprising at least one of: instructions for preparing compounds according to the invention from supplied precursors, instructions for using the composition to image cells or tissues expressing PSMA, or instructions for using the composition to image glutamatergic neurotransmission in a patient suffering from a stress-related disorder, or instructions for using the composition to image prostate cancer.

E. Pharmaceutical Compositions and Administration

In another aspect, the present disclosure provides a pharmaceutical composition including a compound of Formula (I) alone or in combination with one or more additional therapeutic agents in admixture with a pharmaceutically acceptable excipient. One of skill in the art will recognize that the pharmaceutical compositions include the pharmaceutically acceptable salts of the compounds described above. Pharmaceutically acceptable salts are generally well known to those of ordinary skill in the art, and include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent or by ion exchange, whereby one basic counterion (base) in an ionic complex is substituted for another. Examples of pharmaceutically acceptable base addition salts include sodium, potassium, calcium, ammonium, organic amino, or magnesium salt, or a similar salt.

When compounds of the present disclosure contain relatively basic functionalities, acid addition salts can be obtained by contacting the neutral form of such compounds with a sufficient amount of the desired acid, either neat or in a suitable inert solvent or by ion exchange, whereby one acidic counterion (acid) in an ionic complex is substituted for another. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-toluenesulfonic, citric, tartaric, methanesulfonic, and the like. Also included are salts of amino acids such as arginate and the like, and salts of organic acids like glucuronic or galactunoric acids and the like (see, for example, Berge et al, "Pharmaceutical Salts", Journal of Pharmaceutical Science, 1977, 66, 1-19). Certain specific compounds of the present disclosure contain both basic and acidic functionalities that allow the compounds to be converted into either base or acid addition salts.

Accordingly, pharmaceutically acceptable salts suitable for use with the presently disclosed subject matter include, by way of example but not limitation, acetate, benzenesulfonate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy ($20^{th}$ ed.) Lippincott, Williams & Wilkins (2000).

In therapeutic and/or diagnostic applications, the compounds of the disclosure can be formulated for a variety of modes of administration, including systemic and topical or localized administration. Techniques and formulations generally may be found in Remington: The Science and Practice of Pharmacy ($20^{th}$ ed.) Lippincott, Williams & Wilkins (2000).

Depending on the specific conditions being treated, such agents may be formulated into liquid or solid dosage forms and administered systemically or locally. The agents may be delivered, for example, in a timed- or sustained-slow release form as is known to those skilled in the art. Techniques for formulation and administration may be found in Remington: The Science and Practice of Pharmacy ($20^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intrasternal, intra-synovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances, such as saline; preservatives, such as benzyl alcohol; absorption promoters; and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein. Generally, the compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, the bioavailability of the compound(s), the adsorption, distribution, metabolism, and excretion (ADME) toxicity of the compound(s), and the preference and experience of the attending physician.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

II. General Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of Formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group on a molecule, provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted at one or more positions).

Where substituent groups or linking groups are specified by their conventional chemical formulae, written from left to right, they equally encompass the chemically identical substituents that would result from writing the structure from right to left, e.g., —$CH_2O$— is equivalent to —$OCH_2$—; —C(=O)O— is equivalent to —OC(=O)—; —OC(=O)NR— is equivalent to —NRC(=O)O—, and the like.

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless otherwise explicitly defined, a "substituent group," as used herein, includes a functional group selected from one or more of the following moieties, which are defined herein:

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, isopropyl, cyclopropyl, allyl, vinyl, n-butyl, tert-butyl, ethynyl, cyclohexyl, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_1$-$C_{10}$ means one to ten carbons, including 1, 2, 3, 4, 5, 6, 7, 8, 9, and 10 carbons). In particular embodiments, the term "alkyl" refers to $C_{1-20}$ inclusive, including 1, 2, 3, 4, 5, 6, 7, 8, 9, 10, 11, 12, 13, 14, 15, 16, 17, 18, 19, and 20 carbons, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_{25}$—S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, —CH=CH—N($CH_3$)—$CH_3$, O—$CH_3$, —O—$CH_2$—$CH_3$, and —CN. Up to two or three heteroatoms may be consecutive, such as, for example, —CH$_2$—NH—OCH$_3$ and —CH$_2$—O—Si(CH$_3$)$_3$.

As described above, heteroalkyl groups, as used herein, include those groups that are attached to the remainder of the molecule through a heteroatom, such as —C(O)NR', —NR'R", —OR', —SR, —S(O)R, and/or —S(O$_2$)R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, unsubstituted alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{1-20}$ inclusive straight or branched hydrocarbon moiety having at least one carbon-carbon double bond by the removal of a single hydrogen molecule. Alkenyl groups include, for example, ethenyl (i.e., vinyl), propenyl, butenyl, 1-methyl-2-buten-1-yl, pentenyl, hexenyl, octenyl, allenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, and heptynyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)$_3$—); cyclohexylene (—C$_6$H$_{10}$—); —CH=CH—CH=CH—; —CH=CH—CH$_2$—; —CH$_2$CH$_2$CH$_2$CH$_2$—, —CH$_2$CH=CHCH$_2$—, —CH$_2$CsCCH$_2$—, —CH$_2$CH$_2$CH(CH$_2$CH$_2$CH$_3$)CH$_2$—, —(CH$_2$)$_q$—N(R)—(CH$_2$)$_1$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH$_2$—O—); and ethylenedioxyl (—O—(CH$_2$)$_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms also can occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxy, arylthioxy, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

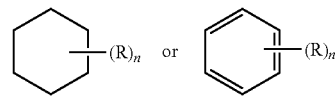

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

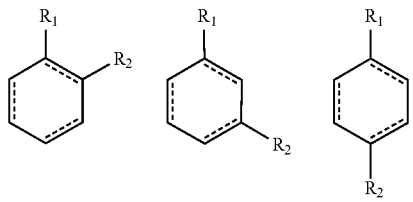

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol ($\sim\!\sim\!\sim$) denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such groups. R', R", R'" and R"" each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R''' and R'''' groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', —SiR'R"R', —OC(O)R', —C(O)R', —CO$_2$R', —C(O)NR'R", —OC(O)NR'R", —NR"C(O)R', —NR'—C(O)NR"R''', —NR"C(O)OR', —NR—C(NR'R"R''')=NR'''', —NR—C(NR'R")=NR''' —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxo, and fluoro(C$_1$-C$_4$)alkyl, in a number ranging from zero to the total number of open valences on aromatic ring system; and where R', R", R' and R'''' may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R''' and R'''' groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'— (C"R''')$_d$—, where s and d are independently integers of from 0 to 3, and X' is —O—, —NR'—, —S—, —S(O)—, —S(O)$_2$—, or —S(O)$_2$NR'—. The substituents R, R', R" and R''' may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocyclic, heterocyclic, or aromatic heterocyclic group as defined herein). As such, the term "acyl" specifically includes arylacyl groups, such as a 2-(furan-2-yl) acetyl)- and a 2-phenylacetyl group. Specific examples of acyl groups include acetyl and benzoyl. Acyl groups also are intended to include amides, —RC(=O)NR', esters, —RC(=O)OR', ketones, —RC(=O)R', and aldehydes, —RC(=O)H.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include C$_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, tert-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl, i.e., C$_6$H$_5$—CH$_2$—O—. An aralkyloxyl group can optionally be substituted.

"Alkoxycarbonyl" refers to an alkyl-O—C(=O)— group. Exemplary alkoxycarbonyl groups include methoxycarbonyl, ethoxycarbonyl, butyloxycarbonyl, and tert-butyloxycarbonyl.

"Aryloxycarbonyl" refers to an aryl-O—C(=O)— group. Exemplary aryloxycarbonyl groups include phenoxy- and naphthoxy-carbonyl.

"Aralkoxycarbonyl" refers to an aralkyl-O—C(=O)— group. An exemplary aralkoxycarbonyl group is benzyloxycarbonyl.

"Carbamoyl" refers to an amide group of the formula —C(=O)NH$_2$. "Alkylcarbamoyl" refers to a R'RN—C(=O)— group wherein one of R and R' is hydrogen and the other of R and R' is alkyl and/or substituted alkyl as previously described. "Dialkylcarbamoyl" refers to a R'RN—C(=O)— group wherein each of R and R' is independently alkyl and/or substituted alkyl as previously described.

The term carbonyldioxyl, as used herein, refers to a carbonate group of the formula —O—C(=O)—OR.

"Acyloxyl" refers to an acyl-O— group wherein acyl is as previously described.

The term "amino" refers to the —NH$_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R'", wherein R', R", and R'" are each independently selected from the group consisting of alkyl groups. Additionally, R', R", and/or R'" taken together may optionally be —(CH$_2$)$_k$— where k is an integer from 2 to 6. Examples include, but are not limited to, methylamino, dimethylamino, ethylamino, diethylamino, diethylaminocarbonyl, methylethylamino, isopropylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —C(=O)— group, and can include an aldehyde group represented by the general formula R—C(=O)H.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —NO$_2$ group.

The term "thio" refers to a compound described previously herein wherein a carbon or oxygen atom is replaced by a sulfur atom.

The term "sulfate" refers to the —SO$_4$ group.

The term thiohydroxyl or thiol, as used herein, refers to a group of the formula —SH.

More particularly, the term "sulfide" refers to compound having a group of the formula —SR.

The term "sulfone" refers to compound having a sulfonyl group —S(O$_2$)R.

The term "sulfoxide" refers to a compound having a sulfinyl group —S(O)R The term ureido refers to a urea group of the formula —NH—CO—NH$_2$.

The term "protecting group" in reference to compounds of formula (I) refers to a chemical substituent which can be selectively removed by readily available reagents which do not attack the regenerated functional group or other functional groups in the molecule. Suitable protecting groups are known in the art and continue to be developed. Suitable protecting groups may be found, for example in Wutz et al. ("Greene's Protective Groups in Organic Synthesis, Fourth Edition," Wiley-Interscience, 2007). Protecting groups for protection of the carboxyl group, as described by Wutz et al. (pages 533-643), are used in certain embodiments. In some embodiments, the protecting group is removable by treatment with acid. Representative examples of protecting groups include, but are not limited to, benzyl, p-methoxybenzyl (PMB), tertiary butyl (t-Bu), methoxymethyl (MOM), methoxyethoxymethyl (MEM), methylthiomethyl (MTM), tetrahydropyranyl (THP), tetrahydrofuranyl (THF), benzyloxymethyl (BOM), trimethylsilyl (TMS), triethylsilyl (TES), t-butyldimethylsilyl (TBDMS), and triphenylmethyl (trityl, Tr). Persons skilled in the art will recognize appropriate situations in which protecting groups are required and will be able to select an appropriate protecting group for use in a particular circumstance.

Throughout the specification and claims, a given chemical formula or name shall encompass all tautomers, congeners, and optical- and stereoisomers, as well as racemic mixtures where such isomers and mixtures exist.

Certain compounds of the present disclosure may possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as D- or L- for amino acids, and individual isomers are encompassed within the scope of the present disclosure. The compounds of the present disclosure do not include those which are known in art to be too unstable to synthesize and/or isolate. The present disclosure is meant to include compounds in racemic, scalemic, and optically pure forms. Optically active (R)- and (S)-, or D- and L-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures with the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present disclosure, whether radioactive or not, are encompassed within the scope of the present disclosure.

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent or by ion exchange. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Overview

The use of PSMA binding ureas conjugated to chelated radiometals via various linking groups for imaging and possible radiotherapy of PSMA expressing tumors have been previously reported in several patent applications and publications (Tykvart et al. (2015) *Journal of medicinal chemistry* 58, 4357-63; Banerjee et al. (2015) *Journal of nuclear medicine* 56, 628-34; Benesova et al. (2015) *Journal of nuclear medicine* 56, 914-20; Weineisen et al. (2014) *EJNMMI* Res 4, 1-15; WO 2009002529 A2; WO 2009070302 A1). A new class of high affinity binding agent has been prepared by modifying the urea linker at epsilon amine position with p-Br-benzyl group. Structures of the presently disclosed compounds are shown in FIG. 1.

Without wishing to be bound to any one particular theory, it is believed that radiometal-chelated Glu-Lysine urea-based theranostic agents targeting prostate-specific membrane antigen (PSMA), when modified with p-Br-benzyl group on the epsilon amino group of lysine of Lys-Glu-urea moiety, demonstrate high binding affinity for PSMA and high uptake in PSMA-expressing tumors and low renal uptake in standard mouse model of prostate cancer. One embodiment, $^{177}$Lu-1, showed significant radiotherapeutic efficacy, about 50% remission of PSMA+ PC3 tumor bearing mice.

Example 2

Material and Methods

Chemical Synthesis of 8. The synthesis of compound 1 is described in Scheme 1. Bromobenzaldehyde (121.0 mg, 0.654 mmol) was slowly added to a stirred solution of Boc-protected urea, 4, (300.0 mg, 0.615 mmol) in 5 ml of methanol at ice-cold bath and allowed to warm to room temperature. After one hour, sodium cyanoborohydride (158.0 mg, 2.5 mmol) was added and the reaction was left to stir overnight. Crude reaction mixture was evaporated, redissolved in dichloromethane, purified by normal phase silica chromatography (95:5, methylene chloride:methanol), and dried in vacuo to provide 5 in good yield. Yield: 80%. ESI-MS: 656.56 [M+H]$^+$, found: 656.5. TSTU (32.6 mg, 108 µmol), Boc-5-aminovaleric acid (23.5 mg, 108 µmol), and DIPEA (37.7 µL, 216 µmol) were dissolved in 300 µL DMF and stirred at room temperature. After one hour, compound 5 (71.0 mg, 108 µmol) was added with three rinses of DMF (50 µL each). The reaction mixture was stirred for four hours and stored at 4° C. overnight. Crude reaction mixture was purified by semi-preparative HPLC on C$_{18}$ column (40% water (0.1 TFA)/60% ACN (0.1 TFA)/for 5 min, 60-90% over 20 minutes. R$_t$ 21 minutes. Purified fractions were combined, evaporated, and dried under high vacuum for 10 minutes. ESI-MS: 572.44 [M+H]+, found: 572.4. Compound 6 was dissolved in dichloromethane (1.5 mL) and chilled in an ice bath. After equilibration, TFA (1.5 mL) was added and the mixture was stirred for 3 hours allowing to warm to room temperature in the process. Mixture was spurge to dryness under a nitrogen stream, dissolved in water, and lyophilized to yield 31.8 mg of compound 7. Yield: 54 µmol, 54%. p-SCN-bn-DOTA (12.2 mg, 17.7 µmol) was added to a stirred solution of 6 (12.2 mg of TFA salt) and DIPEA (15.2 µL, 87.0 µmol) in DMSO (130 µL) equilibrated to 40° C. Reaction mixture was stirred at 40° C. for four hours and stored at 4° C. overnight. Reaction mixture was purified by reverse phase HPLC (hold 20% ACN for 5 min, then 20-40% over 19 minutes). Rt approximately 12 minutes. Purified fractions were combined, rotoevaporated to decrease volume, and then lyopholized. ESI-MS: 1138.37 [M+H]$^+$, found: 1138.5. The compound 1 was further purified by HPLC with gradient method The HPLC method is a gradient method containing a mobile phase 88% water (containing 0.1% TFA) and 22% CH$_3$CN (0.1% TFA) for 1-5 min followed by 0-5 min water 88% water (containing 0.1% TFA) and 12% CH$_3$CN (0.1% TFA), and from 5-25 min 88% water to 44% water and 12% acetonitrile to 56% acetonitrile with flow rate 8 mL/min.

Chemical Synthesis of 2. This compound was synthesized by using the same intermediate 7 and conjugated with a commercially available DOTA-NHS ester. ESI-MS: 974.86. [M+H]$^+$, found: 974.5

Chemical Synthesis of 3. This compound was synthesized by using the intermediate 4 and coupled with commercially available Boc-5-aminovaleric acid and DOTA-NHS ester. ESI-MS: 970.05[M+H]$^+$, found: 970.1.

Radiolableing of $^{177}$Lu-1. 1.0 µl of $^{177}$LuCl$_3$ (1 mCi) in 0.1 N HCl was added 70 µl NH$_4$OAc buffer (0.2 M, pH 4) and to 5 µl of 2 mM in 0.2M NH$_4$OAc. The pH of the mixture was about 4.0. The mixture was kept at 80° C. for an hour and purified by HPLC. The HPLC method is a gradient method containing a mobile phase 77% water (containing 0.1% TFA) and 23% CH$_3$CN (0.1% TFA) for 1-5 min followed by 5-25 min water, 77% to 57% and acetonitrile, 23% to 43%; 25.01-30 min water 5% to 5% and acetonitrile, 95% to 95%, 30.01 to 37 min, water 77% to 77% and acetonitrile, 23% to 23%. Flow rate: 1.0 ml/min; k: 200 nm, and a C$_s$ column (25×4.6 mm), Varian microsob-MV 100-5. Radiolabeled $^{177}$Lu-1 was eluted at 17.1-20 min whereas unlabeled chelating agent was eluted at 21-22 min.

The HPLC method was used to prepare $^{177}$Lu-1 and $^{177}$Lu-7: The HPLC method is a gradient method containing a mobile phase 88% water (containing 0.1% TFA) and 22% CH$_3$CN (0.1% TFA) for 1-5 min followed by 5-27 min water, 88% to 75% and acetonitrile, 12% to 25%; 27.01-32 min water 5% to 5% and acetonitrile, 95% to 95%, 32.01 to 37 min, water 88% to 18% and acetonitrile, 12% to 22%. Flow rate: 1.0 ml/min; λ: 200 nm, and a C$_8$ column (25×4.6 mm), Varian microsob-MV 100-5. Radiolabeled $^{177}$Lu-2 was eluted at 13.1-15.0 min whereas unlabeled chelating agent was eluted at 16-17 min. Radiolabeled $^{177}$Lu-3 was eluted at 13.1-15.0 min whereas unlabeled chelating agent was eluted at 10-12 min a 18-20 min and the unlabeled agent came 14-16 min.

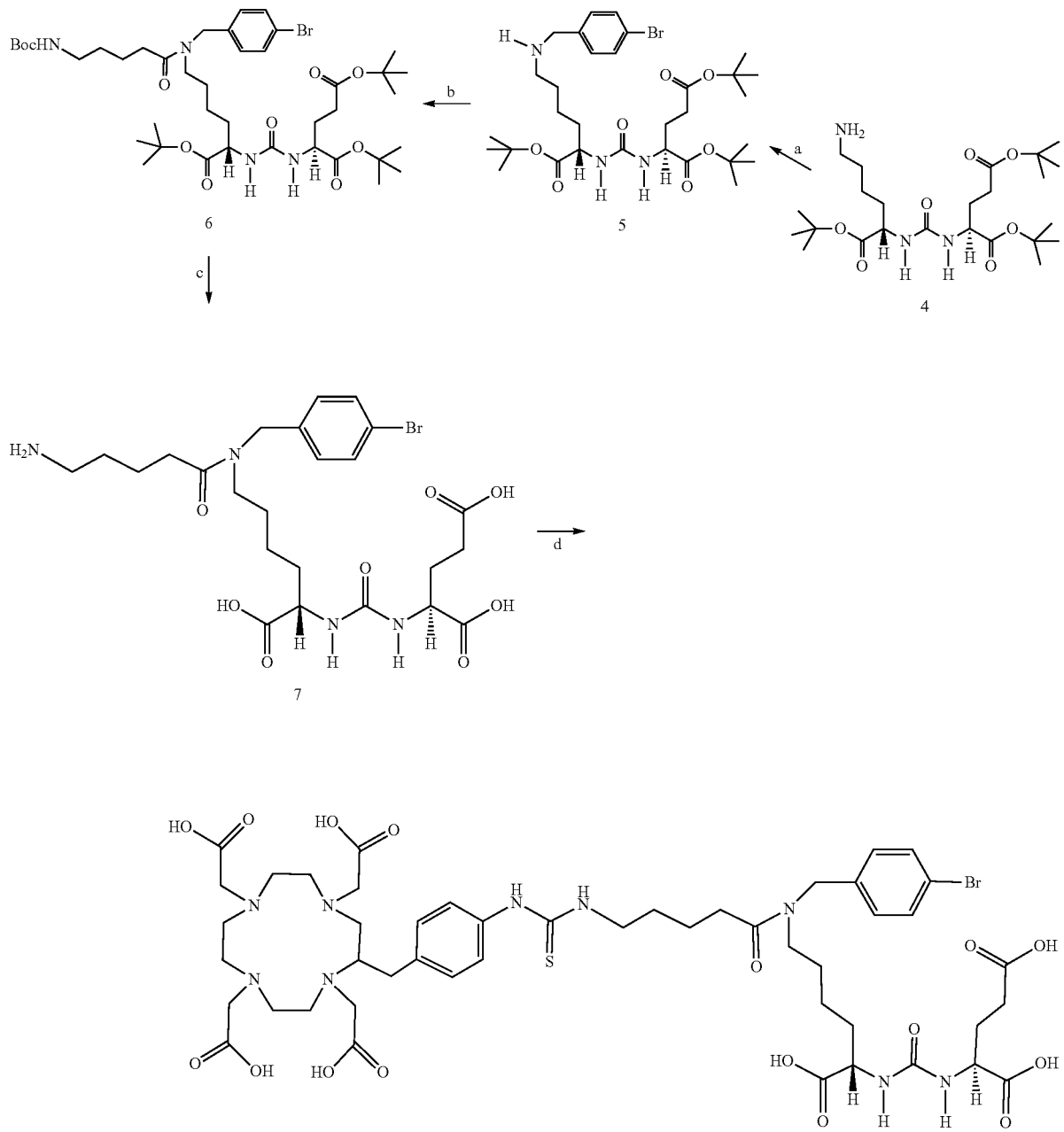

a. 4-Bromobenzaldehyde, NaBH$_3$CN, MeOH, 1% acetic acid;
b. BocNH(CH$_2$)$_4$CO$_2$H, HATU, DIEA, DMF; c. TFA/CH$_2$Cl$_2$;
d. DOTA-Bn-SCN, DMSO, DIEA

Example 3

Results and Discussion

Chemical and Radiochemical Syntheses and Characterization. p-Bromobenzyl group modified of Glu-Lys urea (2) was prepared by reductive alkylation of 2 with p-Bromobenzaldehyde in presence of sodium cyanoborohydride in methanol in good yield to provide 4 following a literature procedure (Tykvart et al. (2015) *Journal of medicinal chemistry* 58, 4357-63). A small aliphatic linker, Boc-5-aminovaleric acid was coupled on the same ε-Lys amine of 4 followed by removal of BOC group and conjugation with commercially available DOTA-Bn-SCN with 6 to provide 1 in moderate yield. The compound 2 was synthesized by using DOTA-NHS ester as the chelating agent and coupling with the same intermediate 6. Compound 3 was synthesized as a control agent, without any p-Bromobenzyl group. All three agents were radiolabeled with $^{177}$Lu in good yield and purity at pH 4 in ammonium acetate buffer at 80° C. Binding affinities of the new compounds are listed in Table 1. Both 1 and 2 modified with p-Bromo-benzyl group showed higher binding affinity compared to 3.

TABLE 1

Binding affinities of the representative agents

| | Compound | | | | |
|---|---|---|---|---|---|
| | 1 | 2 | 3 | ZJ43 (for 2) | ZJ43 (for 1, 3) |
| IC50 (nM) | 0.57 nM | 0.64 nM | 2.16 nM | 1.91 nM | 2.7 nM |
| Ki (nM) | 1.15 nM | 1.28 nM | 0.43 nM | 0.38 nM | 0.66 nM |
| ClogD | −4.6 | −3.5 | −4.1 | nd | nd |
| LogPoct/water | −3.0 | −3.53 | −3.2 | nd | nd |
| Polar Surface area | 359 | 327 | 368 | nd | nd |

Cell-Binding properties. The $^{177}$Lu agents were further evaluated in cells and animals using standard isogenic cell lines PSMA+ PC3 PIP and PSMA-negative PC3 flu cells. Both $^{177}$Lu-1 and $^{177}$Lu-2 demonstrated higher uptake in PSMA+ PC3 cells compared to $^{177}$Lu-3. Further internalization studies revealed that $^{177}$Lu-1 has higher nearly 2-fold higher internalized activity compared to $^{177}$Lu-3. All three agents showed significantly low uptake in PSMA-negative PC3 flu cells. The $^{177}$Lu-1 was further evaluated for treatment efficacy in a clonogenic assay and compared with previous lead compound SR6 (Banerjee et al. (2015) *Journal of nuclear medicine* 56, 628-34) and agents in the clinical trials including $^{177}$Lu-PSMA-617 (Benesova et al. (2015) *Journal of nuclear medicine* 56, 914-20) and $^{177}$Lu PSMA-I&T (Weineisen et al. (2014) EJNMMI Res 4, 1-15). $^{177}$Lu-1 was able to produce about 100% cell killing efficacy using 10 μCi dose in PSMA+ PC3 PIP cells whereas no significant toxicity was seen for PSMA− PC3 flu cells.

TABLE 2

Cell binding properties of the agents at 4 h incubation (values are expressed as percent incubated dose per one million cells) (n = 3)

| | Compound | | |
|---|---|---|---|
| | $^{177}$Lu-1 | $^{177}$Lu-2 | $^{177}$Lu-3 |
| Cell uptake PSMA+ PC3 PIP | 42.60 | 40.6 | 24.50 |
| Cell uptake PSMA− PC3 flu | 0.09 | 0.12 | 0.05 |
| Internalization (cell lysate) | 15.88 | n.d. | 8.75 |
| Cell surface | 27.68 | n.d. | 12.50 |

Biodistribution. In vivo tissue biodistribution studies were done for $^{177}$Lu-1 and $^{177}$Lu-2 and are listed in Table 3 and 4. $^{177}$Lu-1 showed higher uptake and retention in PSMA+ PC3 PIP tumor uptake than $^{177}$Lu-2. Significantly $^{177}$Lu-2 agent showed 5-fold lower renal uptake than $^{177}$Lu-1 and as shown in FIG. 3 tumor/kidney of the presently disclosed compounds were compared with previous lead $^{177}$Lu—SR6, $^{177}$Lu-PSMA-617 and $^{177}$Lu-PSMA-I&T. The PSMA+ PC3 PIP tumor-to-kidney ratio for $^{177}$Lu-2 was higher than $^{177}$Lu-1. Due to the higher tumor uptake and retention, $^{177}$Lu-1 was further evaluated for theranostic efficacy (imaging and therapeutic effect) in a pilot study using a small group of animals.

TABLE 3

In vivo tissue biodistribution of $^{177}$Lu-1, Values expressed as percent injected dose per gram ± standard deviation) (N = 4)

| Tissue | 2 h | 24 h | 48 h | 72 h |
|---|---|---|---|---|
| Blood | 0.68 ± 0.25 | 0.01 ± 0.01 | 0.00 ± 0.01 | 0.00 ± 0.04 |
| Heart | 0.28 ± 0.08 | 0.02 ± 0.05 | 0.01 ± 0.00 | 0.01 ± 0.00 |
| Lung | 1.12 ± 0.33 | 0.06 ± 0.01 | 0.04 ± 0.01 | 0.04 ± 0.02 |
| Liver | 0.39 ± 0.13 | 0.11 ± 0.01 | 0.09 ± 0.02 | 0.07 ± 0.00 |
| Stomach | 0.87 ± 0.63 | 0.04 ± 0.01 | 0.05 ± 0.04 | 0.04 ± 0.00 |
| Pancreas | 0.28 ± 0.09 | 0.02 ± 0.00 | 0.01 ± 0.01 | 0.01 ± 0.00 |
| Spleen | 3.76 ± 0.70 | 0.15 ± 0.05 | 0.08 ± 0.03 | 0.08 ± 0.02 |
| Fat | 0.35 ± 0.10 | 0.08 ± 0.15 | 0.01 ± 0.01 | 0.06 ± 0.07 |
| Kidney | 87.10 ± 25.99 | 1.65 ± 0.30 | 1.02 ± 0.58 | 0.62 ± 0.04 |
| Muscle | 0.68 ± 0.98 | 0.01 ± 0.00 | 0.00 ± 0.00 | 0.02 ± 0.02 |
| Sm. Int. | 0.51 ± 0.32 | 0.03 ± 0.01 | 0.02 ± 0.00 | 0.02 ± 0.01 |
| Sal. Gl | 1.09 ± 0.08 | 0.09 ± 0.02 | 0.05 ± 0.03 | 0.05 ± 0.02 |
| Bladder | 3.39 ± 2.78 | 0.31 ± 0.13 | 0.12 ± 0.07 | 0.06 ± 0.03 |
| PC-3 PIP | 55.04 ± 7.23 | 40.61 ± 7.00 | 27.00 ± 7.03 | 24.90 ± 2.27 |
| PC-3 Flu | 0.39 ± 0.03 | 0.10 ± 0.02 | 0.05 ± 0.01 | 0.06 ± 0.01 |

TABLE 4

In vivo tissue biodistribution of $^{177}$Lu-2, Values expressed as percent injected dose per gram ± standard deviation (N = 4)

| Tissue | 2 h | 24 h | 48 h |
|---|---|---|---|
| Blood | 0.81 ± 0.80 | 0.01 ± 0.01 | 0.00 ± 0.00 |
| Heart | 0.31 ± 0.19 | 0.02 ± 0.01 | 0.01 ± 0.01 |
| Lung | 0.39 ± 0.13 | 0.02 ± 0.00 | 0.02 ± 0.00 |
| Liver | 0.19 ± 0.05 | 0.04 ± 0.01 | 0.04 ± 0.00 |
| Stomach | 7.95 ± 4.17 | 0.03 ± 0.02 | 0.03 ± 0.01 |
| Pancreas | 0.19 ± 0.08 | 0.02 ± 0.02 | 0.01 ± 0.00 |
| Spleen | 1.10 ± 0.62 | 0.05 ± 0.02 | 0.04 ± 0.01 |
| Fat | 0.70 ± 0.54 | 0.11 ± 0.10 | 0.03 ± 0.04 |
| Kidney | 14.04 ± 8.19 | 0.73 ± 0.70 | 0.24 ± 0.07 |
| Muscle | 0.20 ± 0.05 | 0.01 ± 0.00 | 0.00 ± 0.00 |
| Sm. Int. | 2.02 ± 2.86 | 0.06 ± 0.09 | 0.02 ± 0.00 |
| Salivary gland | 0.89 ± 0.51 | 0.04 ± 0.02 | 0.02 ± 0.01 |
| Bladder | 3.48 ± 1.66 | 0.17 ± 0.06 | 0.08 ± 0.02 |
| Bone | 0.46 ± 0.10 | 0.10 ± 0.01 | 0.08 ± 0.02 |
| PC-3 PIP | 43.18 ± 5.32 | 24.76 ± 5.13 | 20.13 ± 3.35 |
| PC-3 Flu | 0.29 ± 0.02 | 0.08 ± 0.04 | 0.05 ± 0.01 |

Small Animal SPECT Imaging and Therapeutic Effect. FIG. 4 shows SPECT imaging of $^{177}$Lu-1 during treatment studies for 1-8 days post-injection. A single dose of 3 mCi was injected via tail-vain injection in mice (n=10) bearing PSMA+ PC3 PIP tumor (size 3-5 mm). Saline was injected to another group of mice (n=10) for control study. Mice were monitored for body weight tumor size measure for two times per week. The control group of mice was euthanized after 4-8 weeks as the size of tumors over were >12 mm. For the treatment group, 50% of mice showed complete eradication of tumors. These mice were initially gone through an initial body weight which was regained after 2 weeks. Results are shown in FIG. 5. FIG. 6A and FIG. 6B demonstrated therapeutic efficacy (decrease in tumor volume) of $^{177}$Lu-1 compared to the control group using saline. Five mice are showed complete remission of the disease, and surviving for more than five months.

In summary, the radiometal-chelated Glu-Lysine urea-based theranostic agents targeting prostate-specific membrane antigen (PSMA) when modified with p-Br-benzyl group on the epsilon amino group of lysine of Lys-Glu-urea moiety demonstrated high binding affinity for PSMA and high uptake in PSMA-expressing tumors and low renal uptake in standard mouse model of prostate cancer. One representative compounds, $^{177}$Lu-1, showed significant radiotherapeutic efficacy, about 50% remission of PSMA+ PC3 tumor bearing mice.

Example 4

PSMA-Based High-LET Agents for Prostate Cancer

Overview. In some embodiments, the presently disclosed subject matter relates to the pharmacokinetic optimization of radiometal-based agents targeting PSMA. Previous work in this area is described in international PCT patent application publication numbers WO2009/002529 A2 and WO2010/108125A2, each of which is incorporated by reference in their entirety. More particularly, in some embodiments, the presently disclosed subject matter provides PSMA-targeted low-molecular-weight (LMW) theranostic agents labeled with an α-emitting radiometal including, but not limited to, $^{213}$Bi ($t_{1/2}$ 46 min, $E_{mean}$ 8.4 MeV), $^{212}$Pb ($t_{1/2}$ 10.6 h, $E_{mean}$ 7.8 MeV), and $^{225}$Ac ($t_{1/2}$ 10 d, $E_{mean}$ 6 MeV, 4α), with a goal of reducing off-target effects that currently hamper widespread dissemination of this promising therapy.

The presently disclosed rationally designed α-emitting agents and methods of use thereof have been developed through an in-depth investigation with careful attention to pharmacokinetics (PK), physical half-life of the radiometals, and by receptor blockade to reduce normal tissue uptake. The guidance of α-camera imaging has been utilized to quickly identify the sub-organ localization (hot-spots) and their blockade prior to the therapeutic studies.

Accordingly, in some embodiments, the presently disclosed subject matter includes radiometal-chelated Glu-Lysine urea-based theranostic agents modified with a p-Br-benzyl group on the epsilon amino group of the lysine of the Lys-Glu-urea moiety targeting prostate-specific membrane antigen (PSMA). These compounds exhibit a higher binding affinity for PSMA and showed significantly lower renal uptake and high tumor uptake in PSMA-expressing tumors in a standard mouse model of prostate cancer. These optimized agents have been radiolabeled with the highly toxic radiometals $^{213}$Bi, $^{212}$Pb, and $^{225}$Ac.

Examples

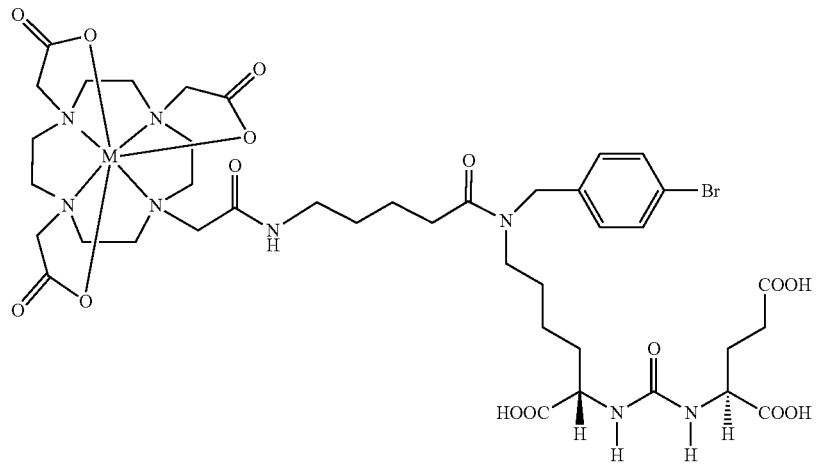

$^{177}$Lu-1/$^{225}$Ac-1/$^{213}$Bi-1/$^{203}$Pb-1

M = $^{177}$Lu/$^{225}$Ac/$^{213}$Bi/$^{203}$Pb

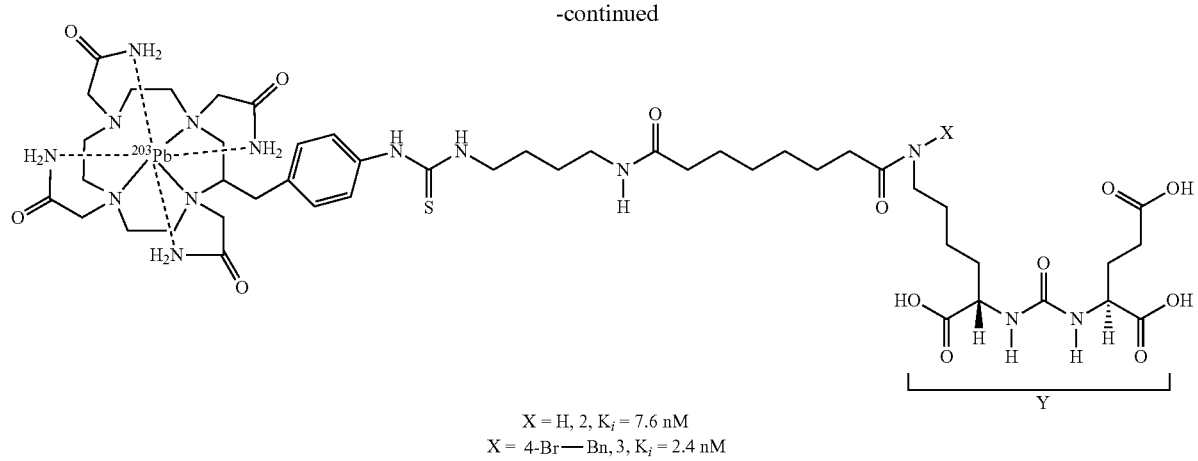
X = H, 2, $K_i$ = 7.6 nM
X = 4-Br—Bn, 3, $K_i$ = 2.4 nM
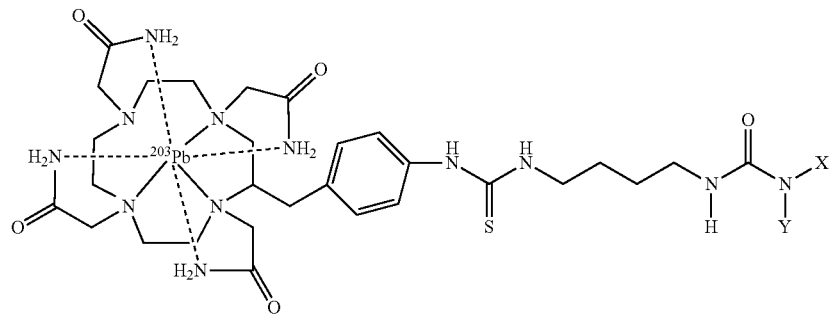
X = 4-Br—Bn, 4, $K_i$ = 2.0 nM
The ligand was synthesized as provided hereinabove. The following compounds also could be synthesized by the presently disclosed methods:
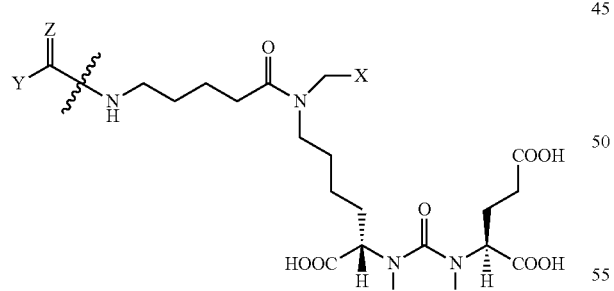
Z = O/S
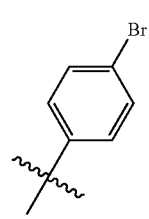
X1
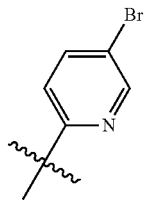
X2
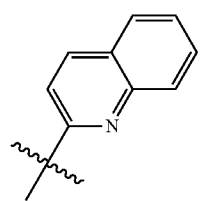
X3

X4

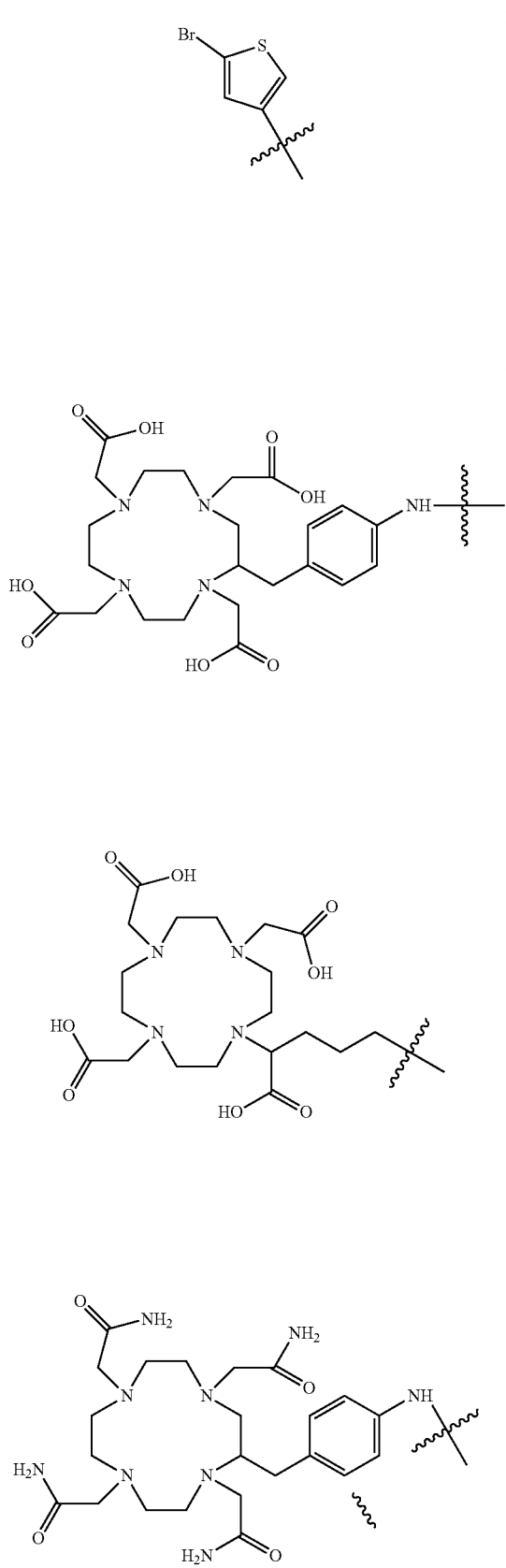

Y1

Y2

Y3

Y4

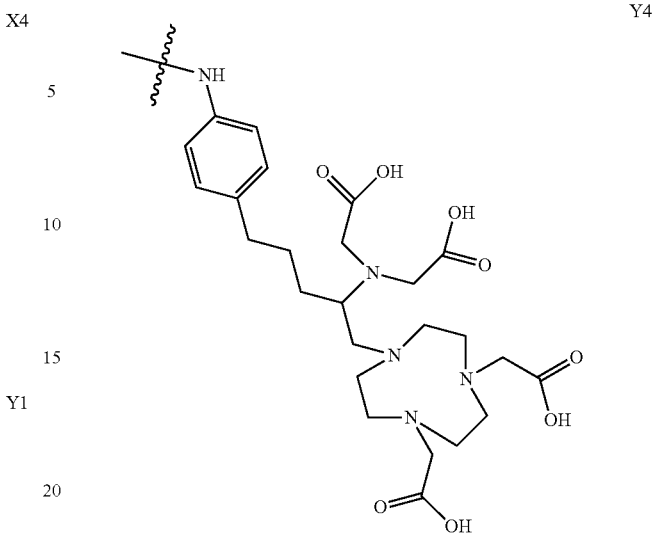

Radiolabeling of $^{213}$Bi-1/$^{225}$Ac-1/$^{203}$Pb-1. All radiolabeled compounds were prepared following a general method as described for $^{213}$Bi-1. $^{213}$Bi was eluted from an $^{225}$Ac/$^{213}$Bi-generator produced by Oak Ridge National Laboratory. Freshly eluted $^{213}$Bi (18.2 MBq) was added to 10 μg of 1 solution and was adjusted to 4 to 5 using 3M NH$_4$OAc solution. The solution was heated in a microwave oven for 5 minutes at 95° C. for 5 min at power 40 watt. Next, a 10 μL of 1 mM Na-DTPA solution was added to complex-free $^{213}$Bi. The specific activity of $^{213}$Bi-1 was >7.4 MBq/μg for all experiments. $^{213}$Bi-1 was purified using a Phenomenex C$_{18}$ Luna 10×250 mm$^2$ column and a Varian Prostar System (Palo Alto, Calif.), equipped with a Varian ProStar 325 UV-Vis variable wavelength detector and a Bioscan (Poway, Calif.) Flowcount in-line radioactivity detector, all controlled by Galaxie software. Flow rate was 1 mL/min with water (0.1% TFA) (A) and CH$_3$CN (0.1% TFA) (B) as the eluting solvents. To ensure uniform purity isocratic solution of 80% A and 20% B was used to separate excess ligand from the radiolabeled compound. The specific radioactivity was calculated as the ratio of the radioactivity eluting at the retention time of product during the preparative HPLC purification to the mass corresponding to the area under the curve of the UV absorption. The purity of tested compounds as determined by analytical HPLC with absorbance at 254 nm was >95%. Radiolabeling yield was also assessed using Silica Gel instant TLC (ITLC) with 0.9% sodium chloride as the mobile phase. The radiolabeled samples were diluted with 10 mM diethylenetriaminepentaacetic acid (DTPA) at a pH of approximately 4. Three microliters of the diluted sample were spotted on an ITLC silica gel strip and allowed to develop in a chromatography chamber. Upon completion of the migration to the solvent front, the ITLC sample strips were allowed to dry, cut in half, and counted on a Wallac Wizard γ-counter (Perkin-Elmer, Boston, Mass.) to determine the radiolabeling yield. Radiochemical purity was assessed via high-performance liquid chromatography (HPLC) analysis.

In vitro and in vivo characterization are shown in FIGS. 7, 8, 9, 10, 11, and 12. Table 5 shows the biodistribution of $^{225}$Ac-1.

TABLE 5

Biodistribution of $^{225}$Ac-1.

| | $^{225}$Ac-1 | | | | | | | |
|---|---|---|---|---|---|---|---|---|
| | 2 h | 8 h | 24 h | 48 h | 72 h | 96 h | 120 h | 8 d |
| Blood | 0.3 ± 0.3 | 0.1 ± 0.1 | 0.1 ± 0.0 | 0.1 ± 0.2 | 0.0 ± 0.1 | 0.1 ± 0.2 | 0.1 ± 0.1 | 0.0 ± 0.1 |
| Heart | 1.7 ± 2.3 | 0.4 ± 0.1 | 0.2 ± 0.1 | 0.1 ± 0.0 | 0.1 ± 0.1 | 0.1 ± 0.1 | 0.0 ± 0.0 | 0.0 ± 0.0 |
| Lung | 1.1 ± 0.6 | 0.4 ± 0.1 | 0.2 ± 0.0 | 0.1 ± 0.1 | 0.1 ± 0.0 | 0.1 ± 0.0 | 0.0 ± 0.0 | 0.0 ± 0.0 |
| Liver | 2.7 ± 1.7 | 3.9 ± 1.1 | 3.1 ± 0.8 | 1.9 ± 0.9 | 1.6 ± 0.4 | 2.7 ± 1.0 | 1.9 ± 0.5 | 2.1 ± 0.4 |
| Stomach | 0.9 ± 0.7 | 0.4 ± 0.2 | 0.4 ± 0.1 | 0.1 ± 0.1 | 0.1 ± 0.1 | 0.1 ± 0.1 | 0.1 ± 0.0 | 0.0 ± 0.1 |
| Pancreas | 0.6 ± 0.6 | 0.1 ± 0.0 | 0.0 ± 0.0 | 0.0 ± 0.0 | 0.0 ± 0.1 | 0.0 ± 0.0 | 0.1 ± 0.1 | 0.0 ± 0.0 |
| Spleen | 1.4 ± 1.2 | 0.6 ± 0.2 | 0.5 ± 0.5 | 0.4 ± 0.1 | 0.2 ± 0.3 | 0.5 ± 0.2 | 0.2 ± 0.1 | 0.3 ± 0.5 |
| Fat | 0.3 ± 0.3 | 0.2 ± 0.3 | 0.3 ± 0.1 | 0.2 ± 0.2 | 0.1 ± 0.1 | 0.1 ± 0.1 | 0.0 ± 0.0 | 0.0 ± 0.1 |
| Kidney | 27.5 ± 14.9 | 3.1 ± 0.9 | 1.5 ± 0.5 | 0.5 ± 0.4 | 0.5 ± 0.3 | 0.6 ± 0.4 | 0.3 ± 0.1 | 0.2 ± 0.2 |
| Muscle | 0.3 ± 0.2 | 0.1 ± 0.0 | 0.1 ± 0.1 | 0.1 ± 0.0 | 0.0 ± 0.1 | 0.0 ± 0.0 | 0.0 ± 0.0 | 0.0 ± 0.1 |
| Sm. Int. | 0.6 ± 0.4 | 0.3 ± 0.1 | 0.5 ± 0.5 | 0.1 ± 0.1 | 0.2 ± 0.2 | 0.0 ± 0.2 | 0.1 ± 0.1 | 0.3 ± 0.5 |
| Sal. Glands | 0.3 ± 0.1 | 0.1 ± 0.0 | 0.2 ± 0.1 | 0.1 ± 0.1 | 0.0 ± 0.1 | 0.1 ± 0.1 | 0.0 ± 0.0 | 0.0 ± 0.0 |
| Bladder | 2.4 ± 2.7 | 0.2 ± 0.1 | 0.5 ± 0.5 | 0.5 ± 0.4 | 0.0 ± 0.2 | 1.0 ± 1.3 | 0.0 ± 0.1 | 0.1 ± 0.2 |
| Bone | 0.8 ± 0.5 | 2.1 ± 1.0 | 0.5 ± 0.3 | 0.5 ± 0.4 | 0.2 ± 0.2 | 0.5 ± 0.4 | 0.5 ± 0.3 | 0.3 ± 0.3 |
| PC-3 PIP | 45.8 ± 17.9 | 44.5 ± 12.9 | 49.0 ± 17.9 | 22.0 ± 7.5 | 18.3 ± 4.1 | 19.2 ± 6.4 | 12.6 ± 3.2 | 10.0 ± 2.2 |
| PC-3 Flu | 0.6 ± 0.2 | 0.2 ± 0.1 | 0.3 ± 0.2 | 0.3 ± 0.2 | 0.1 ± 0.1 | 0.1 ± 0.1 | 0.1 ± 0.0 | 0.1 ± 0.1 |
| Laclm Gln | 1.1 ± 1.1 | 0.5 ± 0.5 | 0.3 ± 0.2 | 0.2 ± 0.2 | 0.1 ± 0.2 | 0.1 ± 0.2 | 0.0 ± 0.1 | 0.1 ± 0.1 |

Development of receptor blockade for normal organs. The blocking effect of 1 was quantified in normal tissues using $^{177}$Lu-1. A drastic reduction of renal uptake was observed while maintaining high uptake in PSMA(+) tumors (FIG. 12). Although lowering of salivary gland uptake was observed in these blocking studies, the results were not statistically significant, likely due to high experimental error associated with very low uptake (<0.5% at 2 h) for $^{177}$Lu-1. Blocking strategies. All blocking studies will be performed using a best performing $^{225}$Ac-labeled agent (e.g., $^{225}$Ac-1) due to its long half-life and related toxicity due to decayed daughters $^{213}$Bi and $^{221}$Fr. These daughters, once formed, are unlikely to associate with the chelate construct due to high atomic recoil-energy as a result of α-decay. Without wishing to be bound to any one particular theory, it is thought that acute salivary gland toxicity caused by $^{225}$Ac-PSMA-617 is most likely due to PSMA-based internalization of the agent followed by daughter release in striated duct or acini. Both biodistribution data and α-camera imaging will be used to interpret the data. Different pharmacologic agents will be evaluated to avoid renal and salivary gland radio toxicity. In addition to com-injection, it will be investigated whether 15 min of 30 min pre-injection blockade will provide any significant change due to the short blood half-life of the agent. Two or three effective blocking formulations will be combined to check if a combined formulation displays any improvement.

The following experiments can be carried out within the scope of the presently disclosed subject matter:

A receptor blockading (self-blocking) experiment, for example, free ligand 1 for $^{225}$Ac-1 (as in FIG. 12);

A competitive blocking with dithiol chelating to scavenge $^{213}$Bi in PSMA-expressing normal tissues to provide synergistic receptor blockade and metal-ion capture;

Use of dithiol chelating agent to remove free $^{213}$Bi by employing 2,3-dimercapto-1-propanesulfonic acid (DMPS) off target effect as DMPS since dithiol chelators have been shown to enhance $^{213}$Bi or other heavy metal excretion in various animal, as well as human, studies;

Francium (Fr), is an alkali metal like sodium and potassium, and therefore may be absorbed by salivary glands ducts by Na$^+$/K$^+$/2Cl-co-transporter (NKCC1) transporter, a key transporter, for acinar cells fluid and electrolyte secretion. Therefore, FDA-approved diuretics furosemide and bumetanide can be used to accelerate the elimination of $^{221}$Fr by preventing its reabsorption similar like Na$^+$ and K$^+$ as reported; and Competitive metal blocking by bismuth subnitrate suspension (100 mg/kg) as reported. The effectiveness of competitive metal blockade either $^{213}$Bi or cold Bi$^{+3}$ uptake or its binding sites (metallothionein-like proteins) in the renal tubular cells can be evaluated.

Example 5

$^{177}$Lu-Labeled Low-Molecular Weight Compounds for PSMA-Based Radiopharmaceutical Therapy 5.1 Overview Prostate-specific membrane antigen (PSMA) is an important target for radionuclide therapy for the treatment of metastatic castration-resistant prostate cancer. One goal of the presently disclosed subject matter is to develop an optimized agent employing the low linear energy transfer radiation of β-particles for targeted radionuclide therapy of metastatic castration-resistant prostate cancer. To this end, novel PSMA-based $^{177}$Lu-labeled radioligands have been synthesized and evaluated for in vitro binding affinity and in vivo tumor targeting. Radiolabeling of the new ligands were synthesized in high (>98%) radiochemical yield and specific activity. Cell uptake and internalization data indicated specific uptake in PSMA(+) PC3 PIP cells for the agents for all agents. Clonogenic cell survival assay was performed for selected agents. A significant decrease in PSMA(+) PC3 PIP cell survival was observed compared to PSMA(−) PC3 flu cells only after 48 h incubation. Selected compounds were further evaluated in a direct comparison studies with the clinical agents $^{177}$Lu-PSMA-617 and $^{177}$Lu-PSMA-I&T for in vivo pharmacokinetics and treatment effect in a primary prostate cancer model. Biodistribution data revealed comparable tumor uptake in PSMA-expressing PC3 PIP tumor for the new agents up to 72 hours. These agents also demonstrated efficient tumor regression at 8-weeks after intravenous administration of 111 MBq (3 mCi) compare to untreated mice (n=10). A representative compound, $^{177}$Lu-L1, demonstrated significantly high survival improvement. Necropsy studies after eight-week post-treatment in tumor bearing mice for the selected agents and one-year post-treatment in tumor-free mice ($^{177}$Lu-L1, 111 MBq) did not reveal any radiation nephropathy.

5.2 Background

Prostate-specific membrane antigen (PSMA), also known as glutamate carboxypeptidase II [GCPII] or N-acetyl-1-aspartyl-1-glutamate peptidase I [NAALADase I], is a type II cell surface metalloenzyme, and has proven to be a valuable clinical biomarker of prostate cancer.[1, 2] Over approximately 80% of prostate tumors, as well as other solid tumors, exhibit a strong PSMA expression within the newly formed vessels resembling tumor related angiogenesis. Lower levels are found in physiologically normal tissues such as the kidneys, salivary glands, and small intestine. Differential PSMA expression in prostate tumors has led clinicians and radiochemists to explore the use of PSMA as a target for delivering a wide range of diagnostic and therapeutic radionuclides using PET, SPECT, nanoparticles, optical agents, and the like. PSMA-based low molecular weight PET imaging agents, $^{68}$Ga-PSMA-11[3] and $^{18}$F-DCFPyL[4] have revolutionized the early diagnosis of men with prostate cancer and are likely to undergo the New Drug Application process at the FDA within the next few years. The therapeutic potential of recently introduced PSMA-based radionuclide therapeutic agents $^{177}$Lu-PSMA-617 and $^{177}$Lu-PSMA-I&T[5-11] (Table 6) and halogen $^{131}$I-MIP1095[2, 12, 13] although showing promising, needs more extensive investigation for safe and effective administration as required for radionuclide therapy. For example, grade 1-3 hematological toxicity was reported with $^{131}$I-MIP1095 along with intense accumulation in the salivary glands that led to xerostomia and mucositis.[13] An $^{225}$Ac-based LMW agent is also in the clinical trials showing similar complications related to salivary glands.[14] Prospective data collected in well-designed clinical trials are still lacking to address long-term nephrotoxicity for PSMA-based radionuclide therapy, a major safety concern for these LMW radiotherapeutic agents.

The pharmacokinetics of the agents with high tumor/background ratios for safe and effective clinical application (FIG. 13) have been investigated for both imaging and therapy of prostate cancer. The overall biologic profile of those agents is not only determined by receptor-specific binding, but also by nonspecific interactions and may be related to molecular weight, charge, hydrophilicity, and metabolic stability. So far two general classes of high affinity agents ($K_i$<20 nM) emerged from our studies: (i) Type I agents. These agents demonstrate high PSMA-specific tumor uptake and long retention, however, with high uptake in many PSMA-expressing normal tissues including renal cortex and spleen.[15] Examples include $^{99m}$Tc-oxo,[16] $^{64}$Cu-1,4,7-triazacyclononane-1,4,7-2-triacetic acid (NOTA)[17] (FIG. 13A), $^{68}$Ga-PSMA-11,[18] and agents $^{68}$Ga—/$^{177}$Lu-PSMA-I&T, second generation) (FIG. 13B), which have been administered to patients[6, 7, 19, 20] in several clinical trials. These agents were generated merely by changing the chelating agent or linker on the original linker/urea construct[21], leading to an improvement in PSMA affinity. Recently developed several high affinity radioligands that displayed high tumor retention using albumin-binding p-(iodophenyl)butyric acid moiety[22-25] also lead to an extended high radiation dose in murine renal cortical and other normal organs. (ii) Type II agents. These agents display high tumor uptake and retention and fast clearance from most normal tissues including kidney and salivary glands, thus producing high tumor-to-background ratios.[16, 17] Type II agents include agents, developed by the inventors (FIG. 13A)[26] and PSMA-617,[5] (FIG. 13B). Agent II underwent a recent first-in-man-study.[27] A similar pattern of faster renal clearance from PSMA-expressing kidney than PSMA+ tumor has been observed, presumably associated with more rapid flow through normally organized renal vasculature compared to the relatively disorganized vasculature of the xenografts.[26, 28, 29]

The presently disclosed subject matter includes, in part, the preclinical evaluation of a new series of low molecular weight compounds targeting PSMA for the development of targeted theranostic radiopharmaceutical therapy for the treatment of metastatic prostate cancer. The 4-halo-benzyl derivative of Lys-urea-Glu was investigated over other urea-based candidates because of sustained tumor uptake for at least 48 h in human PC xenografts of 2-[3-[l-carboxy-5-(4-$^{125}$I-iodo-benzoylamino)-pentyl]-ureido]-pentanedioic acid ($^{125}$I-DCIBzL) and the agent demonstrated significant tumor regression owing to its high linear energy transfer and short range of emission of Auger electrons (<10 mm).[30] DCIBzL is a one of the most potent PSMA binding agents known in the art ($K_i$=0.01 nM). Additionally, the α-particle emitting $^{211}$At-labeled version of DCIBzL showed significant treatment effect in both flank tumor model and micrometastatic model.[31] Accordingly, the presently disclosed metal-based radiotherapeutics were designed to contain a halo-benzyl-urea-Glu derived from the structure of DCIBzL with some rational modifications to the linker and chelating agents to improve the binding affinity and pharmacokinetics of the agents. Several representative compounds were synthesized to evaluate the tumor-targeting and pharmacokinetic properties of the agents. This approach can lead to an optimized agent with reduced off-target effect for $^{177}$Lu, $^{212}$Pb or $^{225}$Ac for PSMA-based targeted radionuclide therapy.

5.3 Results

5.3.1 Synthesis Schemes

A series of representative compounds were synthesized for structure and activity relationships (SAR) study based on the high affinity agent DCIBzL as shown in FIG. 13. All ligands were designed to contain a (Br/I)-Benzyl Lys-urea-Glu targeting moiety, except for ligands L8 and L14, which were designed as control agents. Ligands L1-L4, L7-L9 and L13 were designed to possess a short and flexible linker while L12 contains a rigid aromatic linker. In contrast, ligands L5, L6 and L14 were designed to have longer linkers similar to previous lead agents.[26] The effect of chelating agents was investigated in ligands L7 and L8, by replacing chelating agent DOTA-monoamide as in L1 by DOTA-Bn-SCN and in L9 using a DOTAGA chelating agent. Ligands L10 and L11 were designed to have a rigid cyclohexyl linker as in PSMA-617 with DOTA-monoamide and DOTAGA chelating agent for checking the effect on rigid linker and chelator compared to L1 and L9 respectively. Ligand L13 was designed to possess a different targeting moiety, by replacing Br-Benzyl Lys-urea-Glu with a Br-pyridyl Lys-urea-Glu derived from the clinical PET imaging agent $^{18}$F-DCFPYL.[32] The ligand L14 was designed to have an albumin binding moiety 4-(p-iodophenyl)butyric acid on the previously reported PSMA-binding targeting platform as recently studied by several research groups[22-25, 33] to investigate the effect of 4-(p-Iodophenyl) on the biodistribution properties.

All compounds were synthesized in solution phase chemistry based on well-established methods to prepare Glu-Lys urea derivatives and related conjugation chemistry for linker and chelating agents. Ligand L1 and L2 were synthesized as described in Scheme 2.

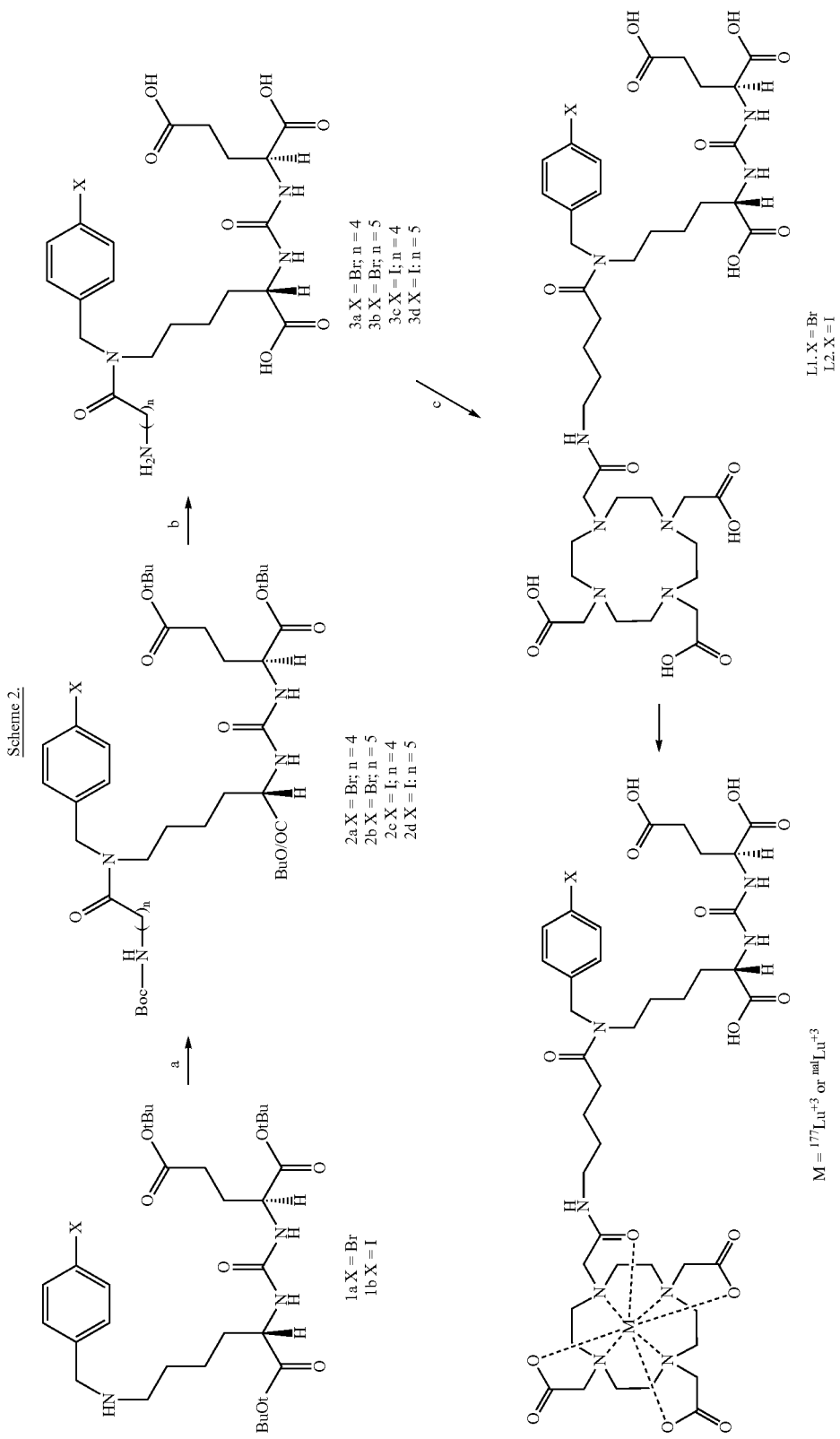

Urea-lysine intermediate Di-tert-butyl (((S)-1-(tert-butoxy)-6-((4-iodo/bromobenzyl)amino)-1-oxohexan-2-yl)carbamoyl)-L-glutamate, 1a or 1b (5-X-Bn)-Lys-urea-Glu (X=Br/I) were synthesized following some modification of the literature method.[34] These two intermediate compounds were also used to synthesize L3, L4, L5, L6, L8, L9, L10, L11 and L12. Briefly, Boc-5-amino valeric acid was conjugated to 1a and 1b to provide 2a and 2c followed by simultaneous removal of tert-But and N-Boc groups to generate 3a and 3c respectively in >90% yields. Compounds 3a and 3c were then reacted with the N-hydroxysuccinimide (NHS)-ester of DOTA-monoamide to provide the target ligands L1 and L2 in high yields. Ligands L3 and L4 were synthesized as shown in Scheme 3.

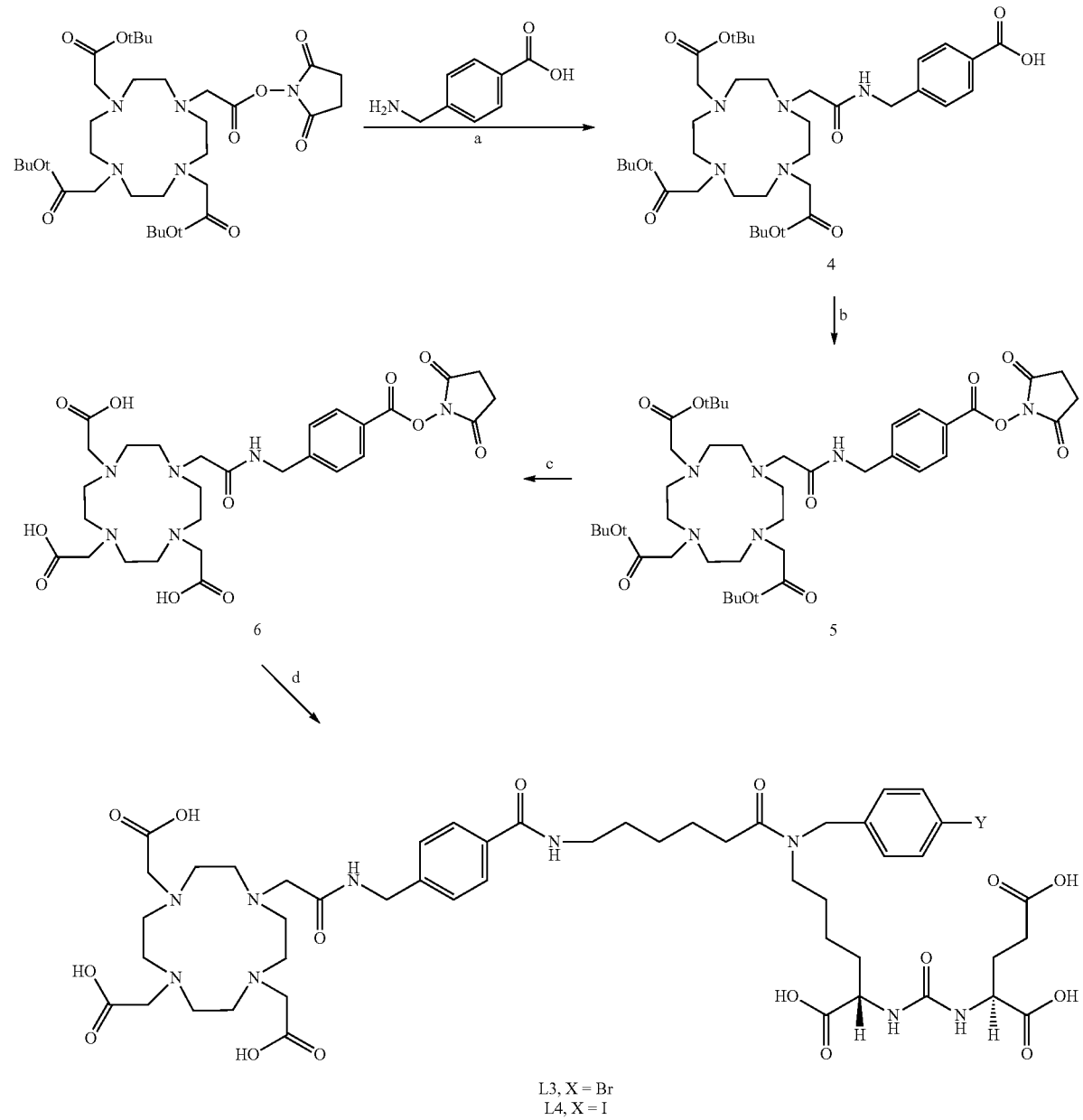

L3, X = Br
L4, X = I

[a]Reagents and conditions: (a) DIPEA, DMF, rt, 16 h; (b) TSTU, TEA, DMSO, 4 h; (c) 50% TFA/CH$_2$Cl$_2$; (d) 3b or 3d, DIPEA, DMSO.

A conjugation reaction was performed using the rigid linker p-aminomethyl benzoic acid and DOTA-monoamide NHS ester to provide compound 4 in quantitative yield. Next, compound 5 was obtained by treating compound 4 with TSTU in presence of trimethylamine and followed by removal of tert-Butyl group using TFA/CH$_2$Cl$_2$ to produce a reactive intermediate 6 in high yield. Ligands L3 and L4 were obtained in good yields after a simple conjugation reaction between 6 with 3b and 3d. Ligands L5 and L6 were synthesized following a synthetic route as shown in Scheme 4.

Scheme 4.

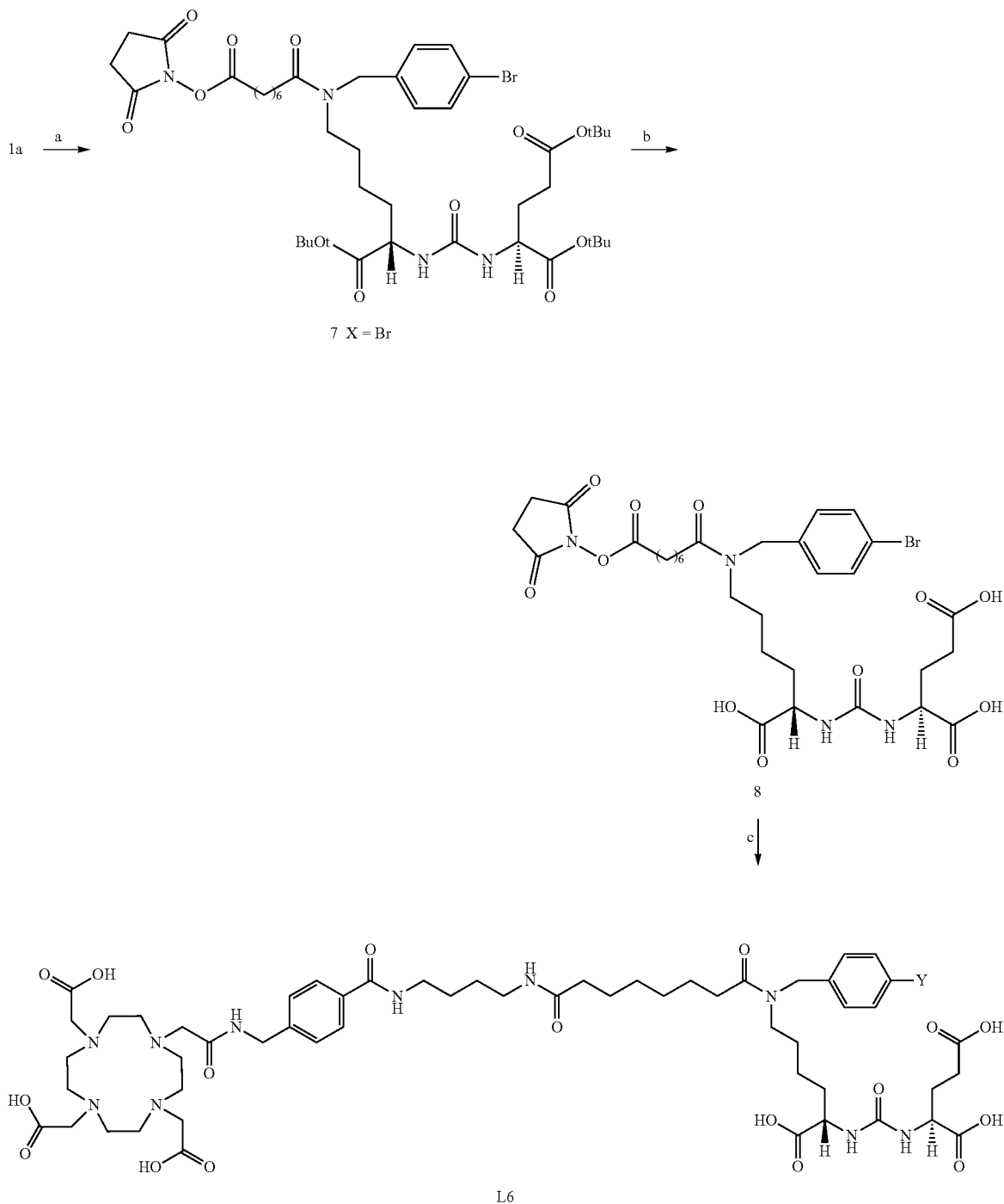

*Reagents and conditions: (a) DSS, TEA, DMF; (b) 50% TFA/TFA/CH₂Cl₂; (c) 4, DIPEA, DMSO, 3 h.

First, compound 7 was synthesized by reacting 1a and disuccinimidyl suberate (DSS) as previously reported.[35] Compound 7 was then treated with 50% TFA/CH$_2$Cl$_2$ to remove t-butyl groups to synthesized compound 8, which was then coupled with Boc-5-amino valeric acid followed by removal of Boc group and coupling to compound 6 to provide L5. Additionally, three analogs of L1 were synthesized by replacing DOTA-monoamide with DOTA-Bn-SCN (L7 and L8) and DOTAGA (L9) following the synthetic route as described in Scheme 2. The conjugation reactions of DOTA-Bn-SCN were performed at 40° C. for 4 h. In contrast, for the chelating agent DOTAGA, the reaction mixture was initially sonicated at room temperature for 1 h to provide a high yield conjugation reaction. Two ligands L10 and L11, analogs of L1 using cyclohexyl linker, were also synthesized as shown in Scheme 5.

Scheme 5.

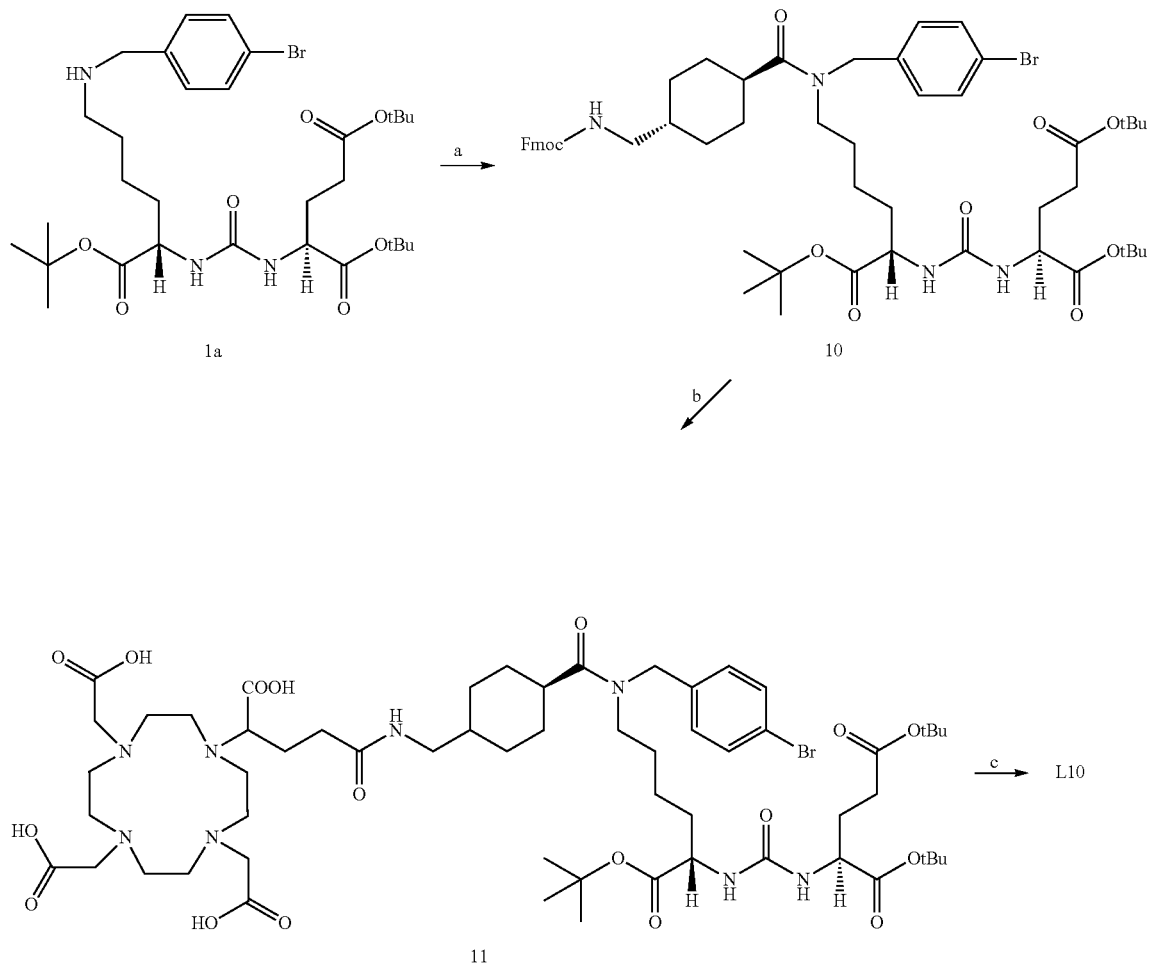

<sup>a</sup>Reagents and conditions: (a) (i)trans-4-(Fmoc-aminomethylcyclohexanecarboxylic acid), TSTU, DIPEA, DMF, RT for 1 h; (ii) 20% piperidine/DMF; (c) DOTA-GA anhydride, DIPEA, DMSO, 3 h (c) 50% TFA/CH₂Cl₂.

At first, NHS-ester of trans-4-(Fmoc-aminomethylcyclohexanecarboxylic acid) was synthesized in situ which was then reacted with 1a to provide 10. After the sequential removal of Fmoc and tert-butyl groups and coupling with the corresponding chelating agents, DOTAGA and DOTA-monoamide, L10 and L11 were obtained in excellent yield. The ligand L12 was synthesized as shown in Scheme 6. In brief, compound 1a was reacted with the intermediate 6 followed by the removal of tert-Butyl groups from Lys-urea-Glu to provide L12 in >80% yields.

Scheme 6.

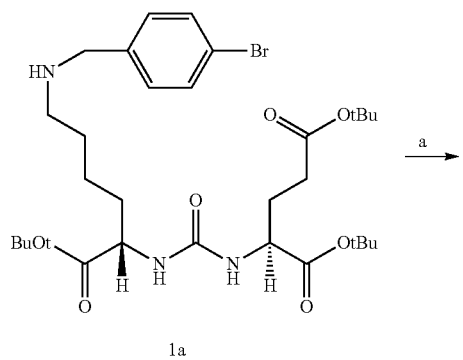

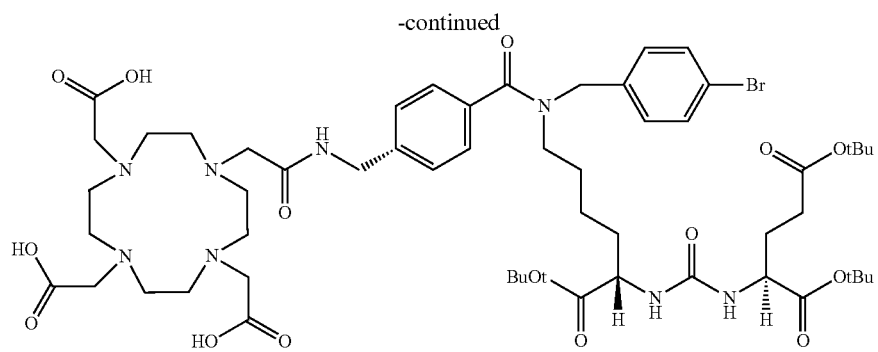

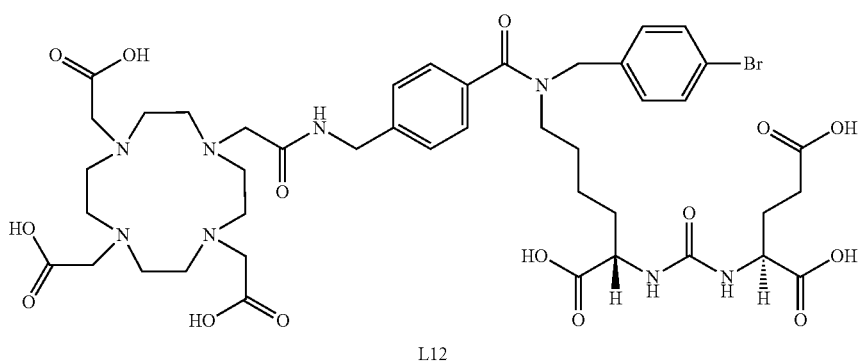

L12

(a) 6, DIPEA, DMSO; (b) 50%TFA/CH$_2$Cl$_2$.

Ligand L13 was also synthesized following Scheme 7, however, by replacing p-bromobenzyl with p-bromopyridyl group to investigate the effect of pharmacophore on the tumor targeting and pharmacokinetics of the agents. The ligand L14 was synthesized following Scheme 7. First NHS-ester of p-(iodophenyl)butyric, compound 12, was synthesized in quantitative yield which was reacted with our previously reported bifunctional compound 14[35] to provide L14 in excellent. All newly synthesized ligands were purified by HPLC and lyophilized to provide colorless hygroscopic solid compound and characterized by standard spectroscopic tools including mass spectrometry and NMR. All ligands were found to be stable at least for 6 months at −20° C.

Scheme 7.

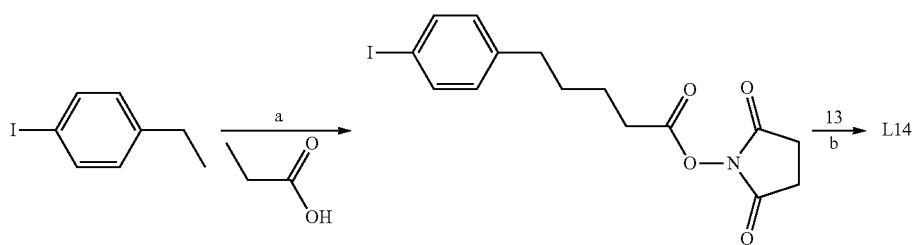

-continued

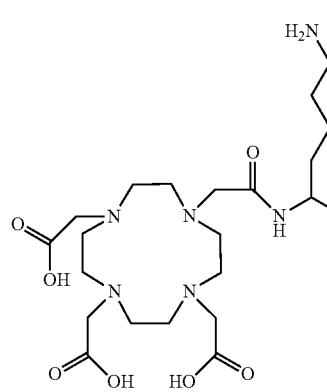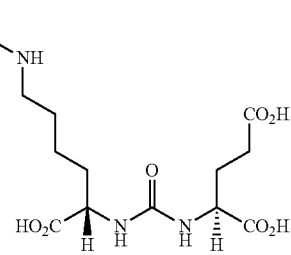

13

*a*Reagents and conditions: (a) TSTU, DIEA, DMF; (b) 13, DIPEA, DMSO, 2 h.

All new ligands were radiolabeled with $^{177}$Lu in high yield at 70° C. for 1 h incubation followed by HPLC purification to remove the unreacted ligand from the radiolabeled compounds to ensure highest radiochemical purity>99% and specific activity (>37 MBq/nmol). Additionally, a fast and convenient microwave assisted radiolabeling method has been developed for L1 and the related ligands including L7, L8, L9, L11, L12 and L13 to synthesize new $^{177}$Lu-labeled agents ($^{177}$Lu-L) in excellent yields (>90%) within 5 min at pH~4 at 40° C. The microwave-assisted method generated multiple radiolabeled products for the ligands with p-iodobenzyl urea derivatives (e.g., L4 and L6), ligands with a long linker (e.g., L3 and L5) and a rigid linker (e.g., L12). All $^{177}$Lu-labeled compounds were found stable up to 4 h at room temperature and 24 h at 4° C. without any significant radiolysis. However, to ensure high stability, L-ascorbic acid was added to the radiolabeled compounds in the final formulation and used for the in vitro and vivo experiments reported here. Cell uptake and internalization experiments were performed immediately without any addition of L-ascorbic acid.

5.3.2 In Vitro Binding and Cell Uptake

All new ligands demonstrated high binding affinity to PSMA with $K_i$ values ranging from 0.03 to 8 nM (Table 6). A stable lutetium analog of L1 (Lu-L1) was synthesized, which displayed 3-fold improvement in binding affinity over L1 (Table 6). Comparative cell uptake studies at 2 h incubation involving L1 to L14 revealed approximately 100-fold higher uptake in PSMA+ PC3 PIP cells relative to PSMA− PC3 flu cells. Cell uptake and internalization data for selected compounds are presented in FIG. 14 and Table 7. Total uptake and internalization for the compounds slowly increased from 1 h to 24 h. Both $^{177}$Lu-PSMA-I&T and $^{177}$Lu-PSMA-617 displayed significantly higher total uptake within the PSMA(+) PC3 PIP cells, ~60% and ~40% of the incubated dose respectively, whereas $^{177}$Lu-L1, $^{177}$Lu-L3 and $^{177}$Lu-L5 showed displayed uptake within the range of 30%. However, percent of internalization was in the same range for the compounds ~18-24% at 1 h to 25-30% at 24 h. The uptake in PSMA(+) PC3 PIP cells could be blocked by treatment with an excess of known PSMA inhibitor, ZJ43 for all compounds (Table 7). Cell internalization of $^{177}$Lu-7 and $^{177}$Lu-8 were also studied up to 24 h post-incubation. Bromo-benzyl group modified $^{177}$Lu-8 displayed nearly >1.5-fold higher internalization compared to ligand $^{177}$Lu-7 without it at all time-points. Significantly, $^{177}$Lu-9 with DOTAGA chelating displayed cell uptake and internalization (~70%) comparable to $^{177}$Lu-PSMA-I&T containing the same chelating agent (Table 7). In contrast, $^{177}$Lu-10 with a DOTAGA chelating agent when modified with a rigid cyclohexyl linker, showed lower uptake and internalization compared to $^{177}$Lu-8 and $^{177}$Lu-9. Similarly, DOTA-mono-amide modified $^{177}$Lu-L11, which also contains a cyclohexyl linker showed >1.5-fold lower uptake compared to $^{177}$Lu-L1 and lower uptake compared to $^{177}$Lu-10. Additionally, $^{177}$Lu-L12 with a rigid aromatic linker displayed low uptake compared to the most agents from the series. The p-bromopyridyl modified $^{177}$Lu-13 displayed comparable cell uptake and internalization properties as $^{177}$Lu-1. The albumin-binding 4-(p-iodophenyl)-butyric acid modified $^{177}$Lu-14 displayed relatively higher uptake in PSMA(+) PC3 PIP cells at 2 h.

TABLE 6

Physical properties and PSMA binding activity of the new compounds and selected clinical agents

| Compound | Molecular Weight | Ki [nM] | Specific Cell Surface Binding [% IA/10⁶ cells] | specific internalization [% IA/10⁶ cells] | POctanol/water co-efficient |
|---|---|---|---|---|---|
| L1 | 973.87 | | 36.49 ± 0.50 | 23.68 ± 0.16 | −3.09 |
| L2 | 1020.87 | 0.20-0.33 nM | 29.23 ± 0.80 | 24.96 ± 0.90 | |
| L3 | 1121.05 | 0.09-34 nM | 36.65 ± 0.50 | 22.03 ± 0.60 | −3.50 |
| L4 | 1168.05 | 0.14-0.39 nM | | | |

TABLE 6-continued

Physical properties and PSMA binding activity of the new compounds and selected clinical agents

| Compound | Molecular Weight | Ki [nM] | Specific Cell Surface Binding [% IA/$10^6$ cells] | specific internalization [% IA/$10^6$ cells] | POctanol/water co-efficient |
|---|---|---|---|---|---|
| L5 | 1234.21 | 0.46-0.63 nM | 36.65 ± 0.50 | 22.03 ± 0.60 | |
| L6 | 1281.21 | 0.35-0.93 nM | | | |
| L7 | 969.41 | 0.29-0.81 nM | | | |
| L8 | 1138.5 | 0.08-0.16 nM ZJ43 (0.28-1.08 nM) | | 20.06 | |
| L9 | 1045.9360 | 0.02-0.05 nM | | 7.80 | −3.53 |
| L10 | 1086.0010 | 0.43-1.2 nM | | | |
| L11 | 1013.94 | | | | |
| L12 | 1007.8900 | 0.22-4.03 nM 0.25-0.56 nM (ZJ43) | | | |
| L13 | 973.34 | 0.23-8.10 nM ZJ43 (0.28-1.07 nM) | | | |
| L14 | 1390.34 | | 53.0 ± 1.3 | | −2.95 |
| SR-VI-71 | | | 22.28 | | −3.02 |
| PSMA-617 | | | 44.6 ± 1.0 | 21.1 ± 0.9 | −3.2 |
| PSMA I&T | | | 64.5 ± 2.3 | 21.1 ± 0.7 | −2.59 |

TABLE 7

Cell uptake and internalization data for the selected compounds in PSMA(+) PC3 PIP and PSMA(−) PC3 flu cells. For blocking studies, ZJ43, a known PSMA inhibitor was used in final concentration of 10 μM. (data expressed in % incubated dose per 1 × $10^6$ cells)

| | | $^{177}$Lu-PSMA I & T | $^{177}$Lu-PSMA-617 | $^{177}$Lu-L1 | $^{177}$Lu-L3 | $^{177}$Lu-L5 |
|---|---|---|---|---|---|---|
| 1 h | PC3 PIP | 60.0 ± 0.2 | 42.2 ± 0.80 | 32.1 ± 0.1 | 27.0 ± 1.3 | 26.6 ± 0.6 |
| | PC3 PIP cell Int | 21.1 ± 0.7 | 18.8 ± 1.2 | 18.8 ± 0.8 | 21.4 ± 1.4 | 24.1 ± 0.5 |
| | PC3 flu | 0.2 ± 0.1 | 0.1 ± 0.01 | 0.2 ± 0.0 | 0.1 ± 0.0 | 0.2 ± 0.1 |
| | Blockade PC3 PIP | 0.2 ± 0.1 | 0.1 ± 0.0 | 0.2 ± 0.0 | 0.1 ± 0.0 | 0.0 ± 0.0 |
| 2 h | PC3 PIP | 60.0 ± 0.2 | 44.6 ± 1. | 36.7 ± 0.5 | 36.5 ± 0.3 | 29.23 ± 0.8 |
| | | 25.1 ± 1.5 | 21.1 ± 0.9 | 22.0 ± 0.6 | 23.7 ± 0.2 | 25.0 ± 0.9 |
| | PC3 flu | 0.1 ± 0.0 | 0.1 ± 0.0 | 0.1 ± 0.0 | 0.1 ± 0.0 | 0.0 ± 0.0 |
| 4 h | PC3 PIP | 72.2 ± 0.4 | 47.6 ± 1.13 | 39.1 ± 0.5 | 32.6 ± 8.5 | 34.4 ± 1.2 |
| | PC3 PIP cell int | 25.7 ± 0.7 | 26.1 ± 1.0 | 26.6 ± 1.2 | 24.9 ± 3.4 | 26.1 ± 1.0 |
| | PC3 flu | 0.3 ± 0.0 | 0.1 ± 0.06 | 0.1 ± 0.0 | 0.1 ± 0.1 | 0.1 ± 0.0 |
| 24h | PC3 PIP | 80.0 ± 1.3 | 54.2 ± 0.21 | 46.2 ± 0.2 | 45.2 ± 1.2 | 49.8 ± 1.4 |
| | PC3 PIP cell int | 28.3 ± 1.2 | 26.4 ± 0.8 | 24.6 ± 0.2 | 30.0 ± 0.7 | 27.9 ± 0.8 |
| | PC3 flu | 0.4 ± 0.1 | 0.1 ± 0.01 | 0.2 ± 0.1 | 0.1 ± 0.0 | 0.1 ± 0.0 |

TABLE 8

Summary of pilot radiotherapy study

| | Average Initial body weight (gram) | Average final body weight (gram) | Average Initial tumor volume (mm$^3$) | Average relative tumor growth after week 8 post-treatment ($V_t/V_0$) | Median survival After 8 weeks post-treatment |
|---|---|---|---|---|---|
| Control group | 23.7 ± 2.7 | 21.4 ± 2.3 | 84.2 ± 38.4 | 41 ± 22 | 33 days |
| $^{177}$Lu-PSMA-617 | 23.5 ± 1.9 | 24.6 ± 3.6 | 84.2 ± 20.6 | Tumor disappear 5 Death one tumor > 4 | Not reached |

TABLE 8-continued

Summary of pilot radiotherapy study

| | Average Initial body weight (gram) | Average final body weight (gram) | Average Initial tumor volume (mm³) | Average relative tumor growth after week 8 post-treatment ($V_t/V_0$) | Median survival After 8 weeks post-treatment |
|---|---|---|---|---|---|
| $^{177}$Lu-PSMAI&T | 22.7 ± 2.73 | 24.0 ± 2.9 Lost body weight >15% after 2 weeks treatment regained within 8 weeks | 84.4 ± 24.7 | Mouse death 1 Tumor disappear 7 No tumor > 5 | Not reached |
| $^{177}$Lu-L1 | 24.1 ± 1.4 | 26.1 ± 1.4 | 83.2 ± 22.8 | Tumor disappear 7 Death 1 | Not reached |
| $^{177}$Lu-L3 | 24.7 ± 1.7 | 25.8 ± 2.6 | 85.2 ± 24.1 | Mouse death 3 Two tumor > 4 | Not reached |
| $^{177}$Lu-L5 | 24.5 ± 2.2 | 27.5 ± 1.9 | 85.7 ± 20.5 | Mouse death 3 one tumor > 5 | Not reached |

5.3.3 Biodistribution Studies

Tumor uptake and in vivo pharmacokinetics of the newly developed $^{177}$Lu compounds were evaluated by performing biodistribution assay using male NOD-SCID mouse bearing both PSMA+P PIP and PSMA− PC flu tumors on the upper flanks. A radiotracer dose~1.67±0.2 MBq (~45±5 µCi) was administered intravenously for all studies presented here. Based on the initial biodistribution study at 24 post-injection, several ligands were selected for detail biodistribution study for longer time-point up to 72-96 h. Except for compounds $^{177}$Lu-7 (without Br-benzyl modified urea group) and with rigid linker $^{177}$Lu-11 and $^{177}$Lu-12, all compounds demonstrated high PSMA(+) tumor uptake>18% ID/g after 24 h post-injection. Tissue biodistribution of $^{177}$Lu-PSMA-617, $^{177}$Lu-PSMA-I&T, $^{177}$Lu-1, $^{177}$Lu-3 and $^{177}$Lu-5 in male NOD-SCID mice are as shown in FIG. 15 and FIG. 16. Mouse body-weight and tumors weights were provided in Table 9.

TABLE 9

Average mouse body weight and average tumor weight at each time-point used for the biodistribution study. Data expressed in mean ± s.d (n = 4).

| Time | | $^{177}$Lu-PSMA-I & T | $^{177}$Lu-PSMA-617 | $^{177}$Lu-1 | $^{177}$Lu-3 | $^{177}$Lu-5 |
|---|---|---|---|---|---|---|
| 3 h | Body Wt. | 24.12 ± 1.04 | 20.83 ± 1.77 | 19.8 ± 1.39 | 21.60 ± 0.32 | 20.80 ± 1.61 |
| | PC3 PIP | 0.06 ± 0.02 | 0.10 ± 0.03 | 0.12 ± 0.04 | 0.04 ± 0.02 | 0.06 ± 0.01 |
| 24 h | Body Wt. | 19.73 ± 0.89 | 22.08 ± 0.95 | 19.70 ± 0.77 | 22.56 ± 0.42 | 20.45 ± 1.01 |
| | PC3 PIP | 0.07 ± 0.01 | 0.040 ± 0.01 | 0.09 ± 0.01 | 0.13 ± 0.05 | 0.05 ± 0.01 |
| 48 h | Body Wt. | 21.83 ± 1.01 | 22.6 ± 0.36 | 20.73 ± 1.24 | 21.95 ± 0.77 | 19.63 ± 0.25 |
| | PC3 PIP | 0.08 ± 0.02 | 0.09 ± 0.02 | 0.15 ± 0.03 | 0.11 ± 0.06 | 0.08 ± 0.02 |
| 72 h | Body Wt. | 22.98 ± 0.57 | 20.50 ± 0.91 | 20.35 ± 0.86 | 22.2 ± 0.84 | 19.03 ± 0.63 |
| | PC3 PIP | 0.13 ± 0.06 | 0.14 ± 0.04 | 0.11 ± 0.04 | 0.13 ± 0.05 | 0.07 ± 0.02 |

At 3 h post-injection significantly higher tumor uptake was observed for $^{177}$Lu-3, 52.6±4.9% ID/g, and $^{177}$Lu-5 (56.3±18.3) while the tumor uptake in $^{177}$Lu-1 was comparable to $^{177}$Lu-PSMA-617 and $^{177}$Lu-PSMA-I&T. However, after 24 h, both $^{177}$Lu-3 and $^{177}$Lu-5 showed fast clearance of activity from the PSMA+ PC3 PIP tumor uptake, causing tumor uptake comparable to $^{177}$Lu-PSMA-617 and $^{177}$Lu-PSMA-I&T. In contrast, $^{177}$Lu-1 displayed significantly lower tumor uptake compared to $^{177}$Lu-PSMA-617. At 72 h post-injection we have not observed significant difference in tumor uptake for the compounds. Uptake in the PC3 flu tumor was low (<0.3% ID/g) for all compounds starting at 3 h post injection demonstrating high specificity of the compounds consistent with the high binding affinity of the ligands.

Although the agents demonstrated nearly similar tumor uptake up to 72 h post-injection, significant changes were observed in the normal tissue uptake for the agents. PSMA-expressing normal organs, for example, kidneys and salivary glands and spleen were significantly higher for $^{177}$Lu-PSMA-I&T. Kidney uptake was 93.39±13.35% ID/g, at 3 h post-injection for $^{177}$Lu-PSMA-I&T while the rest of the agents from the series displayed uptake<10% ID/g; $^{177}$Lu-PSMA-617 (9.81±6.54% ID/g), $^{177}$Lu-1 (5.17±2.38% ID/g), $^{177}$Lu-3 (7.49±3.21% ID/g). Although $^{177}$Lu-PSMA-I&T demonstrated fast kidney clearance, 30.39±12.49% ID/g at 24 h, the data revealed that the agent showed ~3-fold decrease in the kidney uptake in every 24 h up to 72 h. In contrast, $^{177}$Lu-3 and rest of the compounds displayed much faster rate of renal clearance, ~10-fold clearance, resulting kidney uptake<0.5 ID/g after 24 h. Except for $^{177}$Lu-PSMA-I&T, blood and normal tissue uptake, including liver, lung, stomach, pancreas, spleen, fat, adrenal glands, muscle, small and large intestine, bone and salivary glands of the $^{177}$Lu-labeled agents were <0.5% ID/g after 3 h of the administered dose. $^{177}$Lu-PSMA-I&T demonstrated high uptake in spleen and salivary glands at 3 h, nonetheless, displayed fast clearance within 24 h displaying comparable uptake (<1% ID/g) in those tissues as demonstrated by the other agents of the series.

Selected tissue biodistribution data of the p-iodobenzyl analog of $^{177}$Lu-1 and ligands without any halobenzyl modified urea-targeting moiety, $^{177}$Lu-L7 and $^{177}$Lu-L14, and bromobenzyl modified agents, $^{177}$Lu-L8, $^{177}$Lu-L9 and $^{177}$Lu-L10 are shown in FIG. 17. The agent $^{177}$Lu-2 showed significantly higher tumor uptake at 3 h post-injection compared to $^{177}$Lu-L1, but maintained tumor uptake and retention up to 72 h. While both $^{177}$Lu-L7 and $^{177}$Lu-L8 were modified with DOTA-Bn-SCN chelating agent, tumor uptake and retention of $^{177}$Lu-L8 were significantly higher at all time compared to $^{177}$Lu-L7, further emphasizes the importance of bromobenzyl group on tumor retention (55.4±7.2 vs. 25.4±7.2% ID/g at 2 h; 40.6±7.0 vs. 7.0±1.5% ID/g at 24 h; 27.0±7.0 vs. 7.0±3.3% ID/g at 48 h and 24.9±2.3 vs. 2.3±0.0% ID/g). Also, both agents demonstrated much faster kidney clearance compared to $^{177}$Lu-PSMA-I&T. $^{177}$Lu-L9 with a DOTAGA chelating agent, displayed significantly higher tumor uptake and retention compared to $^{177}$Lu-PSMA-I&T up to 72 h post-injection while showing much faster kidney clearance, ~30-fold renal clearance within 24 h (149.7±32.0 at 2 h vs. 5.9±2.7% ID/g at 24 h). The rigid cyclohexyl linker did not generate high cell uptake, $^{177}$Lu-L10 and $^{177}$Lu-L11, compared to L1 and showed similar or lower uptake compared to $^{177}$Lu-L9 and $^{177}$Lu-L1 respectively. The agent $^{177}$Lu-L13 with different targeting ligand (2-pyridyl) ligand showed much faster normal tissue clearance while maintaining similar tumor uptake as $^{177}$Lu-L1.

Biodistribution of $^{177}$Lu-14 was consistent with the reported albumin binding agents with highest tumor uptake reached at 24 h post-injection and displayed high up to 48 h. Although the agent initially displayed lower initial kidney uptake, 49.49±19.55% ID/g compared to $^{177}$Lu-PSMA-I&T, only ~3-fold clearance of activity was observed, 17.47±4.18% ID/g at 48 h compared to 10-fold lowering of activity (93.39±13.35% ID/g at 24 h vs 9.55±3.85% ID/g at 48 h). The agent also showed the highest blood uptake from the series, 16.13±2.33% ID/g at 2 h post-injection followed by 5.05±0.05% ID/g at 2 h and 2.48±0.44% ID/g at 48 h. Both spleen and salivary glands displayed highest non-specific uptake from the series.

5.3.4 SPECT/CT Imaging

SPECT/CT imaging with $^{177}$Lu-1 and $^{177}$Lu-14 were also performed to check in vivo pharmacokinetics. As expected from the biodistribution data, SPECT/CT images during 2-192 h after administration with $^{177}$Lu-1 confirmed high uptake in the PSMA+ PC3 PIP tumors (right) but not in the PSMA− PC3 flu tumors (left), as expected. Also, consistent with the biodistribution data, the ligand displayed very low uptake in the kidneys and all normal tissues. Status of the PSMA expression within the PSMA(+) PC3 PIP tumors were also investigated during the imaging experiments. As shown in FIG. 18B, compared to control tumor (no radioactivity injection), a significant lowering of PSMA(+) staining within the PC3 PIP tumors after day 1 to day 12 of the treated tumor with $^{177}$Lu-1 (37 MBq) was observed. This could be partially due to treatment effect that generated down regulation of PSMA expression and due to the binding of $^{177}$Lu-1 in a significant number of PSMA-binding sites in the treated tumor. Although low, nonetheless, relatively higher staining after 8 days and 12 days are consistent with clearance of $^{177}$Lu-1 from the tumor.

A comparison of hematologic and blood chemistry parameters for the mice groups (n=3) treated with 111 MBq(3 mCi) of $^{177}$Lu-PSMA 617, $^{177}$Lu-2, $^{177}$Lu-4 and $^{177}$Lu-6 after eight-weeks is provided in Table 10.

TABLE 10

| | $^{177}$Lu-1 | $^{177}$Lu-3 | $^{177}$Lu-5 | $^{177}$Lu-PSMA-617 | Control |
|---|---|---|---|---|---|
| Red blood cells (M/µL) | 9.1 ± 0.4 | 8.6 ± 0.2 | 9.2 ± 0.7 | 8.2 ± 0.7 | 9.3 ± 0.0 |
| Hemoglobin (g/dL) | 14.3 ± 0.8 | 13.6 ± 0.4 | 14.3 ± 1.0 | 12.8 ± 1.0 | 14.0 ± 0.1 |
| Hematocrit % | 48.7 ± 2.7 | 45.6 ± 0.9 | 49.7 ± 2.4 | 42.9 ± 4.5 | 47.1 ± 1.1 |
| Mean Corpuscular Value(MCV) fl | 53.4 ± 0.6 | 53.1 ± 0.7 | 54.1 ± 1.4 | 52.2 ± 1.6 | 50.6 ± 1.0 |
| Platelets (K/µL) | 1297 ± 231.4 | 1440.7 ± 92.0 | 1415.3 ± 88.5 | 916.0 ± 141.6 | 1503 ± 190.9 |
| White blood cells (K/µL) | 2.4 ± 0.5 | 3.3 ± 1.7 | 2.9 ± 1.8 | 5.05 ± 4.1 | 4.8 ± 0.8 |
| Neutrophils (K/µL) | 1.2 ± 0.3 | 2.6 ± 1.9 | 2.0 ± 1.8 | 3.5 ± 3.8 | 2.6 ± 0.1 |
| Lymphocytes (K/µL) | 0.5 ± 0.1 | 0.5 ± 0.2 | 0.4 ± 0.1 | 0.7 ± 0.1 | 1.7 ± 0.5 |
| Total protein (g/dL) | 5.8 ± 0.2 | 5.5 ± 0.3 | 5.9 ± 0.6 | 5.5 ± 0.5 | 5.7 ± 0.1 |
| Albumin (g/dL) | 3.1 ± 0.0 | 3.1 ± 0.2 | 3 ± 0.4 | 2.9 ± 0.2 | 3.1 ± 0.3 |
| Blood urea nitrogen(mg/dL) | 24 ± 2.4 | 27.7 ± 1.2 | 22.7 ± 3.2 | 23.3 ± 2.5 | 25.5 ± 0.7 |

5.3.5 Radionuclide Therapy in Cells and Animal Model

The clonogenic efficiency of PSMA(+) PC3 PIP cells after incubation $^{177}$Lu-1 and $^{177}$Lu-8 for 48 h is shown in FIG. 26. Cell surviving fraction was >0.8 for the agents when the cells were incubated for 2 h and 24 h. Significant loss of colony survival was observed after 48 h incubation. The D$_0$ of (37% survival) of $^{177}$Lu-1 and $^{177}$Lu-8 were in the same range 0.3-0.6 µCi/mL.

A pilot treatment study using NOD/SCID mice (n=10 per group) bearing PSMA+ PC3 PIP tumors with a single intravenous dose of 111 MBq (3 mCi) of agents $^{177}$Lu-PSMA-617, $^{177}$Lu-1, $^{177}$Lu-3 and $^{177}$Lu-5 and the control group (with saline treatment) were performed (Table 8). Volume of the all control group mice reached >5-fold of their initial tumor volume within 14 days. Mouse euthanized for treated group within 4 weeks of post-injection was mainly due to sudden body weight loss and not related to tumor growth. All treated group showed significant tumor regression up to eight weeks. The difference among treatment groups was statistically significant (P=0.002) by the log-rank test compared to the untreated group. As shown in Table 8, only one mouse from the group treated with $^{177}$Lu-3 and $^{177}$Lu-PSMA-617 reached tumor volume>4 and two mice from $^{177}$Lu-4 with this high dose. After 8-weeks, three mice from each treated group were used for detailed blood analysis and necropsy study. Selected metabolic and complete blood count data are provided in Table 3, FIG. 24 and FIG. 25. All animals underwent radiotherapy study had normal creatinine (0.3-0.4 mg/dL) and blood urea nitrogen levels. As shown in FIG. 11, only one mouse displayed elevated neutrophil counts (up to 3.5±3.8 K/mL after; control, 2.6 K/mL) from the group treated $^{177}$Lu-PSMA-617. Additionally, a significant lowering of platelet for all three treated mice from $^{177}$Lu-PSMA-617 compared control group and other treated groups.

Pathologic examination of H&E staining of a wide panel normal tissues revealed only moderate changes in the treated group compared to the control group. Significant and concerning changes were identified in testes, and lacrimal grands primarily (FIG. 25) for all treated groups. One mouse with $^{177}$Lu-5 and all three mice treated with $^{177}$Lu-PSMA-617 showed the most significant changes in testis. Changes in kidneys are minimal, only modest tubule changes were seen for all treated group. Parotid glands, usually adjacent to exorbital lacrimal gland, are conspicuously spared and there were mild changes in the group treated $^{177}$Lu-PSMA-617. Additionally, infraorbital lacrimal glands displayed similar changes to exorbital lacrimal glands especially evident within the mice treated with $^{177}$Lu-PSMA-617. One mouse treated with $^{177}$Lu-5 had a thymic lymphoma, morphology is consistent with thymic T lymphoblastic lymphoma which is an expected cause of death in NOD/SCID mice, usually beginning at about 6 month. T lymphoblastic lymphoma is accelerated by irradiation and some carcinogens, and is associated with interactions of endogenous retroviruses/retroelements in NOD/SCID mouse strains. One mouse from the group treated with $^{177}$Lu-PSMA-617 showed tumor and metastases in lung (<1 mm), as well as tumor cells intravascular, in body cavities, serosal surfaces (carcinomatosis), and evident on blood smear. The cells are large up to 25 μm, with very large nuclei (for a mouse) usually 2-3 nucleoli, and a high mitotic rate. Testis and lacrimal gland degenerative changes indicate that this animal did receive a treatment similar to other treated mice.

All animals tested had normal creatinine values (0.3-0.4 mg/dL) and blood urea nitrogen level.

While treatment monitoring was terminated for $^{177}$Lu-4 and $^{177}$Lu-6, the treatment study was continued for $^{177}$Lu-1 and $^{177}$Lu-PSMA-617 until the predefined end-point was reached (tumor volume 1800 mm$^3$ and body weight loss>15%). FIG. 18 displays the survival data of $^{177}$Lu-1 and $^{177}$Lu-PSMA-617. Median survival for the $^{177}$Lu-PSMA-617 was 133 days vs. 234 days for $^{177}$Lu-1. In contrast the treatment group did not to show any change. Individual tumor volume measurements for each animal are shown in FIG. 24. Given that $^{177}$Lu-1 demonstrated good treatment effect, a growth delay study was performed using escalated dose from 18.5 MBq (0.5 mCi), 37 MBq (1 mCi) and 111 mMBq (3 mCi) (n=5 per group) up to 90 days. As shown in FIG. 23, $^{177}$Lu-1, indeed show significant tumor growth delay for the all treated groups was observed compared to untreated group. While four out of five mice treated with 0.5 mCi dose reached the relative volume>5 at 8 weeks post-treatment, only one mouse from the group treated with 37 MBq dose demonstrated similar effect. Three mice from treated both 37 MBq and III MBq showed complete tumor regression up to 120 days, demonstrating nearly similar treatment effect as was observed from the first treat experiment.

A theranostic (SPECT/CT imaging and treatment) study was also performed $^{177}$Lu-8 (n=10) using 111 MBq dose after 24 h post-treatment to 192 h using a PC3 PIP flank tumor model. SPECT/CT imaging revealed very similar profile as $^{177}$Lu-1, low normal tissue and kidney uptake, nonetheless, relatively higher background uptake compared to $^{177}$Lu-1 as anticipated from the biodistribution data. While unexpected death of three mice (used for SPECT/CT imaging) was observed, only two mice showed tumor growth with relative volume>5 after 8 weeks. The remaining treated mice survived tumor-free for 10 months and were evaluated for toxicity.

5.3.6 Discussion

The SAR of a new series of PSMA-based low molecular weight $^{177}$Lu-labeled theranostic agents was investigated for the treatment of patient with metastatic prostate cancer. $^{177}$Lu is the current beta-emitting isotope of choice for PSMA-targeted and other cancer therapeutic applications as it has more favorable emission properties, production feasibility, and radiation safety issues than $^{131}$I and $^{90}$Y. A major motivation of this investigation involves a need to understand the molecular and structural origins, i.e., interaction of the PSMA-targeting moiety Lys-Glu-urea in the PSMA-binding site that accounts for the vastly different PK of Type I vs. Type II agents. This understanding will guide research into a Type II agent with reduced radiation-related side effects compared to $^{177}$Lu-PSMA-617 and $^{177}$Lu-PSMA I&T. The presently disclosed theranostic agents are built upon the well-studied, long linker-based targeting platform[17, 21, 26, 36-42]. From a strictly synthetic standpoint, it was intended to extend the scope of radiotheranostic agents and chemical space for compounds that bind to PSMA. Other similarly intensive synthetic efforts toward developing low molecular weight, PSMA-based radionuclide therapy are not known in the art.

The presently disclosed compounds were synthesized using optimized solution phase chemistry. Therefore, the presently disclosed methodologies can be readily adapted for industrial scale preparation and anticipated to be less expensive compared to the solid-phase peptide synthetic schemes. These radiolabeled therapeutics were synthesized with highest possible specific radioactivity by separating the free ligand from the radioactive peaks. Also microwave assisted radiolabeling method generated fast and high radiolabeling at low temperature 40° C. Systematic cell uptake and internalization followed by tissue biodistribution studies revealed several important findings.

First, the attachment of p-halobenzyl moiety to the PSMA-targeting Glu-Lys-urea provided high tumor uptake and low non-specific normal tissue binding. Second, the SAR study demonstrated that agents with the macrocyclic chelating agents DOTA-Bn-SCN ($^{177}$Lu-8) and DOTAGA ($^{177}$Lu-9) with four acetate donor arms provided higher tumor uptake and retention compared to the DOTA-monamide chelating agents (e.g., $^{177}$Lu-1) with three acetylate arms. These agents also displayed higher blood plasma binding compared to $^{177}$Lu-1 and also higher initial kidney uptake and much faster kidney clearance compared to $^{177}$Lu-PSMA I&T. Third, compared to a rigid linker, agents with p-bromobenzyl moiety showed higher tumor uptake and retention with the linear linkers (e.g., $^{177}$Lu-1 vs $^{177}$Lu-11 and $^{177}$Lu-9 vs $^{177}$Lu-10). This observation is also reflected in the cell uptake study even though higher amount of internalization was found with cyclohexyl linker bearing $^{177}$Lu-10/$^{177}$Lu-11.

Fourth, attachment of an albumin binding moiety provided longer tumor retention for $^{177}$Lu-14 by increasing serum half-life[43, 44] as recently reported by others. However, as reported by others these agents are associated with significantly higher kidney retention compared to clinical agents $^{177}$Lu-PSMA-617 or $^{177}$Lu-PSMA-I&T. Given that these agents showed distinct characteristics related to Type I agents, these agents are anticipated to display much higher salivary gland and lacrimal gland uptake compared to $^{177}$Lu- PSMA-617 as it was seen for $^{131}$I-MIP1095[2, 12, 13]. The necropsy study revealed that the lacrimal glands could be used as a surrogate organ for these $^{177}$Lu-PSMA agents since severe abnormality in normal organ were seen in the lacrimal glands. Although most preclinical study did not report lacrimal gland uptake, indeed an albumin binding agent CTT1403 displayed high uptake in the lacrimal glands.[22]

Fifth, self-blockading study revealed that [177]Lu-1 with low kidney uptake resulted no significant change in tumor uptake to generate 10-fold kidney blockade while for [177]Lu-9 with high initial kidney uptake resulted significant tumor uptake blockade to generate similar effect. This is an import finding since amino acid-based renal protecting agents such as D-lysine/polyglutamate were shown not to be successful in providing improvement in lowering renal uptake for $^{177}$Lu-PSMA I&T.[45] That result confirmed that uptake in renal proximal tubules cells is partially due to PSMA-expression.[46] While kidney toxicity is not a major issue for $^{177}$Lu-PSMA radionuclide therapy but the blocking strategy can be useful for salivary gland related radiation toxicity for PSMA-based α-particle therapy with [225]Ac-PSMA-617[47] and long-term renal toxicity that obtains often with α-particle-based RPT[31, 48].

5.4 Materials and Methods

Solvents and chemicals purchased from commercial sources were of analytical grade or better and used without further purification. Diisopropylethylamine (DIEA), triethylamine (TEA), lutetium (III) nitrate, N,N,N',N'-Tetramethyl-O—(N-succinimidyl)uronium tetrafluoroborate (TSTU), p-aminomethyl benzoic acid, Boc-5-amino valeric acid, Boc-6-aminohexanoic acid-N-hydroxy succinimide and disuccinimidyl suberate were purchased from Sigma-Aldrich. DOTA-tris(t-butyl ester)-monoacid (B270) and DOTA-NHS-ester (B280) were purchased from Macrocyclics, Inc. (Dallas, Tex.). Carrier-free [$^{177}$Lu]Cl$_3$ (NEZ307000MC) was purchased from PerkinElmer Health Sciences Inc (Shelton, Conn., USA). Analytical thin-layer chromatography (TLC) was performed using Aldrich aluminum-backed 0.2 mm silica gel Z19, 329-1 plates and visualized by ultraviolet light (254 nm), 12 and 1% ninhydrin in EtOH. Flash chromatography was performed using silica gel purchased from Bodman (Aston Pa.), MP SiliTech 32-63 D 60 Å. All experiments were performed in duplicate or triplicate to ensure reproducibility. HPLC purification of non-radiolabeled compounds was performed using a Phenomenex C$_{18}$ Luna 10×250 mm$^2$ column on an Agilent 1260 infinity LC system (Santa Clara, Calif.) and elution with water (0.1% TFA) (A) and CH$_3$CN (0.1% TFA) (B). A gradient HPLC method was employed which contained a mobile phase 88/22 water/CH$_3$CN for 1-5 min followed by 0-5 min water 88/12 water/CH$_3$CN and from 5-25 min 88/22 water/CH$_3$CN to 44/56 water/acetonitrile with flow rate 8 mL/min. $^1$H NMR spectra were recorded on a Bruker Ultrashield™ 500 MHz spectrometer. Chemical shifts (δ) are reported in ppm downfield by reference to proton resonances resulting from incomplete deuteration of the NMR solvent. Low resolution ESI mass spectra were obtained on a Bruker Daltonics Esquire 3000 Plus spectrometer. High resolution mass spectra were obtained by the University of Notre Dame Mass Spectrometry & Proteomics Facility, Notre Dame, Ind. using ESI either by direct infusion on a Bruker micrOTOF-II or by LC elution via an ultra-high pressure Dionex RSLC with C18 column coupled with a Bruker micrOTOF-Q II. The compounds, Di-tert-butyl (((S)-6-((4-bromobenzyl)amino)-1-(tert-butoxy)-1-oxohexan-2-yl)carbamoyl)-L-glutamate, 5a, and Di-tert-butyl (((S)-1-(tert-butoxy)-6-((4-iodobenzyl)amino)-1-oxohexan-2-yl)carbamoyl)-L-glutamate, 5b, were prepared using following a reported method with minor modification.[49] The crude product was purified using C$_{18}$ column chromatography eluting with 70-80% MeOH/H$_2$O to provide 0.90 g (62%) of oily material.

5.4.1 Analytical Data for Representative Compounds

Representative compounds of Formula (I) are provided in Chart 1.

Chart 1:

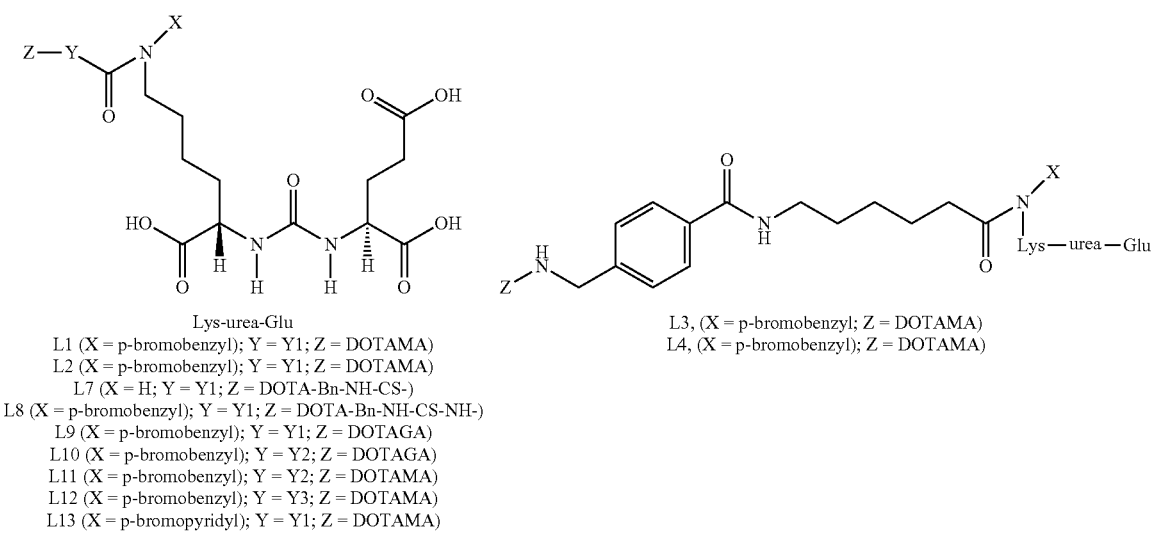

Lys-urea-Glu
L1 (X = p-bromobenzyl); Y = Y1; Z = DOTAMA)
L2 (X = p-bromobenzyl); Y = Y1; Z = DOTAMA)
L7 (X = H; Y = Y1; Z = DOTA-Bn-NH-CS-)
L8 (X = p-bromobenzyl); Y = Y1; Z = DOTA-Bn-NH-CS-NH-)
L9 (X = p-bromobenzyl); Y = Y1; Z = DOTAGA)
L10 (X = p-bromobenzyl); Y = Y2; Z = DOTAGA)
L11 (X = p-bromobenzyl); Y = Y2; Z = DOTAMA)
L12 (X = p-bromobenzyl); Y = Y3; Z = DOTAMA)
L13 (X = p-bromopyridyl); Y = Y1; Z = DOTAMA)

L3, (X = p-bromobenzyl; Z = DOTAMA)
L4, (X = p-bromobenzyl; Z = DOTAMA)

-continued
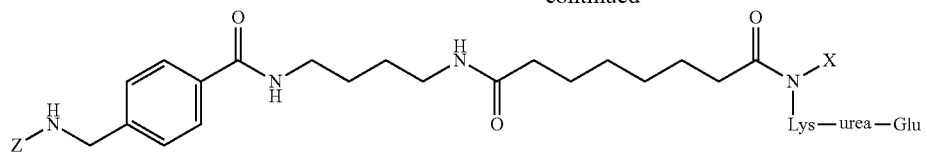
L5, (X = p-bromobenzyl; Z = DOTAMA)
L6, (X = p-bromobenzyl); Z = DOTAMA)
Linker
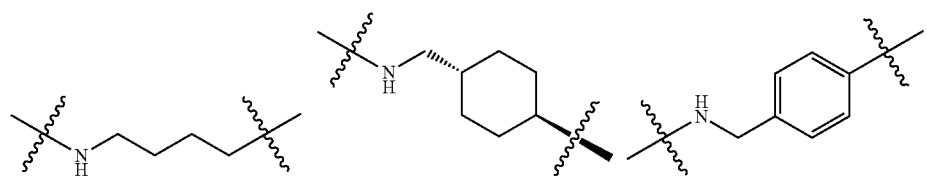
Y1   Y2   Y3
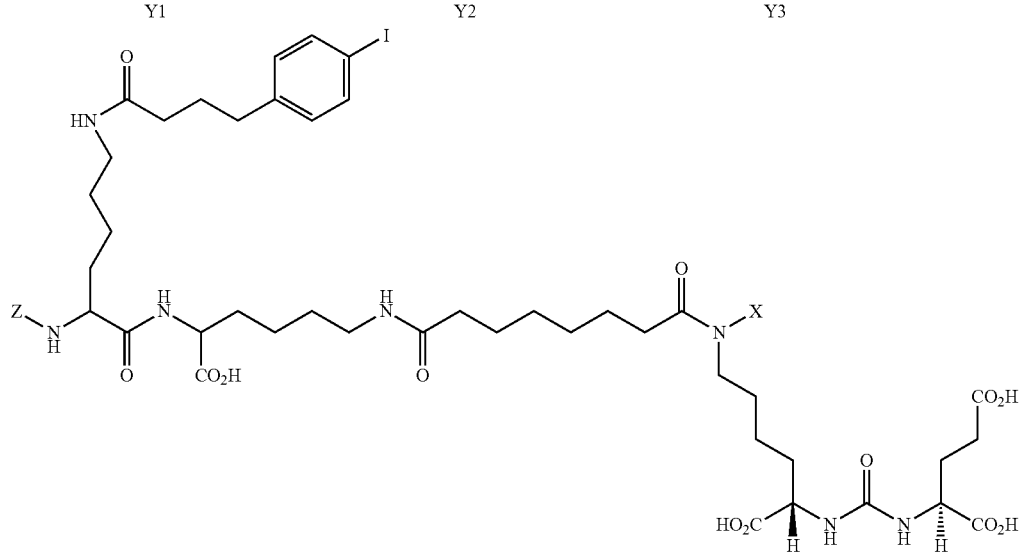
L14 (X = H; Z = DOTAMA)
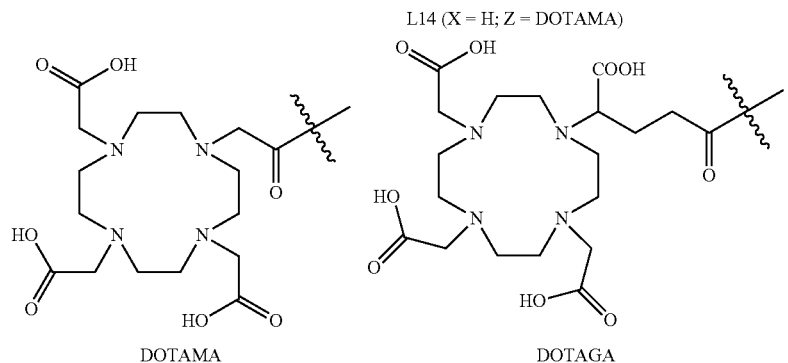
DOTAMA   DOTAGA
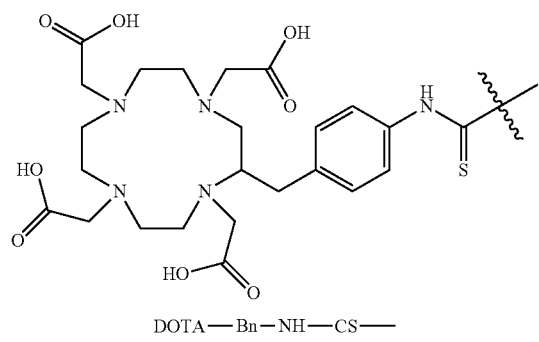
DOTA—Bn—NH—CS—

The following compounds are representative of compounds of Formula (I):
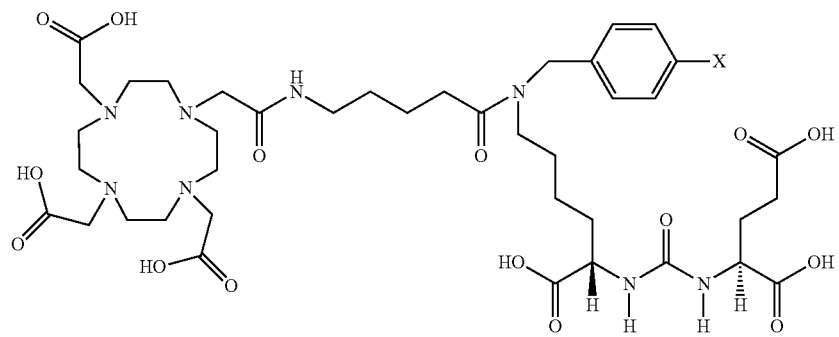
L1, X = Br
L2, X = I
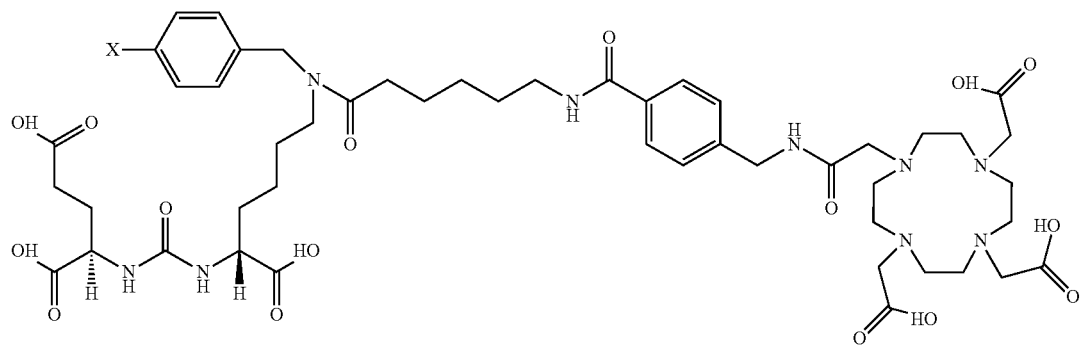
L3, Y = Br
L4, Y = I
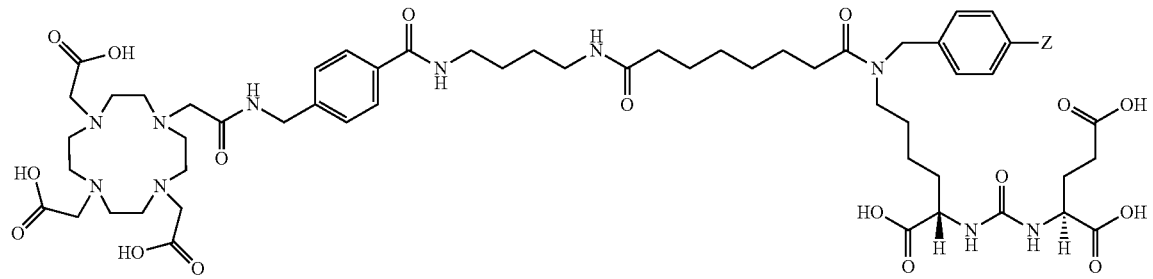
L5, Z = Br
L6, Z = I
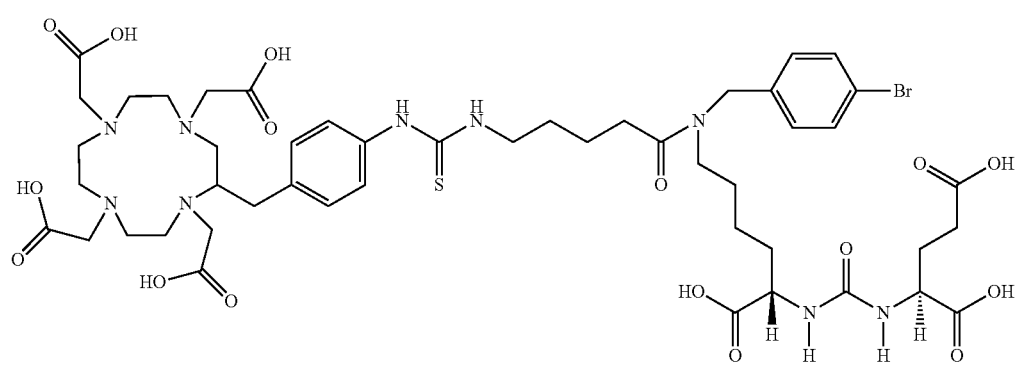
L8

-continued
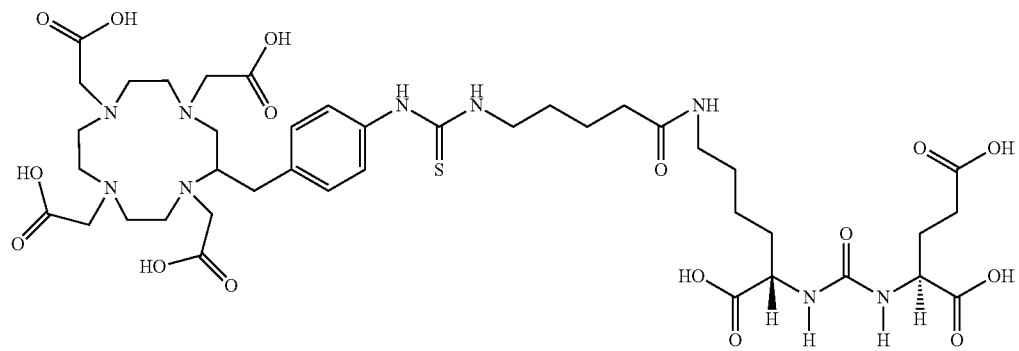
L7
Chemical Formula: C₄₁H₆₃N₉O₁₆S
Exact Mass: 969.41
Molecular Weight: 970.06
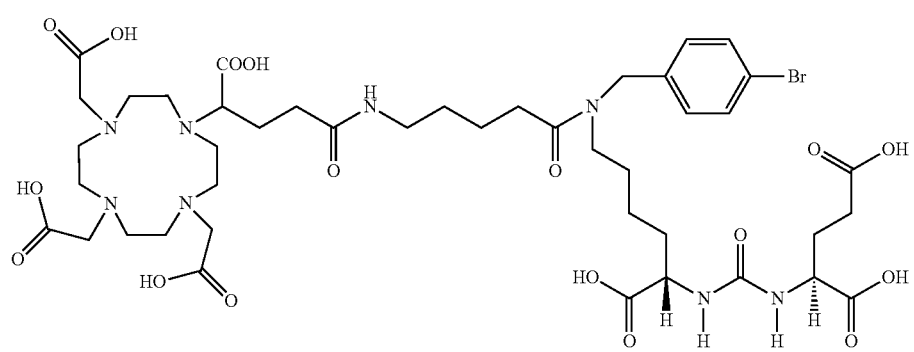
L9
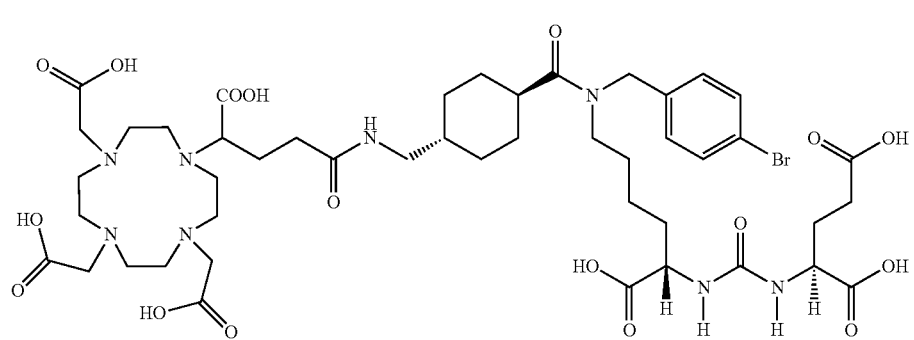
L10
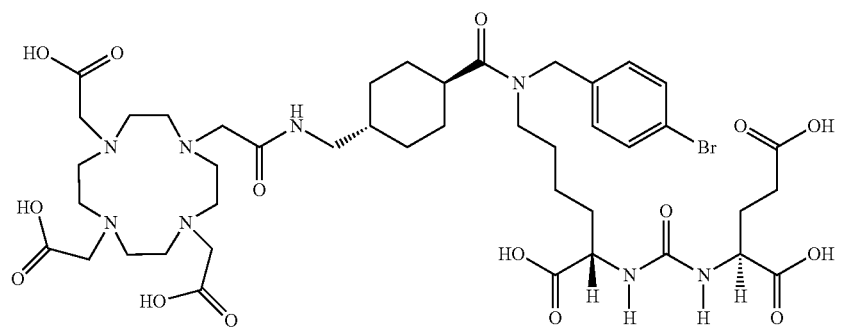
L11

-continued

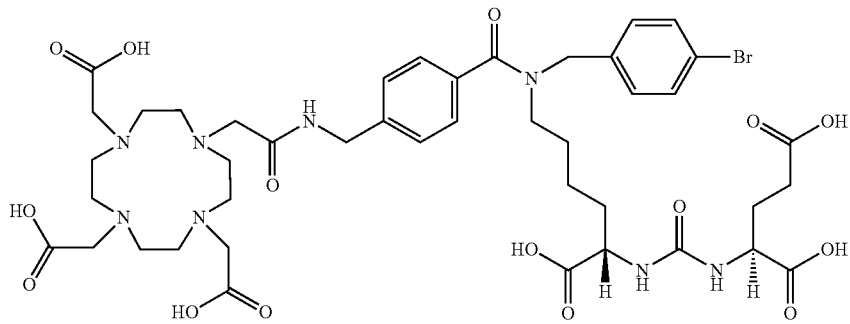
L12

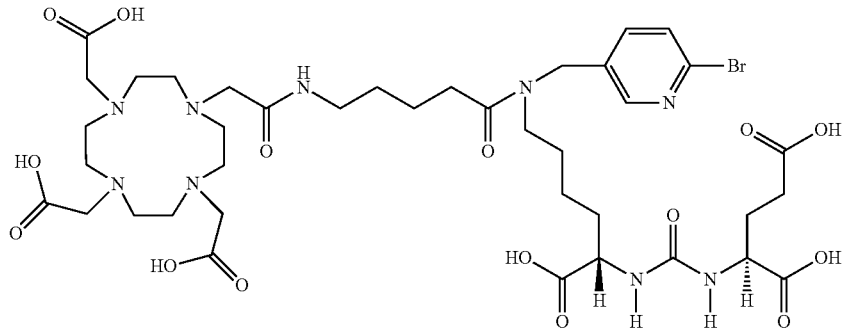
L13

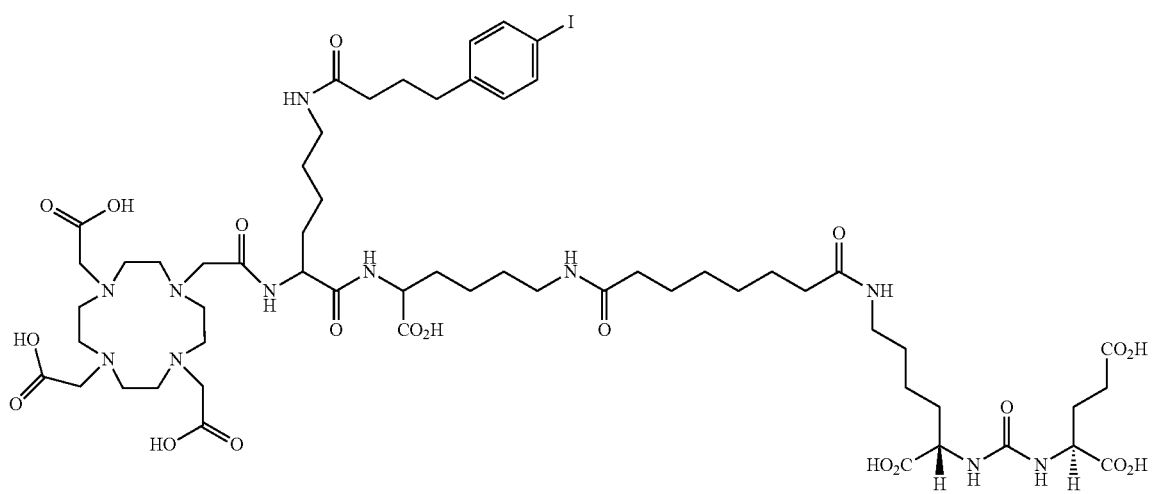
L14

Ligand L1, and L2 were synthesized following a general synthetic route as shown in Scheme 2. A detailed description for L2 is given below.

(14S,18S)-9-(4-Bromobenzyl)-2,8,16-trioxo-1-(4,7,10-tris(carboxymethyl)-1,4,7,10-tetraazacyclododecan-1-yl)-3,9,15,17-tetraazaicosane-14,18,20-tricarboxylic acid (L1)

A mixture of Boc-5-amino valeric acid (0.087 g, 0.40 mmol), TSTU (0.121 g, 0.40 mmol) and DIPEA (0.103 g, 0.80 mmol) were stirred in DMF (1 mL) at RT for 1 h. Compound 1a (0.264 g, 0.40 mmol) was added dropwise after dilution with DMF (1 mL). The reaction mixture was stirred for 4 h, concentrated and purified by $C_{18}$ column chromatography eluting with 100% (in 0.1% TFA) provided 0.151 g (44%) of oily material as compound 2a. $^1$H NMR (500 MHz, DMSO-d6) δ ppm 7.95 (s, 1H), 7.40 (d, J=10 Hz, 1H), 7.34 (d, J=10 Hz, 1H), 7.24 (s, 1H), 7.04 (d, J=5 Hz, 1H), 6.97 (d, J=10 Hz, 1H), 5.48-5.44 (m, 1H), 4.87-4.83 (m, 1H), 4.48-4.36 (m, 2H), 4.26-4.21 (m, 2H), 3.66-3.63 (m, 1H), 3.12-2.95 (m, 4H), 2.90 (s, 1H), 2.81 (s, 1H), 2.73 (s, 2H), 2.33-2.27 (s, 1H), 2.26-2.23 (m, 3H), 2.00-1.98 (m, 1H), 1.77 (m, 1H), 1.66-1.60 (m, 2H), 1.37 (s, 36H), 1.26-1.07 (m, 2H); ESMS m/z: 857.3 (M+H)$^+$. A cold solution of 50% TFA/CH$_2$Cl$_2$ (2 mL) was added to 2a (0.145 g, 0.17 mmol) and stirred at RT for 2 h. The reaction mixture was concentrated and purified by $C_{18}$ column chromatography eluting with 40% acetonitrile/water and lyophilized to provide 0.067 g (67%) of white solid product as compound 3. $^1$H NMR (500 MHz, DMSO-d6) δ ppm 7.55 (d, J=5.0 Hz, 1H), 7.48 (d, J=5.0 Hz, 1H), 7.19-7.15 (m, 2H), 4.62-4.53 (m, 2H), 4.33-4.27 (m, 2H), 3.40 (s, 1H), 2.98-2.92 (m, 2H), 2.83 (s, 1H), 2.56 (s, 1H), 2.44 (s, 3H), 2.16 (bs, 1H), 1.93-1.84 (m, 2H), 1.74 (s, 2H), 1.67-1.60 (m, 5H), 1.41-1.40 (m, 2H); ESMS m/z: 589.1 (M+H)$^+$. A reaction mixture of DOTA-NHS-ester (0.090 g, 0.12 mmol), 3a (0.069 g, 0.08 mmol) and DIPEA (0.102 g, 0.79 mmol) were stirred at RT for 3 h. The reaction mixture was concentrated and purified by HPLC to provide the desired ligand L1. $^1$H NMR (500 MHz, DMSO-d6) δ ppm 12.50 (bs, 5H), 8.38 (bs, 1H), 7.57 (d, J=5 Hz, 1H), 7.51 (d, J=5 Hz, 1H), 7.18-7.12 (m, 2H), 6.55 (bs, 1H), 6.37-6.29 (m, 2H), 4.53 (s, 1H), 4.46 (s, 1H), 4.11-4.04 (m, 3H), 3.80 (bs, 4H), 3.25-2.77 (m, 10H), 2.39-2.37 (m, 2H), 2.27-2.20 (m, 4H), 1.94-1.92 (m, 1H), 1.72-1.63 (m, 2H), 1.65-1.39 (m, 9H), 1.28-1.22 (m, 4H); HRESI-MS: Calcd. for $C_{40}H_{62}BrN_8O_{15}$, 973.3513 [M+H]$^+$, found: 973.3542.

(14S,18S)-9-(4-iodobenzyl)-2,8,16-trioxo-1-(4,7,10-tris(carboxymethyl)-1,4,7,10-tetraazacyclododecan-1-yl)-3,9,15,17-tetraazaicosane-14,18,20-tricarboxylic acid (L2)

Compound L3 was prepared following the same steps as in Scheme 3 by employing 1b as the starting reactant and 2c and 3c as the intermediates. Compound 7c was prepared using the same method as described for 7a, using 5b as the starting material. The crude product was purified using column chromatography eluting with 10% acetone/$CH_2Cl_2$ to provide colorless oily material. $^1$H NMR (500 MHz, DMSO-d6) δ ppm 7.45 (m, 1H), 7.35 (t, J=5 Hz, 1H), 7.29 (m, 1H), 7.21 (m, 1H), 7.15 (d, J=5 Hz, 1H), 5.70 (m, 1H), 4.58-4.47 (m, 1H), 4.35-4.27 (m, 2H), 4.09 (m, 1H), 3.40-3.30 (m, 1H), 3.16-3.08 (m, 2H), 2.80 (s, 2H), 2.41-2.26 (m, 4H), 2.09-2.04 (1H), 1.85-1.80 (m, 1H), 1.75-1.62 (m, 4H), 1.58-1.52 (m, 3H), 1.44 (m, 27H), 1.35 (m, 6H).

Compound 3c was prepared using the same method as described for 3a, using 2c as the starting material. The crude product was purified using HPLC. Spectral data for L2: $^1$H NMR (500 MHz, DMSO-d6) δ ppm 8.39 (bs, 1H), 7.38 (t, J=10 Hz, 1H), 7.31 (m, 1H), 7.21-7.18 (m, 2H), 6.36-6.29 (m, 2H), 4.56-4.50 (m, 2H), 4.11-4.01 (m, 3H), 3.82 (s, 3H), 3.59 (s, 4H), 3.19-3.17 (m, 9H), 3.06 (s, 9H), 2.39 (t, J=5 Hz, 1H), 2.30-2.23 (m, 3H), 1.91 (m, 1H), 1.73 (m, 1H), 1.63-1.39 (m, 8H), 1.24 (m, 2H); HRESI-MS: Calcd. for $C_{40}H_{61}IN_8O_{15}$, 1020.3301 [M+H]$^+$.

(14S,18S)-9-(4-Bromobenzyl)-1,8,16-trioxo-1-(4-((2-(4,7,10-tris(carboxymethyl)-1,4,7,10-tetraazacyclododecan-1-yl)acetamido)methyl)phenyl)-2,9,15,17-tetraazaicosane-14,18,20-tricarboxylic acid (L3)

7b was prepared following the same method as described for 7a and by replacing Boc-5-amino valeric acid by Boc-6-aminohexanoic acid-N-hydroxy succinimide. Yield 0.115 g (46%) of oily material. $^1$H NMR (500 MHz, DMSO-d6) δ ppm 7.41 (d, J=10 Hz, 1H), 7.35 (d, J=10 Hz, 1H), 7.04 (d, J=5 Hz, 1H), 6.97 (d, J=10 Hz, 1H), 5.47 (d, J=10 Hz, 1H), 5.10-5.03 (m, 1H), 4.63-4.56 (m, 1H), 4.44 (s, 1H), 4.39 (s, 1H), 4.27-4.22 (m, 2H), 3.29-3.21 (m, 1H), 3.07-3.01 (m, 5H), 2.30-2.19 (m, 4H), 2.03-1.98 (m, 1H), 1.80-1.75 (m, 1H), 1.66-1.58 (m, 7H), 1.49-1.45 (m, 4H), 1.38 (m, 27H), 1.27-1.04 (m, 5H); ESMS m/z: 871.3 (M+H)$^+$. Compound 3b was prepared using the same method as described for 3a, using 2b as the starting material. The crude product was used as such for next step without further purification. $^1$H NMR (500 MHz, DMSO-d6) δ ppm 7.73 (bs, 3H), 7.76 (d, J=10.0 Hz, 1H), 7.50 (d, J=10.0 Hz, 1H), 7.18-7.14 (m, 2H), 6.34 (m, 2H), 4.53 (s, 1H), 4.46 (m, 2H), 3.22-3.17 (m, 2H), 2.82-2.73 (m, 2H), 2.51 (s, 1H), 2.37 (s, 1H), 2.25 (m, 2H), 1.93 (s, 1H), 1.74-1.71 (m, 1H), 1.64 (m, 6H), 1.35-1.33 (m, 1H), 1.25 (s, 4H); ESMS in/z: 603.2 (M+H)$^+$. A reaction mixture of 4 (0.065 g, 0.08 mmol), 3b (0.047 g, 0.08 mmol) and DIPEA (0.101 g, 0.80 mmol) were stirred in DMSO (1 mL) at RT for 3 h. The reaction mixture was concentrated and purified by HPLC. $^1$H NMR (500 MHz, DMSO-d6) δ ppm 12.65 (brs, 5H), 8.42-8.39 (m, 1H), 7.84-7.81 (m, 2H), 7.56 (d, J=10.0 Hz, 1H), 7.49 (d, J=10.0 Hz, 1H), 7.38 (d, J=5.0 Hz, 2H), 7.17-7.12 (m, 2H), 6.36-6.30 (m, 2H), 4.53 (m, 3H), 4.46-4.40 (m, 5H), 4.10-3.98 (m, 9H), 3.63 (bs, 5H), 3.26-3.14 (m, 13H), 2.38 (m, 2H), 2.31-2.20 (m, 3H), 1.93-1.92 (m, 1H), 1.72-1.71 (m, 1H), 1.63-1.41 (m, 8H), 1.34 (m, 1H), 1.25 (brs, 3H); HRESI-MS: Calcd. for $C_{49}H_{71}BrN_9O_{16}$, 1120.4197 [M+H]$^+$, found: 1120.4200.

(14S,18S)-9-(4-Iodobenzyl)-1,8,16-trioxo-1-(4-((2-(4,7,10-tris(carboxymethyl)-1,4,7,10-tetraazacyclododecan-1-yl)acetamido)methyl)phenyl)-2,9,15,17-tetraazaicosane-14,18,20-tricarboxylic acid (L4)

The intermediate compound 2d was prepared following the same method as described for 2a by replacing Boc-5-amino valeric acid by Boc-6-aminohexanoic acid-N-hydroxy succinimide and also replacing 1a by 1b as a reactant. Spectral data for 2d. $^1$H NMR (500 MHz, DMSO-d6) δ ppm 7.66 (brs, 1H), 7.61 (d, J=10 Hz, 1H), 7.55 (d, J=10 Hz, 1H), 7.15 (brs, 1H), 6.90 (d, J=5 Hz, 1H), 6.84 (d, J=10 Hz, 1H), 5.30 (m, 1H), 5.09-5.03 (m, 1H), 4.63-4.58 (m, 1H), 4.43 (s, 1H), 4.39-4.35 (m, 1H), 4.26-4.20 (m, 3H), 3.07-3.00 (m, 3H), 2.30-2.22 (m, 5H), 2.00-1.98 (m, 1H), 1.80-1.74 (m, 2H), 1.70-1.64 (m, 3H), 1.62-1.61 (m, 2H), 1.38 (s, 36H), 1.32-1.09 (m 3H); ESMS m/z: 917.3 (M+H)$^+$. Spectral data for 3d. $^1$H NMR (500 MHz, DMSO-d6) δ ppm 7.87 (d, J=10 Hz, 1H), 7.72 (d, J=10 Hz, 1H), 7.66 (d, J=10 Hz, 1H), 7.30 (d, J=10 Hz, 1H), 7.04-6.99 (m, 1H), 4.59-4.51 (m, 1H), 4.32-4.25 (m, 3H), 3.69-3.66 (m, 1H), 3.38-3.35 (m, 1H), 3.09 (m, 1H), 2.96-2.89 (m, 1H), 2.51-2.45 (m, 1H), 2.43-2.39 (m, 3H), 2.17-2.14 (m, 1H), 1.91-1.72 (m, 2H), 1.71-1.62 (m, 6H), 1.45-1.28 (m, 8H); ESMS m/z: 649.2 (M+H)$^+$. Spectral data for L4. $^1$H NMR (500 MHz, DMSO-d6) δ ppm 9.16 (bs, 4H), 8.41 (m, 4H), 7.82 (t, J=10.0 Hz, 2H), 7.72 (d, J=10.0 Hz, 1H), 7.66 (d, J=10.0 Hz, 1H), 7.37 (d, J=10.0 Hz, 2H), 7.01 (d, J=5.0 Hz, 2H), 6.37-6.30 (m, 2H), 4.44-4.39 (m, 8H), 4.11-3.97 (m, 9H), 3.66-3.61 (m, 5H), 3.16-3.08 (m, 13H), 2.30 (m, 1H), 2.29-2.20 (m, 2H), 1.94-1.92 (m, 1H), 1.71 (m, 1H), 1.66-1.64 (m, 2H), 1.55-1.47 (m, 8H); HRESI-MS: Calcd. for $C_{49}H_{71}IN_9O_{16}$, 1168.4058 [M+H]$^+$, found: 1168.4045.

(21S,25S)-16-(4-Bromobenzyl)-1,8,15,23-tetraoxo-1-(4-((2-(4,7,10-tris(carboxymethyl)-1,4,7,10-tetraazacyclododecan-1-yl)acetamido)methyl)phenyl)-2,7,16,22,24-pentaazaheptacosane-21,25,27-tricarboxylic acid (L5)

Ligand L5 was prepared following a multi-step organic synthesis method as depicted in Scheme 4. A solution of 1a (0.190 g, 0.29 mmol), Et$_3$N (0.029 g, 0.29 mmol) and DMF (1 mL) was added dropwise to a stirred solution of disuccinimidyl suberate (0.223 g, 0.61 mmol) in DMF (1 mL). The reaction mixture was stirred overnight, concentrated and purified by flash column chromatography eluting with 30% acetonitrile/$CH_2Cl_2$ provided 0.120 g (46%) of oily material. ESMS m/z: 911.3 (M+H)$^+$. Compound 8 was prepared using the same method as described for 10. The crude product was purified by column chromatography eluting with 40-60% acetonitrile/$CH_2Cl_2$ to provide 0.090 g (40%) of oily material. $^1$H NMR (500 MHz, CDCDMSOd6) δ ppm 7.70 (brs, 1H), 7.62 (d, J=5.0 Hz, 1H), 7.55 (d, J=10.0 Hz, 1H), 6.91 (d, J=5.0 Hz, 1H), 6.85 (d, J=5.0 Hz, 1H), 5.41 (d, J=5.0 Hz, 1H), 5.33 (d, J=10.0 Hz, 1H), 5.09-5.02 (m, 1H), 4.45-4.35 (m, 2H), 4.25-4.19 (m, 3H), 3.41-3.34 (m, 1H), 3.12-3.05 (m, 2H), 2.57-2.50 (m, 2H), 2.31-2.18 (m, 5H), 1.97 (m, 1H), 1.86-1.77 (m, 3H), 1.71-1.63 (m, 5H), 1.57-1.46 (m, 5H), 1.37 (m, 27H); ESMS m/z: 957.2 (M+H)$^+$. Compound 12 was prepared using the same method as described for 3a. The crude product was purified by C-18 column chromatography eluting with 40-50% acetonitrile/water to provide 0.057 g (58%) of product. ESMS m/z: 743.2 (M+H)$^+$. Compound L6 was prepared using the same method as described for L1, using compounds 1a and 12 as the starting material. The reaction mixture was concentrated and purified by HPLC. $^1$H NMR (500 MHz, DMSO-d6) δ ppm 8.97 (brs, 1H), 8.43 (t, J=5.0 Hz, 1H), 7.83 (d, J=10.0 Hz, 2H), 7.78-7.73 (m, 1H), 7.56 (d, J=10.0 Hz, 1H), 7.50 (d, J=10.0 Hz, 2H), 7.38 (d, J=10.0 Hz, 2H), 7.17-7.14 (m, 2H), 6.36-6.30 (m, 2H), 4.52-4.39 (m, 8H), 4.09-4.00 (m, 6H), 3.65-3.60 (m, 5H), 3.26-3.08 (m, 11H), 3.07-3.04 (m, 3H), 2.36-2.33 (m, 1H), 2.27-2.22 (m, 2H), 2.06-2.01 (m, 2H), 1.93-1.92 (m, 1H), 1.73-1.64 (m, 2H), 1.51-1.43 (m, 11H), 1.26-1.19 (m, 6H); HRESI-MS: Calcd. for $C_{55}H_{82}BrN_{10}O_{17}$, 1233.5037 [M+H]$^+$, found: 1233.5029.

(21S,25S)-16-(4-Iodobenzyl)-1,8,15,23-tetraoxo-1-(4-((2-(4,7,10-tris(carboxymethyl)-1,4,7,10-tetraazacyclododecan-1-yl)acetamido)methyl)phenyl)-2,7,16,22,24-pentaazaheptacosane-21,25,27-tricarboxylic acid (L6)

Compound L7 was prepared using the same method as described for L5. The crude product was purified by HPLC. $^1$H NMR (500 MHz, DMSO-d6) δ ppm 8.97 (brs, 1H), 8.43 (t, J=5.0 Hz, 1H), 7.83 (d, J=10.0 Hz, 2H), 7.78-7.72 (m, 2H), 7.67 (d, J=5, 1H), 7.55 (bs, 1H), 7.39 (d, J=10.0 Hz, 2H), 7.03-6.99 (m, 2H), 6.36-6.30 (m, 2H), 4.52-4.39 (m, 4H), 4.11-4.00 (m, 6H), 3.64 (m, 4H), 3.26-3.04 (m, 14H), 2.35-2.33 (m, 1H), 2.27-2.22 (m, 3H), 2.20-2.01 (m, 2H), 1.93-1.92 (m, 1H), 1.73-1.62 (m, 2H), 1.51-1.43 (m, 11H), 1.26-1.19 (m, 6H); HRESI-MS: Calcd. for $C_{55}H_{82}IN_{10}O_{17}$, 1281.4899 [M+H]$^+$, found: 1281.4889.

(13S,17S)-8-(4-bromobenzyl)-7,15-dioxo-1-((4-((1,4,7,10-tetrakis(carboxymethyl)-1,4,7,10-tetraazacyclododecan-2-yl)methyl)phenyl)amino)-1-thioxo-2,8,14,16-tetraazanonadecane-13,17,19-tricarboxylic acid (L8)

p-SCN-Bn-DOTA (12.2 mg, 17.7 μmol) was added to a stirred solution of 5a (12.2 mg) and DIPEA (15.2 μL, 87.0 umol) in DMSO (130 μL) equilibrated to 40° C. Reaction mixture was stirred at 40° C. for four hours and stored at 4° C. overnight. Reaction mixture was purified by reverse phase HPLC (hold 20% ACN for 5 min, then 20-40% over 19 minutes). R$_t$ approximately 12 minutes. Purified fractions were combined, rotoevaporated to decrease volume, and then lyopholized. ESI-MS: 1138.37 [M+H]$^+$, found: 1138.5. The compound 1 was further purified by HPLC with gradient method The HPLC method is a gradient method containing a mobile phase 88% water (containing 0.1% TFA) and 22% CH$_3$CN (0.1% TFA) for 1-5 min followed by 0-5 min water 88% water (containing 0.1% TFA) and 12% CH$_3$CN (0.1% TFA), and from 5-25 min 88% water to 44% water and 12% acetonitrile to 56% acetonitrile with flow rate 8 mL/min.

(13S,17S)-7,15-dioxo-1-((4-((1,4,7,10-tetrakis(carboxymethyl)-1,4,7,10-tetraazacyclododecan-2-yl)methyl)phenyl)amino)-1-thioxo-2,8,14,16-tetraazanonadecane-13,17,19-tricarboxylic acid (L7) p-SCN-Bn-DOTA (8.0 mg, 11.6 umol) was added to a stirred solution of 5a and DIPEA (10.1 uL, 58 umol) in DMSO (150 uL) equilibrated to 40° C. Reaction mixture was stirred at 40° C. for four hours followed by cooled to room temperature, dilution with water and finally was purified by reverse phase HPLC (hold 12% ACN for 5 min, then 12-32% over 20 minutes). R$_t$ approximately 12 minutes. Purified fractions were combined, evaporated to reduce volume, and then lyopholized. M/Z calcd, 970.41. M/Z found, 970.4. ESI-MS: 970.05[M+H]$^+$, found: 970.1.

(3S,7S)-12-(4-Bromobenzyl)-5,13,19-trioxo-22-(4,7,10-tris(carboxymethyl)-1,4,7,10-tetraazacyclododecan-1-yl)-4,6,12,18-tetraazadocosane-1,3,7,22-tetracarboxylic acid (L9)

A suspension of DOTA-GA anhydride (0.087 g, 0.19 mmol), 8a (0.075 g, 0.13 mmol) and DIPEA (0.066 g, 0.51 mmol) sonicated at room temperature for 1 h then stirred further for 2 h at room temperature. The reaction mixture was concentrated and purified via HPLC. ESMS m/z: 1047.2 (M+H)$^+$. $^1$H NMR (500 MHz, DMSO-d6) δ ppm 12.66 (bs, 4H), 7.86-7.82 (m, 1H), 7.56 (d, J=10 Hz, 1H), 7.50 (d, J=10 Hz, 1H), 7.15 (m, 2H), 6.34-6.29 (m, 2H), 4.52 (s, 1H), 4.45 (s, 2H), 4.12-4.04 (m, 5H), 3.50 (m, 4H), 3.29 (m, 3H), 3.19 (m, 3H), 3.07-2.90 (m, 8H), 2.38 (m, 3H), 2.25 (m, 3H), 1.94-1.90 (m, 3H), 1.71 (m, 2H), 1.53-1.43 (m, 6H), 1.42 (m, 1H), 1.41-1.23 (m, 3H); ESMS m/z: 1047.2 (M+H)$^+$. HRESI-MS: Calcd. for $C_{43}H_{65}BrN_8O_{17}$, 1047.3714 [M+H]$^+$, found: 1045.3705.

((((1S)-5-((1R,4r)-N-(4-bromobenzyl)-4-((4-carboxy-4-(4,7,10-tris(carboxymethyl)-1,4,7,10-tetraazacyclododecan-1-yl)butanamido)methyl)cyclohexane-1-carboxamido)-1-carboxypentyl)carbamoyl)-L-glutamic acid (L11) (VK03-51)

A mixture of trans-4-(Fmoc-aminomethylcyclohexanecarboxylic acid) (0.069 g, 0.18 mmol), TSTU (0.055 g, 0.18 mmol) and DIPEA (0.064 g, 0.50 mmol) were stirred in DMF (1 mL) at RT for 1 h. Compound 5a (0.110 g, 0.17 mmol) was added dropwise after dilution with DMF (1 mL). The reaction mixture was stirred for 4 h, concentrated and purified by silica gel chromatography eluting with 2% MeOH/CH$_2$Cl$_2$ to provide 0.90 g (52.94%) of oily product. $^1$H NMR (500 MHz, CDCl$_3$) δ ppm 8.02 (s, 1H), 7.78 (d, J=5.0 Hz, 3H), 7.60 (d, J=10.0 Hz, 3H), 7.41 (t, J=10.0 Hz, 4H), 7.33 (d, J=10.0 Hz, 3H), 7.08 (m, 1H), 4.79 (m, 1H), 4.46 (m, 3H), 4.22 (m, 3H), 3.15 (m, 1H), 3.08 (m, 2H), 2.81 (s, 1H), 2.59 (t, J=10.0 Hz, 1H), 2.32 (in, 1H), 2.20 (s, 2H), 2.08 (m, 1H), 1.85 (m, 4H), 1.60-1.44 (m, 27H), 1.26 (s, 1H), 1.05-0.88 (m, 3H). The oily product was then dissolved in a solution of 20% piperidine/DMF and stirred for 3 h at RT under N$_2$. The reaction mixture was concentrated and chromatographed using 10% MeOH/CH$_2$Cl$_2$ as eluent to provide 0.030 g (yield=42.8%) of product. ESMS m/z: 795.2 (M+H)$^+$. The product (0.030 g, 0.04 mmol) was the added in a suspension of DOTA-GA anhydride (0.028 g, 0.05 mmol in 1 mL), and DIPEA (0.024 g, 0.18 mmol) and was sonicated at rt for 1 h followed by stirring for 2 h at RT. The reaction mixture was concentrated and purified via Sep-Pak column using 70-80% ACN/H$_2$O as eluent. ESMS m/z: 1253.4 (M+H)$^+$.

(((S)-5-(N-(4-Bromobenzyl)-4-((2-(4,7,10-tris(carboxymethyl)-1,4,7,10-tetraazacyclododecan-1-yl)acetamido)methyl)benzamido)-1-carboxypentyl)carbamoyl)-L-glutamic acid (L12)

L1 was synthesized following a multi-step organic synthesis as described in Scheme 2. To a solution of DOTA-tBu-ester, 1 (0.4 g, 0.5 mmol in 7 mL DMF) was added p-aminomethyl benzoic acid (0.076 g, 0.5 mmol) and the solution was stirred overnight at room temperature. The resultant solution was evaporated under high vacuum. The solid residue was dissolved in 20/80 acetonitrile/water and was purified by a C$_{18}$ SepPak column. The product was eluted with 60/40 and 50/50 and 40/60 acetonitrile/water fractions. The fractions were combined together and evaporated followed by lyophilization to provide a colorless solid. Yield: 0.36 g (80%). ESMS m/z: 706.5 (M+H)$^+$. To a solution of the compound 2 (0.2 g, 0.29 mmol in DMF) was added TSTU (0.1 g, 0.34 mmol) and DMAP (0.17 g, 0.1 mmol) and was stirred overnight at room temperature. The solution was evaporated under high vacuum. The solid residue was dissolved in 20/80 acetonitrile/water and was purified by a C$_{18}$ SepPak column. The product, compound 3, was eluted with 50/50 and 40/60 acetonitrile/water fractions and was lyophilized to obtain a colorless solid. Yield: 0. 23 g, 90%, ESMS m/z: 802.96 (M+H)$^+$. Compound 3 (0.2 g, 0.23 mmol) was with dissolved in ice-cold TFA/CH$_2$Cl$_2$ (1:1) and stirred overnight stirring for 18 h. The reaction mixture was concentrated and purified by C$_{18}$ column chromatography eluting with 50-60% acetonitrile/water to obtain 4 in good yield (0.16 g, ~60%) after lyphilization. $^1$H NMR (500 MHz, DMSO-d$_6$) δ ppm 9.03 (bs, 1H), 8.09 (d, J=10.0 Hz, 2H), 7.93 (d, J=10.0 Hz, 1H), 7.59 (d, J=5.0 Hz, 3H), 7.43 (d, J=10.0 Hz, 1H), 4.49 (m, 3H), 4.04-3.99 (m, 6H), 3.66 (m, 5H), 2.91 (s, 6H), 2.09 (s, 1H), 1.54 (s, 3H), 1.23 (s, 1H); ESMS m/z: 635.3 (M+H)$^+$. Compound 6 was synthesized by adding 4 (0.200 g, 0.36 mmol) and 5a$^{49}$ (0.050 g, 0.16 mmol) in DMSO (1 mL) followed by addition of DIPEA (0.406 g, 3.65 mmol) and the reaction mixture was stirred at RT for overnight. The crude product was concentrated and used without further purification. A cold solution of 50% TFA/CH$_2$Cl$_2$ (2 mL) was added to 6 (0.050 g, 0.04 mmol) and stirred at RT for 2 h. The reaction mixture was concentrated and purified by HPLC to obtain the final product L1 in good yield. $^1$H NMR (500 MHz, DMSO-d6) δ ppm 12.80 (brs, 3H), 8.94 (s, 1H), 7.56 (m, 3H), 7.38-7.34 (m, 4H), 7.15 (m, 1H), 6.35 (d, J=10 Hz, 2H), 4.64 (m, 4H), 4.43-4.39 (m, 5H), 4.13-3.99 (m, 7H), 3.63 (bs, 4H), 3.14 (m, 9H), 2.37-2.18 (m, 2H), 1.95-1.89 (m, 1H), 1.74-1.68 (m, 1H), 1.55-1.49 (m, 3H), 1.39-1.30 (m, 2H), 1.05 (m, 1H); HRESI-MS: Calcd. for C$_{43}$H$_{60}$BrN$_8$O$_{15}$, 1007.3356 [M+H]$^+$, found: 1007.3367.

(14S,18S)-9-((6-Bromopyridin-3-yl)methyl)-2,8,16-trioxo-1-(4,7,10-tris(carboxymethyl)-1,4,7,10-tetraazacyclododecan-1-yl)-3,9,15,17-tetraazaicosane-14,18,20-tricarboxylic acid (L13) (VK02-112)

$^1$H NMR (500 MHz, DMSO-d$_6$) δ ppm 7.21 (m, 1H), 7.13 (m, 2H), 6.12 (bs, 1H), 5.90 (bs, 1H), 4.29 (s, 1H), 4.19-4.15 (m, 2H), 3.26 (m, 1H), 2.93 (m, 2H), 2.34-2.23 (m, 3H), 2.07-2.02 (m, 1H), 1.82-1.76 (m, 1H), 1.70-1.64 (m, 3H), 1.56-1.53 (m, 1H), 1.43-1.37 (m, 27H), 1.27 (d, J=5 Hz, 2H); ESMS m/z: 657.2 (M+H)$^+$. Product was purified using 70-90% ACN/H$_2$O on C-18 Sep-Pak column. $^1$H NMR (500 MHz, DMSO-d$_6$) δ ppm 8.25 (s, 1H), 7.49 (m, 1H), 7.43 (m, 1H), 5.95 (m, 1H), 5.36 (m, 1H), 4.80 (s, 1H), 4.51 (m, 2H), 4.36-4.33 (m, 3H), 3.24-3.09 (m, 5H), 2.40-2.29 (m, 6H), 2.10-2.05 (m, 2H), 1.85-1.76 (m, 3H), 1.72-1.66 (m, 3H), 1.60-1.36 (m, 36H); ESMS m/z: 856.3 (M+H)$^+$. Product was purified on silica gel using 3% MeOH/CH$_2$Cl$_2$ as eluent. Yield 17.4% Product was purified using 50-60% ACN/H$_2$O on C-18 Sep-Pak column. Yield 82.6% $^1$H NMR (500 MHz, DMSO-d$_6$) δ ppm 8.27 (s, 1H), 7.80 (m, 1H), 7.26-7.13 (m, 1H), 6.41-6.36 (m, 1H), 4.48 (dd, J=2.0, 1.5 Hz, 1H), 4.11 (m, 2H), 3.23 (m, 1H), 2.79 (bs, 2H), 2.42 (s, 1H), 2.33-2.21 (m, 3H), 1.94 (m, 1H), 1.75-1.65 (m, 2H), 1.57-1.42 (m, 6H), 1.28-1.23 (m, 3H), 1.10 (dd, J=5, 2.5, 1.5 Hz, 1H); ESMS m/z: 588.2 (M+H)$^+$.

(3S,7S,26S,29R)-38-(4-iodophenyl)-5,13,20,28,35-pentaoxo-29-(2-(4,7,10-tris(carboxymethyl)-1,4,7,10-tetraazacyclododecan-1-yl)acetamido)-4,6,12,21,27,34-hexaazaoctatriacontane-1,3,7,26-tetracarboxylic acid (L14) (SR—IX-14 A)

5.4.2 Radiolabeling and Serum Stability

For each radiolabeling reaction, approximately 1 nmol of radioligand per mCi of $^{177}$Lu in 200 mM NaOAc (pH 4-5) was heated in a microwave for 5 min at 95° C. and power 40 w. The reaction solution was diluted with 300 μL water. Complexation was monitored by injecting aliquots of 20-40 μL of the solution onto the HPLC. The radiolabeled product [$^{177}$Lu]X was obtained in ~98% radiochemical yield and the radiochemical purity was >99%. All radiolabeled compounds were purified using a Phenomenex C$_{18}$ Luna 10×250 mm$^2$ column and a Agilent Prostar System (Palo Alto, Calif.), equipped with a Varian ProStar 325 UV-Vis variable wavelength detector and a Bioscan (Poway, Calif.) Flow count in-line radioactivity detector, all controlled by Galaxie software. Flow rate was 1 mL/min with water (0.1% TFA) (A) and CH$_3$CN (0.1% TFA) (B) as the eluting solvents. To ensure uniform purity isocratic solution was used to separate excess ligand from the radiolabeled compound. The specific radioactivity was calculated as the ratio of the radioactivity eluting at the retention time of product during the preparative HPLC purification to the mass corresponding to the area under the curve of the UV absorption. The purity of tested compounds as determined by analytical HPLC with absorbance at 254 nm was >95%.

HPLC methods and HPLC chromatograms of radiolabeled were obtained (data not shown). The specific activity of the compounds was >37 MBq/nmol (n>12). The acidic eluate was neutralized with 50 μL 1 M Na$_2$CO$_3$ solution and the volume of the eluate was reduced under vacuum to dryness. The solid residue was diluted with saline and 2 μl of ascorbic acid (200 mg/mL) to the desired radioactivity concentration for all biological studies including biodistribution, imaging and treatment studies. Radiolabeling yield was also assessed using Silica Gel instant TLC (ITLC) with 10 mM diethylenetriaminepentaacetic acid (DTPA) at the mobile phase. Three microliters of the diluted sample were spotted on an ITLC silica gel strip and allowed to develop in a chromatography chamber. Upon completion of the migration to the solvent front, the ITLC sample strips were allowed to dry, cut in half, and counted on a Wallac Wizard γ-counter (Perkin-Elmer, Boston, Mass.) to determine the radiolabeling yield. Radiochemical purity was assessed via high-performance liquid chromatography (HPLC) analysis.

5.4.3 Cell Lines

Sublines of the androgen-independent PC3 human prostate cancer cell line, originally derived from an advanced androgen independent bone metastasis, were used. Those sublines have been modified to express high levels of PSMA [PSMA-positive (+) PC3 PIP] or are devoid of target [PSMA-negative (−) PC3 flu]. They were generously provided by Dr. Warren Heston (Cleveland Clinic). Cells were grown in RPMI 1640 medium (Corning Cellgro, Manassas, Va.) containing 10% fetal bovine serum (FBS) (Sigma-Aldrich, St. Louis, Mo.) and 1% penicillin-streptomycin (Corning Cellgro, Manassas, Va.). PSMA+ PC3 PIP cells were grown in the presence of 20 µg/mL of puromycin to maintain PSMA expression. All cell cultures were maintained in an atmosphere containing 5% carbon dioxide ($CO_2$), at 37.0° C. in a humidified incubator.

5.4.4 Determination of Cell Uptake and Internalization

Cell uptake studies were performed as previously reported.[50] Cells (1 million) were incubated with 37 kBq/mL (1 µCi/mL) of each radiolabeled agent in the growth medium in 6-well plates. To determine specific cell uptake, cells were pre-blocked with ZJ43 to a final concentration of 10 µM. Cellular uptake was terminated by washing with 1 mL of ice-cold PBS. After incubation at 37° C. for 20 min and 60 min, cells were washed with binding buffer, trypsinized using nonenzymatic buffer, and cell-associated activity was determined in a γ-spectrometer (1282 Compugamma CS; Pharmacia/LKB Nuclear, Inc.). For internalization assays, cells were detached using nonenzymatic buffer, and aliquots of 1 million cells per tube were incubated with 37 kBq (1 µCi) of each radiolabeled agent per milliliter for 1, 2, 4 and 24 h at 37° C. Assuming minimal receptor endocytosis at 4° C., the internalization assay was performed only with cells incubated at 37° C. At 1, 2, 4 and 24 h interval, the medium was removed and cells were washed once with binding buffer followed by a mild acidic buffer (50 mM glycine, 150 mM NaCl [pH 3.0]) at 4° C. for 5 min. Then the acidic buffer was collected, and cells were washed twice with binding buffer. Pooled washes (containing cell surface-bound $^{177}$Lu-labeled agent) and cell pellets (containing internalized $^{177}$Lu-labeled) were counted in an automated γ-counter along with the standards. All of the radioactivity values were converted into percentage of incubated dose (% ID) per million cells. Experiments were performed in triplicate and repeated 3 times. Data were fitted according to linear regression analysis using PRIZM software.

5.4.5 Biodistribution

Mice bearing PSMA(+) PC3 PIP and PSMA(−) PC3 flu tumor xenografts were injected via the tail vein with 1.11-1.85 MBq (30-50 µCi) of $^{177}$Lu—X in 150 µL of saline (n=4). At 10 min, 30 min, 60 min and 120 min post-injection, mice were sacrificed by cervical dislocation and the blood was immediately collected by cardiac puncture. The heart, lungs, liver, stomach, pancreas, spleen, fat, kidney, muscle, small and large intestines, urinary bladder, PSMA(+) PC3 PIP and PSMA(−) PC3 flu tumors were collected. Each organ was weighed, and the tissue radioactivity was measured with an automated gamma counter (1282 Compugamma CS, Pharmacia/LKBNuclear, Inc., Mt. Waverly, Vic. Australia). The percentage of injected dose per gram of tissue (% ID/g) was calculated by comparison with samples of a standard dilution of the initial dose. All measurements were corrected for decay.

5.4.6 Blood Plasma Protein Binding Studies and Metabolism In Vivo

Mice (n=2/group) were administered with $^{177}$Lu-1 and $^{177}$Lu-9 radiotracers (3.7 mBq in 150 µL saline) via intravenous tail vein injections. Mice were killed 2 h post-administration. Blood was collected in heparinized tubes and centrifuged (5 minutes, 1700 g) for plasma isolation. Plasma samples (50 µL) were transferred to an ultrafiltration device [Centrifree ultrafiltration device (Millipore Sigma, USA)], and centrifuged to separate proteins. Samples of the filtrate and protein fraction were measured in the gamma counter. Additionally, ITLC was performed to evaluate radiotracer stability in the soluble blood fraction.

5.4.7 Small Animal SPECT/CT Imaging

Selected radiotracers ($^{177}$Lu-1 and $^{177}$Lu-14) were imaged using the same xenograft models (n=2) bearing both PSMA(+) PC3 PIP and PSMA(−) PC3 flu tumor bearing model as used for the biodistribution studies. SPECT-CT imaging for the radiotherapeutic were performed using only PSMA(+) PC3 PIP tumor bearing mouse. Mice were anesthetized using 1% isoflurane gas in oxygen flowing at 0.6 L/min prior to and during radiopharmaceutical injection.

Mice were injected via the tail vein with approximately 37 MBq (1 mCi) or 111 MBq (3 mCi, for the treatment study) of $^{177}$Lu—X formulated in 150 µL of saline, pH 7. After allowing for 2 h of radiopharmaceutical uptake, anesthetized mice were placed on the scanner gantry and secured with medical tape while the anesthetic flow was increased to 0.8 L/min. Body temperature of the mice was maintained by covering them with several layers of Chux disposable pads and illumination with a dissection lamp during scanning. Single-pinhole median-energy (PHME) collimators with aperture size of 1.0 mm, and stepwise rotation for 64 projection angles in a full 360° rotation, 45 s increments were used for SPECT imaging. The radius of rotation (ROR) was set at 6.5 cm, which provided a field of view of 7.5 cm to cover the mouse body from head to bladder. A CT 14 scan was performed prior to scintigraphy for both anatomical coregistration and attenuation correction. A total of 512 projections were acquired in a 2-min continuous rotation mode covering a full 3600 rotation. Data were reconstructed and fused using commercial software from the vendor (GammaMedica). Data were analyzed using AMIDE software.

5.4.8 Tumor Radiopharmaceutical Therapy

Antitumor efficacy studies were performed in PC3 PIP flank tumor growth delay model to evaluate the therapeutic efficacy of a single dose intravenous injection of $^{177}$Lu-L1, $^{177}$Lu-L3, $^{177}$Lu-L5 and $^{177}$Lu-PSMA-617 vs. saline. This was a head-to-head comparison study and same batch of tumor-bearing mice and radioactivity. The study was commenced 14-18 days post-inoculation of the xenografts, when all the mice had tumor volume of about ~60-85 mm$^3$ (Table 8). All the living mice were monitored for 8 weeks to monitor the growth delay. Mice body weight and tumor volume were monitored every 3 days throughout the experiment. Endpoint criteria defined by the institute ACUC was weight loss≥15%, a tumor volume>1800 mm³, active ulceration of the tumor or abnormal behavior indicating pain or unease. After 8-weeks, three mice from each group were submitted for detail necropsy and blood analysis. Mice group treated with $^{177}$Lu-1 and $^{177}$Lu-PSMA-617 were continued to monitor until the endpoint. These definitions were also used for Kaplan-Meier analysis. The probability of reaching 5 times the initial tumor volume was characterized using Kaplan-Meier curves, and comparison was performed using the log-rank test. The formula used for calculation of tumor volume was V=width²×length/2. Toxicity of the $^{177}$Lu-treatment groups after 8-weeks and in healthy CD-1 (n=3) mice treated with 111 MBq was evaluated by pathologic examination at the Johns Hopkins Pathology Core facility with serum metabolic panel, blood counts, and full necropsy including detailed histopathology of kidneys, salivary glands and lacrimal glands.

5.4.9 Data Analysis

Data are expressed as mean±standard deviation (SD). Prism software (GraphPAD, San Diego, Calif.) was used to determine statistical significance. Statistical significance was calculated using a paired t test. A P-value<0.05 was considered significant.

5.5 References

1. Kiess, A. P.; Banerjee, S. R.; Mease, R. C.; Rowe, S. P.; Rao, A.; Foss, C. A.; Chen, Y.; Yang, X.; Cho, S. Y.; Nimmagadda, S.; Pomper, M. G. Prostate-specific membrane antigen as a target for cancer imaging and therapy. *Quarterly journal of nuclear medicine and molecular imaging* 2015, 59, 241-68.
2. Haberkorn, U.; Eder, M.; Kopka, K.; Babich, J. W.; Eisenhut, M. New Strategies in Prostate Cancer: Prostate-Specific Membrane Antigen (PSMA) Ligands for Diagnosis and Therapy. *Clinical cancer research* 2016, 22, 9-15.
3. Sterzing, F.; Kratochwil, C.; Fiedler, H.; Katayama, S.; Habl, G.; Kopka, K.; Afshar-Oromieh, A.; Debus, J.; Haberkorn, U.; Giesel, F. L. (68)Ga-PSMA-11 PET/CT: a new technique with high potential for the radiotherapeutic management of prostate cancer patients. *Eur J Nucl Med Mol Imaging* 2016, 43, 34-41.
4. Rowe, S. P.; Macura, K. J.; Ciarallo, A.; Mena, E.; Blackford, A.; Nadal, R.; Antonarakis, E. S.; Eisenberger, M. A.; Carducci, M. A.; Ross, A. E.; Kantoff, P. W.; Holt, D. P.; Dannals, R. F.; Mease, R. C.; Pomper, M. G.; Cho, S. Y. Comparison of Prostate-Specific Membrane Antigen-Based 18F-DCFBC PET/CT to Conventional Imaging Modalities for Detection of Hormone-Naïve and Castration-Resistant Metastatic Prostate Cancer. *Journal of nuclear medicine* 2016, 57, 46-53.
5. Benesova, M.; Schafer, M.; Bauder-Wust, U.; Afshar-Oromieh, A.; Kratochwil, C.; Mier, W.; Haberkorn, U.; Kopka, K.; Eder, M. Preclinical Evaluation of a Tailor-Made DOTA-Conjugated PSMA Inhibitor with Optimized Linker Moiety for Imaging and Endoradiotherapy of Prostate Cancer. *Journal of Nuclear Medicine* 2015, 56, 914-20.
6. Herrmann, K.; Bluemel, C.; Weineisen, M.; Schottelius, M.; Wester, H. J.; Czernin, J.; Eberlein, U.; Beykan, S.; Lapa, C.; Riedmiller, H.; Krebs, M.; Kropf, S.; Schirbel, A.; Buck, A. K.; Lassmann, M. Biodistribution and radiation dosimetry for a probe targeting prostate-specific membrane antigen for imaging and therapy. *Journal of nuclear medicine* 2015, 56, 855-61.
7. Weineisen, M.; Schottelius, M.; Simecek, J.; Baum, R. P.; Yildiz, A.; Beykan, S.; Kulkarni, H. R.; Lassmann, M.; Klette, I.; Eiber, M.; Schwaiger, M.; Wester, H. J. 68Ga- and 177Lu-labeled PSMA I&T: Optimization of a PSMA targeted theranostic concept and first proof of concept human studies. *Journal of nuclear medicine* 2015, 56, 1169-76.
8. Kratochwil, C.; Giesel, F. L.; Eder, M.; Afshar-Oromieh, A.; Benesova, M.; Mier, W.; Kopka, K.; Haberkorn, U. [(1)(7)(7)Lu]Lutetium-labelled PSMA ligand-induced remission in a patient with metastatic prostate cancer. *Eur J Nucl Med Mol Imaging* 2015, 42, 987-8.
9. Afshar-Oromieh, A.; Hetzheim, H.; Kratochwil, C.; Benesova, M.; Eder, M.; Neels, O. C.; Eisenhut, M.; Kubler, W.; Holland-Letz, T.; Giesel, F. L.; Mier, W.; Kopka, K.; Haberkorn, U. The Theranostic PSMA Ligand PSMA-617 in the Diagnosis of Prostate Cancer by PET/CT: Biodistribution in Humans, Radiation Dosimetry, and First Evaluation of Tumor Lesions. *Journal of Nuclear Medicine* 2015, 56, 1697-1705.
10. Soydal, C.; Ozkan, E.; Akyurek, S.; Kucuk, N. O. Marked Response to 177Lu Prostate-Specific Membrane Antigen Treatment in Patient With Metastatic Prostate Cancer. *Clinical nuclear medicine* 2016, 41, 159-60.
11. Baum R. P., K., H. R., Schuchardt C., Singh A., Weineisen M., Wiessalla S., Schottelius M., Mueller D., Klette I., Wester H.-J. Lutetium-177 PSMA Radioligand Therapy of Metastatic Castration-Resistant Prostate Cancer: Safety and Efficacy. *Journal of nuclear medicine* 2016, In Press.
12. Hillier, S.; Rubino, K.; Maresca, K.; Marquis, J.; Tesson, M.; Zimmerman, C.; Eckelman, W.; Mairs, R.; Joyal, J.; Babich, J. [131I]MIP-1466, a small molecule prostate-specific membrane antigen (PSMA) inhibitor for targeted radiotherapy of prostate cancer (PCa). *Journal of nuclear medicine meeting abstract* 2012, 53, 170.
13. Zechmann, C. M.; Afshar-Oromieh, A.; Armor, T.; Stubbs, J. B.; Mier, W.; Hadaschik, B.; Joyal, J.; Kopka, K.; Debus, J.; Babich, J. W.; Haberkorn, U. Radiation dosimetry and first therapy results with a (124)I/(131)I-labeled small molecule (MIP-1095) targeting PSMA for prostate cancer therapy. *Eur J Nucl Med Mol Imaging* 2014, 41, 1280-92.
14. Haberkorn, U.; Afshar-Oromieh, A.; Giesel, F.; Kopka, K.; Eder, M.; Babich, J.; Kratochwil, C. P8.01PSMA ligands for diagnosis and therapy of prostate cancer. *Annals of Oncology* 2015, 26, ii33.
15. Trover, J. K.; Beckett, M. L.; Wright, G. L. Detection and characterization of the prostate-specific membrane antigen (PSMA) in tissue extracts and body fluids. *International Journal of Cancer* 1995, 62, 552-558.
16. Ray Banerjee, S.; Pullambhatla, M.; Foss, C. A.; Falk, A.; Byun, Y.; Nimmagadda, S.; Mease, R. C.; Pomper, M. G. Effect of chelators on the pharmacokinetics of (99m)Tc-labeled imaging agents for the prostate-specific membrane antigen (PSMA). *Journal of medicinal chemistry* 2013, 56, 6108-21.
17. Banerjee, S. R.; Pullambhatla, M.; Foss, C. A.; Nimmagadda, S.; Ferdani, R.; Anderson, C. J.; Mease, R. C.; Pomper, M. G. (6)(4)Cu-labeled inhibitors of prostate-specific membrane antigen for PET imaging of prostate cancer. *Journal of medicinal chemistry* 2014, 57, 2657-69.
18. Eder, M.; Schaefer, M.; Bauder-Wuest, U.; Hull, W.-E.; Waengler, C.; Mier, W.; Haberkorn, U.; Eisenhut, M. 68Ga-Complex Lipophilicity and the Targeting Property of a Urea-Based PSMA Inhibitor for PET Imaging. *Bioconjugate Chemistry* 2012, 23, 688-697.
19. Afshar-Oromieh, A.; Haberkorn, U.; Schlemmer, H. P.; Fenchel, M.; Eder, M.; Eisenhut, M.; Hadaschik, B. A.; Kopp-Schneider, A.; Rothke, M. Comparison of PET/CT and PET/MRI hybrid systems using a 68Ga-labelled PSMA ligand for the diagnosis of recurrent prostate cancer: initial experience. *Eur J Nucl Med Mol Imaging* 2014, 41, 887-97.
20. Afshar-Oromieh, A.; Avtzi, E.; Giesel, F.; Holland-Letz, T.; Linhart, H.; Eder, M.; Eisenhut, M.; Boxler, S.; Hadaschik, B.; Kratochwil, C.; Weichert, W.; Kopka, K.; Debus, J.; Haberkorn, U. The diagnostic value of PET/CT imaging with the 68Ga-labelled PSMA ligand HBED-CC in the diagnosis of recurrent prostate cancer. *European Journal of Nuclear Medicine and Molecular Imaging* 2015, 42, 197-209.
21. Banerjee, S. R.; Foss, C. A.; Castanares, M.; Mease, R. C.; Byun, Y.; Fox, J. J.; Hilton, J.; Lupold, S. E.; Kozikowski, A. P.; Pomper, M. G. Synthesis and evaluation of technetium-99m- and rhenium-labeled inhibitors of the prostate-specific membrane antigen (PSMA). *Journal of medicinal chemistry* 2008, 51, 4504-17.
22. Choy, C. J.; Ling, X.; Geruntho, J. J.; Beyer, S. K.; Latoche, J. D.; Langton-Webster, B.; Anderson, C. J.; Berkman, C. E. (177)Lu-Labeled Phosphoramidate-Based PSMA Inhibitors: The Effect of an Albumin Binder on Biodistribution and Therapeutic Efficacy in Prostate Tumor-Bearing Mice. *Theranostics* 2017, 7, 1928-1939.
23. Benesova, M.; Umbricht, C. A.; Schibli, R.; Muller, C. Albumin-Binding PSMA Ligands: Optimization of the Tissue Distribution Profile. *Mol Pharm* 2018, 15, 934-946.
24. Umbricht, C. A.; Benesova, M.; Schibli, R.; Muller, C. Preclinical Development of Novel PSMA-Targeting Radioligands: Modulation of Albumin-Binding Properties To Improve Prostate Cancer Therapy. *Mol Pharm* 2018.
25. Kelly, J.; Amor-Coarasa, A.; Ponnala, S.; Nikolopoulou, A.; Williams, C., Jr.; Schlyer, D.; Zhao, Y.; Kim, D.; Babich, J. W. Trifunctional PSMA-targeting constructs for prostate cancer with unprecedented localization to LNCaP tumors. *Eur J Nucl Med Mol Imaging* 2018.
26. Banerjee, S. R.; Foss, C. A.; Pullambhatla, M.; Wang, Y.; Srinivasan, S.; Hobbs, R. F.; Baidoo, K. E.; Brechbiel, M. W.; Nimmagadda, S.; Mease, R. C.; Sgouros, G.; Pomper, M. G. Preclinical evaluation of 86Y-labeled inhibitors of prostate-specific membrane antigen for dosimetry estimates. *Journal of nuclear medicine* 2015, 56, 628-34.
27. Kulkarni, H. R.; Singh, A.; Schuchardt, C.; Niepsch, K.; Sayeg, M.; Leshch, Y.; Wester, H. J.; Baum, R. P. PSMA-Based Radioligand Therapy for Metastatic Castration-Resistant Prostate Cancer: The Bad Berka Experience Since 2013. *Journal of nuclear medicine* 2016, 57, 97s-104s.
28. Hillier, S. M.; Kern, A. M.; Maresca, K. P.; Marquis, J. C.; Eckelman, W. C.; Joyal, J. L.; Babich, J. W. 123I-MIP-1072, a small-molecule inhibitor of prostate-specific membrane antigen, is effective at monitoring tumor response to taxane therapy. *Journal of nuclear medicine* 2011, 52, 1087-93.
29. Chen, Y.; Pullambhatla, M.; Foss, C. A.; Byun, Y.; Nimmagadda, S.; Senthamizhchelvan, S.; Sgouros, G.; Mease, R. C.; Pomper, M. G. 2-(3-{1-Carboxy-5-[(6-[18F]fluoro-pyridine-3-carbonyl)-amino]-pentyl}-ureido)-pen tanedioic acid, [18F]DCFPyL, a PSMA-based PET imaging agent for prostate cancer. *Clinical cancer research* 2011, 17, 7645-53.
30. Chen, Y.; Foss, C. A.; Byun, Y.; Nimmagadda, S.; Pullambahatla, M.; Fox, J. J.; Castanares, M.; Lupold, S. E.; Babich, J. W.; Mease, R. C.; Pomper, M. G. Radiohalogenated Prostate-Specific Membrane Antigen (PSMA)-Based Ureas as Imaging Agents for Prostate Cancer. *Journal of Medicinal Chemistry* 2008, 51, 7933-7943.
31. Kiess, A. P.; Minn, I.; Vaidyanathan, G.; Hobbs, R. F.; Josefsson, A.; Shen, C.; Brummet, M.; Chen, Y.; Choi, J.; Koumarianou, E.; Baidoo, K.; Brechbiel, M. W.; Mease, R. C.; Sgouros, G.; Zalutsky, M. R.; Pomper, M. G. (2S)-2-(3-(1-Carboxy-5-(4-211At-Astatobenzamido)Pentyl)Ureido)-Pentanedioic Acid for PSMA-Targeted alpha-Particle Radiopharmaceutical Therapy. *Journal of nuclear medicine* 2016, 57, 1569-1575.
32. Szabo, Z.; Mena, E.; Rowe, S.; Plyku, D.; Nidal, R.; Eisenberger, M.; Antonarakis, E.; Fan, H.; Dannals, R.; Chen, Y.; Mease, R.; Vranesic, M.; Bhatnagar, A.; Sgouros, G.; Cho, S.; Pomper, M. Initial Evaluation of [18F]DCFPyL for Prostate-Specific Membrane Antigen (PSMA)-Targeted PET Imaging of Prostate Cancer. *Molecular Imaging and Biology* 2015, 1-10.
33. Muller, C.; Struthers, H.; Winiger, C.; Zhernosekov, K.; Schibli, R. DOTA conjugate with an albumin-binding entity enables the first folic acid-targeted $^{177}$Lu-radionuclide tumor therapy in mice. *J Nucl Med* 2013, 54, 124-31.
34. Tykvart, J.; Schimer, J.; Barinkova, J.; Pachl, P.; Postova-Slavetinska, L.; Majer, P.; Konvalinka, J.; Sacha, P. Rational design of urea-based glutamate carboxypeptidase II (GCPII) inhibitors as versatile tools for specific drug targeting and delivery. *Bioorganic & medicinal chemistry* 2014, 22, 4099-108.
35. Banerjee, S. R.; Pullambhatla, M.; Byun, Y.; Nimmagadda, S.; Foss, C. A.; Green, G.; Fox, J. J.; Lupold, S. E.; Mease, R. C.; Pomper, M. G. Sequential SPECT and optical imaging of experimental models of prostate cancer with a dual modality inhibitor of the prostate-specific membrane antigen. *Angewandte Chemie International Edition* 2011, 50, 9167-70.
36. Banerjee, S. R.; Pullambhatla, M.; Byun, Y.; Nimmagadda, S.; Green, G.; Fox, J. J.; Horti, A.; Mease, R. C.; Pomper, M. G. 68Ga-labeled inhibitors of prostate-specific membrane antigen (PSMA) for imaging prostate cancer. *Journal of medicinal chemistry* 2010, 53, 5333-41.
37. Banerjee, S. R.; Pullambhatla, M.; Byun, Y.; Nimmagadda, S.; Foss, C. A.; Green, G.; Fox, J. J.; Lupold, S. E.; Mease, R. C.; Pomper, M. G. Sequential SPECT and Optical Imaging of Experimental Models of Prostate Cancer with a Dual Modality Inhibitor of the Prostate-Specific Membrane Antigen. *Angewandte Chemie* 2011, 50, 9167-70.
38. Banerjee, S. R.; Pullambhatla, M.; Shallal, H.; Lisok, A.; Mease, R. C.; Pomper, M. G. A modular strategy to prepare multivalent inhibitors of prostate-specific membrane antigen (PSMA). *Oncotarget* 2011, 2, 1244-53.
39. Chen, Y.; Dhara, S.; Banerjee, S. R.; Byun, Y.; Pullambhatla, M.; Mease, R. C.; Pomper, M. G. A low molecular weight PSMA-based fluorescent imaging agent for cancer. *Biochemical and biophysical research communications* 2009, 390, 624-9.
40. Chen, Y.; Pullambhatla, M.; Banerjee, S. R.; Byun, Y.; Stathis, M.; Rojas, C.; Slusher, B. S.; Mease, R. C.; Pomper, M. G. Synthesis and biological evaluation of low molecular weight fluorescent imaging agents for the prostate-specific membrane antigen. *Bioconjug Chem* 2012, 23, 2377-85.

41. Ray Banerjee, S.; Pullambhatla, M.; Foss, C. A.; Falk, A.; Byun, Y.; Nimmagadda, S.; Mease, R. C.; Pomper, M. G. Effect of chelators on the pharmacokinetics of (99m)Tc-labeled imaging agents for the prostate-specific membrane antigen (PSMA). *J Med Chem* 2013, 56, 6108-21.

42. Shallal, H. M.; Minn, I.; Banerjee, S. R.; Lisok, A.; Mease, R. C.; Pomper, M. G. Heterobivalent agents targeting PSMA and integrin-alphavbeta3. *Bioconjug Chem* 2014, 25, 393-405.

43. Dennis, M. S.; Jin, H.; Dugger, D.; Yang, R.; McFarland, L.; Ogasawara, A.; Williams, S.; Cole, M. J.; Ross, S.; Schwall, R. Imaging tumors with an albumin-binding Fab, a novel tumor-targeting agent. *Cancer research* 2007, 67, 254-61.

44. Dennis, M. S.; Zhang, M.; Meng, Y. G.; Kadkhodayan, M.; Kirchhofer, D.; Combs, D.; Damico, L. A. Albumin binding as a general strategy for improving the pharmacokinetics of proteins. *The Journal of biological chemistry* 2002, 277, 35035-43.

45. Chatalic, K. L.; Heskamp, S.; Konijnenberg, M.; Molkenboer-Kuenen, J. D.; Franssen, G. M.; Clahsen-van Groningen, M. C.; Schottelius, M.; Wester, H. J.; van Weerden, W. M.; Boerman, O. C.; de Jong, M. Towards Personalized Treatment of Prostate Cancer: PSMA I&T, a Promising Prostate-Specific Membrane Antigen-Targeted Theranostic Agent. *Theranostics* 2016, 6, 849-61.

46. Chang, S. S. Overview of Prostate-Specific Membrane Antigen. *Reviews in Urology* 2004, 6, S13-S18.

47. Kratochwil, C.; Bruchertseifer, F.; Rathke, H.; Bronzel, M.; Apostolidis, C.; Weichert, W.; Haberkorn, U.; Giesel, F. L.; Morgenstern, A. Targeted Alpha Therapy of mCRPC with 225Actinium-PSMA-617: Dosimetry estimate and empirical dose finding. *Journal of Nuclear Medicine* 2017.

48. Song, H.; Hobbs, R. F.; Vajravelu, R.; Huso, D. L.; Esaias, C.; Apostolidis, C.; Morgenstern, A.; Sgouros, G. Radioimmunotherapy of breast cancer metastases with alpha-particle emitter 225Ac: comparing efficacy with 213Bi and 90Y. *Cancer Res* 2009, 69, 8941-8.

49. Tykvart, J.; Schimer, J.; Bařinková, J.; Pachl, P.; Poštová-Slavětínská, L.; Majer, P.; Konvalinka, J.; Šácha, P. Rational design of urea-based glutamate carboxypeptidase II (GCPII) inhibitors as versatile tools for specific drug targeting and delivery. *Bioorganic & Medicinal Chemistry* 2014, 22, 4099-4108.

50. Ray Banerjee, S.; Chen, Z.; Pullambhatla, M.; Lisok, A.; Chen, J.; Mease, R. C.; Pomper, M. G. Preclinical Comparative Study of (68)Ga-Labeled DOTA, NOTA, and HBED-CC Chelated Radiotracers for Targeting PSMA. *Bioconjugate chemistry* 2016, 27, 1447-55.

REFERENCES

All publications, patent applications, patents, and other references mentioned in the specification are indicative of the level of those skilled in the art to which the presently disclosed subject matter pertains. All publications, patent applications, patents, and other references (e.g., websites, databases, etc.) mentioned in the specification are herein incorporated by reference in their entirety to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

International PCT Patent Application No. PCT/US2008/007947 to Pomper, M. G., Ray, S., Mease, R. C., Foss, C. for Labeled inhibitors of prostate specific membrane antigen (PSMA), biological evaluation, and use as imaging agents, published 2008 Dec. 31 (WO 2009/002529 A2);

International PCT Patent Application No. PCT/US2008/013158 to Chandran S. S., Ray S., Denmeade S. R., Pomper M. G., Mease R. C. for Prostate specific membrane antigen targeted nanoparticles for therapy of prostate cancer, published 2009 Jun. 4 (WO 2009070302 A1);

International PCT Patent Application Publication No. PCT/US2010/028020 to Pomper M. G., Mease R. C.; Ray S., Chen Y. for PSMA-targeting compounds and uses thereof, published 2010 Sep. 23 (WO 2010108125 A2);

Banerjee, S. R., Foss, C. A., Pullambhatla, M., Wang, Y., Srinivasan, S., Hobbs, R. F., Baidoo, K. E., Brechbiel, M. W., Nimmagadda, S., Mease, R. C., Sgouros, G., and Pomper, M. G. (2015) Preclinical evaluation of 86Y-labeled inhibitors of prostate-specific membrane antigen for dosimetry estimates. *Journal of nuclear medicine* 56, 628-34;

Banerjee, S. R., Pullambhatla, M., Byun, Y., Nimmagadda, S., Green, G., Fox, J. J., Horti, A., Mease, R. C., and Pomper, M. G. (2010) 68Ga-labeled inhibitors of prostate-specific membrane antigen (PSMA) for imaging prostate cancer. *J Med Chem* 53, 5333-5341;

Banerjee, S. R., Pullambhatla, M., Byun, Y., Nimmagadda, S., Foss, C. A., Green, G., Fox, J. J., Lupold, S. E., Mease, R. C., and Pomper, M. G. (2011) Sequential SPECT and optical imaging of experimental models of prostate cancer with a dual modality inhibitor of the prostate-specific membrane antigen. *Angewandte Chemie International Edition* 50, 9167-9170;

Banerjee, S. R., Pullambhatla, M., Shallal, H., Lisok, A., Mease, R. C., and Pomper, M. G. (2011) A modular strategy to prepare multivalent inhibitors of prostate-specific membrane antigen (PSMA). *Oncotarget* 2, 1244-1253;

Ray Banerjee, S., Pullambhatla, M., Foss, C. A., Falk, A., Byun, Y., Nimmagadda, S., Mease, R. C., and Pomper, M. G. (2013) Effect of chelators on the pharmacokinetics of (99m)Tc-labeled imaging agents for the prostate-specific membrane antigen (PSMA). *J Med Chem* 56, 6108-6121;

Banerjee, S. R., Pullambhatla, M., Foss, C. A., Nimmagadda, S., Ferdani, R., Anderson, C. J., Mease, R. C., and Pomper, M. G. (2014) (6)(4)Cu-labeled inhibitors of prostate-specific membrane antigen for PET imaging of prostate cancer. *J Med Chem* 57, 2657-2669;

Ray Banerjee, S., Chen, Z., Pullambhatla, M., Lisok, A., Chen, J., Mease, R. C., and Pomper, M. G. (2016) Preclinical Comparative Study of (68)Ga-Labeled DOTA, NOTA, and HBED-CC Chelated Radiotracers for Targeting PSMA. *Bioconjug Chem* 27, 1447-1455;

Benesova, M., Schafer, M., Bauder-Wust, U., Afshar-Oromieh, A., Kratochwil, C., Mier, W., Haberkorn, U., Kopka, K., and Eder, M. (2015) Preclinical Evaluation of a Tailor-Made DOTA-Conjugated PSMA Inhibitor with Optimized Linker Moiety for Imaging and Endoradiotherapy of Prostate Cancer. *Journal of nuclear medicine* 56, 914-20;

Tykvart, J., Schimer, J., Jancarik, A., Barinkova, J., Navratil, V., Starkova, J., Sramkova, K., Konvalinka, J., Majer, P., and Sacha, P. (2015) Design of Highly Potent Urea-Based, Exosite-Binding Inhibitors Selective for Glutamate Carboxypeptidase II. *Journal of medicinal chemistry* 58, 4357-63;

Weineisen, M., Simecek, J., Schottelius, M., Schwaiger, M., and Wester, H.-J. (2014) Synthesis and preclinical evaluation of DOTAGA-conjugated PSMA ligands for functional imaging and endoradiotherapy of prostate cancer. *EJNMMI Res* 4, 1-15.

Although the foregoing subject matter has been described in some detail by way of illustration and example for purposes of clarity of understanding, it will be understood by those skilled in the art that certain changes and modifications can be practiced within the scope of the appended claims.

The invention claimed is:

1. A compound of Formula (I):

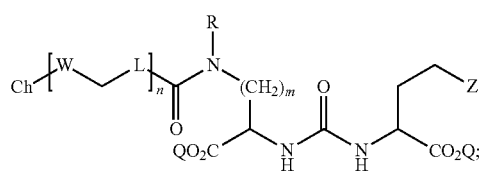

(I)

wherein:
Z is tetrazole or $CO_2Q$;
Q is H or a protecting group;
m is an integer selected from the group consisting of 1, 2, 3, 4, and 5;
R is $-CH_2-R^1$;

$R^1$ is:

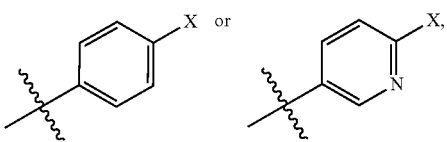

wherein each X is independently Br or I;
L consists of a $C_1$-$C_6$ alkylene linker;
W is $-(C=O)-NR^2-$;
$R^2$ is H or a $C_1$-$C_4$ alkyl;
n is 1;
Ch is a chelating agent having a structure of:

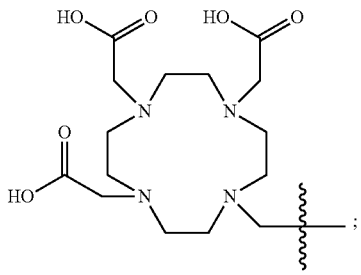 [SMILES: *CN1CCN(CC(=O)O)CCN(CC(=O)O)CCN(CC(=O)O)CC1]

that comprises a radiometal selected from the group consisting of $^{212}Pb$, $^{225}Ac$, $^{213}Bi$, and $^{203}Pb$;
and pharmaceutically acceptable salts thereof.

2. The compound of claim 1, wherein the compound of Formula (I) is selected from the group consisting of:

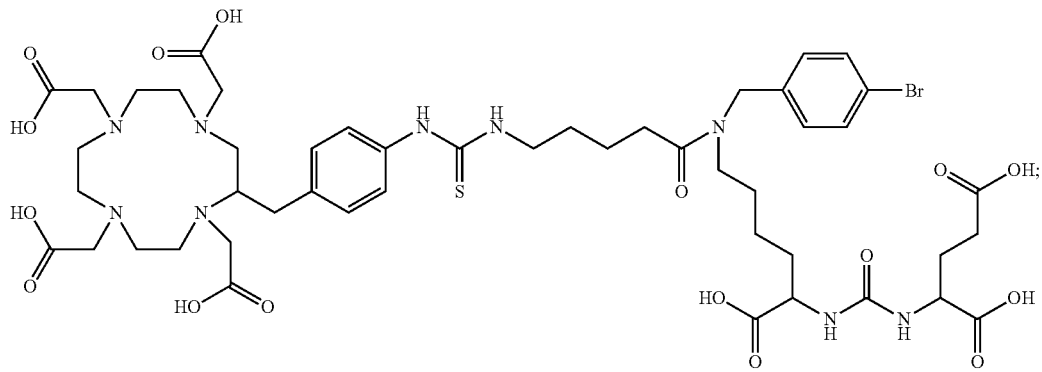

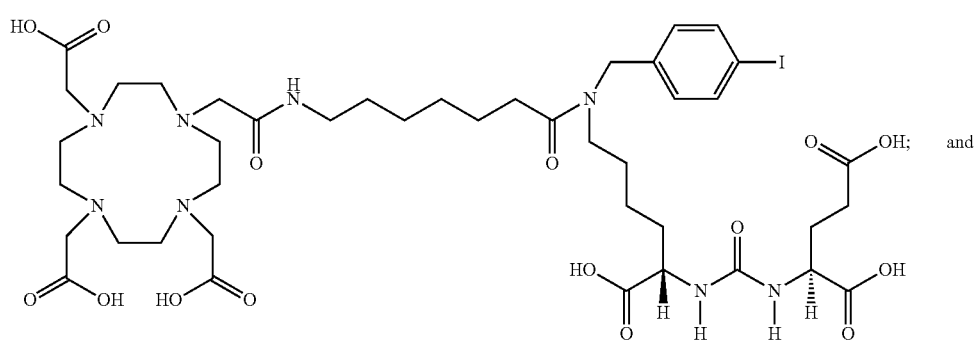

and

P2

-continued

P2

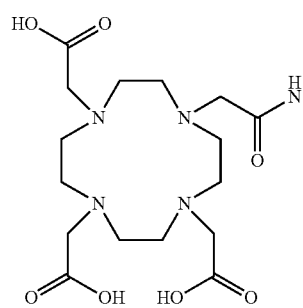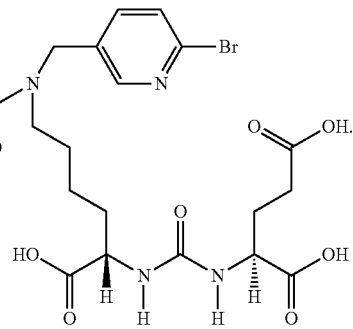

3. A method for treating one or more PSMA expressing tumors or cells, the method comprising contacting the one or more PSMA expressing tumors or cells with an effective amount of a compound of formula (I), the compound of formula (I) comprising:

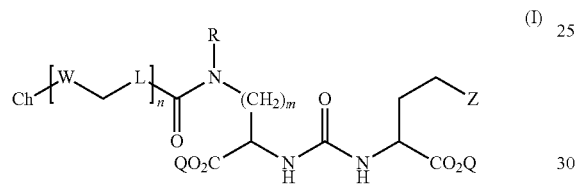

(I)

wherein:
Z is tetrazole or $CO_2Q$;
Q is H or a protecting group;
m is an integer selected from the group consisting of 1, 2, 3, 4, and 5;
R is —$CH_2$—$R^1$;
$R^1$ is:

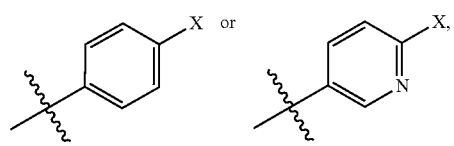

wherein each X is independently Br or I;

L consists of a $C_1$-$C_6$ alkylene linker;
W is —(C=O)—$NR^2$—, and —(C=S)—$NR^2$—;
$R^2$ is H or a $C_1$-$C_4$ alkyl;
n is 1;
Ch is a chelating agent having a structure of:

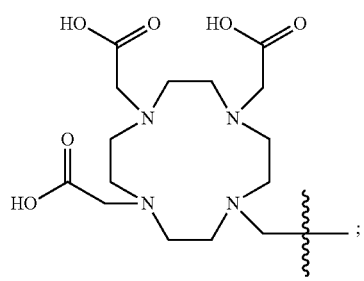 [SMILES: *CN1CCN(CC(=O)O)CCN(CC(=O)O)CCN(CC(=O)O)CC1]

that comprises a radiometal suitable for radiotherapy selected from the group consisting of $^{212}$Pb, $^{225}$Ac, $^{213}$Bi, and $^{203}$Pb;

and pharmaceutically acceptable salts thereof.

4. The method of claim 3, wherein the compound is selected from the group consisting of:

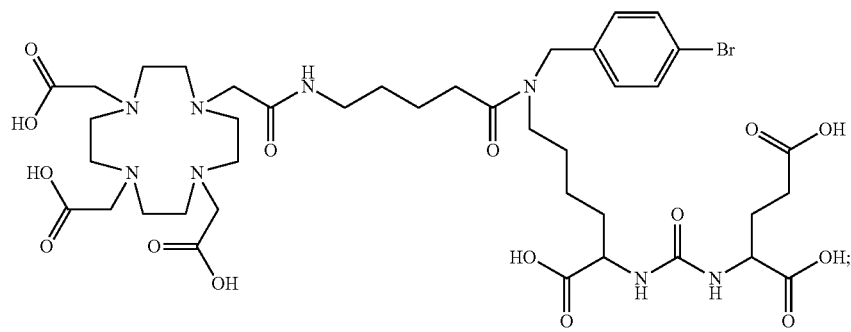

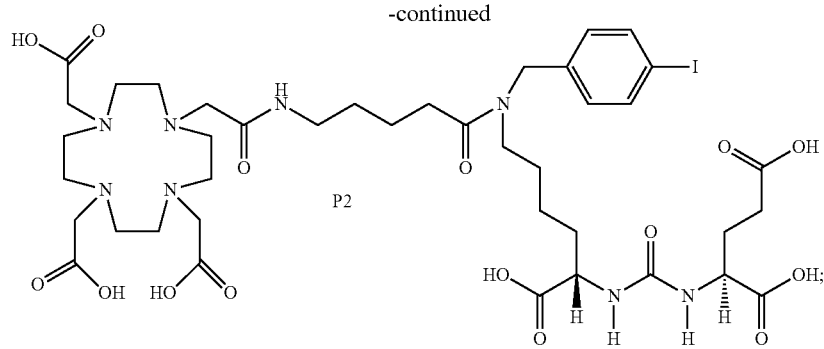

and

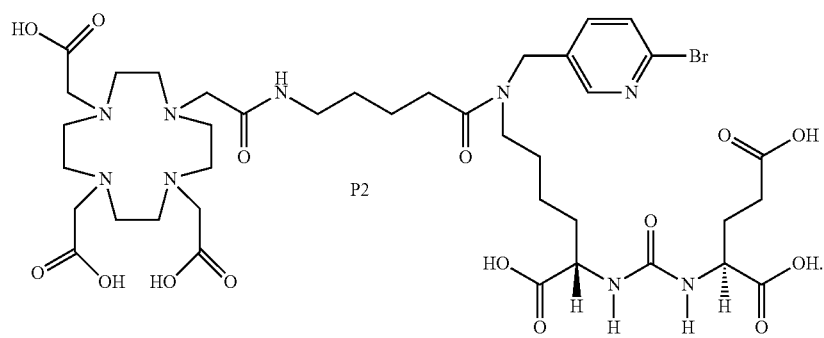

5. The method of claim 3, wherein the one or more PSMA-expressing tumor or cell is selected from the group consisting of: a prostate tumor or cell, a metastasized prostate tumor or cell, a lung tumor or cell, a renal tumor or cell, a glioblastoma, a pancreatic tumor or cell, a bladder tumor or cell, a sarcoma, a melanoma, a breast tumor or cell, a colon tumor or cell, a germ cell, a pheochromocytoma, an esophageal tumor or cell, a stomach tumor or cell, and combinations thereof.

6. The method of claim 3, wherein the one or more PSMA-expressing tumor or cell is a prostate tumor or cell.

7. The method of claim 3, wherein the one or more PSMA-expressing tumor or cell is in vitro, in vivo, or ex vivo.

8. The method of claim 3, wherein the one or more PSMA-expressing tumor or cell is present in a subject.

9. The method of claim 8, wherein the subject is human.

10. The method of claim 3, wherein the method results in inhibition of the tumor growth.

11. The compound of claim 1, wherein the compound of formula (I) is:

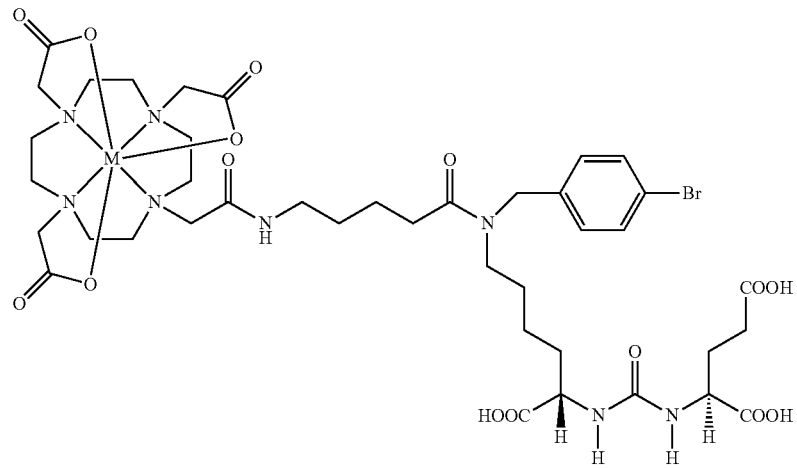

wherein: M is $^{225}$Ac.

12. The method of claim 3, wherein the compound of formula (I) is:
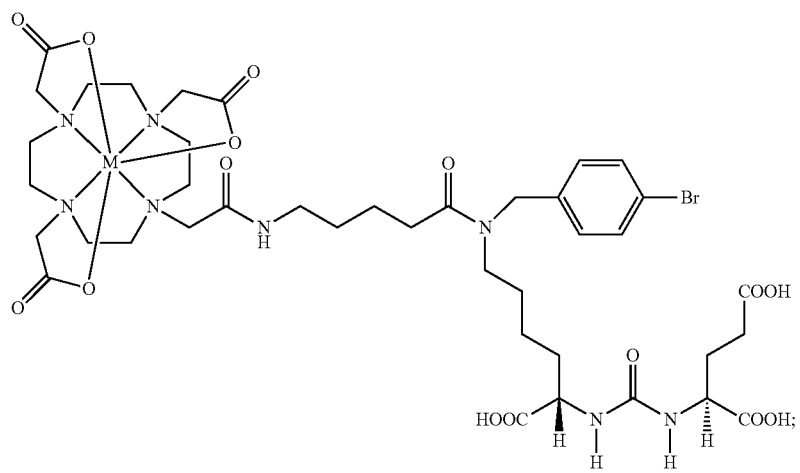
wherein: M is $^{225}$Ac.

UNITED STATES PATENT AND TRADEMARK OFFICE
CERTIFICATE OF CORRECTION

PATENT NO. : 11,478,558 B2  
APPLICATION NO. : 16/617244  
DATED : October 25, 2022  
INVENTOR(S) : Sangeeta Ray and Martin G. Pomper Page 1 of 1

It is certified that error appears in the above-identified patent and that said Letters Patent is hereby corrected as shown below:

In the Claims

1st compound for Claim 2, Column 161-162 insert:

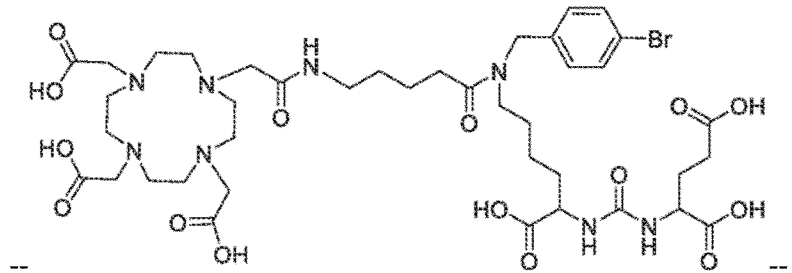

Signed and Sealed this  
Twenty-fourth Day of January, 2023

Katherine Kelly Vidal  
*Director of the United States Patent and Trademark Office*